(12) United States Patent
Grosman et al.

(10) Patent No.: US 12,268,846 B2
(45) Date of Patent: Apr. 8, 2025

(54) REGULATING DELIVERY OF INSULIN TO A BODY OF A USER BY A FLUID DELIVERY DEVICE

(71) Applicant: Medtronic MiniMed, Inc., Northridge, CA (US)

(72) Inventors: Benyamin Grosman, Winnetka, CA (US); Di Wu, Palo Alto, CA (US); Anirban Roy, Agoura Hills, CA (US); Neha J. Parikh, Pleasanton, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 0 days.

(21) Appl. No.: 18/638,352

(22) Filed: Apr. 17, 2024

(65) Prior Publication Data
US 2024/0277932 A1    Aug. 22, 2024

Related U.S. Application Data

(63) Continuation of application No. 18/118,964, filed on Mar. 8, 2023, now Pat. No. 11,986,633, which is a
(Continued)

(51) Int. Cl.
*A61M 5/172* (2006.01)
*A61B 5/00* (2006.01)
(Continued)

(52) U.S. Cl.
CPC ....... *A61M 5/1723* (2013.01); *A61B 5/14503* (2013.01); *A61B 5/14532* (2013.01);
(Continued)

(58) Field of Classification Search
CPC ............ A61M 5/1723; A61M 5/14244; G16H 20/17; G16Z 99/00; A61B 5/14503; A61B 5/14532; A61B 5/4839; A61B 5/746
See application file for complete search history.

(56) References Cited

U.S. PATENT DOCUMENTS

| 3,631,847 A | 1/1972 | Hobbs, II |
| 4,212,738 A | 7/1980 | Henne |

(Continued)

FOREIGN PATENT DOCUMENTS

| CN | 1859943 A | 11/2006 |
| CN | 1914715 A | 2/2007 |

(Continued)

OTHER PUBLICATIONS

Abel, P. et al., "Experience With an Implantable Glucose Sensor as a Prerequisite of an Artificial Beta Cell", Biomed Biochim Acta, 1984, vol. 43, No. 5, pp. 577-584.
(Continued)

*Primary Examiner* — Tammara R Peyton
(74) *Attorney, Agent, or Firm* — Weaver Austin Villeneuve & Sampson LLP

(57) ABSTRACT

Techniques related to temporary setpoint values are disclosed. The techniques may involve causing operation of a fluid delivery device in a closed-loop mode for automatically delivering fluid based on a difference between a first setpoint value and an analyte concentration value during operation of the fluid delivery device in the closed-loop mode. Additionally, the techniques may involve obtaining a second setpoint value. The second setpoint value may be a temporary setpoint value to be used for a period of time to regulate fluid delivery, and the second setpoint value may be greater than the first setpoint value. The techniques may further involve causing operation of the fluid delivery device for automatically reducing fluid delivery for the period of time based on the second setpoint value.

20 Claims, 55 Drawing Sheets

Related U.S. Application Data continuation of application No. 16/156,801, filed on Oct. 10, 2018, now Pat. No. 11,628,250, which is a continuation of application No. 15/138,540, filed on Apr. 26, 2016, now Pat. No. 10,130,767, which is a continuation-in-part of application No. 13/870,907, filed on Apr. 25, 2013, now abandoned.

(60) Provisional application No. 61/812,874, filed on Apr. 17, 2013, provisional application No. 61/694,961, filed on Aug. 30, 2012, provisional application No. 61/694,950, filed on Aug. 30, 2012.

(51) Int. Cl.
*A61B 5/145* (2006.01)
*A61M 5/142* (2006.01)
*G16H 20/17* (2018.01)
*G16Z 99/00* (2019.01)

(52) U.S. Cl.
CPC ............ *A61B 5/4839* (2013.01); *A61B 5/746* (2013.01); *A61M 5/14244* (2013.01); *G16H 20/17* (2018.01); *G16Z 99/00* (2019.02); *A61M 2005/14208* (2013.01); *A61M 2205/52* (2013.01); *A61M 2230/005* (2013.01); *A61M 2230/201* (2013.01)

(56) References Cited

U.S. PATENT DOCUMENTS

| | | |
|---|---|---|
| 4,270,532 A | 6/1981 | Franetzki et al. |
| 4,282,872 A | 8/1981 | Franetzki et al. |
| 4,373,527 A | 2/1983 | Fischell |
| 4,395,259 A | 7/1983 | Prestele et al. |
| 4,433,072 A | 2/1984 | Pusineri et al. |
| 4,443,218 A | 4/1984 | DeCant, Jr. et al. |
| 4,494,950 A | 1/1985 | Fischell |
| 4,533,346 A | 8/1985 | Cosgrove, Jr. et al. |
| 4,542,532 A | 9/1985 | McQuilkin |
| 4,550,731 A | 11/1985 | Batina et al. |
| 4,559,037 A | 12/1985 | Franetzki et al. |
| 4,562,751 A | 1/1986 | Nason et al. |
| 4,573,994 A | 3/1986 | Fischell et al. |
| 4,618,408 A | 10/1986 | Malavarca et al. |
| 4,671,288 A | 6/1987 | Gough |
| 4,678,408 A | 7/1987 | Nason et al. |
| 4,685,903 A | 8/1987 | Cable et al. |
| 4,731,051 A | 3/1988 | Fischell |
| 4,731,726 A | 3/1988 | Allen, III |
| 4,755,173 A | 7/1988 | Konopka et al. |
| 4,781,798 A | 11/1988 | Gough |
| 4,803,625 A | 2/1989 | Fu et al. |
| 4,809,697 A | 3/1989 | Causey, III et al. |
| 4,826,810 A | 5/1989 | Aoki |
| 4,871,351 A | 10/1989 | Feingold |
| 4,898,578 A | 2/1990 | Rubalcaba, Jr. |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,485,408 A | 1/1996 | Blomquist |
| 5,497,772 A | 3/1996 | Schulman et al. |
| 5,505,709 A | 4/1996 | Funderburk et al. |
| 5,522,803 A | 6/1996 | Teissen-Simony |
| 5,543,326 A | 8/1996 | Heller et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Iliff |
| 5,609,060 A | 3/1997 | Dent |
| 5,626,144 A | 5/1997 | Tacklind et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Marttila |
| 5,687,734 A | 11/1997 | Dempsey et al. |
| 5,704,366 A | 1/1998 | Tacklind et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,315 A | 9/1998 | Van Antwerp et al. |
| 5,807,336 A | 9/1998 | Russo et al. |
| 5,807,375 A | 9/1998 | Gross et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,861,018 A | 1/1999 | Feierbach |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,951,521 A | 9/1999 | Mastrototaro et al. |
| 5,954,643 A | 9/1999 | Vanantwerp et al. |
| 5,956,501 A | 9/1999 | Brown |
| 5,960,403 A | 9/1999 | Brown |

(56) References Cited

U.S. PATENT DOCUMENTS

| | | |
|---|---|---|
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,011,984 A | 1/2000 | Van Antwerp et al. |
| 6,017,328 A | 1/2000 | Fischell et al. |
| 6,032,119 A | 2/2000 | Brown et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,183,412 B1 | 2/2001 | Benkowski et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,254,586 B1 | 7/2001 | Mann et al. |
| 6,259,937 B1 | 7/2001 | Schulman et al. |
| 6,329,161 B1 | 12/2001 | Heller et al. |
| 6,355,021 B1 | 3/2002 | Nielsen et al. |
| 6,368,141 B1 | 4/2002 | Vanantwerp et al. |
| 6,379,301 B1 | 4/2002 | Worthington et al. |
| 6,408,330 B1 | 6/2002 | DeLahuerga |
| 6,418,332 B1 | 7/2002 | Mastrototaro et al. |
| 6,424,847 B1 | 7/2002 | Mastrototaro et al. |
| 6,461,331 B1 | 10/2002 | Van Antwerp |
| 6,472,122 B1 | 10/2002 | Schulman et al. |
| 6,484,045 B1 | 11/2002 | Holker et al. |
| 6,484,046 B1 | 11/2002 | Say et al. |
| 6,503,381 B1 | 1/2003 | Gotoh et al. |
| 6,514,718 B2 | 2/2003 | Heller et al. |
| 6,544,173 B2 | 4/2003 | West et al. |
| 6,544,212 B2 | 4/2003 | Galley et al. |
| 6,553,263 B1 | 4/2003 | Meadows et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,560,741 B1 | 5/2003 | Gerety et al. |
| 6,565,509 B1 | 5/2003 | Say et al. |
| 6,579,690 B1 | 6/2003 | Bonnecaze et al. |
| 6,591,125 B1 | 7/2003 | Buse et al. |
| 6,591,876 B2 | 7/2003 | Safabash |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say et al. |
| 6,659,980 B2 | 12/2003 | Moberg et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,728,576 B2 | 4/2004 | Thompson et al. |
| 6,733,471 B1 | 5/2004 | Ericson et al. |
| 6,734,162 B2 | 5/2004 | Van Antwerp et al. |
| 6,736,797 B1 | 5/2004 | Larsen et al. |
| 6,746,582 B2 | 6/2004 | Heller et al. |
| 6,747,556 B2 | 6/2004 | Medema et al. |
| 6,749,587 B2 | 6/2004 | Flaherty |
| 6,749,740 B2 | 6/2004 | Liamos et al. |
| 6,752,787 B1 | 6/2004 | Causey, III et al. |
| 6,766,183 B2 | 7/2004 | Walsh et al. |
| 6,801,420 B2 | 10/2004 | Talbot et al. |
| 6,804,544 B2 | 10/2004 | Van et al. |
| 6,809,653 B1 | 10/2004 | Mann et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,916,159 B2 | 7/2005 | Rush et al. |
| 6,932,584 B2 | 8/2005 | Gray et al. |
| 6,932,894 B2 | 8/2005 | Mao et al. |
| 6,942,518 B2 | 9/2005 | Liamos et al. |
| 7,003,336 B2 | 2/2006 | Holker et al. |
| 7,066,909 B1 | 6/2006 | Peter et al. |
| 7,137,964 B2 | 11/2006 | Flaherty |
| 7,153,263 B2 | 12/2006 | Carter et al. |
| 7,153,289 B2 | 12/2006 | Vasko |
| 7,303,549 B2 | 12/2007 | Flaherty et al. |
| 7,396,330 B2 | 7/2008 | Banet et al. |
| 7,442,186 B2 | 10/2008 | Blomquist |
| 7,500,949 B2 | 3/2009 | Gottlieb et al. |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van et al. |
| 8,353,829 B2 | 1/2013 | Say et al. |
| 8,690,820 B2 | 4/2014 | Cinar et al. |
| 8,876,755 B2 | 11/2014 | Taub et al. |
| 9,526,834 B2 | 12/2016 | Keenan et al. |
| 9,878,096 B2 | 1/2018 | Roy et al. |
| 9,943,644 B2 | 4/2018 | Hayter |
| 10,130,767 B2 | 11/2018 | Grosman et al. |
| 10,758,674 B2 | 9/2020 | Keenan et al. |
| 11,241,535 B2 | 2/2022 | Mastrototaro et al. |
| 11,338,086 B2* | 5/2022 | Roy .................. A61M 5/1723 |
| 11,628,250 B2 | 4/2023 | Grosman et al. |
| 11,986,633 B2 | 5/2024 | Grosman et al. |
| 2001/0044731 A1 | 11/2001 | Coffman et al. |
| 2002/0013518 A1 | 1/2002 | West et al. |

(56) References Cited

U.S. PATENT DOCUMENTS

| | | |
|---|---|---|
| 2002/0055857 A1 | 5/2002 | Mault |
| 2002/0082665 A1 | 6/2002 | Haller et al. |
| 2002/0137997 A1 | 9/2002 | Mastrototaro et al. |
| 2003/0060765 A1 | 3/2003 | Campbell et al. |
| 2003/0078560 A1 | 4/2003 | Miller et al. |
| 2003/0088166 A1 | 5/2003 | Say et al. |
| 2003/0144581 A1 | 7/2003 | Conn et al. |
| 2003/0152823 A1 | 8/2003 | Heller |
| 2003/0163223 A1 | 8/2003 | Blomquist |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0208113 A1 | 11/2003 | Mault et al. |
| 2003/0220552 A1 | 11/2003 | Reghabi et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0073095 A1 | 4/2004 | Causey et al. |
| 2004/0074785 A1 | 4/2004 | Holker et al. |
| 2004/0093167 A1 | 5/2004 | Braig et al. |
| 2004/0097796 A1 | 5/2004 | Berman et al. |
| 2004/0102683 A1 | 5/2004 | Khanuja et al. |
| 2004/0111017 A1 | 6/2004 | Say et al. |
| 2004/0122353 A1 | 6/2004 | Shahmirian et al. |
| 2004/0167465 A1 | 8/2004 | Mihai et al. |
| 2004/0263354 A1 | 12/2004 | Mann et al. |
| 2005/0038331 A1 | 2/2005 | Silaski et al. |
| 2005/0038680 A1 | 2/2005 | McMahon |
| 2005/0154271 A1 | 7/2005 | Rasdal et al. |
| 2005/0192557 A1 | 9/2005 | Brauker et al. |
| 2006/0229694 A1 | 10/2006 | Schulman et al. |
| 2006/0238333 A1 | 10/2006 | Welch et al. |
| 2006/0293571 A1 | 12/2006 | Bao et al. |
| 2007/0088521 A1 | 4/2007 | Shmueli et al. |
| 2007/0106135 A1 | 5/2007 | Sloan et al. |
| 2007/0123819 A1 | 5/2007 | Mernoe et al. |
| 2007/0135866 A1 | 6/2007 | Baker et al. |
| 2007/0173761 A1 | 7/2007 | Kanderian et al. |
| 2007/0179671 A1 | 8/2007 | Arimatsu et al. |
| 2007/0276279 A1 | 11/2007 | Echauz et al. |
| 2008/0154503 A1 | 6/2008 | Wittenber et al. |
| 2008/0228056 A1 | 9/2008 | Blomquist et al. |
| 2008/0269723 A1 | 10/2008 | Mastrototaro et al. |
| 2008/0275384 A1 | 11/2008 | Mastrototaro |
| 2009/0081951 A1 | 3/2009 | Erdmann et al. |
| 2009/0082635 A1 | 3/2009 | Baldus et al. |
| 2010/0057040 A1 | 3/2010 | Hayter |
| 2010/0057041 A1 | 3/2010 | Hayter |
| 2010/0160861 A1 | 6/2010 | Causey, III et al. |
| 2010/0185175 A1 | 7/2010 | Kamen et al. |
| 2010/0262117 A1 | 10/2010 | Magni et al. |
| 2011/0028279 A1 | 2/2011 | Chen |
| 2011/0054391 A1 | 3/2011 | Ward et al. |
| 2011/0106011 A1 | 5/2011 | Cinar et al. |
| 2011/0313390 A1 | 12/2011 | Roy et al. |
| 2013/0245547 A1 | 9/2013 | El-Khatib et al. |
| 2014/0066892 A1 | 3/2014 | Keenan et al. |
| 2019/0076600 A1 | 3/2019 | Grosman et al. |
| 2020/0353168 A1 | 11/2020 | Keenan et al. |
| 2022/0118182 A1 | 4/2022 | Mastrototaro et al. |

FOREIGN PATENT DOCUMENTS

| | | |
|---|---|---|
| CN | 1973768 A | 6/2007 |
| CN | 101675438 A | 3/2010 |
| CN | 102056645 A | 5/2011 |
| CN | 102334113 A | 1/2012 |
| CN | 102369032 A | 3/2012 |
| CN | 102576375 A | 7/2012 |
| CN | 102946923 A | 2/2013 |
| DE | 4329229 A1 | 3/1995 |
| EP | 0319268 A2 | 6/1989 |
| EP | 0806738 A1 | 11/1997 |
| EP | 0880936 A2 | 12/1998 |
| EP | 1338295 A1 | 8/2003 |
| EP | 1631036 A2 | 3/2006 |
| GB | 2218831 A | 11/1989 |
| JP | 2006510467 A | 3/2006 |
| JP | 2007516814 A | 6/2007 |
| JP | 2010512945 A | 4/2010 |
| JP | 2010519623 A | 6/2010 |
| JP | 2010521222 A | 6/2010 |
| JP | 2012502693 A | 2/2012 |
| WO | 9620745 A1 | 7/1996 |
| WO | 9625088 A1 | 8/1996 |
| WO | 9636389 A1 | 11/1996 |
| WO | 9637246 A1 | 11/1996 |
| WO | 9721456 A1 | 6/1997 |
| WO | 9820439 A1 | 5/1998 |
| WO | 9824358 A2 | 6/1998 |
| WO | 9842407 A1 | 10/1998 |
| WO | 9849659 A2 | 11/1998 |
| WO | 9856293 A1 | 12/1998 |
| WO | 9859487 A1 | 12/1998 |
| WO | 9908183 A1 | 2/1999 |
| WO | 9910801 A1 | 3/1999 |
| WO | 9918532 A1 | 4/1999 |
| WO | 9922236 A1 | 5/1999 |
| WO | 9929230 A1 | 6/1999 |
| WO | 0010628 A2 | 3/2000 |
| WO | 0018449 A2 | 4/2000 |
| WO | 0019887 A1 | 4/2000 |
| WO | 0035530 A1 | 6/2000 |
| WO | 0048112 A2 | 8/2000 |
| WO | 0078210 A1 | 12/2000 |
| WO | 02058537 A2 | 8/2002 |
| WO | 02066101 A2 | 8/2002 |
| WO | 03001329 A2 | 1/2003 |
| WO | 03094090 A2 | 11/2003 |
| WO | 2005065538 A2 | 7/2005 |
| WO | 2011162970 A1 | 12/2011 |
| WO | 2014035570 A2 | 3/2014 |
| WO | 2014035672 A2 | 3/2014 |

OTHER PUBLICATIONS

Bergman, R.N. et al., "Physiological Evaluation of Factors Controlling Glucose Tolerance in Man", Journal of Clinical Investigation, The American Society for Clinical Investigation, Inc, Dec. 1981, vol. 68, pp. 1456-1467.
Bindra, D.S. et al., "Design and in Vitro Studies of a Needle-type Glucose Sensor for Subcutaneous Monitoring", American Chemistry Society, Sep. 1991, vol. 63, No. 17, pp. 1692-1696.
Bode, B.W. et al., "Reduction in Severe Hypoglycemia With Long-term Continuous Subcutaneous Insulin Infusion in Type I Diabetes", Diabetes Care, Apr. 1996, vol. 19, No. 4, pp. 324-327.
Boguslavsky, L. et al., "Applications of Redox Polymers in Biosensors", Solid State Ionics, Mar. 1993, vol. 60, No. 1-3, pp. 189-197.
Clarke et al., "Closed-Loop Artificial Pancreas Using Subcutaneous Glucose Sensing and Insulin Delivery and a Model-Predictive Control Algorithm: The Virginia Experience," Journal of Diabetes Science and Technology, Sep. 2009, vol. 3(5), pp. 8.
D'Azzo, J. et al., "Linear Control System Analysis and Design with Matlab," Marcel Dekker, Inc, 2003, 31 pages.
Disetronic H-TRON® plus Quick Start Manual, 91 pages, [pre-2012].
Disetronic H-TRON® plus Reference Manual, 83 pages, [pre-2012].
Disetronic My Choice H-TRON plus Insulin Pump Reference Manual, 102 pages, [pre-2012].
Disetronic My Choice. TM D-TRONTM Insulin Pump Reference Manual, 162 pages, [pre-2012].
EP Extended European Search report dated May 11, 2015, in Application No. 15156952.
Garry M. Steil, et al., The Effect of insulin Feedback on Closed Loop Glucose Control, Journal of Clinical Endocrinology Metabolism, May 1, 2011, pp. 1402-1408, vol. 96, Issue No. 5.
Geise, R.J .et al., "Electropolymerized 1,3-Diaminobenzene for the Construction of a 1,1'-Dimethylferrocene Mediated Glucose Biosensor", Analytica Chimica Acta, Sep. 1993, vol. 281, No. 3, pp. 467-473.

(56) References Cited

OTHER PUBLICATIONS

Gernet, S. et al., "A Planar Glucose Enzyme Electrode", Sensors and Actuators, May 1989, vol. 17, No. 3-4, pp. 537-540.
Gernet, S. et al., "Fabrication and Characterization of a Planar Electrochemical Cell and Its Application as a Glucose Sensor", Sensors and Actuators, Jun. 1989, vol. 18, No. 1, pp. 59-70.
Gortan, L. et al., "Amperometric Glucose Sensors Based on Immobilized Glucose-Oxidizing Enymes and Chemically Modified Electrodes," Analytica Chimica Acta, 1991, vol. 249, No. 1, pp. 43-54.
Gorton, L. et al., "Amperometric Biosensors Based on an Apparent Direct Electron Transfer Between Electrodes and Immobilized Peroxiases," Analyst, Aug. 1992, vol. 117, pp. 1235-1241.
Gough, D. A. et al., "Two-Dimensional Enzyme Electrode Sensor for Glucose", Analytical Chemistry, 1985, vol. 57, No. 5, pp. 2351-2357.
Gregg, B. A. et al., "Redox Polymer Films Containing Enzymes. 1. A Redox-Conducting Epoxy Cement: Synthesis, Characterization, and Electrocatalytic Oxidation of Hydroquinone", The Journal of Physical Chemistry, 1991, vol. 95, No. 15, pp. 5970-5975.
Gregg, B.A. et al., "Cross-Linked Redox Gels Containing Glucose Oxidase for Amperometric Biosensor Applications", Analytical Chemistry, 1990, vol. 62, No. 3, pp. 258-263.
Guyton, A.C., "Insulin, Glucagon, and Diabetes Mellitus," Textbook of Medical Physiology, W. B. Saunders Company, Eighth Edition, 1991, Chapter 78, pp. 855-867.
Hashiguchi, Y. et al., "Development of a Miniaturized Glucose Monitoring System by Combining a Needle-Type Glucose Sensor With Microdialysis Sampling Method," Diabetes Care, May 1994, vol. 17, No. 5, pp. 387-396.
Heller, A. et al., "Electrical Wiring of Redox Enzymes", Accounts of Chemical Research, 1990, vol. 23, No. 5, pp. 128-134.
Hirsch, I. B. et al., "Intensive Insulin Therapy for Treatment of Type I Diabetes", Diabetes Care, Dec. 1990, vol. 13, No. 12, pp. 1265-1283.
Hovorak et al., "Manual Closed-loop Insulin Delivery in Children and Adolescents With Type 1 Diabetes: a Phase 2 Randomized Crossover Trial, "Lancet, Feb. 2010, vol. 375(9716), pp. 9.
Hovorka et al., "Overnight Closed-loop Insulin Delivery (Artificial Pancreas) in Adults With Type 1 Diabetes: Crossover Randomized Controlled Studies," BMJ, Apr. 2011, vol. 342, pp. 10.
Hovorka R., "Continuous Glucose Monitoring and Closed-loop Systems," Diabetic Medicine, 2006, vol. 23(1), pp. 1-12.
Hovorka, R. et al., "Nonlinear Model Predictive Control of Glucose Concentration in Subjects with Type 1 Diabetes", Physiological Measurement, Aug. 2004, vol. 25, No. 4, pp. 905-920.
International Preliminary Report on Patentability dated Mar. 12, 2015 in Application No. PCT/US2013/051886.
International Search Report and Written Opinion dated Oct. 14, 2014 in PCT Application No. PCT/US2013/051886.
Jacobs, P., et al., "Development of a Fully Automated Closed Loop Artificial Pancreas Control System With Dual Pump Delivery of Insulin and Glucagon," Annual International Conference of the IEEE Engineering in Medicine and Biology Society, 2011, pp. 397-400.
Jobst, G. et al., "Thin-Film Microbiosensors for Glucose-Lactate Monitoring",Analytical Chemistry, Sep. 15, 1996, vol. 68, No. 18, pp. 3173-3179.
Johnson, K.W. et al., "In Vivo Evaluation of an Electroenzymatic Glucose Sensor Implanted in Subcutaneous Tissue", Biosensors & Bioelectronics, 1992, vol. 7, No. 10, pp. 709-714.
Jonsson, G. et al., "An Electromechanical Sensor for Hydrogen Peroxide Based on Peroxidase Adsorbed on a Spectrographic Graphite Electrode," Electroanalysis, Sep. 1989, vol. 1, No. 5, pp. 465-468.
Kahn, S.E., et al., "Quantification of the Relationship Between Insulin Sensitivity and Beta-Cell Function in Human Subjects. Evidence for a Hyperbolic Function," Diabetes, Nov. 1993, vol. 42 (11), pp. 1663-1672.
Kanapieniene, J. J. et al., "Miniature Glucose Biosensor with Extended Linearity," Sensors and Actuators B: Chemical, Dec. 1992, vol. 10, No. 1, pp. 37-40.
Kaufman, et al., "Type 1 Diabetes Mellitus," Pediatrics in Review, vol. 24, No. 9, Sep. 2003, pp. 291-323.
Kawamori, R. et al., "Perfect Normalization of Excessive Glucagon Responses to Intraveneous Arginine in Human Diabetes Mellitus With the Artificial Beta-Cell", Diabetes, Sep. 1980, vol. 29, No. 9, pp. 762-765.
Kawamura, T. et al., "The importance of carbohydrate counting in the treatment of children with diabetes," Pediatric Diabetes, Jun. 20, 2007, vol. 8, pp. 57-62.
Kazuhiko, T. et al., "Specific Complexation with Mono- and Disaccharides that can be Detected by Circular Dichroism", J. Org. Chem., 1991, vol. 56, pp. 4089-4091.
Kimura, J. et al., "An Immobilized Enzyme Membrane Fabrication Method", Biosensors, 1988, vol. 4, No. 1, pp. 41-52.
Kollind, M., et al., "Insulin Clearance During Hypoglycemia in Patients With Insulin-dependent Diabetes Mellitus," Hormone and Metabolic Research, Jul. 1991, vol. 23 (7), pp. 333-335.
Koudelka, M. et al., "In-vivo Behaviour of Hypodermically Implanted Microfabricated Glucose Sensors", Biosensors & Bioelectronics, 1991, vol. 6, No. 1, pp. 31-36.
Koudelka, M. et al., "Planar Amperometric Enzyme-Based Glucose Microelectrode", Sensors & Actuators, Jun. 15, 1989, vol. 18, No. 2, pp. 157-165.
Ljung, "System Identification: Theory For The User," University ofLinkoeping, Sweden, P T R Prentice Hall, Englewood Cliffs, New Jersey, 1987, pp. 255. (Applicant points out, in accordance with MPEP 609.04(a), that the year of publication, 1987 is sufficiently earlier than the effective U.S. filing date, so that the particular month of publication is not in issue.).
Loutseiko, M. et al., "Closed-Loop Insulin Delivery Utilizing Pole Placement to Compensate for Delays in Subcutaneous Insulin Delivery," Journal of Diabetes Science and Technology, Nov. 2011, vol. 5, No. 6, pp. 1342-1351.
Mastrototaro, J.J. et al., "An Electroenzymatic Glucose Sensor Fabricated on a Flexible Substrate", Sensors and Actuators B: Chemical, Aug. 1991, vol. 5, No. 1-4, pp. 139-144.
Mastrototaro, J.J., et al., "An Electroenzymatic Sensor Capable of 72 Hour Continuous Monitoring of Subcutaneous Glucose", 14th Annual International Diabetes Federation Congress, Washington D.C., Jun. 1991, pp. 23-28.
Mckean, B. D. et al., "A Telemetry-Instrumentation System for Chronically Implanted Glucose and Oxygen Sensors", IEEE Transactions on Biomedical Engineering, Jul. 1988, vol. 35, No. 7, pp. 526-532.
Monroe, D., "Novel Implantable: Glucose Sensors", ACL, Dec. 1989, pp. 8-16.
Morff, R.J., et al., "Microfabrication of Reproducible, Economical, Electroenzymatic Glucose Sensors", Annual International Conference of the IEEE Engineering in Medicine and Biology Society, 1990, vol. 12, No. 2, pp. 483-484.
Moussy, F. et al., "Performance of Subcutaneously Implanted Needle-Type Glucose Sensors Employing a Novel Trilayer Coating," Analytical Chemistry, Aug. 1, 1993, vol. 65, No. 15, pp. 2072-2077.
Mudaliar, S.R., et al., "Insulin Aspart (B28 Asp-Insulin): A Fast-Acting Analog of Human Insulin: Absorption Kinetics and Action Profile Compared with Regular Human Insulin in Healthy Nondiabetic Subjects," Emerging Treatments and Technologies, Diabetes Care, Sep. 1999, vol. 22(9) pp. 1501-1506.
Nakamoto, S. et al., "A Lift-Off Method for Patterning Enzyme-Immobilized Membranes in Multi-Biosensors", Sensors and Actuators , Feb. 1988, vol. 13, No. 2, pp. 165-172.
Nishida, K. et al., "Clinical Applications of the Wearable Artificel Endocrine Pancreas with the Newly Designed Needle-Type Glucose Sensor," Elsevier Sciences B.V., 1994, pp. 353-358.
Nishida, K. et al., "Development of a Ferrocene-mediated Needle-type Glucose Sensor Covered With Newly Designed Biocompatible Membrane, 2-methacryloyloxyethy1phosphorylcholine-co-n-butyl Methacrylate", Medical Progress Through Technology, 1995, vol. 21, No. 2, pp. 91-103.

(56) References Cited

OTHER PUBLICATIONS

O'Grady et al., "The Use of an Automated Portable Glucose Control System for Overnight Glucose Control in Adolescents and Young Adults with Type 1 Diabetes," Diabetes Care, Nov. 2012, vol. 35(11), pp. 2182-2187.
Panteleon, A.E., et al., "Evaluation of the Effect of Gain on the Meal Response of an Automated Closed-Loop Insulin Delivery System," Diabetes, Jul. 2006, vol. 55 (7), pp. 1995-2000.
PCT Search Report PCT/US2002/003299, dated Oct. 31, 2002, Medtronic Minimed, Inc.
Pickup et al., "Continuous Subcutaneous Insulin Infusion at 25 Years," Diabets Care, Mar. 2002, vol. 25(3), pp. 593-598.
Poitout, V. et al., "A Glucose Monitoring System for on Line Estimation in Man of Blood Glucose Concentration Using a Miniaturized Glucose Sensor Implanted in the Subcutaneous Tissue and a Wearable Control Unit", Diabetologia, Jul. 1993, vol. 36, No. 7, pp. 658-663.
Reach, G. et al., "A Method for Evaluating in vivo the Functional Characteristics of Glucose Sensors", Biosensors, 1986, vol. 2, No. 4, pp. 211-220.
Scaramuzza, A., et al., "Use of Integrated Real-time Continuous Glucose Monitoring/insulin Pump System in Children and Adolescents With Type 1 Diabetes: a 3-year Follow-up Study," Diabetes technology & therapeutics, 2011, vol. 13(2), pp. 99-103.
Shaw, G. W. et al., "In Vitro Testing of a Simply Constructed, Highly Stable Glucose Sensor Suitable for Implantation in Diabetic Patients", Biosensors and Bioelectronics, 1991, vol. 6, No. 5, pp. 401-406.
Shichiri, M., "A Needle-Type Glucose Sensor—A Valuable Tool Not Only for a Self-Blood Glucose Monitoring but for a Wearable Artifiical Pancreas", Life Support Systems Proceedings, XI Annual Meeting ESAO, Alpbach-Innsbruck, Austria, Sep. 1984, pp. 7-9.
Shichiri, M. et al., "An Artificial Endocrine Pancreas-problems Awaiting Solution for Long-term Clinical Applications of a Glucose Sensor", Frontiers of Medical and Biological Engineering : the International Journal of the Japan Society of Medical Electronics and Biological Engineering, 1991, vol. 3, No. 4, pp. 283-292.
Shichiri, M. et al., "Closed-loop Glycemic Control With a Wearable Artificial Endocrine Pancreas. Variations in Daily Insulin Requirements to Glycemic Response", Diabetes, Dec. 1984, vol. 33, No. 12, pp. 1200-1202.
Shichiri, M. et al., "Glycaemic Control in Pancreatectomized Dogs With a Wearable Artificial Endocrine Pancreas", Diabetologia, Mar. 1983, vol. 24, No. 3, pp. 179-184.
Shichiri, M. et al., "In Vivo Characteristics of Needle-type Glucose Sensor-measurements of Subcutaneous Glucose Concentrations in Human Volunteers", Hormone and Metabolic Research. Supplement Series, 1988, vol. 20, pp. 17-20.
Shichiri, M. et al., "Membrane Design for Extending the Long-Life of an Implantable Glucose Sensor," Diabetes Nutrition and Metabolism, 1989, vol. 2, No. 4, pp. 309-313.
Shichiri, M. et al., "Normalization of the Paradoxic Secretion of Glucagon in Diabetics Who Were Controlled by the Artificial Beta Cell", Diabetes, Apr. 1979, vol. 28, No. 4, pp. 272-275.
Shichiri, M. et al., "Telemetry Glucose Monitoring Device With Needle-type Glucose Sensor: a Useful Tool for Blood Glucose Monitoring in Diabetic Individuals", Diabetes care, May-Jun. 1986, vol. 9, No. 3, pp. 298-301.
Shichiri, M. et al., "The Wearable Artificial Endocrine Pancreas with a Needle-Type Glucose Sensor: Perfect Glycemic Control in Ambulatory Diabetes," Acta Paediatrica Japonica, 1984, vol. 26, No. 3, pp. 359-370.
Shichiri, M. et al., "Wearable Artificial Endocrine Pancrease With Needle-type Glucose Sensor", Lancet, Nov. 1982, vol. 2, No. 8308, pp. 1129-1131.
Shinkai.S et al., "Molecular Recognition of Mono- and Di-Saccharides by Phenylboronic Acids in Solvent Extraction and as a Monolayer",Journal of the Chemical Society Chemical Communications, Aug. 1991, vol. 15, No. 15, pp. 1039-1041.
Shults, M. C., "A Telemetry-Instrumentation System for Monitoring Multiple Subcutaneously Implanted Glucose Sensors", IEEE Transactions on Bio-medical Engineering, Oct. 1994, vol. 41, No. 10, pp. 937-942.
Soberg, et al., "Chapter 3: Laplace Transforms," Process Dynamics and Control, Second Edition Wiley, (Applicant points out, in accordance with MPEP 609.04(a), that the year of publication, 2004, is sufficiently earlier than the effective U.S. filing date, so that the particular month of publication is not in issue ), 2004, pp. 51-77.
Steil et al., "Closed-loop Insulin Delivery—What Lies Between Where We Are And Where We Are Going?," Expert Opinion on Drug Delivery, vol. 2(2).
Steil, G.M., et al., "Feasibility of Automating Insulin Delivery for the Treatment of Type 1 Diabetes," Diabetes, Dec. 2006, vol. 55 (12), pp. 3344-3350.
Steil, G.M., et al., "Metabolic Modelling and the Closed-Loop Insulin Delivery Problem," Diabetes Research and Clinical Practice, Dec. 2006, vol. 74 Suppl 2, pp. S183-S186.
Steil, G.M. et al., "Modeling Insulin Action for Development of a Closed-loop Artificial Pancreas", Diabetes Technology and Therapeutics, Mary Ann Liebert, Inc., Feb. 2005, vol. 7, No. 1, pp. 94-109.
Sternberg, R. et al., "Study and Development of Multilayer Needle-type Enzyme-based Glucose Microsensors", Biosensors, 1989, vol. 4, pp. 27-40.
Strowig, S. M., "Initiation and Management of Insulin Pump Therapy", The Diabetes Educator, Feb. 1993, vol. 19, No. 1, pp. 50-60.
Tamiya, E. et al., "Micro Glucose Sensors using Electron Mediators Immobilized on a Polypyrrole-Modified Electrode", Sensors and Actuators, 1989, vol. 18, pp. 297-307.
Urban, G., et al., "Miniaturized Multi-enzyme Biosensors Integrated With Ph Sensors on Flexible Polymer Carriers for in Vivo Applications", Biosensors & Bioelectronics, 1992, vol. 7, pp. 733-739.
Urban, G., et al., "Miniaturized Thin-film Biosensors Using Covalently Immobilized Glucose Oxidase", Biosensors Bioelectronics, 1991, vol. 6, pp. 555-562.
U.S Advisory Action dated Oct. 19, 2018 in U.S. Appl. No. 14/731,356.
U.S. Corrected Notice of Allowance dated Feb. 9, 2024 in U.S. Appl. No. 18/118,964.
U.S. Final office Action dated Aug. 16, 2018 in U.S. Appl. No. 14/731,356.
U.S. Final Office Action dated Jul. 18, 2024 in U.S. Appl. No. 16/939,421.
U.S. Final office Action dated Sep. 23, 2015 in U.S. Appl. No. 13/870,907.
U.S. Non-Final Office Action dated Aug. 22, 2022, in U.S. Appl. No. 16/156,801.
U.S. Non-Final Office Action dated Dec. 13, 2018, in U.S. Appl. No. 14/731,356.
U.S. Non-Final Office Action dated Feb. 26, 2020 in U.S. Appl. No. 15/354,451.
U.S. Non-Final Office Action dated Jul. 11, 2019, in U.S. Appl. No. 15/354,451.
U.S. Non-Final Office Action dated Mar. 8, 2018, in U.S. Appl. No. 14/731,356.
U.S. Non-Final Office Action dated Mar. 12, 2024 in U.S. Appl. No. 16/939,421.
U.S. Non-Final office Action dated May 21, 2015 in U.S. Appl. No. 13/870,907.
U.S. Non-Final office Action dated Nov. 3, 2016 in U.S. Appl. No. 13/870,907.
U.S. Non-Final Office Action dated Sep. 22, 2023, in U.S. Appl. No. 18/118,964.
U.S. Notice of Allowance dated Aug. 2, 2019 in U.S. Appl. No. 14/731,356.
U.S. Notice of Allowance dated Feb. 28, 2024 in U.S. Appl. No. 18/118,964.
U.S. Notice of Allowance dated Jan. 31, 2024 in U.S. Appl. No. 18/118,964.

(56) References Cited

OTHER PUBLICATIONS

U.S. Notice of Allowance dated Oct. 2, 2019 in U.S. Appl. No. 14/731,356.

Van Den Berghe, G., et al., "Intensive Insulin Therapy in Critically Ill Patients" The New England Journal of Medicine, Nov. 8, 2001,vol. 345(19), pp. 1359-1367.

Velho, G., et al., "In Vivo Calibration of a Subcutaneous Glucose Sensor for Determination of Subcutaneous Glucose Kinetics", Diab. Nutr. Metab., 1988, vol. 3, pp. 227-233.

Wang, J. et al., "Needle-type Dual Microsensor for the Simultaneous Monitoring of Glucose and Insulin", Analytical Chemistry, Feb. 15, 2001, vol. 73, No. 4, pp. 844-847.

Weinzimer et al., "Effect of Pramlintide on Prandial Glycemic Excursions During Closed-Loop Control in Adolescents andYoung Adults With Type 1 Diabetes," Diabetes Care, Oct. 2012, vol. 35(10), pp. 6.

Weinzimer, S.A., et al., "Fully Automated Closed-Loop Insulin Delivery Versus Semiautomated Hybrid Control in Pediatric Patients With Type 1 Diabetes Using an Artificial Pancreas," Diabetes Care, May 2008, vol. 31 (5), pp. 934-939.

Yamasaki, Y. et al., "Direct Measurement of Whole Blood Glucose by a Needle-type Sensor", Clinica Chimica Acta; International Journal of Clinical Chemistry, Mar. 15, 1989, vol. 180, No. 1, pp. 93-98.

Yokoyama, K. et al., "Integrated Biosensor for Glucose and Galactose", Analytica Chimica Acta, 1989, vol. 218, pp. 137-142.

\* cited by examiner

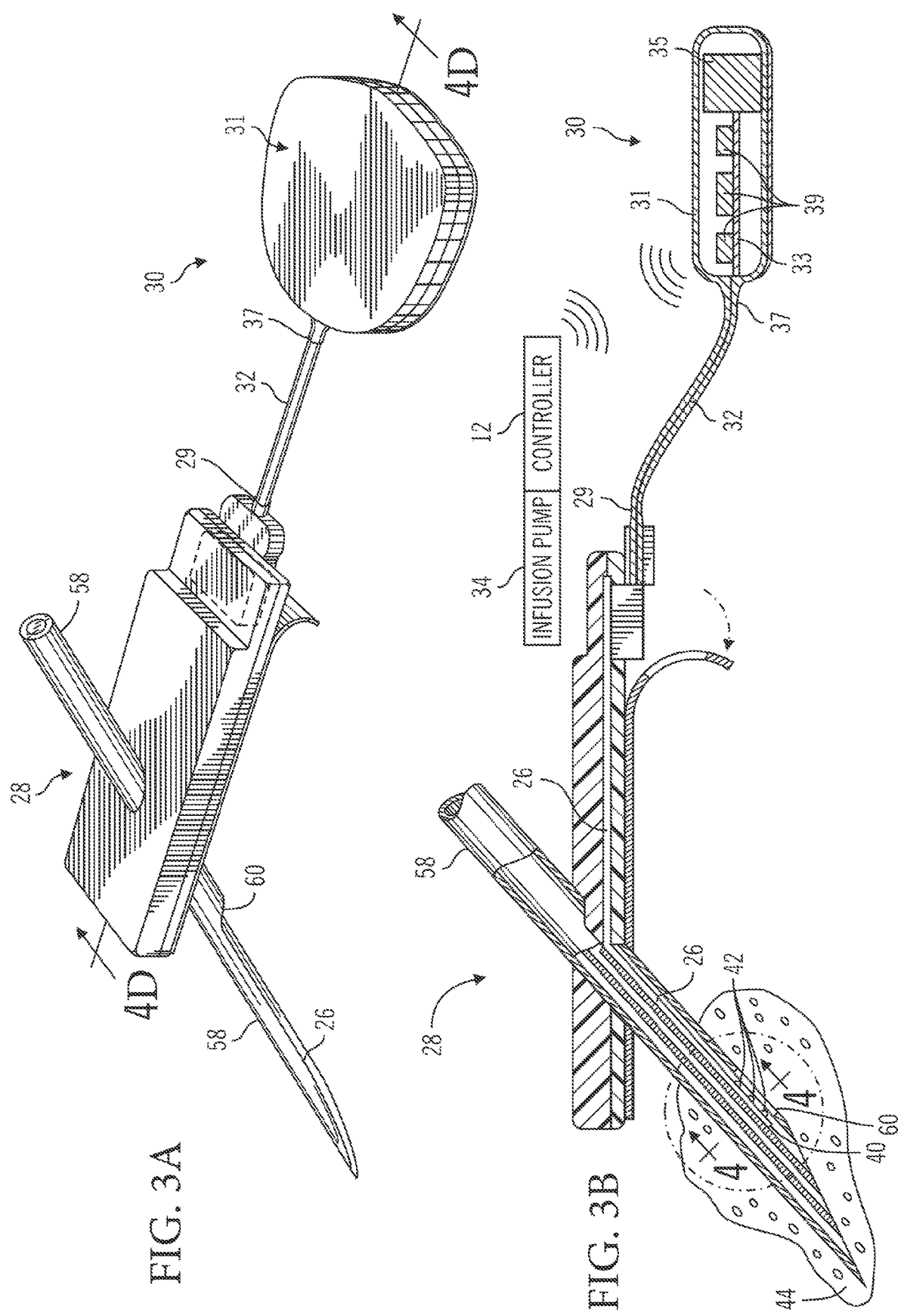

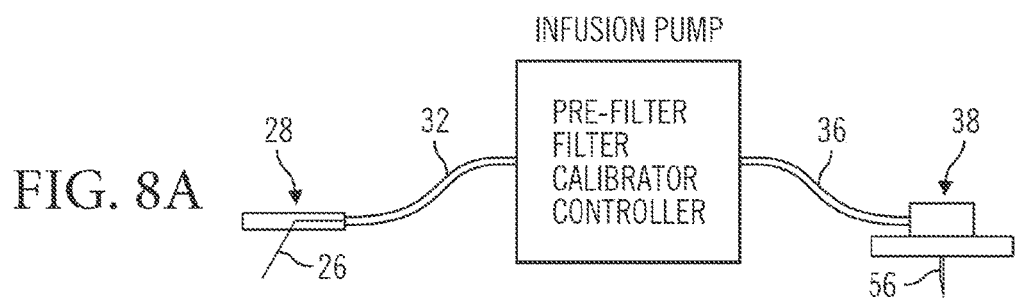
FIG. 8A
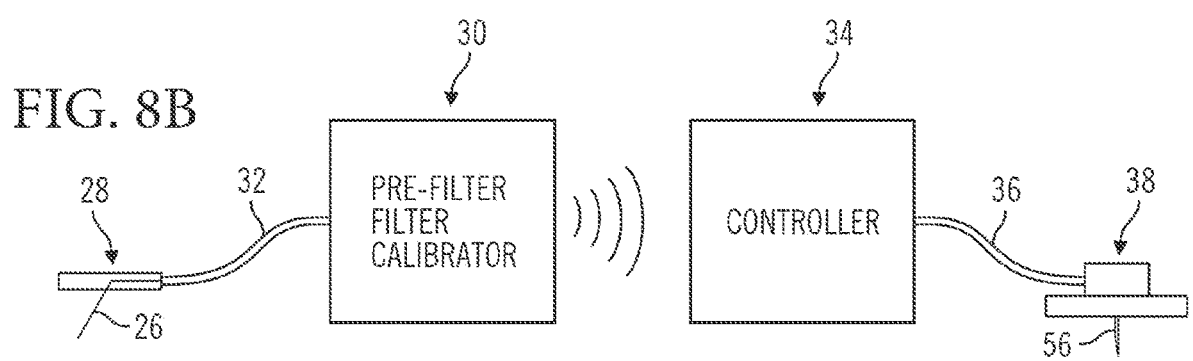
FIG. 8B
FIG. 8C
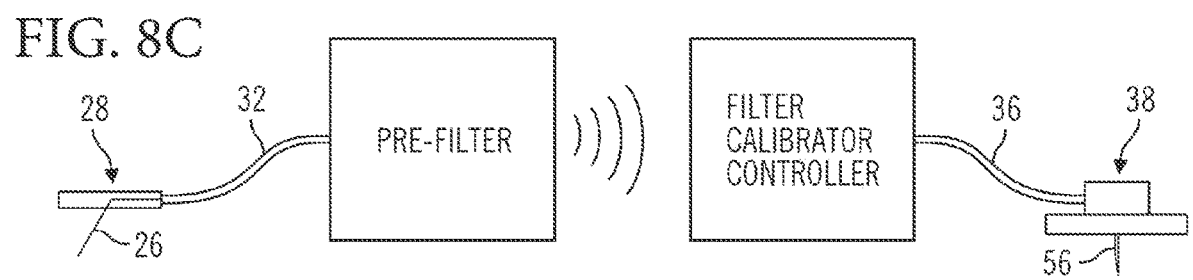
FIG. 8D
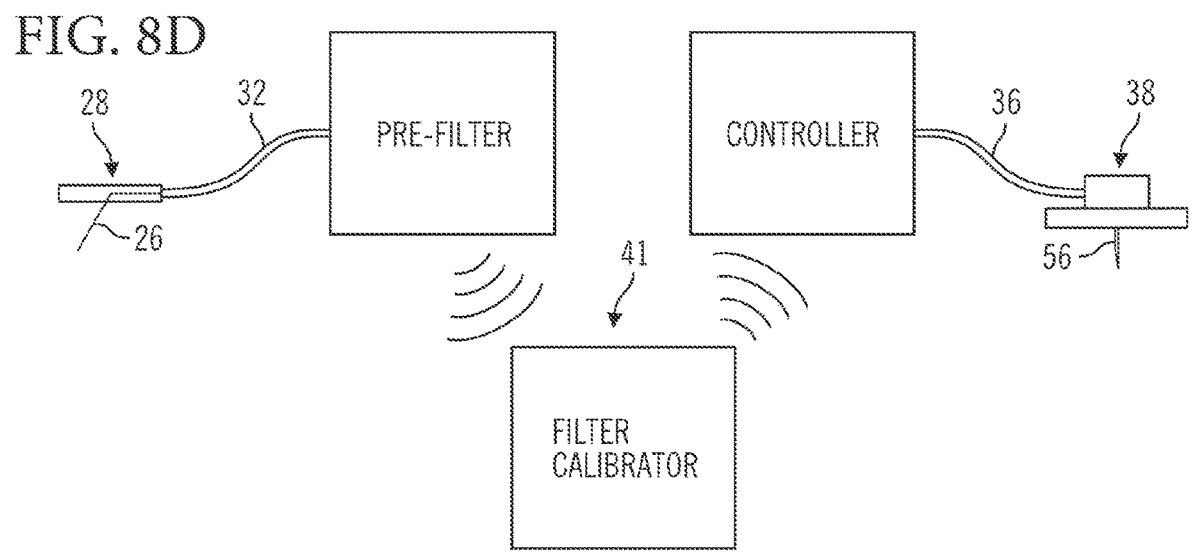

| COMPONENTS | ALTERNATIVE, FIG. 8(a) | | PREFERRED EMBODIMENT, FIG. 8(b) | | ALTERNATIVE, FIG. 8(c) | | ALTERNATIVE, FIG. 8(d) | | |
|---|---|---|---|---|---|---|---|---|---|
| | TELEMETERED CHARACTERISTIC MONITOR TRANSMITTER | INFUSION PUMP | TELEMETERED CHARACTERISTIC MONITOR TRANSMITTER | INFUSION PUMP | TELEMETERED CHARACTERISTIC MONITOR TRANSMITTER | INFUSION PUMP | TELEMETERED CHARACTERISTIC MONITOR TRANSMITTER | SUPPLEMENTAL DEVICE | SUPPLEMENTAL INFUSION PUMP |
| PRE-FILTERS | | X | X | | | X | | X | |
| FILTERS | | X | X | | | X | | X | |
| CALIBRATOR | | X | X | | X | | X | | |
| CONTROLLER | | X | | X | | X | | | X |

FIG. 9

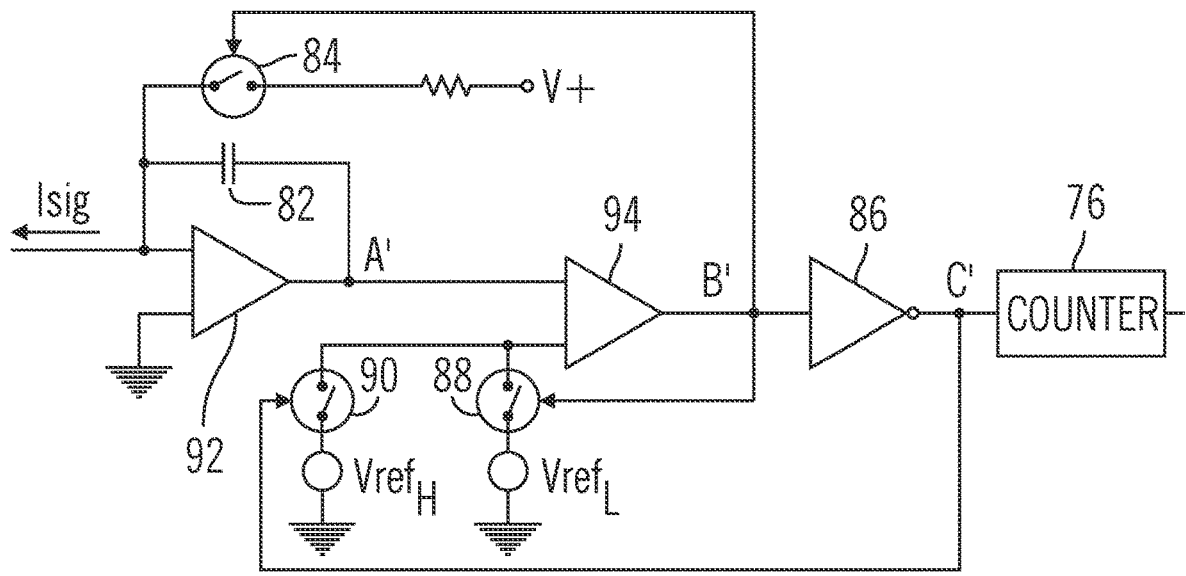
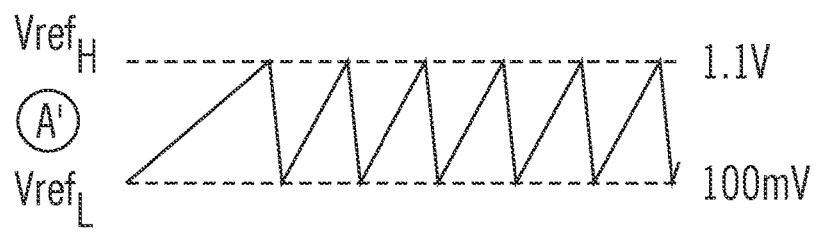
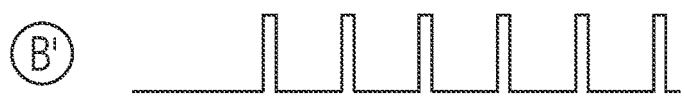
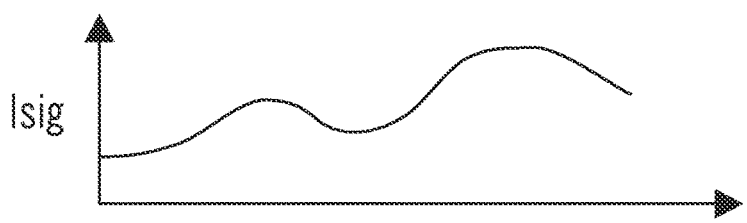
FIG. 12

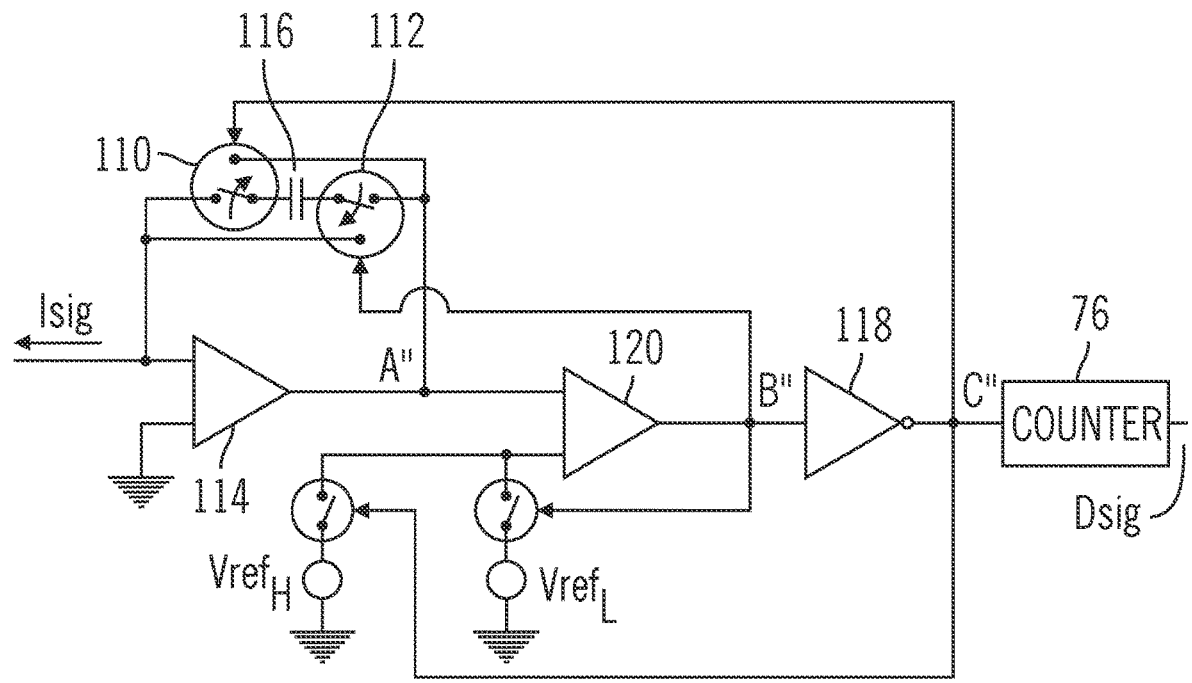
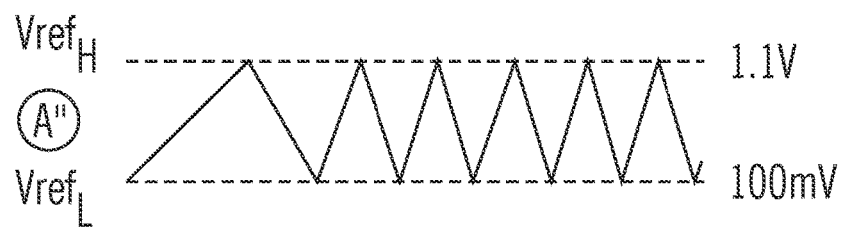
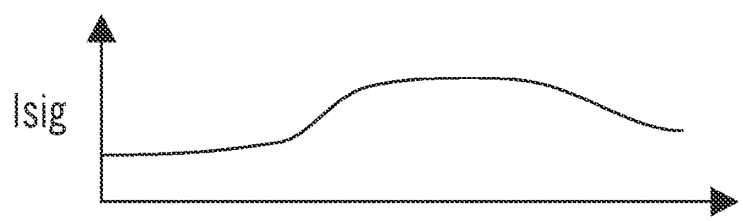
FIG. 13

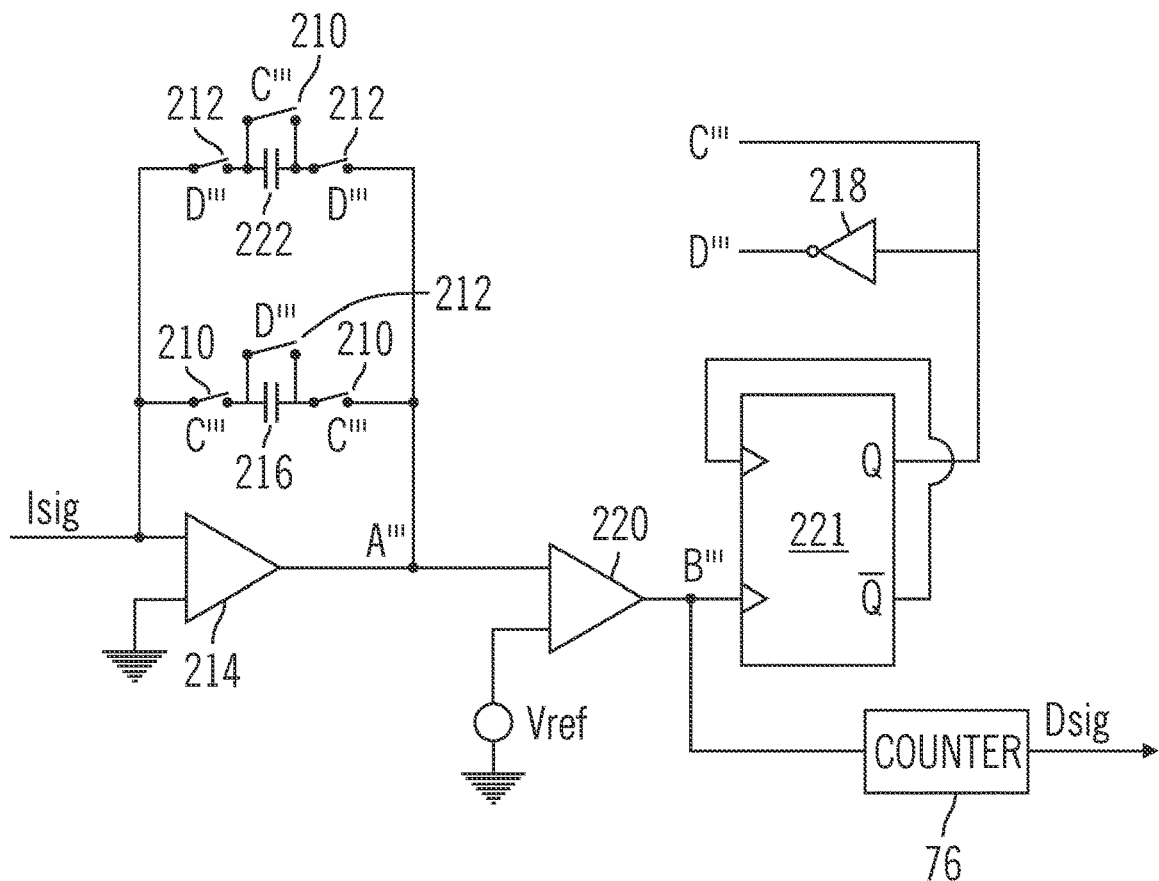
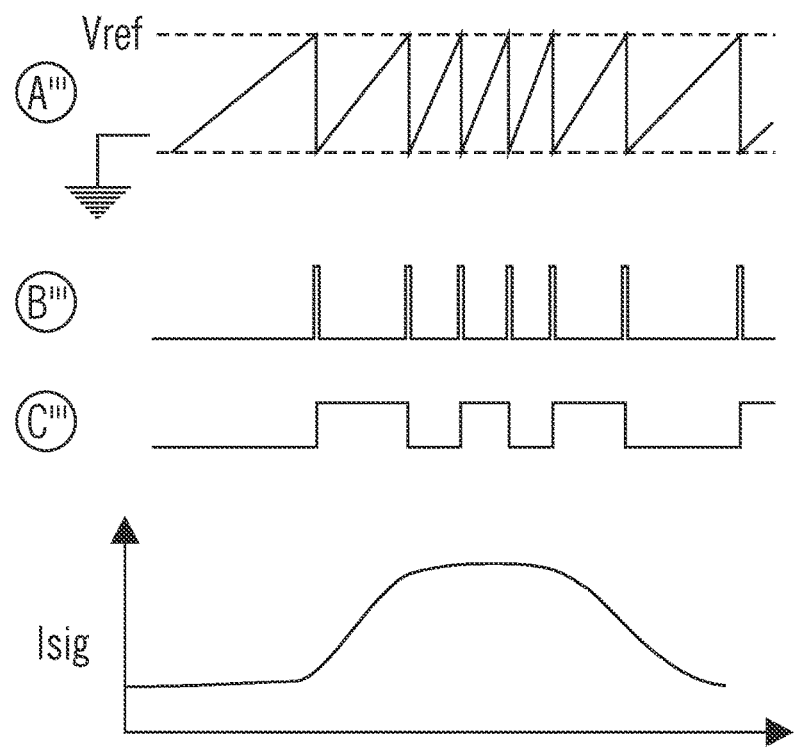
FIG. 14

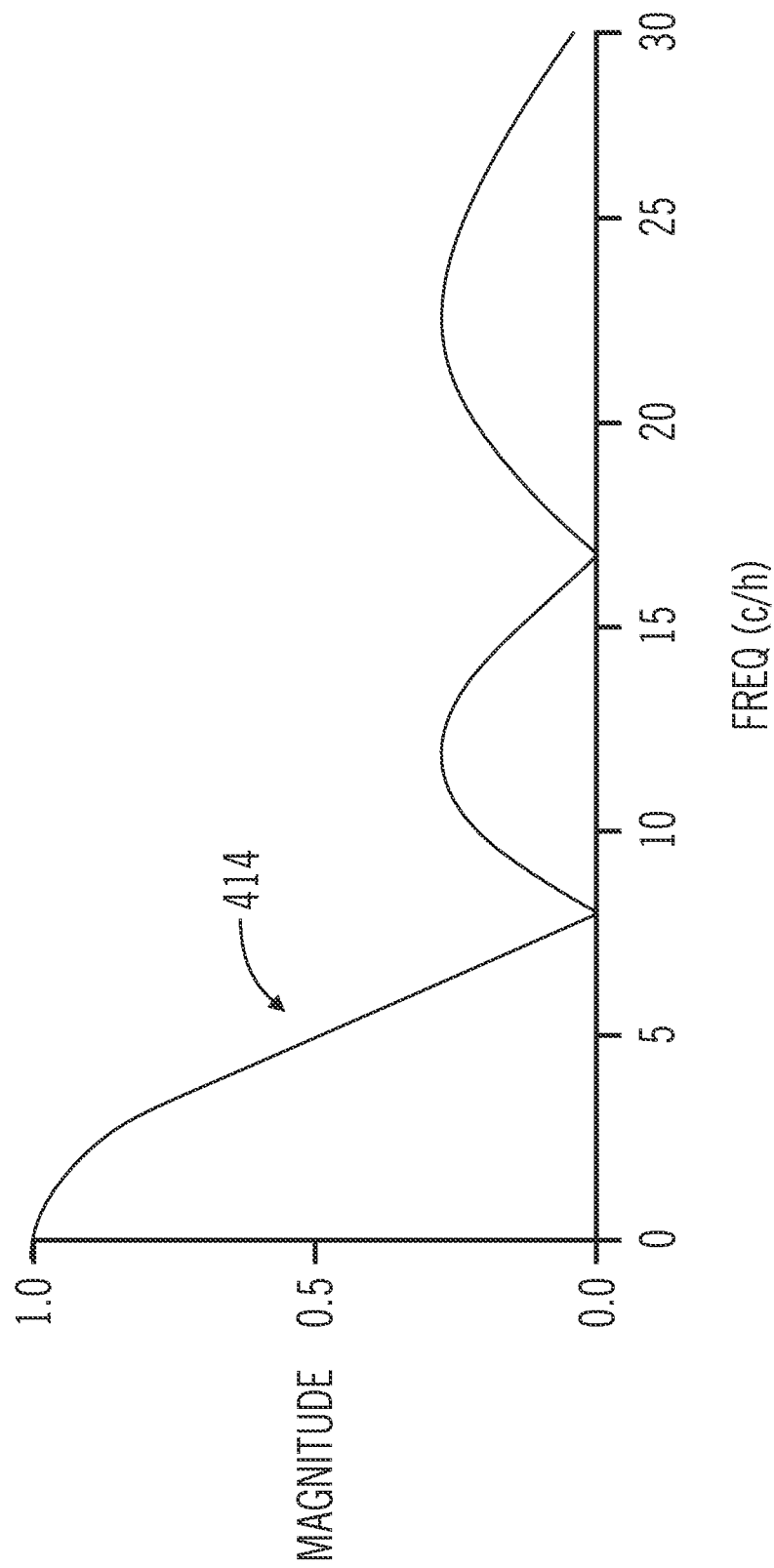

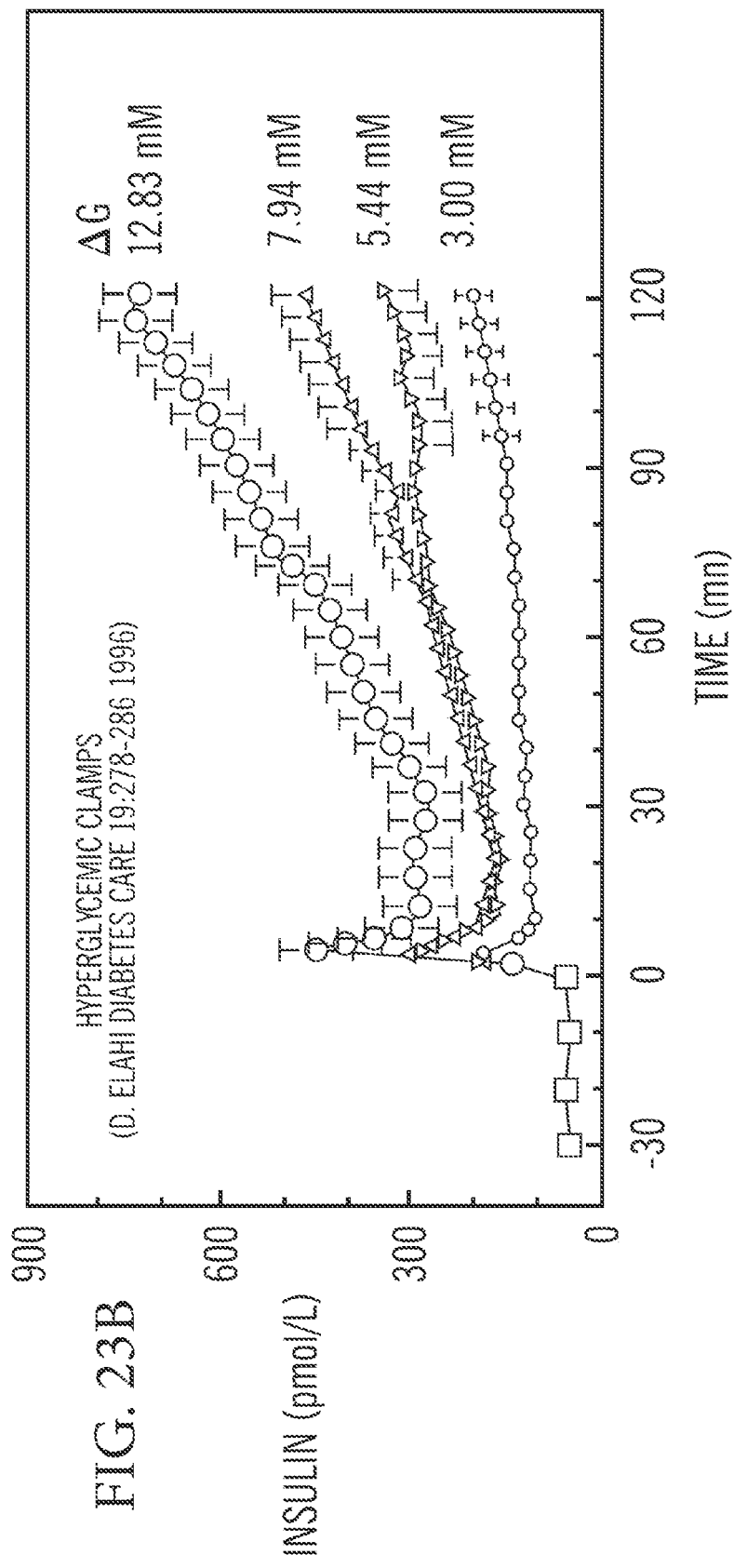

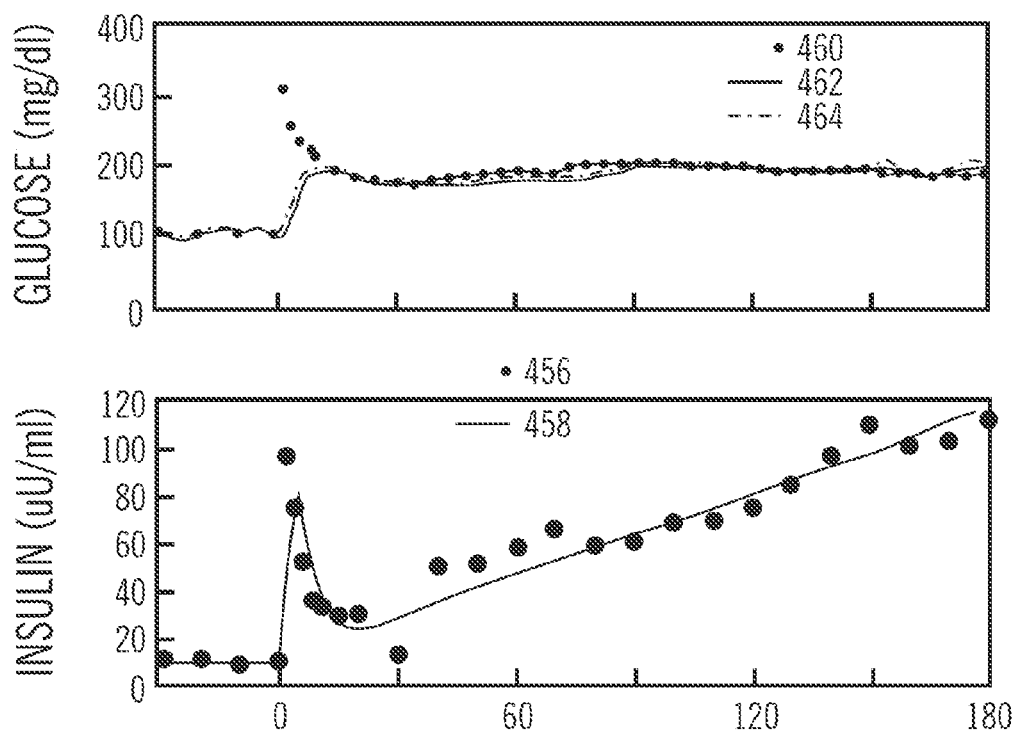
FIG. 29A
FIG. 29B
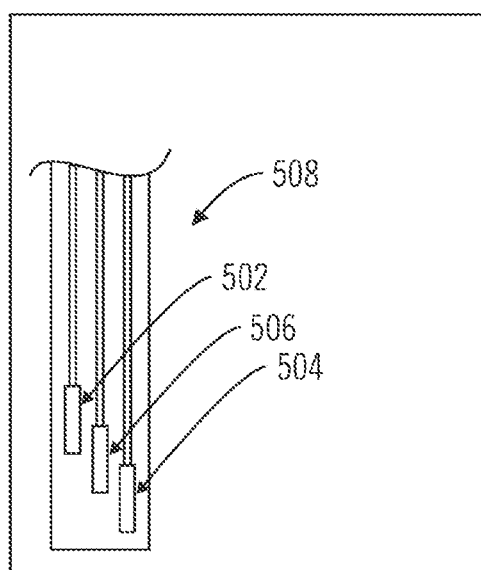
FIG. 30

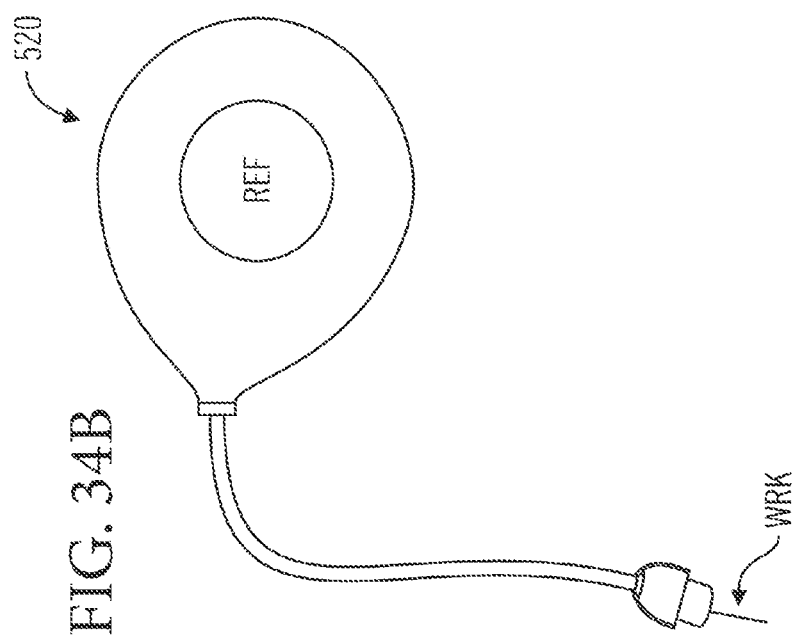
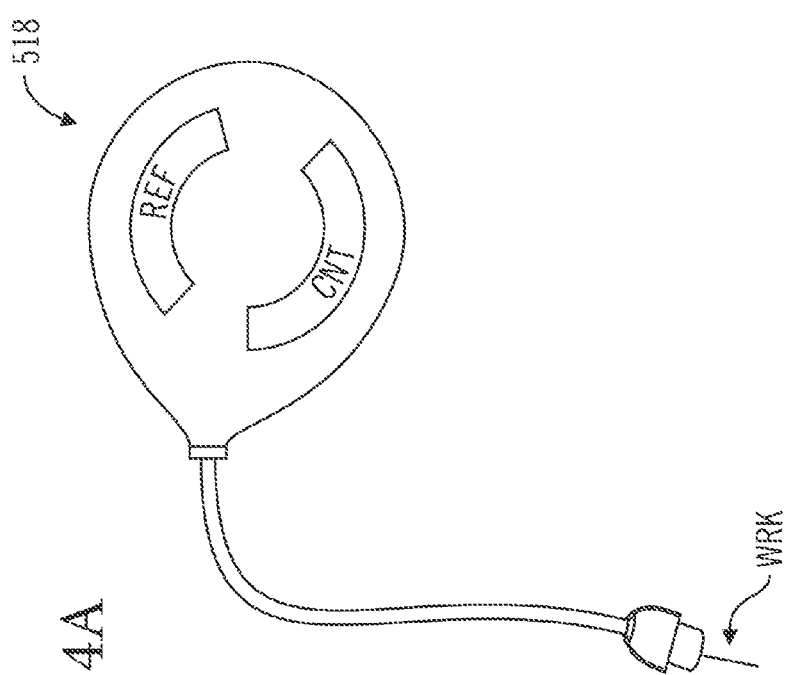

REGULATING DELIVERY OF INSULIN TO A BODY OF A USER BY A FLUID DELIVERY DEVICE

CROSS-REFERENCE TO RELATED APPLICATIONS

This application is a continuation of U.S. patent application Ser. No. 18/118,964, filed Mar. 8, 2023, titled "SENSOR MODEL SUPERVISOR FOR TEMPORARY REDUCTIONS IN FLUID DELIVERY BY A FLUID DELIVERY DEVICE," which is a continuation of U.S. patent application Ser. No. 16/156,801, filed Oct. 10, 2018, titled "TEMPORARY SETPOINT VALUES FOR TEMPORARY REDUCTIONS IN FLUID DELIVERY," which is a continuation of U.S. patent application Ser. No. 15/138,540, filed Apr. 26, 2016, titled "SENSOR MODEL SUPERVISOR FOR A CLOSED-LOOP INSULIN INFUSION SYSTEM," which is a continuation-in-part of U.S. patent application Ser. No. 13/870,907 titled "SENSOR MODEL SUPERVISOR FOR A CLOSED-LOOP INSULIN INFUSION SYSTEM," filed Apr. 25, 2013 and now abandoned. Application Ser. No. 13/870,907 claims the benefit of: U.S. provisional patent application No. 61/694,950, filed Aug. 30, 2012 and titled "Closed Loop System"; U.S. provisional patent application No. 61/694,961, filed Aug. 30, 2012 and titled "Closed Loop Mobile System"; and U.S. provisional patent application No. 61/812,874, filed Apr. 17, 2013 and titled "Closed Loop System". The contents of these related applications are herein incorporated by reference in their entireties for all purposes.

TECHNICAL FIELD

Embodiments of the subject matter disclosed herein generally relate to fluid delivery management and, more specifically, to temporary setpoint values.

BACKGROUND

The pancreas of a normal healthy person produces and releases insulin into the blood stream in response to elevated blood plasma glucose levels. Beta cells (β-cells), which reside in the pancreas, produce and secrete the insulin into the blood stream, as it is needed. If β-cells become incapacitated or die, a condition known as Type I diabetes mellitus (or in some cases if β-cells produce insufficient quantities of insulin, Type II diabetes), then insulin must be provided to the body from another source.

Traditionally, since insulin cannot be taken orally, insulin has been injected with a syringe. More recently, use of infusion pump therapy has been increasing, especially for delivering insulin for diabetics. For example, external infusion pumps are worn on a belt, in a pocket, or the like, and deliver insulin into the body via an infusion tube with a percutaneous needle or a cannula placed in the subcutaneous tissue. As of 1995, less than 5% of Type I diabetics in the United States were using infusion pump therapy. Presently, over 7% of the more than 900,000 Type I diabetics in the United States are using infusion pump therapy, and the percentage of Type I diabetics that use an infusion pump is growing at an absolute rate of over 2% each year. Moreover, the number of Type I diabetics is growing at 3% or more per year. In addition, growing numbers of insulin-using Type II diabetics are also using infusion pumps. Physicians have recognized that continuous infusion provides greater control of a diabetic's condition, and are also increasingly prescribing it for patients. Although offering control, pump therapy can suffer from several complications that make use of traditional external infusion pumps less desirable for the user.

In insulin pumps, it is common to use fast acting insulin as opposed to the slower acting insulin that is used for injections, because pumps allow changing of insulin profiles. As insulin companies develop faster acting insulin, the faster acting insulin is often adopted quickly. However, current pumps are still limited by the speed of the insulin they are using.

BRIEF SUMMARY

Techniques related to temporary setpoint values are disclosed. The techniques may be practiced using a processor-implemented method; a system comprising one or more processors and one or more processor-readable storage media; and/or one or more non-transitory processor-readable storage media.

In some embodiments, the techniques may involve causing operation of a fluid delivery device in a closed-loop mode for automatically delivering fluid based on a difference between a first setpoint value and an analyte concentration value during operation of the fluid delivery device in the closed-loop mode. Additionally, the techniques may involve obtaining a second setpoint value. The second setpoint value may be a temporary setpoint value to be used for a period of time to regulate fluid delivery, and the second setpoint value may be greater than the first setpoint value. The techniques may further involve causing operation of the fluid delivery device for automatically reducing fluid delivery for the period of time based on the second setpoint value.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

FIG. 3A is a perspective view of a glucose sensor system for use in an embodiment of the present invention.

FIG. 3B is a side cross-sectional view of the glucose sensor system of FIG. 3A.

FIG. 8A is a diagram of a single device and its components in accordance with an embodiment of the present invention.

FIG. 8B is a diagram of two devices and their components in accordance with an embodiment of the present invention.

FIG. 8C is another diagram of two devices and their components in accordance with an embodiment of the present invention.

FIG. 8D is a diagram of three devices and their components in accordance with an embodiment of the present invention.

FIG. 9 is a table listing the devices of FIGS. 8A-D and their components.

FIG. 12 is a circuit diagram of an I-F A/D converter of FIG. 10 accompanied by charts of node signals in accordance with an embodiment of the present invention.

FIG. 13 is another circuit diagram of an I-F A/D converter of FIG. 10 accompanied by charts of node signals in accordance with an embodiment of the present invention.

FIG. 14 is still another circuit diagram of an I-F A/D converter of FIG. 10 accompanied by charts of node signals in accordance with an embodiment of the present invention.

FIG. 18 is frequency response chart for a filter of FIG. 16 in accordance with an embodiment of the present invention.

FIG. 23A is a diagram of a glucose clamp (glucose level with respect to time).

FIG. 23B is a plot of insulin concentration in a normal glucose tolerant (NGT) individual in response to various magnitudes of glucose clamps of FIG. 23A.

FIG. 29A is a plot of two different glucose sensor outputs compared to glucose meter readings during a glucose clamp in accordance with an embodiment of the present invention.

FIG. 29B is a plot of actual insulin concentration in blood compared to a controller commanded insulin concentration in response to the glucose clamp of FIG. 29A in accordance with an embodiment of the present invention.

FIG. 30 is a top view of an end of a multi-sensor for measuring both glucose concentration and pH in accordance with an embodiment of the present invention.

FIG. 34A is a bottom view of a telemetered characteristic monitor in accordance with an embodiment of the present invention.

FIG. 34B is a bottom view of a different telemetered characteristic monitor in accordance with an embodiment of the present invention.

DETAILED DESCRIPTION

Figure 1:
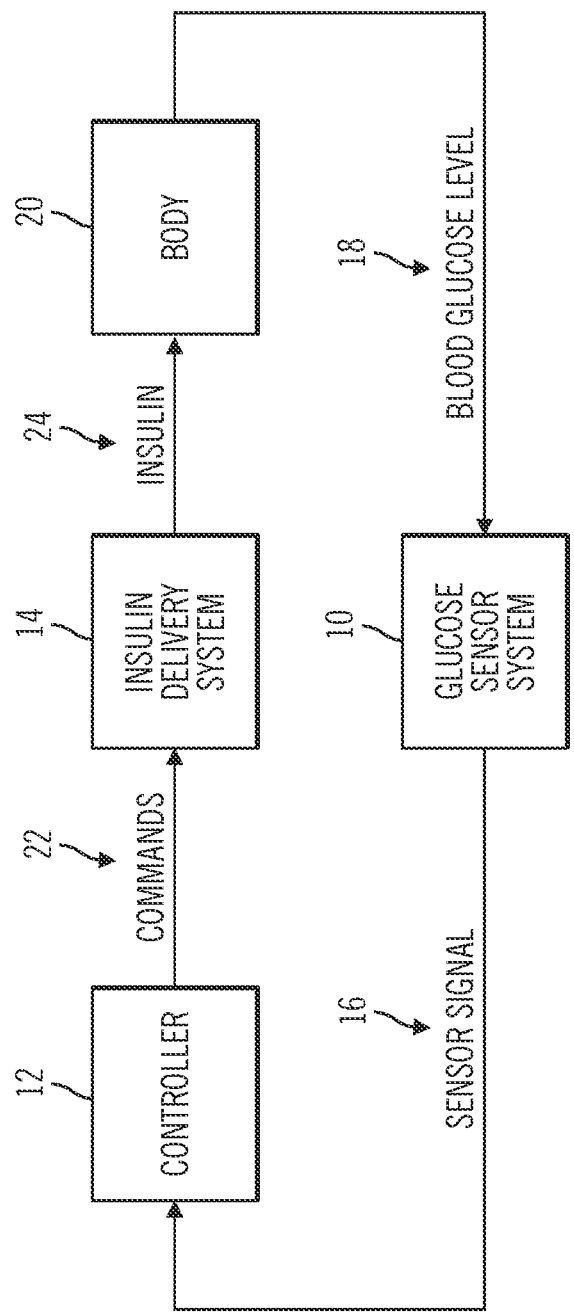
FIG. 1 is a block diagram of a closed loop glucose control system in accordance with an embodiment of the present invention.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Techniques and technologies may be described herein in terms of functional and/or logical block components, and with reference to symbolic representations of operations, processing tasks, and functions that may be performed by various computing components or devices. Such operations, tasks, and functions are sometimes referred to as being computer-executed, computerized, software-implemented, or computer-implemented. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

When implemented in software or firmware, various elements of the systems described herein are essentially the code segments or instructions that perform the various tasks. The program or code segments can be stored in any tangible and non-transitory processor-readable medium. The "processor-readable medium" or "machine-readable medium" may include any medium that can store or transfer information. Examples of the processor-readable medium include an electronic circuit, a semiconductor memory device, a ROM, a flash memory, an erasable ROM (EROM), a floppy diskette, a CD-ROM, an optical disk, a hard disk, or the like.

The various tasks performed in connection with a process described herein may be performed by software, hardware, firmware, or any combination thereof. It should be appreciated that a described process may include any number of additional or alternative tasks, the tasks shown in a particular figure need not be performed in the illustrated order, and a described process may be incorporated into a more comprehensive procedure or process having additional functionality not described in detail herein. Moreover, one or more of the tasks shown in the figures could be omitted from an embodiment of a described process as long as the intended overall functionality remains intact.

As shown in the drawings for purposes of illustration, the invention is embodied in a closed loop infusion system for regulating the rate of fluid infusion into a body of a user based on feedback from an analyte concentration measurement taken from the body. In particular embodiments, the invention is embodied in a control system for regulating the rate of insulin infusion into the body of a user based on a glucose concentration measurement taken from the body. In preferred embodiments, the system is designed to model a pancreatic beta cell (β-cell) In other words, the system controls an infusion device to release insulin into a body of a user in a similar concentration profile as would be created by fully functioning human β-cells when responding to changes in blood glucose concentrations in the body.

Thus, the system simulates the body's natural insulin response to blood glucose levels and not only makes efficient use of insulin, but also accounts for other bodily functions as well since insulin has both metabolic and mitogenic effects. However, the algorithms must model the β-cells closely, since algorithms that are designed to minimize glucose excursions in the body, without regard for how much insulin is delivered, may cause excessive weight gain, hypertension, and atherosclerosis. In preferred embodiments of the present invention, the system is intended to emulate the in vivo insulin secretion pattern and to adjust this pattern consistent with the in vivo β-cell adaptation experienced by normal healthy individuals. The in vivo β-cell response in subjects with normal glucose tolerance (NGT), with widely varying insulin sensitivity ($S_I$, is the optimal insulin response for the maintenance of glucose homeostasis.

Preferred embodiments include a glucose sensor system 10, a controller 12 and an insulin delivery system 14, as shown in FIG. 1. The glucose sensor system 10 generates a sensor signal 16 representative of blood glucose levels 18 in the body 20, and provides the sensor signal 16 to the controller 12. The controller 12 receives the sensor signal 16 and generates commands 22 that are communicated to the insulin delivery system 14. The insulin delivery system 14 receives the commands 22 and infuses insulin 24 into the body 20 in response to the commands 22.

Generally, the glucose sensor system 10 includes a glucose sensor, sensor electrical components to provide power to the sensor and generate the sensor signal 16, a sensor communication system to carry the sensor signal 16 to the controller 12, and a sensor system housing for the electrical components and the sensor communication system.

Typically, the controller 12 includes controller electrical components and software to generate commands for the insulin delivery system 14 based on the sensor signal 16, and a controller communication system to receive the sensor signal 16 and carry commands to the insulin delivery system 14.

Generally, the insulin delivery system 14 includes an infusion device and an infusion tube to infuse insulin 24 into the body 20. In particular embodiments, the infusion device includes infusion electrical components to activate an infusion motor according to the commands 22, an infusion communication system to receive the commands 22 from the controller 12, and an infusion device housing to hold the infusion device.

In preferred embodiments, the controller 12 is housed in the infusion device housing and the infusion communication system is an electrical trace or a wire that carries the commands 22 from the controller 12 to the infusion device. In alternative embodiments, the controller 12 is housed in the sensor system housing and the sensor communication system is an electrical trace or a wire that carries the sensor signal 16 from the sensor electrical components to the controller electrical components. In other alternative embodiments, the controller 12 has its own housing or is included in a supplemental device. In another alternative embodiment, the controller is located with the infusion device and the sensor system all within one housing. In further alternative embodiments, the sensor, controller, and/or infusion communication systems may utilize a cable, a wire, fiber optic lines, RF, IR, or ultrasonic transmitters and receivers, or the like instead of the electrical traces.

System Overview

Figure 2:
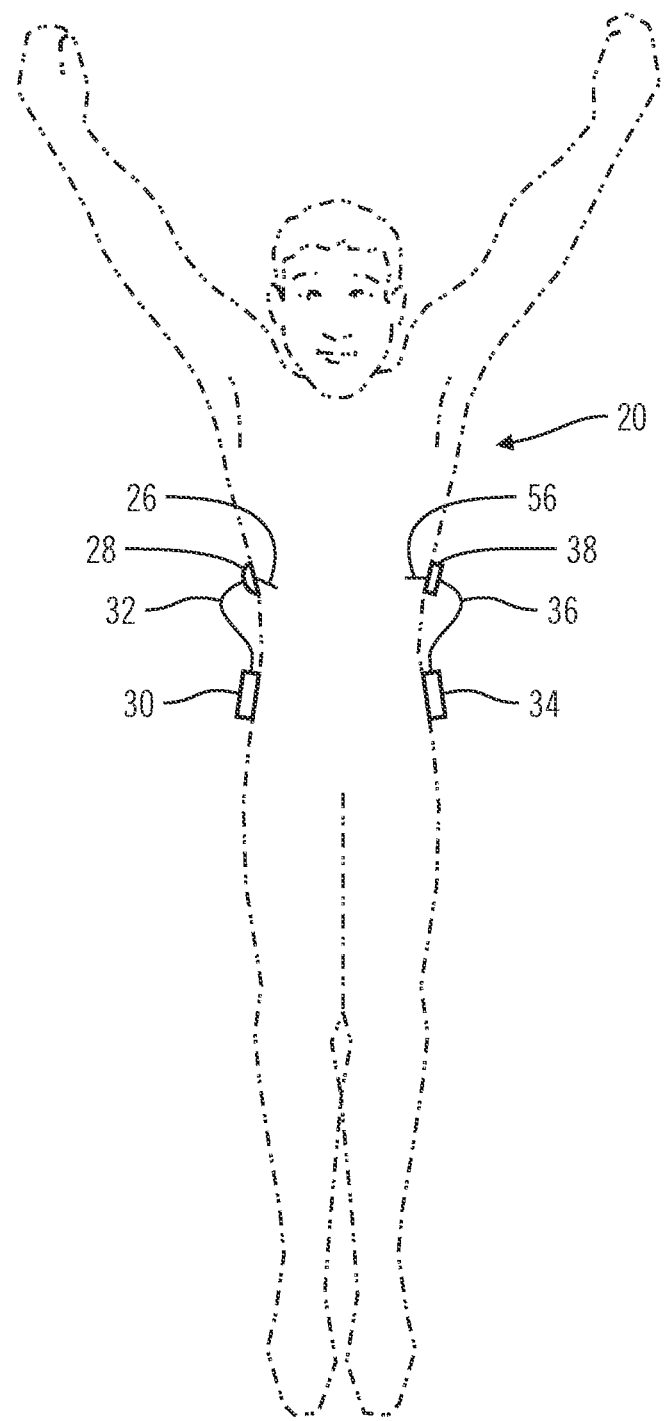
FIG. 2 is a front view of closed loop hardware located on a body in accordance with an embodiment of the present invention.
Figure 3C:
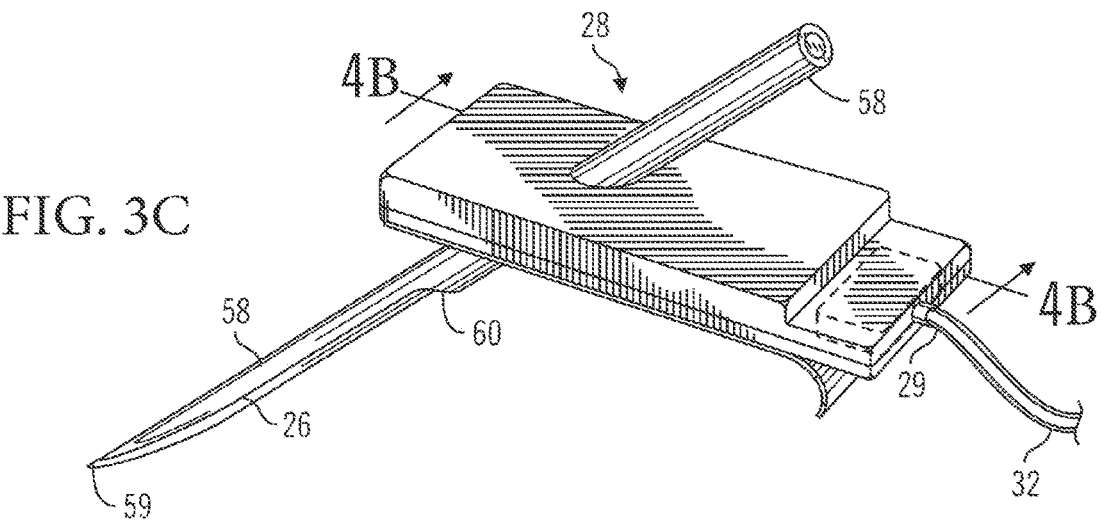
FIG. 3C is a perspective view of a sensor set of the glucose sensor system of FIG. 3A for use in an embodiment of the present invention.
Figure 3D:
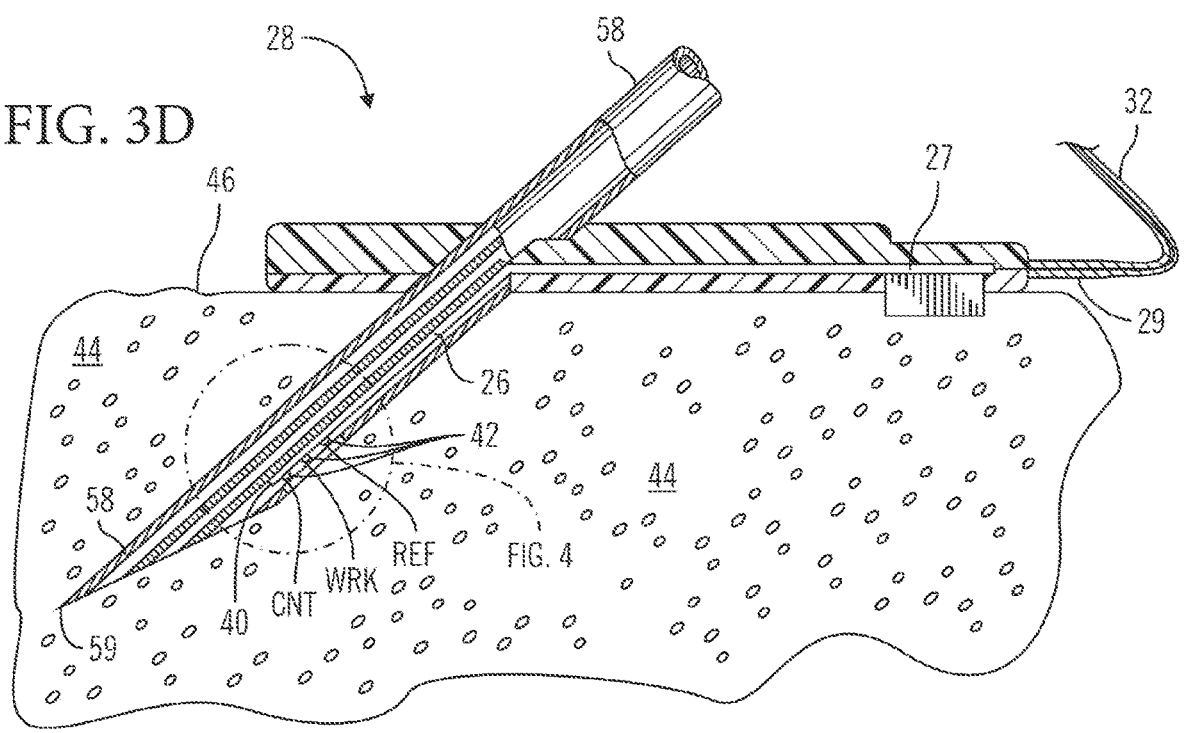
FIG. 3D is a side cross-sectional view of the sensor set of FIG. 3C.
Figure 4:
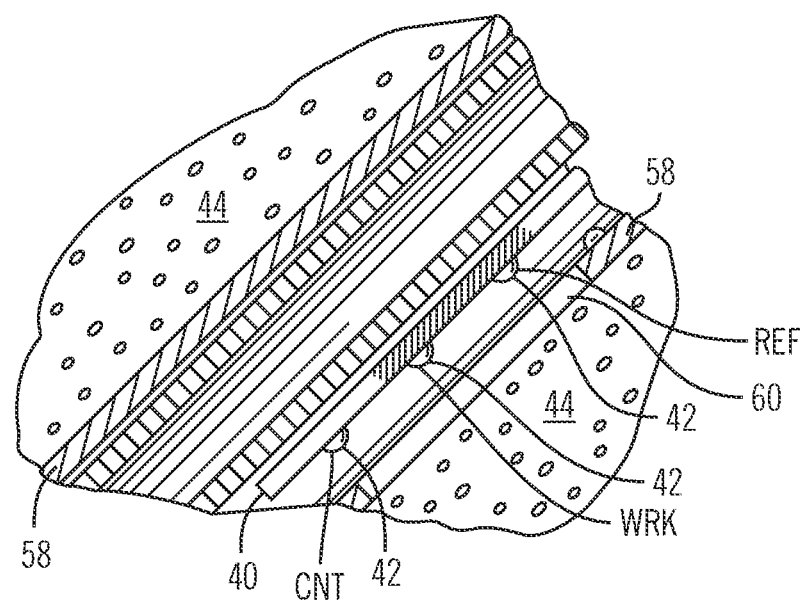
FIG. 4 is a cross sectional view of a sensing end of the sensor of FIG. 3D.

Preferred embodiments of the invention include a sensor 26, a sensor set 28, a telemetered characteristic monitor 30, a sensor cable 32, an infusion device 34, an infusion tube 36, and an infusion set 38, all worn on the body 20 of a user, as shown in FIG. 2. The telemetered characteristic monitor 30 includes a monitor housing 31 that supports a printed circuit board 33, batteries 35, antenna (not shown, and a sensor cable connector (not shown, as seen in FIGS. 3A and 3B. A sensing end 40 of the sensor 26 has exposed electrodes 42 and is inserted through skin 46 into a subcutaneous tissue 44 of a user's body 20, as shown in FIGS. 3D and 4. The electrodes 42 are in contact with interstitial fluid (ISF that is present throughout the subcutaneous tissue 44. The sensor 26 is held in place by the sensor set 28, which is adhesively secured to the user's skin 46, as shown in FIGS. 3C and 3D. The sensor set 28 provides for a connector end 27 of the sensor 26 to connect to a first end 29 of the sensor cable 32. A second end 37 of the sensor cable 32 connects to the monitor housing 31. The batteries 35 included in the monitor housing 31 provide power for the sensor 26 and electrical components 39 on the printed circuit board 33. The electrical components 39 sample the sensor signal 16 and store digital sensor values (Dsig in a memory and then periodically transmit the digital sensor values Dsig from the memory to the controller 12, which is included in the infusion device.

Figure 5:
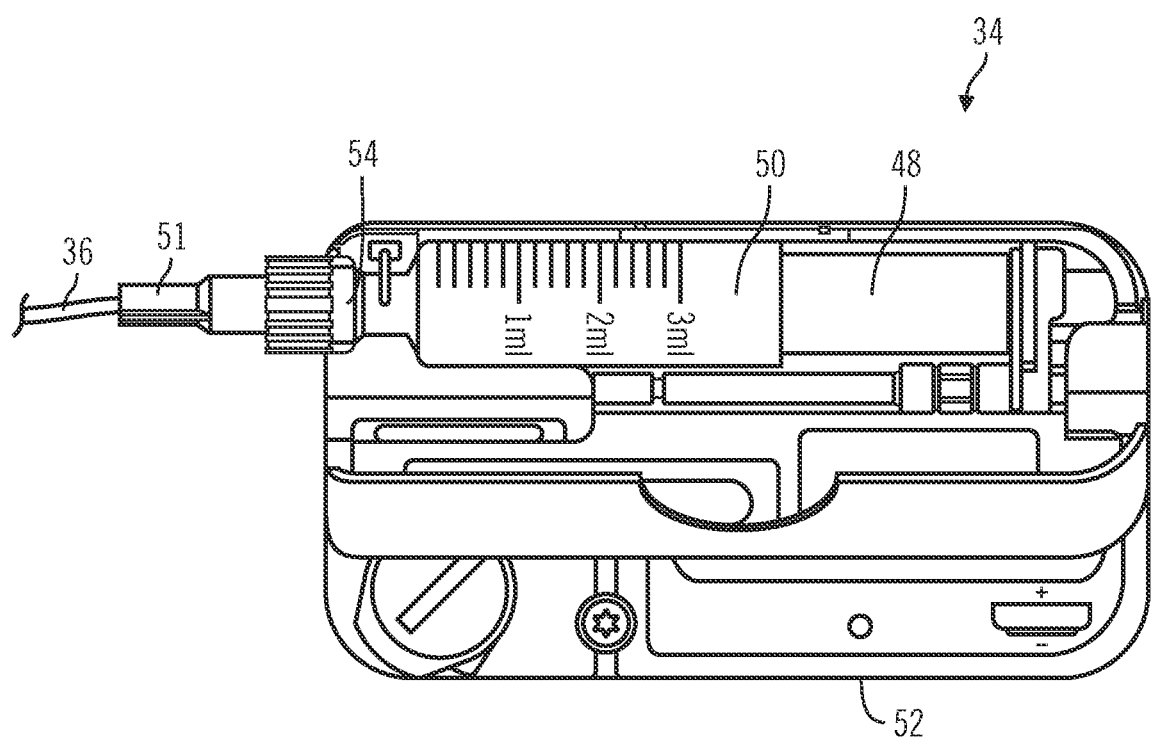
FIG. 5 is a top view of an infusion device with a reservoir door in the open position, for use in an embodiment of the present invention.
Figure 6:
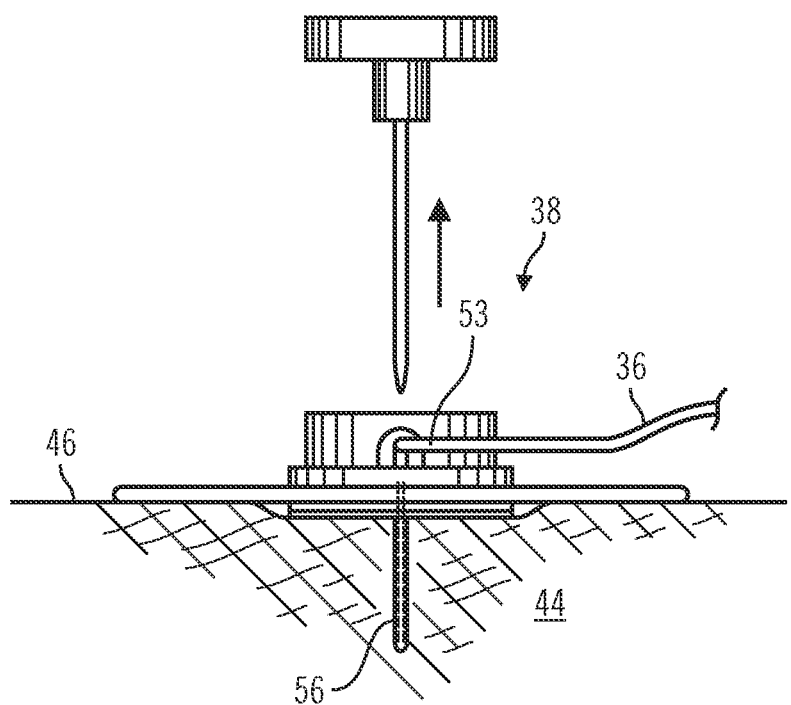
FIG. 6 is a side view of an infusion set with the insertion needle pulled out, for use in an embodiment of the present invention.

The controller 12 processes the digital sensor values Dsig and generates commands 22 for the infusion device 34. Preferably, the infusion device 34 responds to the commands 22 and actuates a plunger 48 that forces insulin 24 out of a reservoir 50 located inside the infusion device 34, as shown in FIG. 5. In particular embodiments, a connector tip 54 of the reservoir 50 extends through the infusion device housing 52 and a first end 51 of the infusion tube 36 is attached to the connector tip 54. A second end 53 of the infusion tube 36 connects to the infusion set 38. Insulin 24 is forced through the infusion tube 36 into the infusion set 38 and into the body 20. The infusion set 38 is adhesively attached to the user's skin 46, as shown in FIG. 6. As part of the infusion set 38, a cannula 56 extends through the skin 46 and terminates in the subcutaneous tissue 44 completing fluid communication between the reservoir 50 and the subcutaneous tissue 44 of the user's body 20.

In alternative embodiments, the closed-loop system can be a part of a hospital-based glucose management system.

Given that insulin therapy during intensive care has been shown to dramatically improve wound healing, reduce blood stream infections, renal failure, and polyneuropathy mortality, irrespective of whether subjects previously had diabetes (See Van den Berghe G. et al., NEJM 345: 1359-67, 2001, which is incorporated by reference herein), the present invention can be used in this hospital setting to control the blood glucose level of a patient in intensive care. In these alternative embodiments, since an intravenous (IV) hookup is typically implanted into a patient's arm while the patient is in an intensive care setting (e.g., ICU), a closed loop glucose control can be established which piggy-backs off the existing IV connection. Thus, in a hospital based system, IV catheters which are directly connected to a patient vascular system for purposes of quickly delivering IV fluids, can also be used to facilitate blood sampling and direct infusion of substances (e.g., insulin, anticoagulants) into the intra-vascular space. Moreover, glucose sensors may be inserted through the IV line to give real-time glucose levels from the blood stream. Therefore, depending on the type of hospital based system, the alternative embodiments would not necessarily need the described system components such as the sensor 26, the sensor set 28, the telemetered characteristic monitor 30, the sensor cable 32, the infusion tube 36, and the infusion set 38 as described in the preferred embodiments. Instead, standard blood glucose meters or vascular glucose sensors as described in provisional application entitled "Multi-lumen Catheter," filed Sep. 27, 2002, Ser. No. 60/414,248, which is incorporated herein in its entirety by reference, can be used to provide the blood glucose values to the infusion pump control and the existing IV connection can be used to administer the insulin to the patient.

Figure 39A:
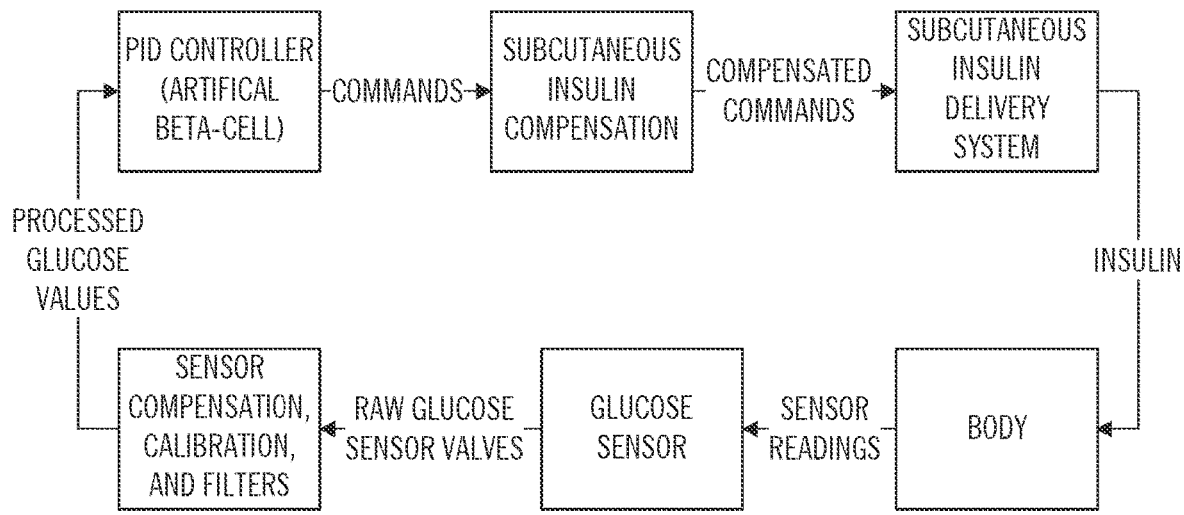
FIGS. 39A and 39B are a block diagrams of a closed loop glucose control system in accordance with embodiments of the present invention.
Figure 39B:
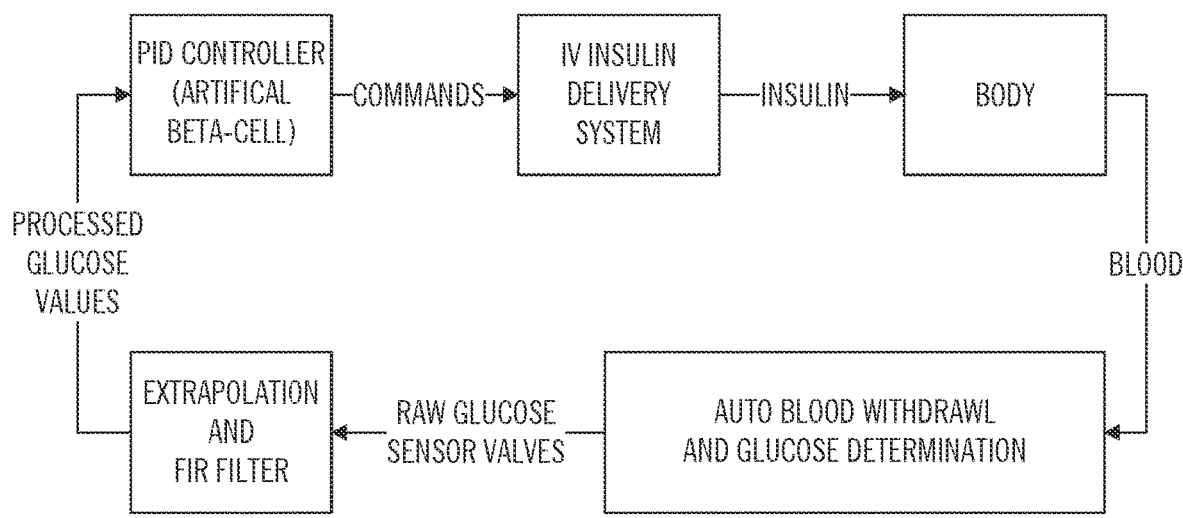
Figure 40:
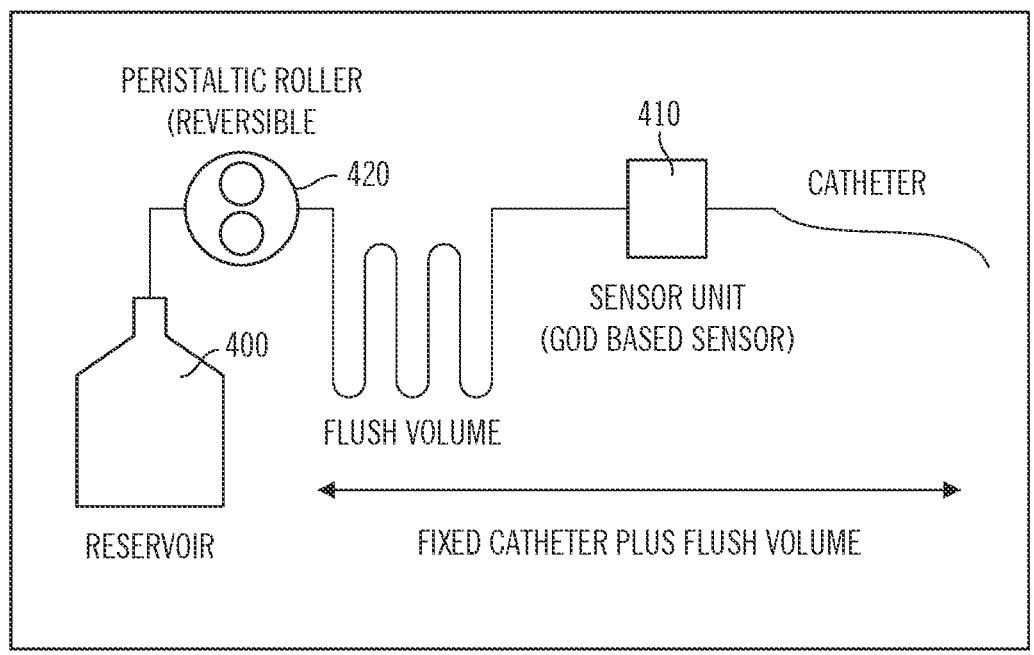
FIG. 40 is a block diagram of auto blood withdrawal and return in accordance with an embodiment of the present invention.

It is important to appreciate that numerous combinations of devices in the hospital-based system can be used with the closed loop controller of the present invention. For example, as described in FIG. 39B compared to the preferred system in FIG. 39A, an auto blood glucose/intravenous insulin infusion system can automatically withdraw and analyze blood for glucose concentration at fixed intervals (preferably 5-20 minutes), extrapolate the blood glucose values at a more frequent interval (preferably 1 minute), and use the extrapolated signal for calculating an IV-insulin infusion according to the controller described below. The modified auto blood glucose/intravenous insulin infusion system would eliminate the need for subcutaneous sensor compensation and subcutaneous insulin compensation (as described with regards to the lead-lag compensator below). The automatic withdrawal of blood, and subsequent glucose determination can be accomplished with existing technology (e.g. VIA or Biostator like blood glucose analyzer) or by the system described in FIG. 40. The system in FIG. 40 uses a peristaltic pump 420 to withdraw blood across an amperometric sensor 410 (the same technology as used in sensor 26) and then return the blood with added flush (0.5 to 1.0 ml) from the reservoir 400. The flush can consist of any makeup of saline, heparin, glucose solution and/or the like. If the blood samples are obtained at intervals longer than 1 minute but less than 20 minutes, the blood glucose determinations can be extrapolated on a minute-to-minute basis with extrapolation based on the present (n) and previous values (n−1) to work with the logic of the controller as described in detail below. For blood samples obtained at intervals greater than 20 minutes, a zero-order-hold would be used for the extrapolation. Based on these blood glucose values, the infusion device can administer insulin based on the closed loop controller described in greater detail below.

In other modifications to the system, a manual blood glucose/intravenous insulin infusion system can be used where frequent manual entry of blood glucose values from a standard blood glucose meter (e.g., YSI, Beckman, etc.) and extrapolate the values at more frequent intervals (preferably 1 min) to create a surrogate signal for calculating IV-insulin infusion. Alternatively, a sensor blood glucose/intravenous insulin infusion system can use a continuous glucose sensor (e.g., vascular, subcutaneous, etc.) for frequent blood glucose determination. Moreover, the insulin infusion can be administered subcutaneously rather than intravenously in any one of the previous examples according to the controller described below.

In still further alternative embodiments, the system components may be combined in a smaller or greater number of devices and/or the functions of each device may be allocated differently to suit the needs of the user.

Controller

Once the hardware for a closed loop system is configured, such as in the preferred embodiments described above, the effects of the hardware on a human body are determined by the controller. In preferred embodiments, the controller 12 is designed to model a pancreatic beta cell (β-cell). In other words, the controller 12 commands the infusion device 34 to release insulin 24 into the body 20 at a rate that causes the insulin concentration in the blood to follow a similar concentration profile as would be caused by fully functioning human β-cells responding to blood glucose concentrations in the body 20. In further embodiments, a "semi-closed-loop" system may be used, in which the user is prompted to confirm insulin delivery before any insulin is actually delivered.

A controller that simulates the body's natural insulin response to blood glucose levels not only makes efficient use of insulin but also accounts for other bodily functions as well since insulin has both metabolic and mitogenic effects. Controller algorithms that are designed to minimize glucose excursions in the body without regard for how much insulin is delivered may cause excessive weight gain, hypertension, and atherosclerosis. In preferred embodiments, of the present invention, the controller 12 is intended to emulate the in vivo insulin secretion pattern and to adjust this pattern to be consistent with in vivo β-cell adaptation. The in vivo β-cell response in subjects with normal glucose tolerance (NGT), with widely varying insulin sensitivity ($S_I$), is the optimal insulin response for the maintenance of glucose homeostasis.

The β-Cell and PID Control

Generally, the in vivo β-cell response to changes in glucose is characterized by "first" and "second" phase insulin responses. This biphasic insulin response is clearly seen during hyperglycemic clamps applied to NGT subjects, as shown in FIG. 23B. During a hyperglycemic clamp the glucose level is rapidly increased from a basal level $G_B$ to a new higher level $G_C$ and then held constant at the higher-level $G_C$ as shown in FIG. 23A. The magnitude of the increase in glucose ($\Delta G$) affects the insulin response. Four insulin response curves are shown for four different glucose clamp levels in FIG. 23B.

The biphasic insulin response of a β-cell can be modeled using components of a proportional, plus integral, plus derivative (PID) controller. A PID controller is selected since PID algorithms are stable for a wide variety of non-medical dynamic systems, and PID algorithms have been found to be stable over widely varying disturbances and changes in system dynamics.

The insulin response of β-cells during a hyperglycemic clamp is diagrammed in FIGS. 24A-E using the components of a PID controller to model the β-cell. A proportional component $U_P$ and a derivative component $U_D$ of the PID controller may be combined to represent a first phase insulin response 440, which lasts several minutes. An integral component $U_I$ of the PID controller represents a second phase insulin response 442, which is a steady increase in insulin release under hyperglycemic clamp conditions. The magnitude of each component's contribution to the insulin response is described by the following equations:

Proportional Component Response: $U_P = K_P(G - G_B)$

Integral Component Response: $U_I = K_I \int_{t_0}^{t}(G - G_B)dt + I_B$, and

Derivative Component Response:

$$U_D = K_D \frac{dG}{dt},$$

Where
$U_P$ is the proportional component of the command sent to the insulin delivery system,
$U_I$ is the integral component of the command sent to the insulin delivery system,
$U_D$ is the derivative component of the command sent to the insulin delivery system,
$K_P$ is a proportional gain coefficient,
$K_I$ is an integral gain coefficient,
$K_D$ is a derivative gain coefficient,
G is a present blood glucose level,
$G_B$ is a desired basal glucose level,
t is the time that has passed since the last sensor calibration,
$t_0$ is the time of the last sensor calibration, and
$I_B$ is a basal insulin concentration at to, or can also be described as $U_I(t_0)$.

Figure 24A:
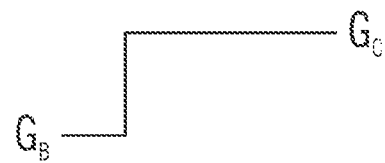
FIG. 24A is a diagram of a glucose clamp.
Figure 24B:
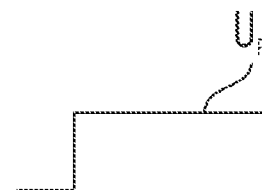
FIG. 24B is a diagram of a proportional insulin response to the glucose clamp of FIG. 24A in accordance with an embodiment of the present invention.
Figure 24C:
FIG. 24C is a diagram of an integral insulin response to the glucose clamp of FIG. 24A in accordance with an embodiment of the present invention.
Figure 24D:
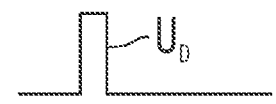
FIG. 24D is a diagram of a derivative insulin response to the glucose clamp of FIG. 24A in accordance with an embodiment of the present invention.
Figure 24E:
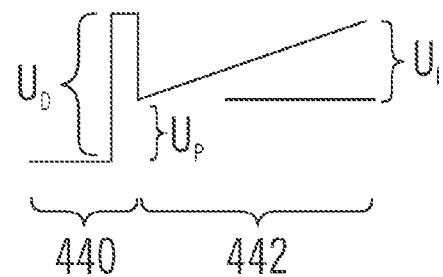
FIG. 24E is a diagram of a combined proportional, integral, and derivative insulin response to the glucose clamp of FIG. 24A in accordance with an embodiment of the present invention.

The combination of the PID components that model the two phases of insulin response by a β-cell is shown in FIG. 24E as it responds to the hyperglycemic clamp of FIG. 24A. FIG. 24E shows that the magnitude of the first phase response 440 is driven by the derivative and proportional gains, $K_D$ and $K_P$. And the magnitude of the second phase response 442 is driven by the integral gain $K_I$.

The components of the PID controller can also be expressed in its discrete form:

Proportional Component Response: $P_{con}^n = K_P(SG_f^n - G_{sp})$

Integral Component Response: $I_{con}^n = I_{con}^{n-1} + K_I(SG_f^n - G_{sp}); I_{con}^0 = I_b$ Derivative Component Response: $D_{con}^n = K_D dGdt_f^n$ Where $K_P$, $K_I$, and $K_D$ are the proportional, integral, and derivative gain coefficients, $SG_f$ and $dGdt_f$ are the filtered sensor glucose and derivative respectively, and the superscript n refers to discrete time.

An acute insulin response is essential for preventing wide postprandial glycemic excursions. Generally, an early insulin response to a sudden increase in glucose level results in less total insulin being needed to bring the glucose level back to a desired basal glucose level. This is because the infusion of insulin increases the percentage of glucose that is taken up by the body. Infusing a large amount of insulin to increase the percentage of glucose uptake while the glucose concentration is high results in an efficient use of insulin. Conversely, infusing a large amount of insulin while the glucose concentration is low results in using a large amount of insulin to remove a relatively small amount of glucose. In other words, a larger percentage of a big number is more than a larger percentage of a small number. The infusion of less total insulin helps to avoid development of insulin resistance in the user. As well, first-phase insulin is thought to result in an early suppression of hepatic glucose output.

Figure 25A:
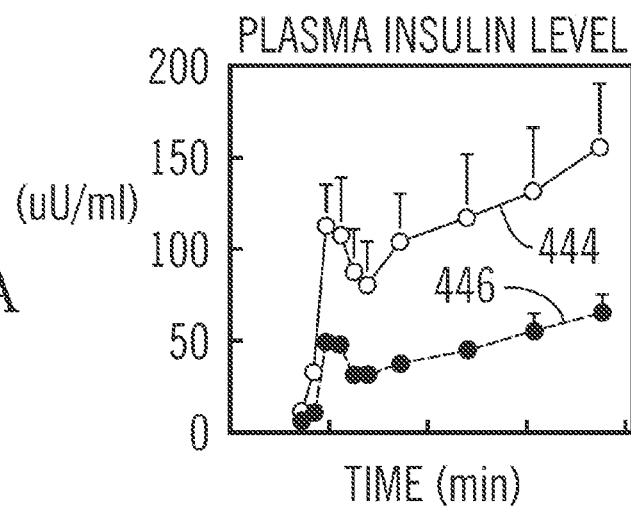
FIG. 25A is a plot of insulin responses to a glucose clamp for exercise trained and normal individuals.
Figure 25B:
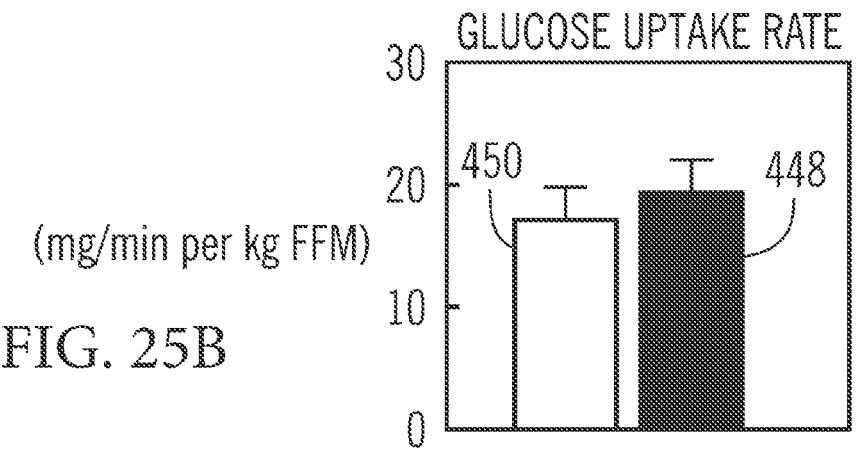
FIG. 25B is a bar chart of glucose uptake rates for exercise trained and normal individuals.

Insulin sensitivity is not fixed and can change dramatically in a body depending on the amount of exercise by the body. In one study, for example, insulin responses in highly exercise-trained individuals (individuals who trained more than 5 days a week) were compared to the insulin responses in subjects with normal glucose tolerance (NGT) during a hyperglycemic clamp. The insulin response in exercise-trained individuals 444 was about one-half of the insulin response of the NGT subjects 446, as shown in FIG. 25A. But the glucose uptake rate for each of the individuals (exercise-trained 448 or normal 450) was virtually identical, as shown in FIG. 25B. Thus, it can be speculated that the exercise-trained individuals have twice the insulin sensitivity and half of the insulin response leading to the same glucose uptake as the NGT individuals. Not only is the first phase insulin response 440 reduced due to the effects of exercise, but the second phase insulin response 442 has also been shown to adjust to insulin sensitivity, as can be seen in FIG. 25A.

Figure 26:
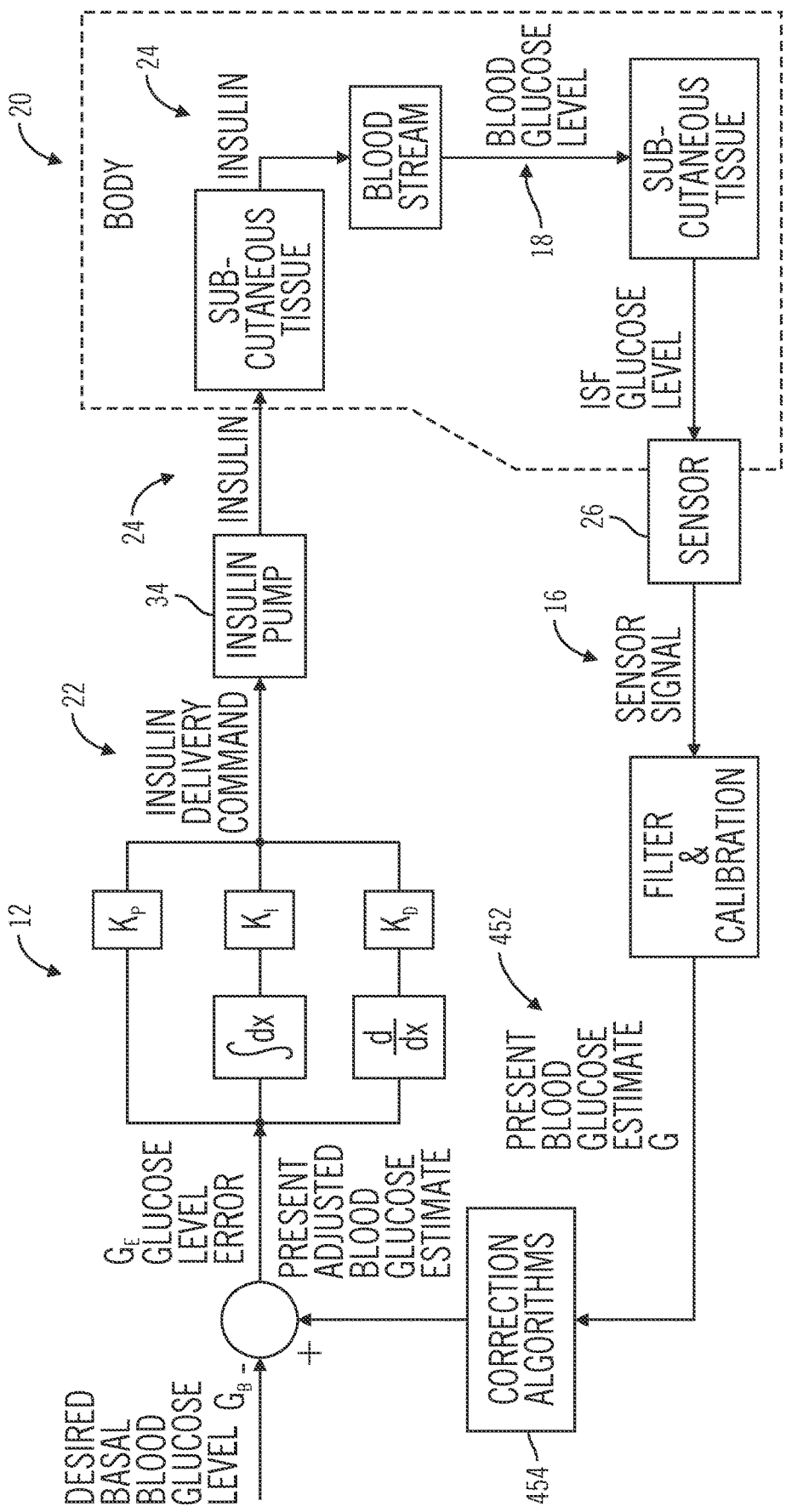
FIG. 26 is a block diagram of a closed loop system to control blood glucose levels through insulin infusion based on glucose level feedback in accordance with an embodiment of the present invention.

In preferred embodiments, a closed loop control system may be used for delivering insulin to a body to compensate for β-cells that perform inadequately. There is a desired basal blood glucose level $G_B$ for each body. The difference between the desired basal blood glucose level $G_B$ and an estimate of the present blood glucose level G is the glucose level error $G_E$ that must be corrected. The glucose level error $G_E$ is provided as an input to the controller 12, as shown in FIG. 26.

If the glucose level error $G_E$ is positive (meaning that the present estimate of the blood glucose level G is higher than the desired basal blood glucose level $G_B$) then the controller 12 generates an insulin delivery command 22 to drive the infusion device 34 to provide insulin 24 to the body 20. In terms of the control loop, glucose is considered to be positive, and therefore insulin is negative. The sensor 26 senses the ISF glucose level and generates a sensor signal 16. The sensor signal 16 is filtered and calibrated to create an estimate of the present blood glucose level 452. In particular embodiments, the estimate of the present blood glucose level G is adjusted with correction algorithms 454 before it is compared to the desired basal blood glucose level $G_B$ to calculate a new glucose level error $G_E$ to start the loop again.

If the glucose level error $G_E$ is negative (meaning that the present estimate of the blood glucose level is lower than the desired basal blood glucose level $G_B$) then the controller 12 reduces or stops the insulin delivery depending on whether the integral component response of the glucose error $G_E$ is still positive.

If the glucose level error $G_E$ is zero, (meaning that the present estimate of the blood glucose level is equal to the desired basal blood glucose level $G_B$) then the controller 12 may or may not issue commands to infuse insulin depending on the derivative component (whether the glucose level is raising or falling) and the integral component (how long and by how much glucose level has been above or below the basal blood glucose level $G_B$). In "semi-closed loop"

embodiments, the user is prompted before the controller 12 issues the commands to infuse insulin. The prompts may be displayed to the user on a display, sounded to the user, or otherwise provide an indication to the user that the system is ready to deliver insulin, for example a vibration or other tactile indication. In addition, the amount of insulin to be delivered may be displayed, with or without other information, such as the total amount infused for the day or the potential effect on the user's blood glucose level by the insulin delivery. In response, the user may indicate that the insulin should or should not be delivered, for example by selecting a button, key, or other input. In further embodiments, there must be at least two keystrokes so that insulin is not delivered by accident.

Figure 27:
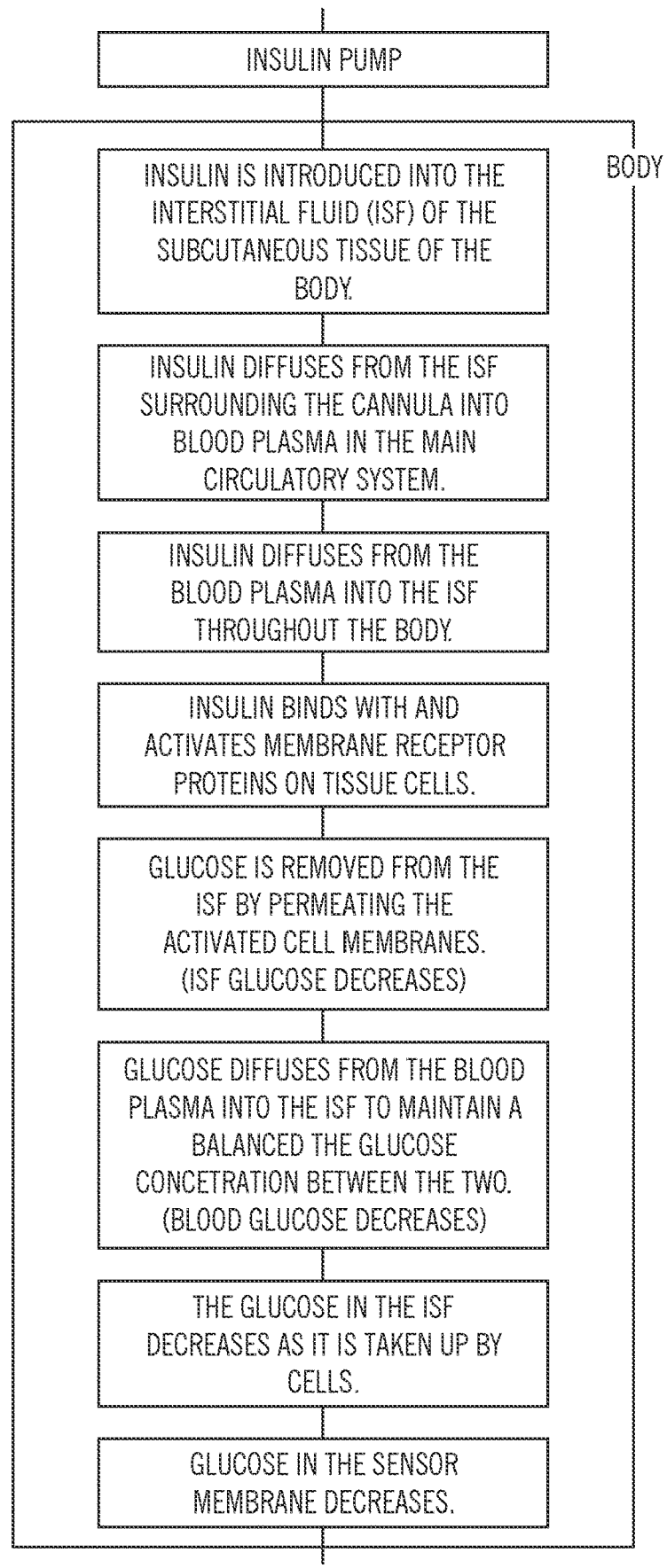
FIG. 27 is a detailed block diagram of the portion of the control loop of FIG. 26 that is in the body in accordance with an embodiment of the present invention.

To more clearly understand the effects that the body has on the control loop, a more detailed description of the physiological effects that insulin has on the glucose concentration in the interstitial fluid (ISF) is needed. In preferred embodiments, the infusion device 34 delivers insulin through the cannula 56 of the infusion set 38 into the ISF of the subcutaneous tissue 44 of the body 20. And the insulin 24 diffuses from the local ISF surrounding the cannula into the blood plasma and then spreads throughout the body 20 in the main circulatory system, as described in the block diagram of FIG. 27. The insulin then diffuses from the blood plasma into the interstitial fluid ISF substantially throughout the entire body. The insulin 24 binds with and activates membrane receptor proteins on cells of body tissues. This facilitates glucose permeation into the activated cells. In this way, the tissues of the body 20 take up the glucose from the ISF. As the ISF glucose level decreases, glucose diffuses from the blood plasma into the ISF to maintain glucose concentration equilibrium. Finally, the glucose in the ISF permeates the sensor membrane and affects the sensor signal 16.

In addition, insulin has direct and indirect effects on liver glucose production. Increased insulin concentration decreases liver glucose production. Therefore, acute and immediate insulin response not only helps the body to efficiently take up glucose but also substantially stops the liver from adding to the glucose in the blood stream. In alternative embodiments, insulin is delivered more directly into the blood stream instead of into the interstitial fluid, such as delivery into veins, arteries, the peritoneal cavity, or the like. And therefore, any time delay associated with moving the insulin from the interstitial fluid into the blood plasma is diminished. In other alternative embodiments, the glucose sensor is in contact with blood or body fluids other than interstitial fluid, or the glucose sensor is outside of the body and measures glucose through a non-invasive means. The embodiments that use alternative glucose sensors may have shorter or longer delays between the blood glucose level and the measured blood glucose level.

Selecting Controller Gains

In preferred embodiments, the controller gains $K_P$, $K_I$, and $K_D$, are selected so that the commands from the controller 12 cause the infusion device 34 to release insulin 24 into the body 20 at a rate, that causes the insulin concentration in the blood to follow a similar concentration profile, as would be caused by fully functioning human β-cells responding to blood glucose concentrations in the body. In preferred embodiments, the gains may be selected by observing the insulin response of several normal glucose tolerant (NGT) individuals, with healthy normally functioning β-cells. The first step in determining a set of controller gains is to take periodic measurements of blood glucose and blood insulin concentrations from the group of NGT individuals. Second, each individual in the group is subjected to a hyperglycemic clamp, while continuing to periodically measure and record the blood glucose and blood insulin concentrations. Third, a least squares curve fit is applied to the recorded blood insulin concentrations measured over time for each individual. The result is a set of curves representing the insulin responses to the hyperglycemic clamp for each individual of the group. Fourth, the curves are used to calculate the controller gains $K_P$, $K_I$, and $K_D$, for each individual. And finally, the proportional gains from each of the individuals are averaged together to obtain an average proportional gain, $K_P$, to be used in a controller 12. Similarly, the integral gains, $K_I$, and the derivative gains, $K_D$, are averaged to obtain an average integral gain, $K_I$, and an average derivative gain, $K_D$, for the controller 12. Alternatively, other statistical values may be used instead of averages such as, maximums, minimums, the high or low one, two or three sigma standard deviation values, or the like. The gains calculated for various individuals in a group may be filtered to remove anomalous data points before statistically calculating the gains to be used in a controller.

Figure 28A:
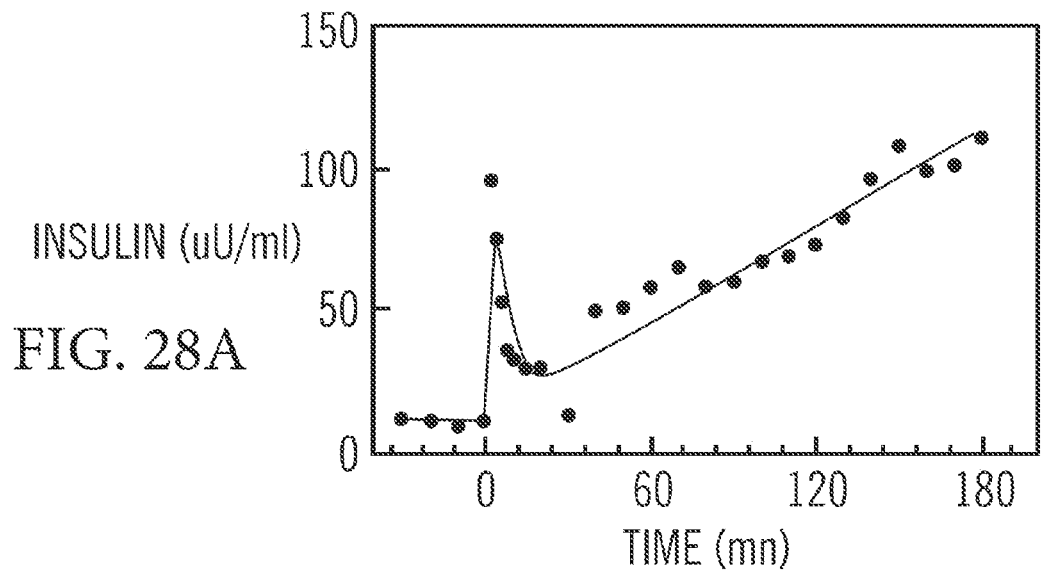
FIGS. 28A and 28B are plots of measured insulin responses of two different normal glucose tolerant (NGT) individuals to a glucose clamp for use with an embodiment of the present invention.
Figure 28B:
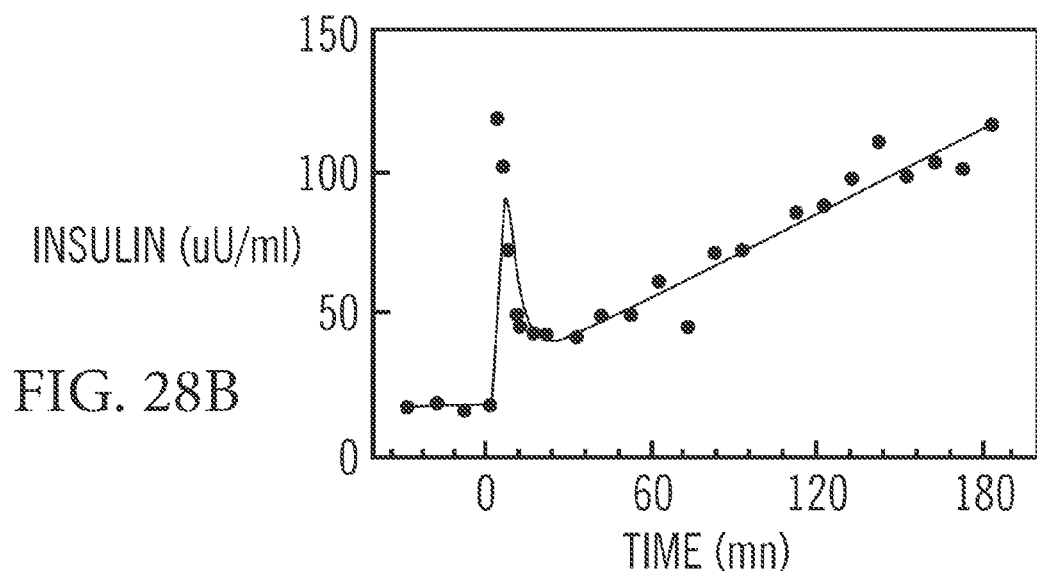

In an example, a least squares curve-fitting method is used to generate representative insulin response curves from two fasted individuals in a group, as shown in FIGS. 28A and B. Then the controller gains were calculated from the insulin response curves of the two representative individuals and are shown in Table 1. When calculating the controller gains, the insulin clearance rate (k), was assumed to be 10 (ml of insulin)/min/(kg. of body weight). The insulin clearance rate k is the rate that insulin is taken out of the blood stream in a body. Finally, the average value for each type of gain is calculated using the measurements from the group, as shown in Table 1.

TABLE 1

| PID Controller Gains Calculated From The Insulin Response Curves Of Two NGT Individuals | | | |
|---|---|---|---|
| Individuals | Proportional Gain, $K_P$ | Integral Gain, $K_I$ | Derivative Gain, $K_D$ |
| a | 0.000406 | 0.005650 | 0.052672 |
| b | 0.000723 | 0.003397 | 0.040403 |
| Average | 0.000564 | 0.004523 | 0.046537 |

The controller gains may be expressed in various units and/or may be modified by conversion factors depending on preferences for British or S. I. Units, floating-point or integer software implementation, the software memory available, or the like. The set of units for the controller gains in Table 1 is:

$K_P$: (mU of insulin)/min/(Kg of body weight) per (mg of glucose)/(dl of plasma);

$K_I$: (mU of insulin)/min/(Kg of body weight) per (mg of glucose)/(dl of plasma) min.; and $K_D$: (mU of insulin)/min/(Kg of body weight) per (mg of glucose)/(dl of plasma)/min.

In alternative embodiments, other curve fitting methods are used to generate the insulin response curves from the measurements of blood insulin concentrations.

An estimate of an insulin clearance rate (k), the individual's body weight (W), and the insulin sensitivity $S_I$ are needed to calculate the controller gains from the insulin response curves for each NGT individual. The insulin clearance rate (k) is generally proportional to body weight and is well documented in literature. The individual's insulin sensitivity $S_I$ may be measured using an intravenous glucose tolerance test, a hyperinsulinemic clamp, or in the case of a diabetic, comparing the individual's daily insulin requirement to their daily carbohydrate intake.

In particular embodiments, two parameters, the insulin sensitivity $S_I$ and the insulin clearance rate k, are measured for each individual. In other embodiments, the insulin clearance rate k is estimated from literature given the individual's body weight. In other particular embodiments, longer or shorter insulin clearance times are used. In still other embodiments, all of the parameters are estimated. In additional embodiments, one or more parameters are measured, while at least one parameter is estimated from literature.

In other alternative embodiments, the controller gains are calculated using a group of individuals with similar body types. For example, the insulin response to a hyperglycemic clamp may be measured for several tall, thin, NGT, males in order to calculate the controller insulin response gains for each individual in the group. Then the gains are statistically combined to generate a set of representative controller gains for tall, thin, NGT, males. The same could be done for other groups such as, but not limited to, short, heavy, NGT, females; medium height, medium weight, highly exercised trained, females; average height and weight 10 year olds; or the like. Then the controller gains are selected for each individual user based on the group that best represents them. In further alternative embodiments, controller gains are uniquely selected for each individual user. In particular embodiments, the controller gains for a user are selected based on measurements of insulin sensitivity, insulin clearing time, insulin appearance time, insulin concentration, body weight, body fat percentage, body metabolism, or other body characteristics such as pregnancy, age, heart conditions, or the like.

In other alternative embodiments, the controller gains are estimated as a function of a user's body weight W and insulin sensitivity $S_I$. A series of observations are used to justify this method. The first observation is that the controller gains are proportional to each other. In other words, small changes in glucose concentration cause a small derivative response $U_D$, a small proportional response $U_P$ and a small integral response $U_I$. And larger changes in glucose concentration cause a proportionally larger derivative response $U_D$, a proportionally larger proportional $U_P$ response and a proportionally larger integral response $U_I$, as shown in FIG. 23B. Changes in the glucose concentration proportionally affect all three components of the controller response $U_{PID}$. The second observation is that the first phase insulin response (φb) is proportional to the derivative gain $K_D$. And the third observation is that two constants may be readily obtained from information in published literature or may be measured from a cross-section of the general population. The two constants are the insulin clearance rate (k) for a human given a body weight and the disposition index (DI) for a human given a change in glucose concentration.

While there are multiple sources for the information needed to calculate the insulin clearance rate k, one source is the article "Insulin clearance during hypoglycemia in patients with insulin-dependent diabetes mellitus", written by Kollind M et al., published in Horm Metab Res, 1991 July; 23(7):333-5. The insulin clearance rate k is obtained from the insulin infused divided by the steady state plasma insulin concentration. An insulin clearance constant $A_k$, which is independent of an individual's body weight, may be obtained by dividing the insulin clearance rate k (measured from a particular individual) by the individual's body weight. The insulin clearance constant $A_k$ is generally the same for all humans, except under extenuating circumstances such as after an individual has contracted HIV, other metabolic affecting diseases, or the like.

The disposition index (DI) for a human given a change in glucose concentration is available from information presented in the article "Quantification of the relationship between insulin sensitivity and beta-cell function in human subjects. Evidence for a hyperbolic function", written by Khan S E et al., published in Diabetes, 1993 November; 42(11):1663-72.

Both the disposition index DI and the insulin clearance rate k may be measured directly from tests. The disposition index DI may be calculated given the first phase insulin response measured form a glucose clamp test and the individual's insulin sensitivity measured from an insulin sensitivity test. The insulin clearance rate k may be measured from an insulin clearance test. The glucose clamp test and the insulin clearance test are described in the above-mentioned articles and are well known in the art. The insulin sensitivity $S_I$ may be measured using an intravenous glucose tolerance test or a hyperinsulinemic clamp test.

Given these observations, then the following parameters may be measured from an NGT individual's insulin response to a glucose clamp: a desired first phase insulin response φ1, the ratio of $K_D$ to $K_P$, and the ratio of $K_D$ to $K_I$. Then the derivative gain $K_D$ may be calculated from the first phase insulin response φ1 using the constants k and DI. And finally $K_P$ and $K_I$ may be calculated using the ratios of $K_D$ to $K_P$ and $K_D$ to $K_I$.

The first phase insulin response φ1 may be observed in a NGT individual as the area under the insulin response curve during approximately the first 10 minutes of a glucose clamp. The increase in the glucose concentration during the glucose clamp is ΔG=(G−GB), where G is equal to Gc, the glucose concentration during the clamp, and $G_B$ is the basal glucose concentration before the clamp.

The importance of the first phase insulin response φ1 has been emphasized by studies indicating that, in subjects with normal glucose tolerance (NGT), the product of first phase insulin response φ1 and insulin sensitivity ($S_I$) is a constant known as the disposition index, DI=φ1 $S_I$. Therefore, $$\phi 1 = \frac{DI}{S_I}.$$

For a different ΔG there is a different φ1 and therefore a different DI. But, the ratio DI/ΔG is substantially constant even for different individuals with different insulin sensitivities.

The insulin sensitivity $S_I$ is defined as the percentage of the glucose concentration that the body tissues will take up for a given amount of insulin. The β-cell naturally adapts to changes in insulin sensitivity by adjusting the amount of insulin it secretes during the first phase insulin response φ1. This suggests that the body naturally seeks an optimal level of glucose tolerance. A controller that mimics this characteristic of the β-cell more accurately simulates the body's natural insulin response.

The instantaneous insulin response (RI) may be calculated given the insulin clearance rate (k) and the first phase insulin response φ1, RI=kφ1.

The insulin clearance rate k is proportional to body weight (W), therefore substituting a proportional constant $A_k$ and the user's body weight W for k and replacing φ1 with the ratio of DI over $S_I$ yields the following equation:

$$R_I = A_k W \frac{DI}{S_I}.$$

The instantaneous insulin response $R_I$ may also be expressed as the product of the derivative gain $K_D$ and the change in glucose concentration $\Delta G$, $R_I = K_D \Delta G$.

Setting the two equations for $R_I$ equal to each other and solving for $K_D$ yields, $$K_D = \frac{W}{S_I} \frac{A_k DI}{\Delta G}.$$

As mentioned above, $DI/\Delta G$ and $A_k$ are constants available or calculated from data in published literature. Combining the constants into a single constant, $Q$, $$Q = \frac{A_k DI}{\Delta G},$$

yields an equation for the derivative gain $K_D$ that is a function of the user's body weight $W$ and the user's insulin sensitivity $$K_D = \frac{W}{S_i} Q.$$

Once the derivative gain $K_D$ is calculated, the proportional and integral gains are calculated using ratios. The ratio of $K_D/K_P$ can be set to the dominant time constant for insulin action, ranging from 10-60 minutes, but more typically 20-40 minutes and preferably 30 minutes. For example, calculating $K_P$ given $K_D$ using a time constant of 30 minutes, yields the following relationship:

$$\frac{K_D}{K_P} = 30 \Rightarrow K_P = \frac{K_D}{30}.$$

In a similar fashion, the ratio of $K_D/K_I$ can be set to the average ratio measured from a population of NGT individuals. And $K_I$ can be calculated from $K_D$.

In particular embodiments, the user enters their body weight $W$ and insulin sensitivity $S_I$ into the device that contains the controller. Then the controller gains are automatically calculated and used by the controller. In alternative embodiments, an individual enters the user's body weight $W$ and insulin sensitivity $S_I$ into a device and the device provides the information to the controller to calculate the gains.

A study was conducted to confirm that the insulin response for an individual could be reproduced using the glucose sensor as an input. In the study, glucose and insulin measurements were taken while a hyperglycemic clamp was applied to a NGT individual. The glucose level measurements, shown in FIG. 29A, were used as the inputs to a mathematical model created to simulate a PID insulin response controller. The insulin dosing commanded by the controller in response to the glucose clamp very closely approximates the actual insulin appearance in the NGT individual, as shown in FIG. 29B. The insulin concentration measured from periodic blood samples 456 taken from the individual during the test are represented by dots in FIG. 29B. The output from the mathematical model simulating the insulin response commanded by the controller is shown as a solid line 458 in FIG. 29B.

Three different devices were used to measure the individual's blood glucose during the study. Blood glucose meter readings 460 from periodic blood samples taken from the individual are represented by the dots in FIG. 29A. Two MiniMed sensors (such as those described in the section entitled "sensor", below) were placed in the individual's subcutaneous tissue, and the sensor readings 462, 464 are shown as lines in FIG. 29A. The sensor readings 462, 464 are slightly delayed compared to the meter readings 460. The delay is most likely due to the delay between blood glucose and interstitial fluid (ISF) glucose and can be substantially corrected through the use of a filter if needed. In this study, the delay was not corrected by a filter and did not significantly affect the controller's ability to command an insulin response that matches the natural response of the NGT individual. This study indicates that the PID insulin response controller model is a good minimal model of insulin secretion that captures the biphasic response of healthy β-cells. Correction of the delay is only expected to increase the accuracy of the model.

Fuzzy Logic to Select Between Multiple Sets of Controller Gains

In preferred embodiments, one set of controller gains is used for a particular individual. In alternative embodiments, more than one set of controller gains is used, and fuzzy logic is used to select between sets of controller gains and to determine when to change from one set of controller gains to another. In particular alternative embodiments, the controller gains are different if the glucose level is above or below the desired glucose basal level. In other alternative embodiments, the controller gains are different if the glucose level is increasing or decreasing. A justification for different sets of gains comes from physiological studies that indicate that β-cells turn off faster than they turn on. In still other alternative embodiments, the controller gains are different depending on whether the glucose level is above or below the desired glucose basal level and whether the glucose level is increasing or decreasing, which results in four sets of controller gains. In additional alternative embodiments, the controller gains change depending on the magnitude of the hypoglycemic excursion. In other words, the controller gains for small changes in glucose are different than those for large changes in glucose.

Self-Tuning Controller Gains

Further embodiments may include a controller that self-tunes one or more the gains, $K_P$, $K_I$, $K_D$ to accommodate changes in insulin sensitivity. In particular embodiments, previous measurements of glucose levels are compared to the desired basal glucose level $G_B$. For example, the desired basal glucose level $G_B$ is subtracted from the previous glucose level measurements. Then any negative values, within a predefined time window, are summed (in essence integrating the glucose level measurements that were below the basal glucose level $G_B$). If the resulting sum is greater than a pre-selected hypoglycemic integral threshold, then the controller gains are increased by a factor $(1+\alpha)$. Conversely, if the integral of the glucose level measurements that were measured above the basal glucose level $G_B$ within the predefined time window is greater than a pre-selected hyperglycemic integral threshold, then the controller gains are decreased by a factor $(1-\alpha)$.

In particular embodiments, the predefined time window over which the glucose concentration integrals are evaluated is generally 24 hours, and the controller gains are adjusted if needed at the end of each predefined time window. In alternative embodiments, the integrals of the glucose level measurements are continuously calculated over a moving window of time, and if either integral exceeds a threshold, the gains are immediately adjusted. In particular embodiments, the moving time window is one hour, and the time window may be restarted whenever the gains are adjusted. In other alternative embodiments, the time window is longer or shorter depending on the sensor accuracy, the rate at which an individual's insulin sensitivity changes, the computational capabilities of the hardware, or the like.

In particular embodiments, the adjustment amount ($\alpha$) is 0.01. In alternative embodiments, the adjustment amount $\alpha$ is greater or smaller depending on the sensor accuracy, the rate at which an individual's insulin sensitivity changes, the rate at which the sensor sensitivity $S_I$ changes, or the like. In still other alternative embodiments, the adjustment amount $\alpha$ is made larger or smaller depending on the amount that the integral of the measured glucose levels exceeds a threshold. In this way, the gains are adjusted by greater amounts if the measured glucose level G is significantly deviating from the desired blood glucose level $G_B$ and less if the measured glucose level G is closer to the desired blood glucose level $G_B$. In additional alternative embodiments, the controller employs a Kalman filter.

State Variable Feedback

While the primary signal determining the β-cell's insulin response is glucose, there also exists a putative effect of insulin per se to inhibit insulin secretion. This effect may be directly related to the concentration of insulin in plasma (IP(t)), or mediated through some signal proportional to insulin effect (IEFF(t)). The β-cell can likely directly sense these signals (i.e., directly sense insulin concentration and secondary signals proportional to insulin effect such as free fatty acid). Feedback from these intermediary signals is analogous to what is known as state variable feedback; that is feedback, whereby the variable being controlled (glucose in this case) is used together with feedback of each intermediary signal that affects the variable (insulin concentration in plasma and interstitial fluid). With this type of feedback, undesirable slow kinetic process can be made to appear much faster than they are. For example, if β-cell insulin secretion were inhibited by a signal proportional to insulin concentration in the interstitial fluid where it acts, the delay between plasma and interstitial insulin could be made to appear to be shorter. For the artificial closed-loop algorithm, or for "semi-closed-loop" algorithms, this beneficial effect can be achieved by using "state observers" (mathematical equations that predict the insulin concentration in various parts of the body knowing the history of past insulin delivery). In "semi-closed loop" algorithms, the algorithms are the same as for closed loop algorithms but there is a user confirmation step before any insulin is actually administered. By using state variable feedback, it is possible to make the insulin in an insulin pump act faster than the insulin actually is.

To estimate subcutaneous insulin concentration, plasma insulin concentration, and insulin effect, the following equations may be used:

$$\frac{dI_{SC}}{dt} = \alpha_1(I_D - I_{SC})$$

$$\frac{dI_P}{dt} = \alpha_2(I_{SC} - I_P)$$

$$\frac{dI_{EF}}{dt} = \alpha_3(I_P - I_{EF})$$

Wherein $I_{SC}$ is the estimate of normalized insulin concentration in the subcutaneous space, $I_P$ is the estimate of normalized insulin concentration in the plasma, $I_{EF}$ is the estimate of insulin effect on glucose, $\alpha_1$ is the rate constant between insulin delivery and the subcutaneous insulin compartment, $\alpha_2$ is the rate constant between subcutaneous insulin and plasma compartments, $\alpha_3$ is the rate constant between the plasma compartment and the insulin effect. ID is the delivered insulin, which can be a function of the three state variables ($I_{SC}$, $I_P$, and $I_{EF}$).

In particular embodiments, an open loop fixed base rate plus user requested bolus would result in the bolus being increased a certain amount and the basal rate subsequently decreased the same amount in accordance to the following formula:

$$I'_D = (1 + \gamma_1 + \gamma_2 + \gamma_3)I_D - \gamma_1 I_{SC} - \gamma_2 I_P - \gamma_3 I_{EF}$$

Wherein $I_D$ is the user requested basal (U/h) plus bolus (U) profile and $I_D'$ is the state feedback adjusted profiles. Note that for a given kinetic excursion the total amount of insulin requested (area under curve of $I_D$) and delivered (area under curve of $I_D'$) is identical. Here, $\gamma_1$, $\gamma_2$, and $\gamma_3$ are state-feedback gains (scalars). Careful choice of these gains the pump to correct its delivery rate to compensate for delays associated with the dispersion of insulin from the bolus injection into the subcutaneous layer of the patient, to the plasma, and to its actual insulin effect/action on the body. Thus, by estimating how much insulin from a bolus is in the subcutaneous layer, the plasma, or is actually acting on the patient's glucose level (state variables $I_{SC}$, $I_P$ and $I_{EF}$), it is possible to optimize delivery of insulin over time to the patient. Using state feedback the bolus is increased by an amount $(1+\gamma_1+\gamma_2+\gamma_3)$ that is gradually taken away from future insulin delivery $(-\gamma_1 I_{SC}-\gamma_2 I_P-\gamma_3 I_{EF})$. As a result, the apparent insulin pharmokinetic curve appears faster. This is akin to developing a faster acting insulin, but it is achieved algorithmically by rearranging the distribution of the insulin delivery per unit bolus by delivering more upfront and removing the extra amount at a later time. The three gains can be chosen to move the time delays ($1/\alpha_1$, $1/\alpha_2$, and $1/\alpha_3$) to any arbitrary locations. In control theory, this is known as pole placement.

State feedback can be used in open loop and closed loop insulin delivery algorithms and with "semi-closed-loop" delivery algorithms. State feedback can be used in conjunction with a Proportional-Integral-Derivative (PID) or any other type of closed loop controller. $\gamma_1$ is the feedback gain multiplied to $I_{SG}$, $\gamma_2$ is the feedback gain multiplied to $I_P$, and $\gamma_3$ is the feedback gain multiplied to $I_{EF}$.

The physical state space form directly taken from the equations above is:

$$\begin{cases} \begin{bmatrix} \dot{I}_{SC} \\ \dot{I}_P \\ \dot{I}_{EF} \end{bmatrix} = \begin{bmatrix} -\alpha_1 & 0 & 0 \\ \alpha_2 & -\alpha_2 & 0 \\ 0 & \alpha_3 & -\alpha_3 \end{bmatrix} \cdot \begin{bmatrix} I_{SC} \\ I_P \\ I_{EF} \end{bmatrix} + \begin{bmatrix} \alpha_1 \\ 0 \\ 0 \end{bmatrix} \cdot I_D \\ I_D = \begin{bmatrix} 0 & 0 & 0 \end{bmatrix} \cdot \begin{bmatrix} I_{SC} \\ I_P \\ I_{EF} \end{bmatrix} + \begin{bmatrix} 1 \\ 0 \\ 0 \end{bmatrix} \cdot I_D \end{cases} \text{ or } \begin{cases} \dot{x} = Ax + Bu \\ y = Cx + du \end{cases}$$

The finite difference form is calculated as follows (wherein ex indicates an exponential function):
Define: $k_1 = e^{-\alpha_1 T}$, $k_2 = e^{-\alpha_2 T}$, $k_3 = e^{-\alpha_1 T}$ $$I_{SC}(i) = (1 - k_1)(I_D(i-1)) + k_1 I_{SC}(i-1) \quad (\text{eq 1b})$$

$$I_P(i) = (1 - k_2)(I_{SC}(i)) + k_2 I_P(i-1) \quad (\text{eq 2b})$$

$$I_{EF}(i) = (1 - k_3)(I_P(i)) + k_3 I_{EF}(i-1) \quad (\text{eq 3b})$$

The Laplace Form is as follows, wherein s represents the Stäckel determinant used in Laplace equations:

$$\frac{I_{SC}}{I_D} = \frac{\alpha_1}{s + \alpha_1} \quad (\text{eq 1c})$$

$$\frac{I_P}{I_{SC}} = \frac{\alpha_2}{s + \alpha_2} \quad (\text{eq 2c})$$

$$\frac{I_{EFF}}{I_P} = \frac{\alpha_3}{s + \alpha_3} \quad (\text{eq 3c})$$

$$\frac{I_P}{I_D} = \frac{\alpha_1 \alpha_2}{(s + \alpha_1)(s + \alpha_2)} \quad (\text{eq 4})$$

$$\frac{I_{EFF}}{I_D} = \frac{\alpha_1 \alpha_2 \alpha_3}{(s + \alpha_1)(s + \alpha_2)(s + \alpha_3)} \quad (\text{eq 5})$$

To obtain the transfer function of insulin delivery with state feedback, the control equation is as follows, wherein E represents the error between the actual glucose concentration and the desired glucose concentration ($G - G_D$):

$$I_D = PID \cdot E - \gamma_1 I_{SC} - \gamma_2 I_P - \gamma_3 I_{EFF} \quad (\text{eq 6})$$

Substituting equations (eq 1c), (eq 4) and (eq 5) into (eq 6) and rearranging, the following transfer functions are obtained, wherein GM is a gain multiplier:

$$\frac{I_D}{E} = \frac{(GM)(PID)(s + \alpha_1)(s + \alpha_2)(s + \alpha_3)}{(s + \alpha_1)(s + \alpha_2)(s + \alpha_3) + \alpha_1 \gamma_1 (s + \alpha_2)(s + \alpha_3) + \alpha_1 \alpha_2 \gamma_2 (s + \alpha_3) + \alpha_1 \alpha_2 \alpha_3 \gamma_3} \quad (\text{eq 7})$$

$$\frac{I_{SC}}{E} = \frac{(GM)(PID)\alpha_1(s + \alpha_2)(s + \alpha_3)}{(s + \alpha_1)(s + \alpha_2)(s + \alpha_3) + \alpha_1 \gamma_1 (s + \alpha_2)(s + \alpha_3) + \alpha_1 \alpha_2 \gamma_2 (s + \alpha_3) + \alpha_1 \alpha_2 \alpha_3 \gamma_3} \quad (\text{eq 8})$$

$$\frac{I_P}{E} = \frac{(GM)(PID)\alpha_1 \alpha_2 (s + \alpha_3)}{(s + \alpha_1)(s + \alpha_2)(s + \alpha_3) + \alpha_1 \gamma_1 (s + \alpha_2)(s + \alpha_3) + \alpha_1 \alpha_2 \gamma_2 (s + \alpha_3) + \alpha_1 \alpha_2 \alpha_3 \gamma_3} \quad (\text{eq 9})$$

$$\frac{I_{EFF}}{E} = \frac{(GM)(PID)\alpha_1 \alpha_2 \alpha_3}{(s + \alpha_1)(s + \alpha_2)(s + \alpha_3) + \alpha_1 \gamma_1 (s + \alpha_2)(s + \alpha_3) + \alpha_1 \alpha_2 \gamma_2 (s + \alpha_3) + \alpha_1 \alpha_2 \alpha_3 \gamma_3} \quad (\text{eq 10})$$

The computation of the gain multiplier is also obtained in the state variable feedback method. When state variable feedback is used, the gain multiplier (GM) is a scalar that forces a step response to reach the same steady value whether state feedback is used or not. In other words, GM ensures that the total amount given per unit of bolus will be the same in both cases. In the case of state feedback, more insulin is given up front, but this extra insulin is taken away later. To calculate GM in particular embodiments, the "final value theorem" from control systems is used. The final value theorem states that to evaluate the steady state of any transfer function T(s) given any input X(s), the steady state output response to the input is given by:

$$y_{SS}(t \to \infty) = \lim_{s \to 0}(sT(s)X(s))$$

The Laplace form of a step input is given by $$X(s) = \frac{1}{s}$$

and the steady state solution of the final value theorem simplifies to:

$$y_{SS}(t \to \infty) = \lim_{s \to 0}(T(s)).$$

In the case when there is no state feedback, ($\gamma_1$, $\gamma_2$ and $\gamma_3 = 0$), the steady state solution may be obtained from equation (eq 7) to be as follows:

$$I_D(t \to \infty) = 1 \quad (\text{eq 11})$$

With state feedback without the gain correction factor, the steady state solution is:

$$I_D(t \to \infty) = \frac{1}{1 + \gamma_1 + \gamma_2 + \gamma_3} \quad (\text{eq}12)$$

GM is then evaluated as the ratio of equation (eq 12) to equation (eq 11) to obtain the following: $GM = 1 + \gamma_1 + \gamma_2 + \gamma_3$.

Using state variable feedback, a closed loop control equation and state feedback gain are determined for pole placement. Specifically, the gains are calculated for the insulin delivery equation shown above. In particular embodiments, they are determined as follows: First, with state feedback, the denominator of equations (eq 7), (eq 8), (eq 9), and (eq 1) is:

$$D = s^3 + (\alpha_1 + \alpha_2 + \alpha_3 + \gamma_1\alpha_1)s^2 + \quad \text{(eq 14)}$$
$$(\alpha_1\alpha_2 + (\alpha_1 + \alpha_2)\alpha_3 + \gamma_2\alpha_1\alpha_2 + (\alpha_2 + \alpha_3)\gamma_1\alpha_1)s +$$
$$(\alpha_1\alpha_2\alpha_3 + \gamma_3\alpha_1\alpha_2\alpha_3 + \gamma_2\alpha_1\alpha_2\alpha_3 + \gamma_1\alpha_1\alpha_2\alpha_3)$$

To get the poles of the system in the equations (eq 7), (eq 8), (eq 9), or (eq 10), D may be set equal to zero yield the characteristic equation:

$$s^3 + (\alpha_1 + \alpha_2 + \alpha_3 + \gamma_1\alpha_1)s^2 + \quad \text{(eq 16)}$$
$$(\alpha_1\alpha_2 + (\alpha_1 + \alpha_2)\alpha_3 + \gamma_2\alpha_1\alpha_2 + (\alpha_2 + \alpha_3)\gamma_1\alpha_1)s +$$
$$(\alpha_1\alpha_2\alpha_3 + \gamma_3\alpha_1\alpha_2\alpha_3 + \gamma_2\alpha_1\alpha_2\alpha_3 + \gamma_1\alpha_1\alpha_2\alpha_3) = 0$$

If the desired system poles or roots of (eq 16) are defined by eigenvalues $\lambda_1$, $\lambda_2$ and $\lambda_3$, then the characteristic equation can be written as:

$$(s - \lambda_1)(s - \lambda_2)(s - \lambda_3) = 0$$

Expanding and collecting like powers of s, (eq 16) can be written as:

$$s^3 - (\lambda_1 + \lambda_2 + \lambda_3)s^2 + (\lambda_1\lambda_2 + \lambda_1\lambda_3 + \lambda_2\lambda_3)s - \lambda_1\lambda_2\lambda_3 = 0 \quad \text{(eq 17)}$$

Setting the coefficients of like powers of s equal to each other we have the system of equations:

$$\alpha_1 + \alpha_2 + \alpha_3 + \gamma_1\alpha_1 = -(\lambda_1 + \lambda_2 + \lambda_3) \quad \text{(eq 18)}$$

$$\alpha_1\alpha_2 + \alpha_1\alpha_3 + \alpha_2\alpha_3 + \gamma_2\alpha_1\alpha_2 + \gamma_1\alpha_1(\alpha_2 + \alpha_3) = \quad \text{(eq 19)}$$
$$\lambda_1\lambda_2 + \lambda_1\lambda_3 + \lambda_2\lambda_3$$

$$\alpha_1\alpha_2\alpha_3 + \gamma_3\alpha_1\alpha_2\alpha_3 + \gamma_2\alpha_1\alpha_2\alpha_3 + \gamma_1\alpha_1\alpha_2\alpha_3 = \lambda_1\lambda_2\lambda_3 \quad \text{(eq 20)}$$

This results in three equations and three unknowns, $\gamma_1$, $\gamma_2$ and $\gamma_3$. Therefore, the unknown gains can be solved for in terms of the desired poles $\lambda_1$, $\lambda_2$, $\lambda_3$, and system time constants, $\alpha_1$, $\alpha_2$ and $\alpha_3$. These formulas enable us to control the desired pharmacokinetics of insulin as it appears in the different compartments:

$$\gamma_1 = \frac{-(\lambda_1 + \lambda_2 + \lambda_3 + \alpha_1 + \alpha_2 + \alpha_3)}{\alpha_1}$$

$$\gamma_2 = \frac{\lambda_1\lambda_2 + \lambda_1\lambda_3 + \lambda_2\lambda_3 - \alpha_1\alpha_2 - \alpha_1\alpha_3 - \alpha_2\alpha_3 + (\lambda_1 + \lambda_2 + \lambda_3 + \alpha_1 + \alpha_2 + \alpha_3)(\alpha_2 + \alpha_3)}{\alpha_1\alpha_2}$$

$$\gamma_3 = \frac{-\lambda_1\lambda_2\lambda_3}{\alpha_1\alpha_2\alpha_3} -$$
$$\frac{\lambda_1\lambda_2 + \lambda_1\lambda_3 + \lambda_2\lambda_3 - \alpha_1\alpha_2 - \alpha_1\alpha_3 - \alpha_2\alpha_3 + (\lambda_1 + \lambda_2 + \lambda_3 + \alpha_1 + \alpha_2 + \alpha_3)(\alpha_2 + \alpha_3)}{\alpha_1\alpha_2} +$$

$$\frac{(\lambda_1 + \lambda_2 + \lambda_3 + \alpha_1 + \alpha_2 + \alpha_3)}{\alpha_1} - 1$$

Thus, through the above calculations, the gains can be calculated and used in the control equation for insulin delivery of:

$$I_D = PID \cdot E - \gamma_1 I_{SC} - \gamma_2 I_P - \gamma_3 I_{EF}$$

PID is the output of a PID controller of any other closed loop (or "semi-closed-loop") controller. The gains are generally calculated just once, but could be calculated more often if desired. The control equation may be calculated on a repeated basis, after predetermined periods of time or continuously. For example, and without limitation, it may be calculated every five, ten, thirty or sixty minutes. Just the state variable portion ($\gamma_1 I_{SC} - \gamma_2 I_P - \gamma_3 I_{EF}$) may be updated or the entire equation may be updated. By updating the control equation, it is possible to continually improve the delivery of insulin to the patient.

Figure 42:
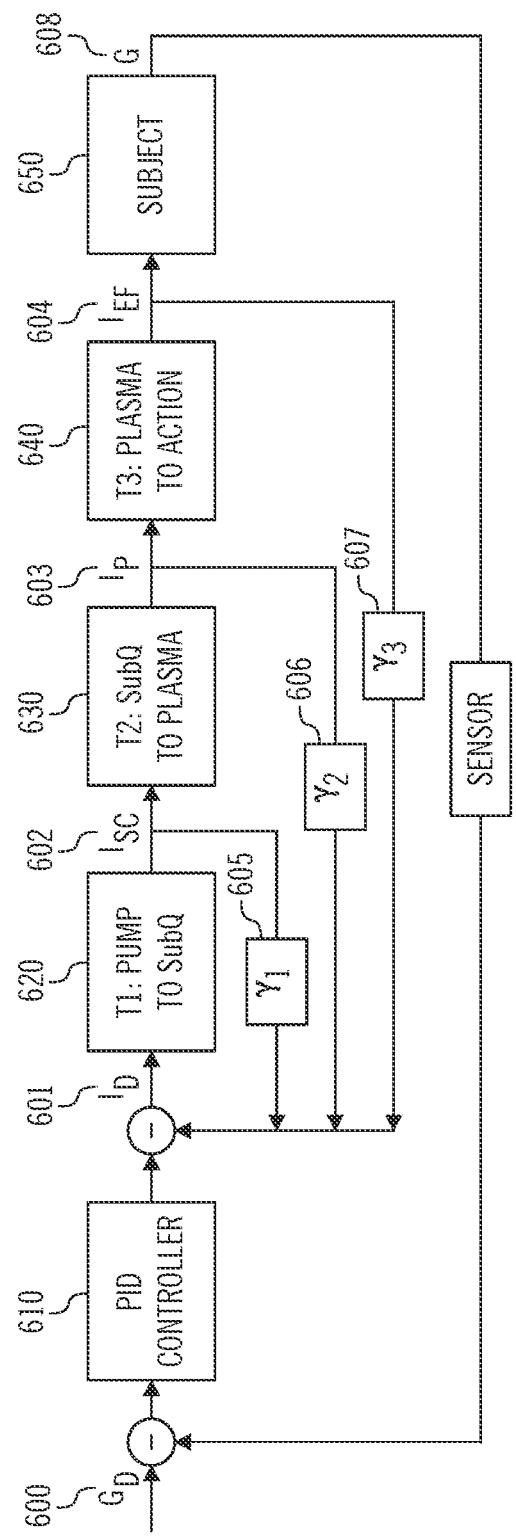
FIG. 42 illustrates a control feedback block diagram of state variable feedback and in accordance with an embodiment of the present invention.

A control feedback block diagram of an embodiment of a pump using state variable feedback is shown in FIG. 42. As shown, the desired glucose GD 600 of the patient is entered into the PID Controller 610. The output of the PID controller is an insulin delivery value $I_D$ 601. The block then calculates how much insulin should actually be delivered to the patient as a bolus in addition to the insulin delivery value and how much should be taken away from the basal rate, as discussed above. At each discrete time interval, Ti, (T1 620, T2 630, and T3 640), the amount of insulin that has entered into the subcutaneous layer from the pump is calculated to provide $I_{SC}$ 602. That value will be multiplied (or otherwise factored by) $\gamma_1$ 605 and subtracted from the output of the PID controller to provide an improved desired insulin value based on the subcutaneous insulin concentration (with the other calculations following). At each discrete time interval Ti, the amount of insulin that has entered into the plasma from the subcutaneous compartment is calculated to provide $I_P$ 603. That value will be multiplied (or otherwise factored by) $\gamma_2$ 606 and subtracted from the output of the PID controller to determine an improved desired insulin value based on the plasma insulin concentration. At each discrete time interval Ti, the amount of insulin actually going into action or the effective insulin compartment from the insulin in the plasma is calculated to provide $I_{EF}$ 604. That value will be multiplied (or otherwise factored by) $\gamma_3$ 607 and subtracted from the output of the PID controller to determine an improved desired insulin value based on the effective insulin. The insulin actually delivered to the subject 650 will then change the blood glucose G of the user 608, which will then be measured by the sensor 660 and compared to the desired glucose 600.

Figure 43:
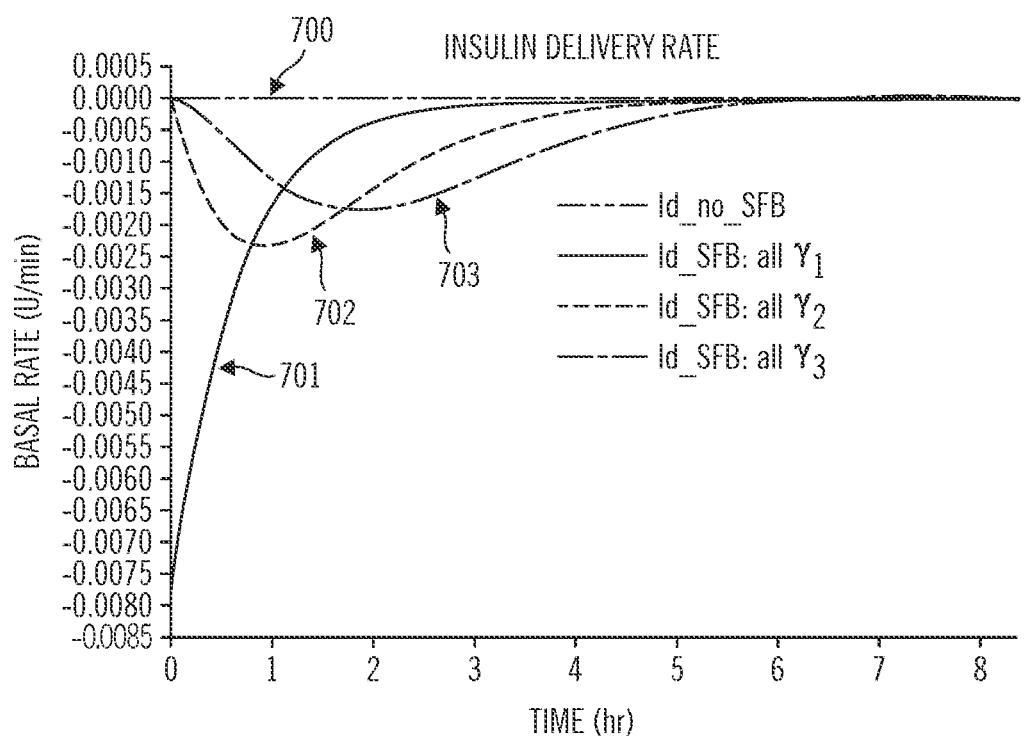
FIG. 43 is a plot of basal insulin delivery rate over time using different control gains in accordance with embodiments of the present invention.

FIGS. 43-46 show graphs with the effect of state feedback. FIG. 43 shows the effect on the basal insulin delivery rate achieved using the algorithm described above. A bolus is given at time zero. Line 700 shows the insulin delivery when no state feedback is used. This line would be the same as a regular delivery of an insulin bolus and is indicated as 0.0000, because it does not change the amount of basal rate being delivered. The other three lines illustrate the change in insulin delivery rate over time when all of the state feedback is placed in one of the gains $\gamma_1$, $\gamma_2$, or $\gamma_3$. As can be seen, if all the state feedback is placed in the gain $\gamma_1$ (for the subcutaneous layer), the basal insulin delivery rate 701 (in relation to the standard basal rate) starts out low and gradually moves to a limit of zero, or the rate without state feedback, as steady state is reached. If all of the state feedback is placed in the gain $\gamma_2$ (for the plasma layer), the basal insulin delivery rate 702 starts at zero, dips lower, and then gradually returns up to a limit of zero as steady state is reached. If all of the state feedback is placed in the gain $\gamma_3$ (for the insulin action/effect), the basal insulin delivery rate 703 starts at zero, dips lower, but more slowly than for the all $\gamma_2$ delivery rate, and then gradually returns up to a limit of zero as steady state is reached. In all cases, the total delivery of insulin is the same.

Figure 44:
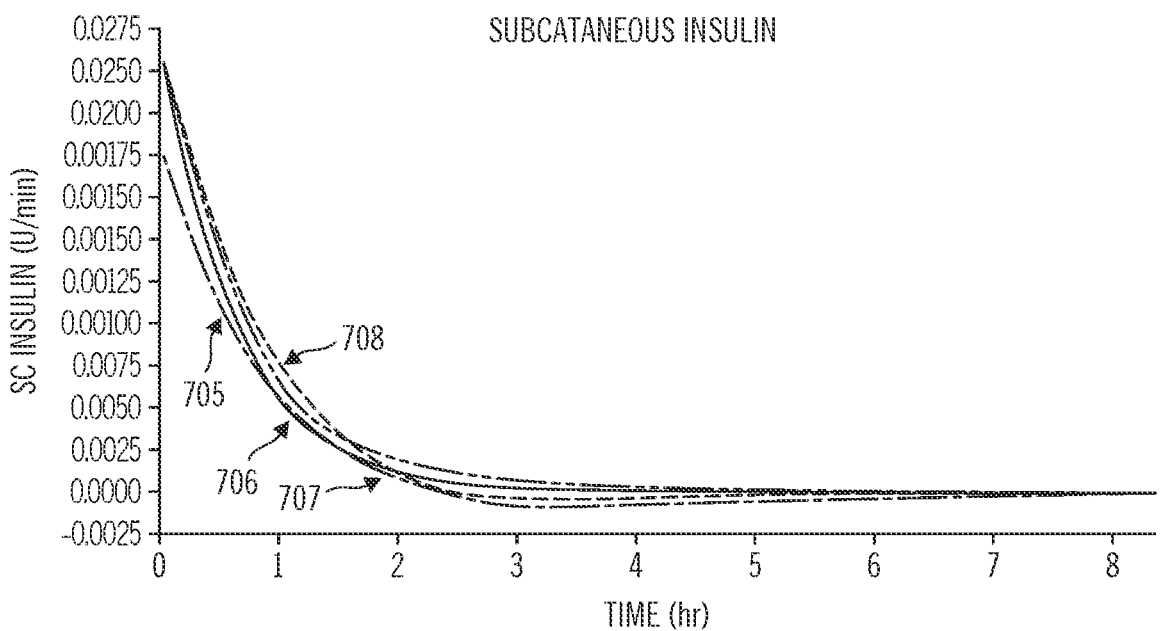
FIG. 44 is a plot of subcutaneous insulin over time using different control gains in accordance with embodiments of the present invention.

FIG. 44 shows the effect of state feedback per unit bolus on the subcutaneous insulin. In other words, a bolus of insulin is given to a patient at time zero and the figure shows the rate in which the amount of insulin in the subcutaneous layer, from that bolus, decreases to zero. Line 705 shows the amount of insulin in the subcutaneous layer over time with no state feedback. Line 706 shows the amount of insulin in the subcutaneous layer over time when all of the state feedback is placed in gain $\gamma_1$. Line 707 shows the amount of insulin in the subcutaneous layer over time when all of the state feedback is placed in gain $\gamma_2$. Line 708 shows the amount of insulin in the subcutaneous layer over time when all of the state feedback is placed in gain $\gamma_3$.

Figure 45:
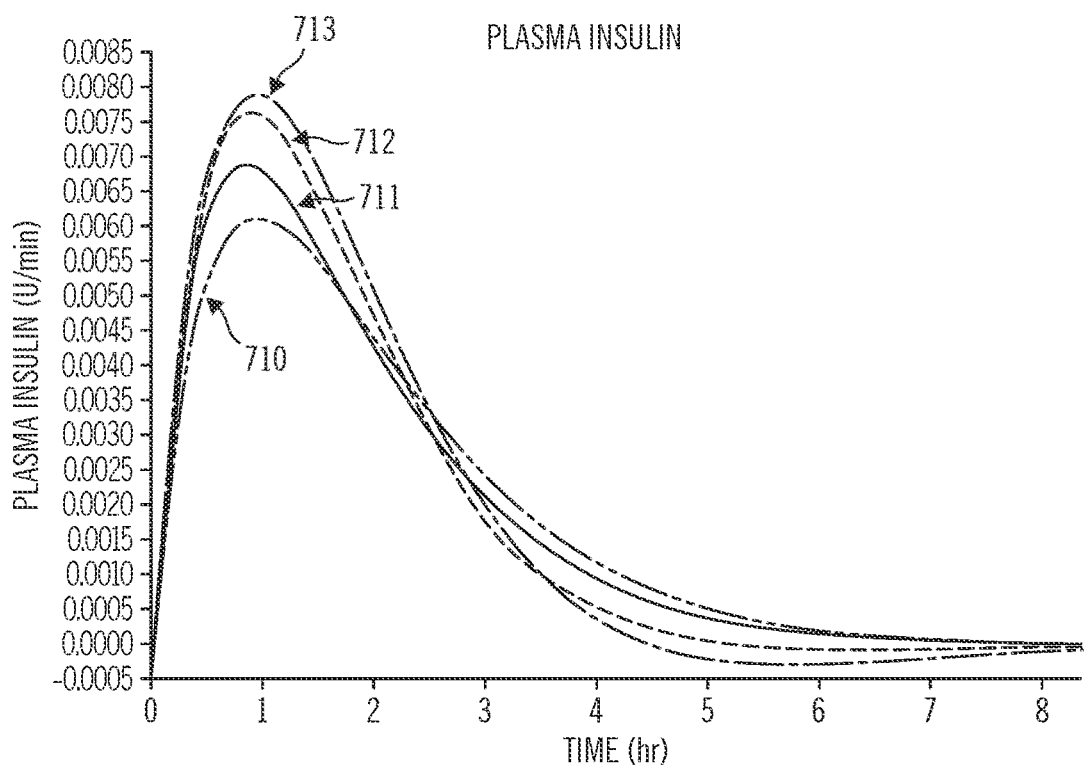
FIG. 45 is a plot of plasma insulin over time using different control gains in accordance with embodiments of the present invention.

FIG. 45 shows the effect of state feedback per unit bolus on the plasma insulin. In other words, a bolus of insulin is given to a patient at time zero and the figure shows the rate in which the amount of insulin in the plasma layer, from that bolus, increases from zero (there is a slight delay from injecting insulin to when the insulin moves into the plasma from the subcutaneous layer), reaches its peak and then returns to zero. Line 710 shows the amount of insulin in the plasma over time with no state feedback. Line 711 shows the amount of insulin in the plasma over time when all of the state feedback is placed in gain $\gamma_1$. Line 712 shows the amount of insulin in the plasma over time when all of the state feedback is placed in gain $\gamma_2$. Line 713 shows the amount of insulin in the plasma over time when all of the state feedback is placed in gain $\gamma_3$.

Figure 46:
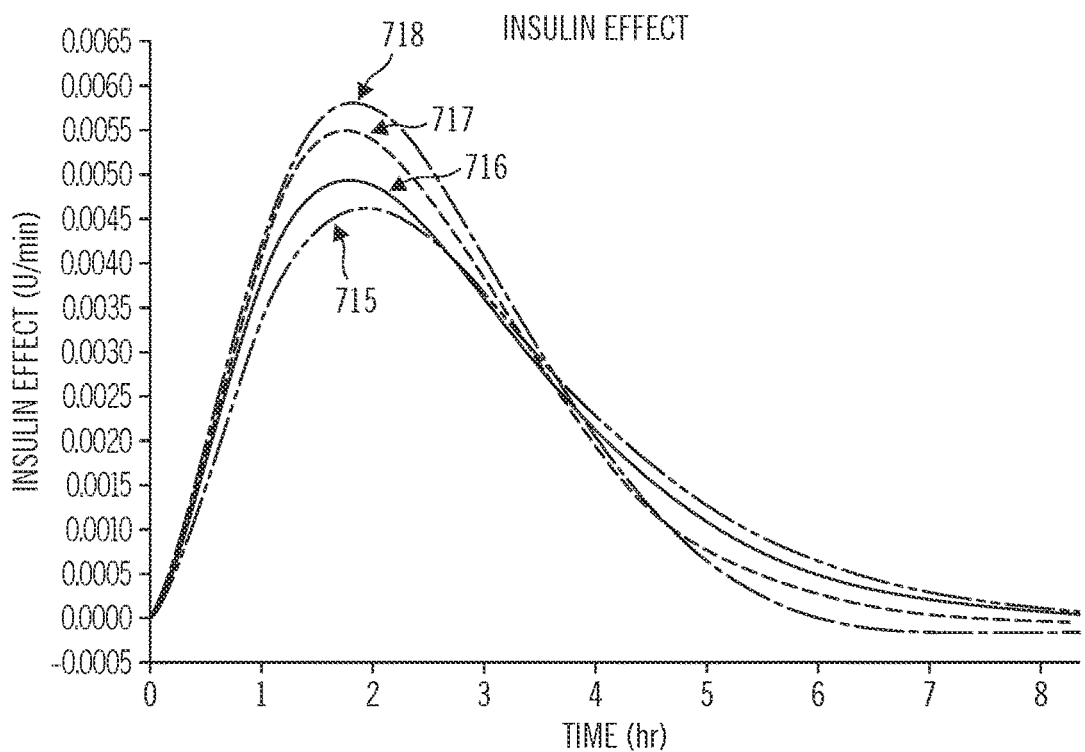
FIG. 46 is a plot of insulin effect over time using different control gains in accordance with embodiments of the present invention.

FIG. 46 shows the effect of state feedback per unit bolus on the insulin effect. In other words, a bolus of insulin is given to a patient at time zero and the figure shows the rate in which the amount of insulin from that bolus creates the insulin effect on the body, starting at zero (there is a delay from the injection of insulin into the subcutaneous layer and through the plasma to the insulin effect), rising to its maximum point, and decreasing to zero. Line 715 shows the insulin effect over time with no state feedback. Line 716 shows the insulin effect over time when all of the state feedback is placed in gain $\gamma_1$. Line 717 shows the insulin effect over time when all of the state feedback is placed in gain $\gamma_2$. Line 718 shows the insulin effect over time when all of the state feedback is placed in gain $\gamma_3$.

Figure 47:
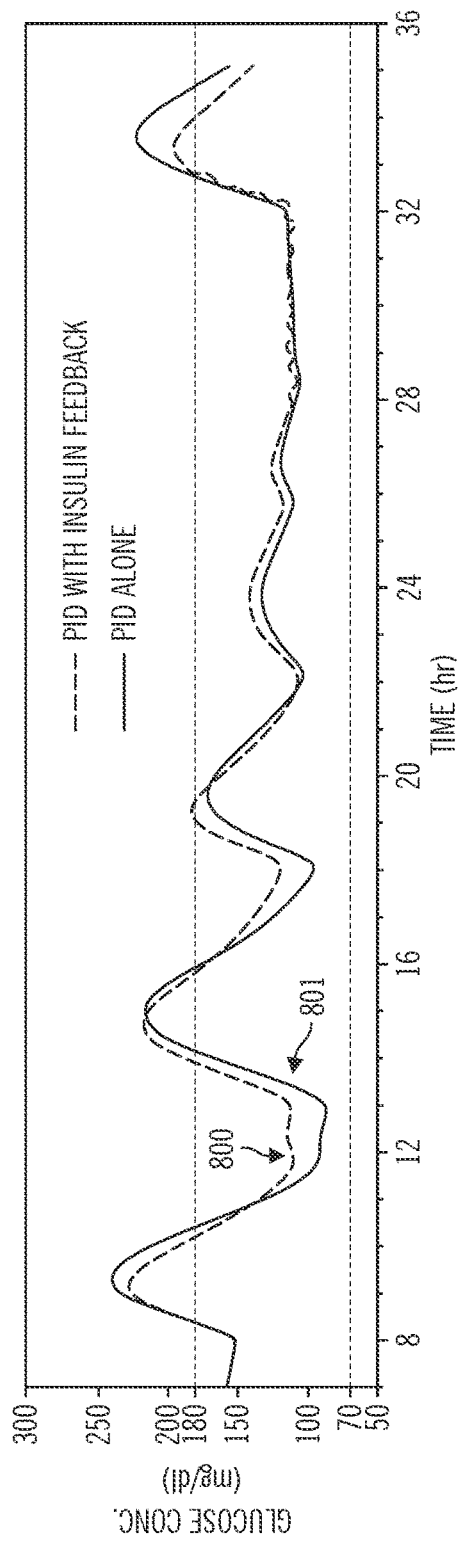
FIG. 47 is a plot of simulated glucose concentration over time using a PID controller with state variable feedback and a PID controller without state variable feedback in accordance with embodiments of the present invention.
Figure 48:
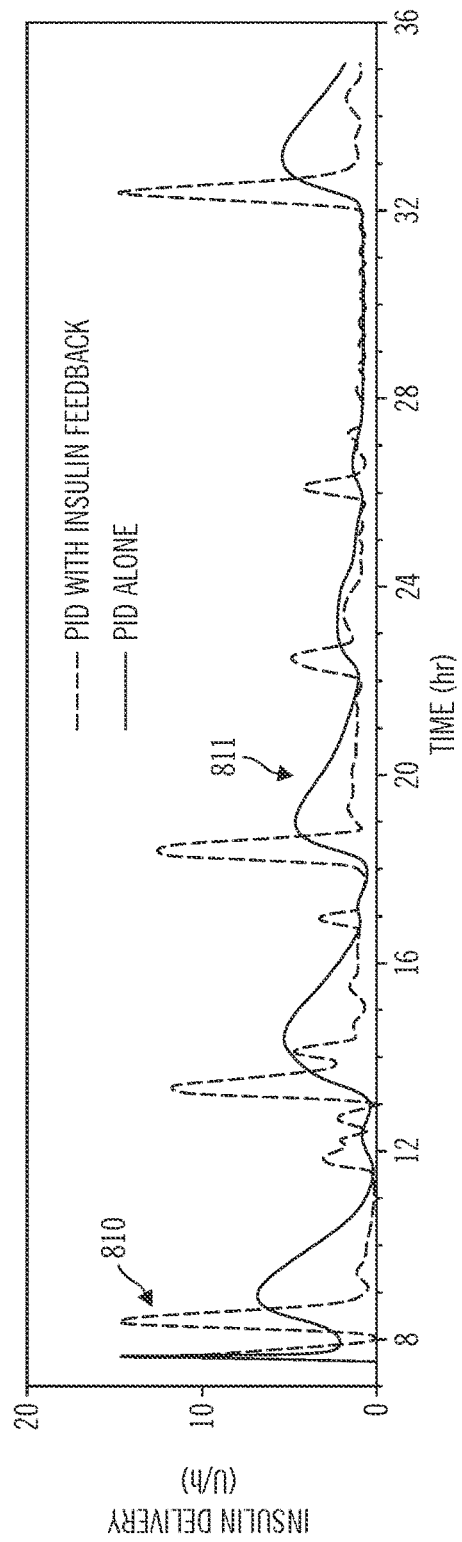
FIG. 48 is a plot of simulated insulin delivery over time using a PID controller with state variable feedback and a PID controller without state variable feedback in accordance with embodiments of the present invention.

FIGS. 47 and 48 compare insulin state variable feedback used in conjunction with a PID closed loop controller as opposed to use of a PID closed loop controller alone (with no insulin state variable feedback). FIG. 47 shows the simulated glucose concentration of a patient over time. Meals are given at 8, 13, 18, 22, and 32 hours. The glucose concentration using the PID with insulin state feedback is shown as line 800. The glucose concentration using the PID without insulin state feedback is shown as line 801. With glucose concentrations, it is always preferable to keep a patient's concentrations from being too high or too low, so the more that the closed loop program can avoid high and low values, the better. As can be seen in FIG. 47, as time goes on, the glucose concentration using the PID with insulin state feedback improves over time (versus the glucose concentration using the PID without insulin state feedback) in that it varies less as time goes on, keeping the patient with a more steady glucose level that will greatly reduce hyper- and hypoglycemic events. FIG. 48 shows average simulated insulin delivery profiles from the same system as FIG. 47. Line 810 represents the insulin delivery using the PID with insulin state feedback. Line 811 represents the insulin delivery using the PID without insulin state feedback. As can be seen, the insulin delivery using the PID with insulin state feedback contains more spikes and dips, resulting from the state feedback.

Modifying the PID Controller to Incorporate an Integrator Leak In preferred embodiments, the PID control response was described with constant gain components, $K_P$, $K_I$, $K_D$. Although the preferred control response guarantees zero steady-state error (i.e., steady state glucose minus a desired basal glucose $(G_B)$=0), inherently, the integral component $U_I = K_I \int_{t_0}^{t} (G-G_B) dt + U_I(t_0)$ destabilizes feedback control because there is no temporal wind down of the insulin response while the integral component models the increase in the insulin response. Without any correction, the integral component has a tendency to over-estimate the increase in the insulin response. Since a small difference between steady-state glucose and $G_B$ is typically acceptable in insulin response control, an alternative modeling of the integral component can incorporate an integrator leak to reduce the magnitude of the destabilizing effect. Specifically, changes in $U_I(t)$ can be described by a term proportional to the error in glucose and a term that leaks in proportion to the magnitude of $U_I$. This can be expressed in the formula:

$$\frac{dU_I}{dt} K_1(G - G_B) - K_{LEAK} U_I;$$

with initial condition $U_I(t_0)$.

The parameter $K_{LEAK}$ is the reciprocal time constant of the rate of leaking ($\tau_{LEAK}$ in min=$1/K_{LEAK}$), where $\tau_{LEAK}$ is a tuning parameter that can be set based on empirical data, and be tied with the other gain components $K_P$, $K_I$, $K_D$. However, the current realization of the artificial β-cell has $\tau_{LEAK}$ as a user input. $U_I$ can also be expressed in discrete form by standard methods.

Post-Controller (Lead/Lag) Compensator

Figure 35A:
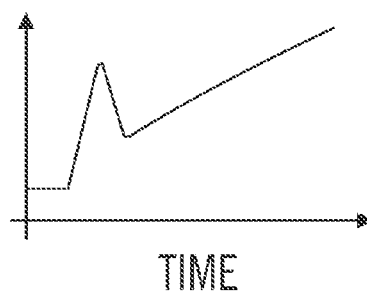
FIG. 35A is a drawing of a blood plasma insulin response to a glucose clamp in a normal glucose tolerant (NGT) individual in accordance with an embodiment of the present invention.
Figure 35B:
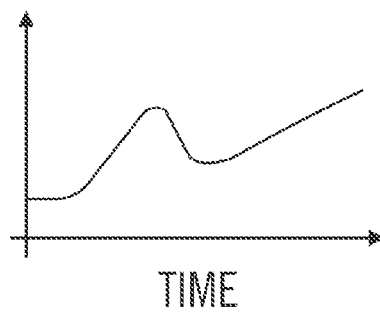
FIG. 35B is a drawing of the blood plasma insulin response of FIG. 35A when delayed due to insulin being delivered to the subcutaneous tissue instead of directly into the blood stream in accordance with an embodiment of the present invention.
Figure 36A:
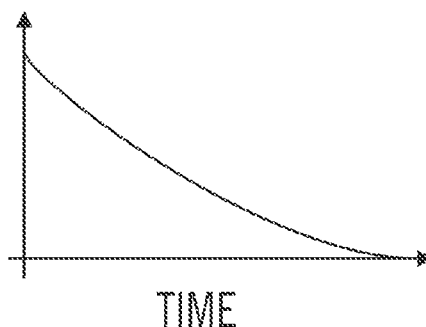
FIG. 36A is a drawing of blood plasma insulin concentration over time after an insulin bolus is delivered directly into the blood stream in accordance with an embodiment of the present invention.

In preferred embodiments, commands are issued from the controller without regard to where in the body the insulin delivery system will infuse the insulin. In essence, the assumption is that the insulin is either delivered directly into the blood stream for immediate use by the body, or that any time delays caused by delivering the insulin somewhere in the body other than the blood stream can be compensated for by adjusting $K_P$, $K_I$, and $K_D$. In this case, the commands generally model a β-cell insulin secretion profile, an example of which is shown in FIG. 35A. And since the β-cells secrete insulin directly into the blood stream, the β-cell insulin secretion profile is the intended blood plasma insulin concentration profile. However, an insulin delivery delay may distort the intended blood plasma insulin concentration profile, as shown in FIG. 35B. The insulin delivery delay is the amount of time between the instant that the command is given to the insulin delivery system to infuse insulin and the time that insulin reaches the blood plasma. An insulin delivery delay may be caused by a diffusion delay, represented by a circle with an arrow 528 in FIG. 20, which is the time required for insulin that has been infused into a tissue to diffuse into the blood stream. Other contributors to insulin delivery delay may include, time for the delivery system to deliver the insulin to the body after receiving a command to infuse insulin, time for the insulin to spread throughout the circulatory system once it has entered the blood stream, and/or by other mechanical or physiological causes. In addition, the body clears insulin even while an insulin dose is being delivered from the insulin delivery system into the body. Since insulin is continuously cleared from the blood plasma by the body, an insulin dose that is delivered to the blood plasma too slowly or is delayed is at least partially, if not significantly, cleared before the entire insulin dose fully reaches the blood plasma. And therefore, the insulin concentration profile in the blood plasma never achieves the same peak (nor follows the same profile) it would have achieved if there were no delay. Given an insulin dose delivered all at once into the blood plasma at time zero, the insulin concentration in the blood plasma is raised virtually instantaneously (not shown) and then would decrease exponentially over time as the body clears (uses or filters out) the insulin, as shown in FIG. 36A per equation:

$$C_P = \frac{I_0}{V_p} e^{-P_1 t},$$

where:
$C_P$ is the concentration of insulin in the blood plasma,
$I_0$ is a mass of the insulin dose delivered directly to the blood plasma at time zero,
$V_P$ is a volume of the blood plasma in the body,
$P_1$ is a reciprocal time constant for insulin clearance, and
t is the time that has passed since the delivery of the insulin dose directly into the blood plasma.

The time constant for insulin clearance Pi may be calculated using the following equation:

$$P_1 = -\frac{k}{V_p},$$

where:
k is the volume insulin clearance rate, and
$V_P$ is a volume of the blood plasma in the body.

Or the time constant for insulin clearance $P_1$ may be obtained by providing insulin to an individual that does not generate his own insulin, and then periodically testing blood samples from the individual for insulin concentration. Then, using an exponential curve fitting routine, generate a mathematical expression for a best-fit curve for the insulin concentration measurements, and observe the time constant in the mathematical expression.

Figure 36B:
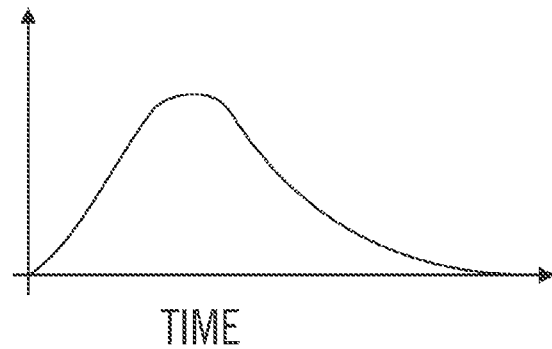
FIG. 36B is a drawing of a blood plasma insulin concentration over time after an insulin bolus is delivered into the subcutaneous tissue in accordance with an embodiment of the present invention.

Given the same insulin dose (delivered at time zero all at once) into the subcutaneous tissue, instead of directly into the blood plasma, the concentration of insulin in the blood plasma would begin to rise slowly as insulin diffuses from the interstitial fluid ISF into the blood plasma, as shown in FIG. 36B. At the same time that insulin is entering the blood plasma, the body is clearing insulin from the blood. While the rate at which insulin is entering the blood plasma exceeds the insulin clearance rate, the insulin concentration in the blood plasma continues to increase. When the insulin clearance rate exceeds the rate at which insulin is entering the blood plasma from the interstitial fluid ISF, the insulin concentration in the blood plasma begins to decrease. So, the result of delivering insulin into the interstitial fluid ISF instead of directly into the blood stream is that the insulin concentration in the blood plasma is spread over time rather than increased virtually instantaneously to a peak followed by a decay.

A bi-exponential equation may be used to model the insulin concentration in blood plasma given an insulin dose delivered to the subcutaneous tissue:

$$C_P = \frac{I_0 D}{V_P V_{ISF}(P_3 - P_2)} \left(e^{-P_2 t} - e^{-P_3 t}\right),$$

where:
$C_P$ is the concentration of insulin in the blood plasma,
$I_0$ is the mass of the insulin dose delivered to the subcutaneous tissue at time zero,
D is a diffusion coefficient (the rate at which insulin diffuses from the interstitial fluid ISF into the blood glucose)
$V_P$ is a volume of the blood plasma in the body,
$V_{ISF}$ is a volume of interstitial fluid ISF that the insulin is delivered to,
$P_2$ is a time constant,
$P_3$ is a time constant greater than or equal to $P_2$, and
t is time since the delivery of the insulin dose into the interstitial fluid ISF.

The time constants may be calculated using the quadratic formula:

$$P_2, P_3 = -\frac{a_1 \pm \sqrt{a_1^2 - 4a_0}}{2}, \text{ where}$$

$$a_1 = \frac{D+K}{V_P} + \frac{D}{v_{ISF}}, \text{ and}$$

$$a_0 = \left(\frac{D+K}{V_P}\right)\left(\frac{D}{C_{ISF}}\right) - \frac{D^2}{V_{ISF} V_P}.$$

Figure 37:
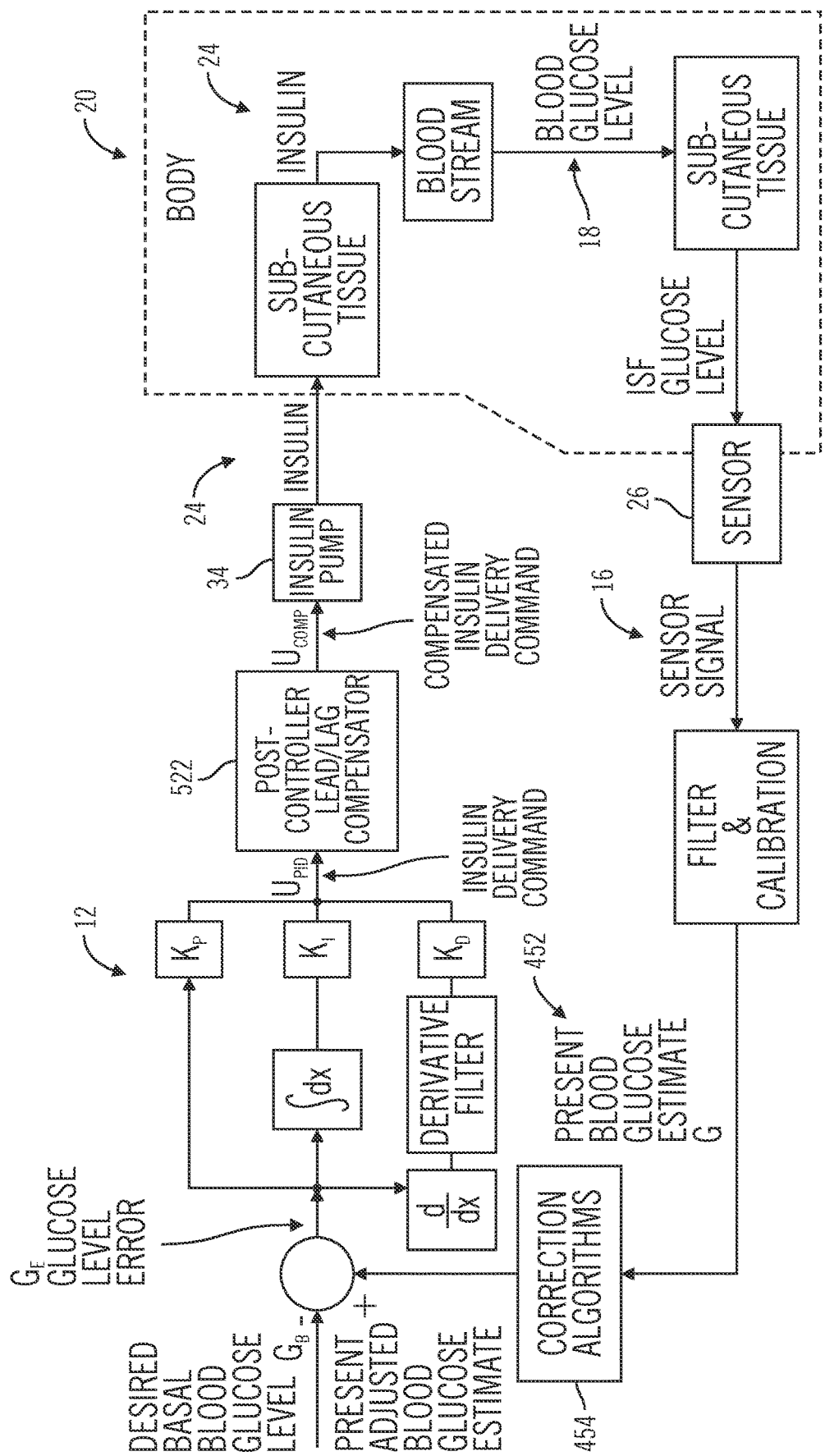
FIG. 37 is a block diagram of the closed loop system of FIG. 26 with the addition of a post-controller compensator and a derivative filter in accordance with an embodiment of the present invention.

In alternative embodiments, a post-controller lead-lag compensator 522 is used to modify the commands ($U_{PID}$) to compensate for the insulin delivery delay and/or the insulin clearance rate k, as shown in FIG. 37. The post-controller lead-lag compensator 522 is of the form $$\frac{U_{COMP}}{U_{PID}} = \frac{s + \alpha}{s + \gamma}$$

where $1/\alpha$ and $1/\gamma$ are the lead and lag constants respectively, s is the Laplace variable, and $U_{COMP}$ is the compensated commands calculated by the lead-lag compensator 522.

The PID controller generates commands ($U_{PID}$) for a desired insulin delivery rate into the blood plasma. The commands $U_{PID}$ are calculated and issued periodically depending on the update rate for the control loop, which is selected based on a maximum anticipated rate of change of the blood glucose level, an insulin delivery system minimum insulin dosage, insulin sensitivity, a maximum and a minimum acceptable glucose concentration, or the like. The commands $U_{PID}$ are used as inputs to the post-controller lead-lag compensator 522.

In particular embodiments, the compensated commands ($U_{COMP}$) issued from the post-controller lead-lag compensator 522 uses more than one value from the controller. In particular embodiments, post-controller lead-lag compensator 522 uses the present command ($U_{PID}^n$) and the previous command ($U_{PID}^{n-1}$) to calculate a compensated command $U_{COMP}$ per a compensation equation:

$$U_{COMP}^n = (1-\gamma)U_{COMP}^{n-1} + U_{PID}^n + (1-\alpha)U_{PID}^{n-1},$$

where:
$U_{PID}^n$ is the present command,
$U_{PID}^{n-1}$ is the previous command,
$U_{COMP}^{n-1}$ is the previous compensated control output,
$\alpha$ is the reciprocal lead time constant in min$^{-1}$, and
$\gamma$ is the reciprocal lag time constant in min$^{-1}$.

This is a first forward difference equation. However, other forms can be used alternatively (e.g., first backward or bilinear), but all result in a compensated control output ($U_{COMP}$) that is comprised of a weighted history of both past PID outputs ($U_{PID}$), and past compensated outputs ($U_{COMP}$).

An alternative method of modifying the commands ($U_{PID}$) to compensate for the insulin delivery delay and/or the insulin clearance can be performed based on a weighted history of past insulin delivery. By giving the most recent delivery history more weight, the weighted history of the previous insulin delivered can then be subtracted from the present PID control output to yield a compensated control output. Expressed in Laplace domain this results in:

$$U_{COMP} = PID\,E - \frac{\lambda}{s+a}U_{COMP},$$

where E is the Laplace transformed error signal (G–G$_B$), $\lambda$ determines how much the PID output is reduce in proportion to the weighted history of past control outputs, and $\alpha$ is the reciprocal time constant determining how long a history is weighted (the preferred value of $\alpha$ would be equal to the reciprocal dominant time constant or subcutaneous insulin appearance, P$_2$). Solving the compensated signals as a function of the error results in:

$$\frac{U(s)}{E(s)} = PID\frac{s+\alpha_w}{s+(\alpha+\lambda)} = PID\frac{s+\alpha_w}{s+\gamma},$$

which is identical to the previously described lead-lag compensation.

In other alternative embodiments, additional previous command values may be used. In still other alternative embodiments, the compensation equation compensates for both time constants P$_2$ and P$_3$.

In still more alternative embodiments, the controller gains are modified to include the effects of the post-controller lead/lag compensator so that the post-controller lead/lag compensator is not needed to modify the commands to account for the insulin delivery delay.

In particular embodiments, the insulin delivery system provides finite insulin doses into the body in response to commands from the controller. The smallest amount of insulin that the insulin delivery system can deliver is the minimum finite insulin dose. The controller may generate commands for a dose of insulin to be delivered that is not a whole number multiple of the minimum finite insulin dose. Therefore, either too much or too little insulin is delivered by the insulin delivery system in response to the commands. In particular alternative embodiments, the post-controller lead-lag compensator truncates the command to the nearest whole number multiple of the minimum finite insulin dose and adds the remaining commanded volume of insulin to the next command. In other alternative embodiments, a compensator rounds the command to the nearest whole number multiple of the minimum finite insulin dose. In still other alternative embodiments, other methods are used to compensate for the difference between the commands and the nearest whole number multiple of the minimum finite insulin dose. In other embodiments, no compensation is needed.

Eliminating the Lead-Lag Compensator with Feedback of Predicted Plasma Insulin

Yet in another alternative embodiment, the PID control commands may be modified to emulate the effect of plasma insulin on a β-cell to determine optimal insulin administration by feeding back a predicted plasma insulin based on the subcutaneous insulin infusion. The net effect of such feedback is to replace an undesired dynamic with a more desirable one and achieve a plasma insulin profile that a β-cell would achieve. This can be seen as follows (using Laplace transformed variables). Assume the relation between glucose above basal (G–G$_B$) and insulin delivery (I$_D$) is described by a linear transfer function D(s)= C(s)(G(s)–G$_B$), where C(s) may be, but is not necessarily, described by the PID controller transfer function. If the β-cell is using peripheral insulin (I$_p$(s)) levels to suppress insulin secretion the predicted rate of insulin delivery would be modified as: D(s)=C(s)(G(s)–G$_B$)–kI$_p$(s).

For portal insulin delivery the relation between I$_D$(s) and plasma insulin I$_P$(s) is known to be approximated by a single time delay:

$$I_p(s) = \frac{k_1}{s+\alpha}ID(s).$$

Substituting I$_p$(s) value into the previous formula and making k large results in:

$$ID(s) = \frac{C(s)(G(s)-G_B)}{1+\frac{kk_1}{s+\alpha}} \approx C(s)\frac{s+\alpha}{kk_1}(G(s)-G_B);\, 1 \ll \frac{kk_1}{s+\alpha},$$

which would completely cancel the undesirable time constant $1/\alpha$. In practice a lower value of k would be used resulting in:

$$ID(s) = C(s)(G(s) - G_B) - \frac{kk_1}{s + \alpha}ID(s) = C(s)\frac{s + \alpha}{s + \gamma}(G(s) - G_B),$$

where $\gamma = \alpha + kk_1$ (i.e., something greater than $\alpha$). Thus, the effect for the β-cell, of adding a plasma insulin feedback is to replace the portal insulin delivery time constant ($\alpha$) with a faster time constant ($\gamma = \alpha + kk_1$; $\gamma > \alpha$). In block diagram form:

$$G - G_B \rightarrow C(s) \cdot \frac{s + \alpha}{s + \gamma} \xrightarrow{ID} \frac{k_1}{s + \alpha} \xrightarrow{I_p}$$

which is equivalent to:

$$G - G_B \rightarrow C(s) \cdot \frac{1}{s + \gamma} \xrightarrow{I_p}$$

To apply this mechanism to subcutaneous insulin delivery all that is needed is the transfer function between sc insulin delivery and plasma insulin. This transfer function is well approximated by a bi-exponential time course (bolus response) or:

$$\frac{I_p(s)}{ID_{SC}(s)} = \frac{k_2}{(s + \alpha_1)(s + \alpha_2)}$$

thus, $$ID(s) = C(s)(G(s) - G_B) - \frac{kk_2}{(s + \alpha_1)(s + \alpha_2)}ID(s)$$

$$= C(s)\frac{1}{1 + \frac{kk_2}{(s + \alpha)(s + \alpha_2)}}(G(s) - G_B)$$

in the limiting case as $kk_2/(s+\alpha_1)(s+\alpha_2) >> 1$ this is approximately equal to $$ID(s) = C(s)\frac{(s + \alpha_1)(s + \alpha_2)}{kk_2}(G(s) - G_B)$$

where again, the undesirable time constants associated with subcutaneous insulin delivery have been eliminated. In practice they would just be replaced with more desirable rate constants (i.e., faster time constants).

Correction of Hypoglycemic Excursion Around ~200 Minutes (Wind-Down)

Figures 41A, 41B:
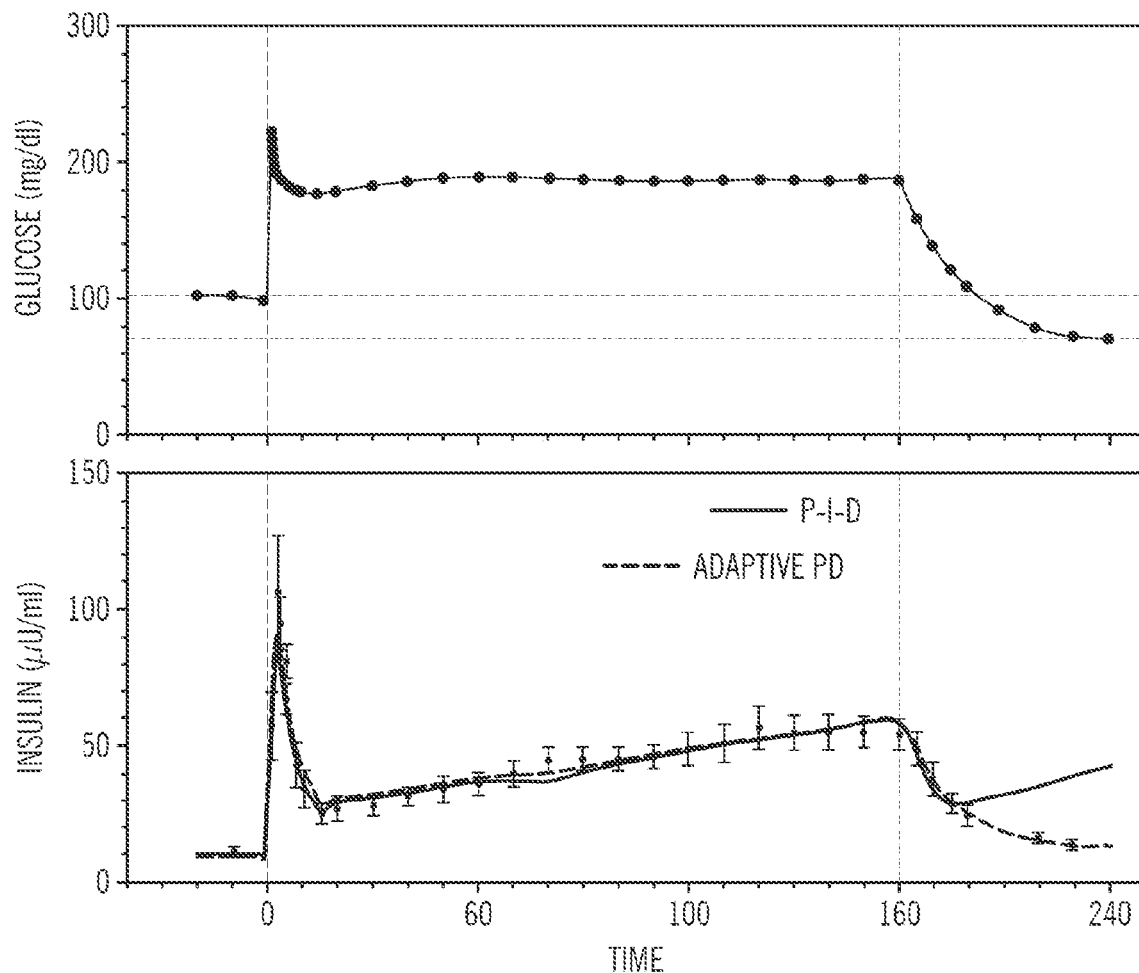
FIG. 41A is a plot actual blood glucose concentration in accordance with an embodiment of the present invention.
FIG. 41B is a plot of actual insulin concentration in blood compared to a controller commanded insulin concentration in response to the blood glucose in FIG. 41A in accordance with an embodiment of the present invention.

Previous modeling of β-cells using a PID controller gave excellent predictability of the "first" and "second" phase insulin responses during prolonged periods of increased glucose appearance. However, if the periods of increased glucose appearance is followed by a rapid decrease in glucose appearance, the PID controller would not be able to correctly predict the wind down of the insulin response to lower glucose levels. FIG. 41B illustrates the insulin response to the blood glucose level of FIG. 41A based on the clinical data (shown as data points), the PID modeling (shown as a solid line), and correction of the PID for the hypoglycemic excursion (shown as a dashed line).

In preferred embodiments, the hypoglycemic excursion is corrected by modifying the PID controller to a PD control with Adaptive Proportional Gain (or Bilinear PID controller), which is modified form of the original PID equations. As described previously, the discrete PID algorithm is as follows:

Proportional Component Response:

$$P_{con}^n = K_P(SG_f^n - G_{sp}),$$

Integral Component Response:

$$I_{con}^n = I_{con}^{n-1} + K_I(SG_f^n - G_{sp}); I_{con}^0 = I_b,$$

and
Derivative Component Response:

$$D_{con}^n = K_D dGdt_f^n,$$

where $K_P$, $K_I$, and $K_D$ are the proportional, integral, and derivative gain coefficients, $SG_f$ and $dGdt_f$ are the filtered sensor glucose and derivative respectively, and the superscript n refers to discrete time.

In the Bilinear PID controller, the proportional gain $K_P$ is based on the integrated error term. The magnitude of each component's contribution to the insulin response is described by the following equations:

$$P_{con}^n = K_P^n(SG_f^n - INT)$$

$$D_{con}^n = K_D dGdt_f^n$$

$$K_P^n = K_P^{n-1} + K_I(SG_f^n - G_{sp}), \text{ where } K_P^0 = K_{P0}$$

Where the proportional gain now integrates at rate $K_I$ (initial value $K_{P0}$) and the proportional component is related to an intercept value (INT) where (INT<$G_{sp}$). The modified formulation can be seen to fit the hypoglycemic glucose excursion without systematic error as the adaptive PD line shown as a dashed line in FIG. 39.

In additional embodiments, the Bilinear PID controller can also incorporate an integrator leak by modifying the formula to multiply the previous $K_P$ with a value such as a as follows:

$$K_P^n = \alpha K_P^{n-1} + K_I(SG_f^n - G_{sp}), \text{ where } \alpha \approx 0.99$$

An alternative method of correcting the hypoglycemic glucose excursion can be performed by integrator clip into the PID control. PID controllers generally have integrator-reset rules that prevent excessive "winding" and such a rule can be used to correct the hypoglycemic glucose excursion. For example, the integrator can be clipped as follows:

If $(SG \leq 60 \text{ mg/dl AND } I_{con}^{n-1} > K_P(SP - 60))$ then $I_{con}^{n-1} = K_P(SP - 60)$ This equation resets the integrator such that if the sensor glucose falls below 60 mg/dl the insulin delivery is zero for all stable or falling sensor glucose signals. The clipping limit represents an absolute threshold, similar to the human counter regulatory response.

However, other approaches that may emulate the β-cell more accurately include the use of piecewise continuous functions. For example, the following function allows for progressive clipping to be tuned:

$$\gamma(SG) = \gamma_0 + (1 - \gamma_0)\left[\frac{T_1 - SG}{T_1 - 60}\right]$$

if $\left(SG \leq T_1 \text{ mg/dl AND } I_{con}^{n-1} > \gamma K_p(SP - 60)\right)$ then $$I_{con}^{n-1} = \gamma K_P(SP - 60)$$

This equation introduces two additional tuning parameters ($\gamma_0$ and $T_1$) and starts to check the integrator output at a higher threshold. For example, if $\gamma_0=5$ and $T_1=100$ mg/dl, the integrator output would be clipped to 4 $K_p 60$ if glucose fell to 90 mg/dl, 3 $K_p 60$ if glucose fell to 80 mg/dl and so forth until glucose reached 60 where it would be clipped at $K_p 60$. Other functions than that proposed in the above equation (e.g. functions based on the rate of fall of glucose, or percent decrease in $I_{con}$) may alternatively be used.

System Configurations

The following sections provide exemplary, but not limiting, illustrations of components that can be utilized with the controller described above. Various changes in components, layout of various components, combinations of elements, or the like may be made without departing from the scope of the embodiments of the invention.

Before it is provided as an input to the controller 12, the sensor signal 16 is generally subjected to signal conditioning such as pre-filtering, filtering, calibrating, or the like. Components such as a pre-filter, one or more filters, a calibrator and the controller 12 may be split up or physically located together, and may be included with a telemetered characteristic monitor transmitter 30, the infusion device 34, or a supplemental device. In preferred embodiments, the pre-filter, filters and the calibrator are included as part of the telemetered characteristic monitor transmitter 30, and the controller 12 is included with the infusion device 34, as shown in FIG. 8B. In alternative embodiments, the pre-filter is included with the telemetered characteristic monitor transmitter 30 and the filter and calibrator are included with the controller 12 in the infusion device, as shown in FIG. 8C. In other alternative embodiments, the pre-filter may be included with the telemetered characteristic monitor transmitter 30, while the filter and calibrator are included in the supplemental device 41, and the controller is included in the infusion device, as shown in FIG. 8D. To illustrate the various embodiments in another way, FIG. 9 shows a table of the groupings of components (pre-filter, filters, calibrator, and controller) in various devices (telemetered characteristic monitor transmitter, supplemental device, and infusion device) from FIGS. 8A-D. In other alternative embodiments, a supplemental device contains some of (or all of) the components.

In preferred embodiments, the sensor system generates a message that includes information based on the sensor signal such as digital sensor values, pre-filtered digital sensor values, filtered digital sensor values, calibrated digital sensor values, commands, or the like. The message may include other types of information as well such as a serial number, an ID code, a check value, values for other sensed parameters, diagnostic signals, other signals, or the like. In particular embodiments, the digital sensor values Dsig may be filtered in the telemetered characteristic monitor transmitter 30, and then the filtered digital sensor values may be included in the message sent to the infusion device 34 where the filtered digital sensor values are calibrated and used in the controller. In other embodiments, the digital sensor values Dsig may be filtered and calibrated before being sent to the controller 12 in the infusion device 34. Alternatively, the digital sensor values Dsig may be filtered, and calibrated and used in the controller to generate commands 22 that are then sent from the telemetered characteristic monitor transmitter 30 to the infusion device 34.

In further embodiments, additional optional components, such as a post-calibration filter, a display, a recorder, and a blood glucose meter may be included in the devices with any of the other components or they may stand-alone. Generally, if a blood glucose meter is built into one of the devices, it will be co-located in the device that contains the calibrator. In alternative embodiments, one or more of the components are not used.

In preferred embodiments, RF telemetry is used to communicate between devices, such as the telemetered characteristic monitor transmitter 30 and the infusion device 34, which contain groups of components. In alternative embodiments, other communication mediums may be employed between devices such as wires, cables, IR signals, laser signals, fiber optics, ultrasonic signals, or the like.

Filtering

Figure 16:
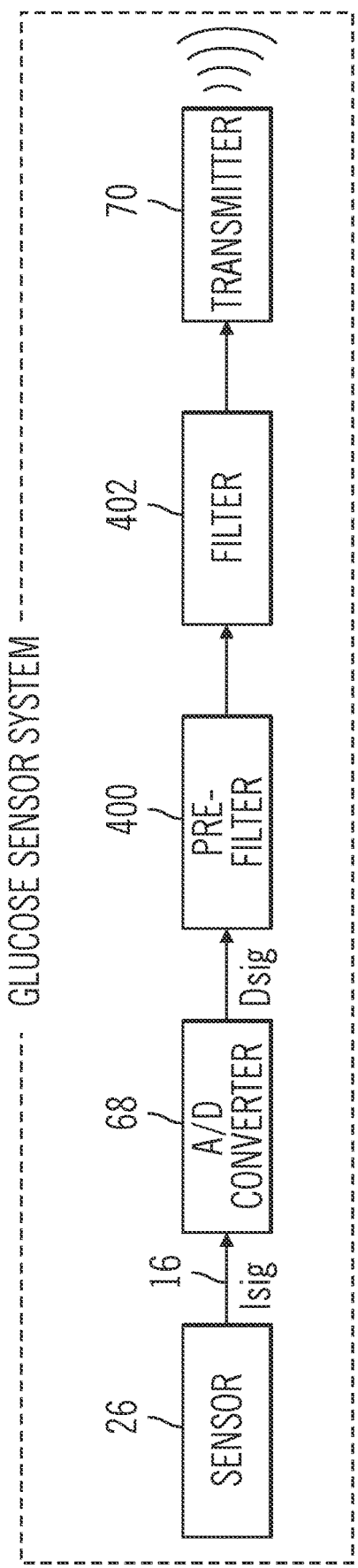
FIG. 16 is a block diagram of the glucose sensor system of FIG. 10 with a pre-filter and a filter in accordance with an embodiment of the present invention.

In preferred embodiments, the digital sensor values Dsig and/or the derivative of the digital sensor values are processed, filtered, modified, analyzed, smoothed, combined, averaged, clipped, scaled, calibrated, or the like, to minimize the effects of anomalous data points before they are provided as an input to the controller. In particular embodiments, the digital sensor values Dsig are passed through a pre-filter 400 and then a filter 402 before they are passed to the transmitter 70, as shown in FIG. 16. The filters are used to detect and minimize the effects of anomalous digital sensor values Dsig. Some causes of anomalous digital sensor values Dsig may include temporary signal transients caused by sensor separation from the subcutaneous tissue, sensor noise, power supply noise, temporary disconnects or shorts, and the like. In particular embodiments, each individual digital sensor value Dsig is compared to maximum and minimum value-thresholds. In other particular embodiments, the differences between consecutive pairs of digital sensor values Dsig are compared with rate-of-change-thresholds for increasing or decreasing values.

Pre-Filter

In particular embodiments, the pre-filter 400 uses fuzzy logic to determine if individual digital sensor values Dsig need to be adjusted. The pre-filter 400 uses a subset of a group of digital sensor values Dsig to calculate a parameter and then uses the parameter to determine if individual digital sensor values Dsig need to be adjusted in comparison to the group as a whole. For example, the average of a subset of a group of digital sensor values Dsig may be calculated, and then noise thresholds may be placed above and below the average. Then individual digital sensor values Dsig within the group are compared to noise thresholds and eliminated or modified if they are outside of the noise thresholds.

Figure 17:
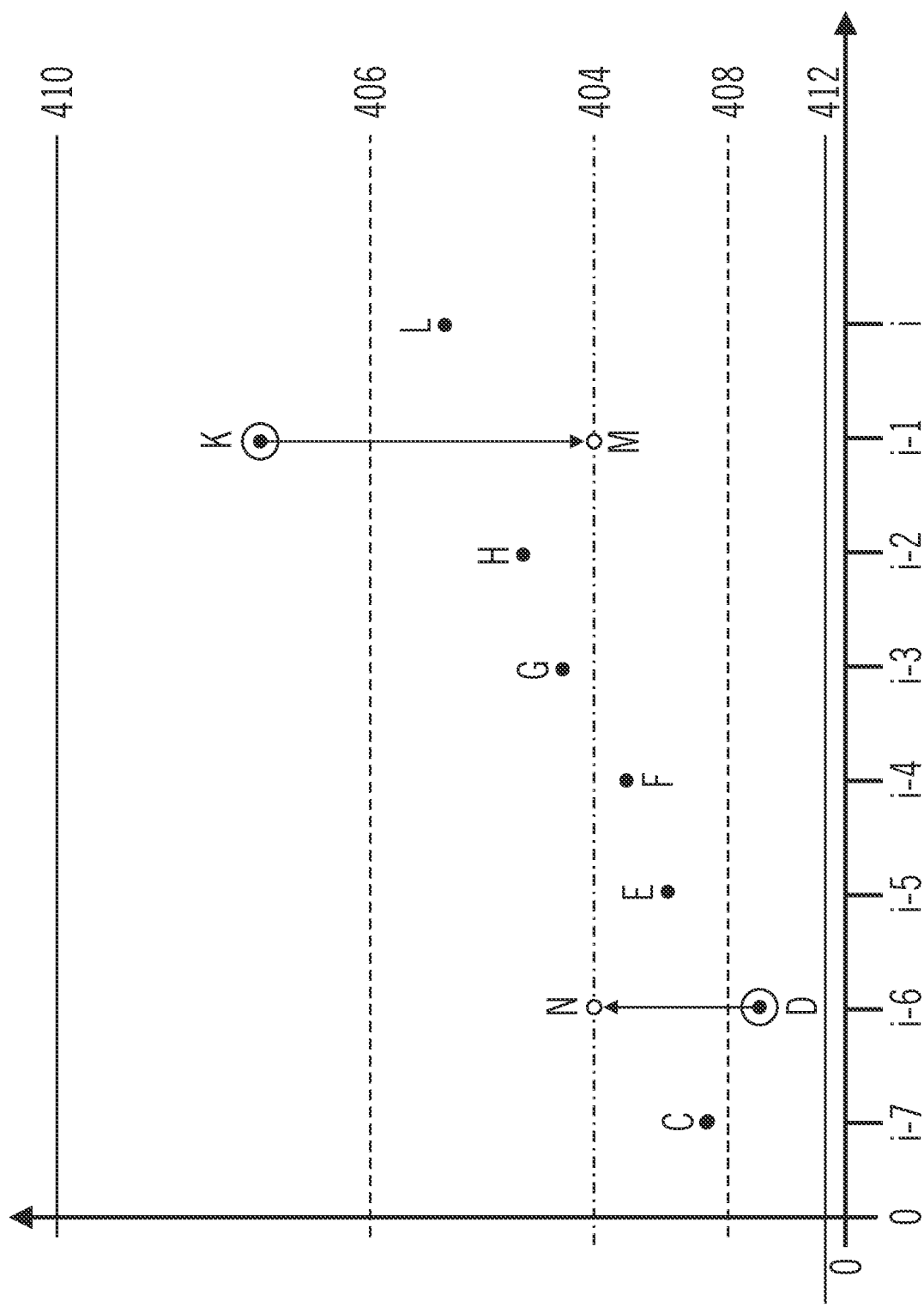
FIG. 17 is a chart of an example of a pre-filter of FIG. 16 and its effects on digital sensor values Dsig in accordance with an embodiment of the present invention.

A more detailed example is provided below to more clearly illustrate, but not limit, an embodiment of a pre-filter. A group of eight digital sensor values Dsig are shown in FIG. 17 including a most recently sampled value, labeled L, sampled from the analog sensor signal Isig at time i, and the seven previous values K, H, G, F, E, D, and C sampled at times (i-1) through (i-7). An average value is calculated using the four temporally middle values in the group, H, G, F, and E sampled at times (i-2) through (i-5). The calculated average value is represented as a dashed/dotted average line 404. A high noise threshold 406 is established at 100% above the average line 404. In other words, the magnitude of the high noise threshold 406 is two times the magnitude of the average line 404. A negative noise threshold 408 is established at 50% below the average line 404. In other words, the magnitude of the negative noise threshold 408 is one half of the magnitude of the average line 404. The individual magnitudes of each of the eight values, L, K, H, G, F, E, D, and C are compared to the high and negative noise thresholds 406 and 408. If a value is above the high noise threshold 406 or below the negative noise threshold 408 then the value is considered anomalous and the anomalous value is replaced with the magnitude of the average line 404. In the example shown in FIG. 17, the value K is above the high noise threshold 406 so it is replaced with the average value M. Also, the value D is below the negative noise threshold 408 so it is replaced with the average value N. In this way noisy signal spikes are reduced. Therefore, in the example, values L, K, H, G, F, E, D, and C are inputs to the pre-filter 400 and values L, M, H, G, F, E, N, and C are outputs from the pre-filter 400. In alternative embodiments, other noise threshold levels (or percentages) may be used. In other alternative embodiments, values outside of the thresholds may be replaced with values other than the average value, such as the previous value, the value of the closest threshold, a value calculated by extrapolating a trend line through previous data, a value that is calculated by interpolation between other values that are inside the thresholds, or the like.

In preferred embodiments, when any of a group's values are outside of the noise thresholds 406 or 408 then a warning flag is set. If one to three values are outside of the noise thresholds 406 or 408, a "noise" flag is set. If more than three values are outside of the noise thresholds 406 or 408, a "discard" flag is set which indicates that the whole group of values should be ignored and not used. In alternative embodiments, more or less values need be outside of the thresholds 406 or 408 to trigger the "noise" flag or the "discard" flag.

In preferred embodiments, each digital sensor value Dsig is checked for saturation and disconnection. To continue with the example of FIG. 17, each individual value is compared to a saturation threshold 410. If a value is equal to or above the saturation threshold 410 then a "saturation" flag is set. In particular embodiments, when the "saturation" flag is set, a warning is provided to the user that the sensor 26 may need calibration or replacement. In further particular embodiments, if an individual digital sensor value Dsig is at or above the saturation threshold 410, the individual digital sensor value Dsig may be ignored, changed to a value equal to the average line 404, or the entire group of values associated with the individual digital sensor value Dsig may be ignored. In preferred embodiments, the saturation threshold 410 is set at about 16% below the maximum value of the range of digital sensor values that may be generated. In preferred embodiments, the maximum digital sensor value represents a glucose concentration greater than 150 mg/dl. In alternative embodiments, the maximum digital sensor value may represent larger or smaller a glucose concentrations depending on the range of expected glucose concentrations to be measured, the sensor accuracy, the sensor system resolution needed for closed loop control, or the like. The full range of values is the difference between the maximum and the minimum digital sensor value that may be generated. Higher or lower saturation threshold levels may be used depending on an expected signal range of the sensor, sensor noise, sensor gains, or the like.

Similarly, in preferred embodiments, if a digital signal value Dsig is below a disconnect threshold 412, then a "disconnect" flag is set indicating to a user that the sensor is not properly connected to the power supply and that the power supply or sensor may need replacement or recalibration. In further particular embodiments, if a digital sensor value Dsig is below the disconnect threshold 412, the individual value may be ignored, changed to a value equal to the average line 404, or the entire group of values associated with the individual digital sensor value Dsig may be ignored. In preferred embodiments, the disconnect threshold 410 is set at about 20% of the full range of values. Higher or lower disconnect threshold levels may be used depending on an expected signal range of the sensor, sensor system noise, sensor gains, or the like.

In alternative embodiments, other methods are used to pre-filter the digital sensor values Dsig such as rate-of-change thresholds, rate-of-change squared thresholds, noise thresholds about a least squares fit line rather than about the average of a subset of a group's values, higher or lower noise threshold lines, or the like.

Noise Filter

After the digital sensor values Dsig are evaluated, and if necessary, modified by the pre-filter 400, the digital sensor values Dsig are passed to the filter 402. The filter 402 may be used to reduce noise in particular frequency bands. Generally the body's blood glucose level 18 changes relatively slowly compared to a rate at which digital sensor values Dsig are collected. Therefore, high frequency signal components are typically noise, and a low pass filter may be used to improve the signal to noise ratio.

Figure 19A:
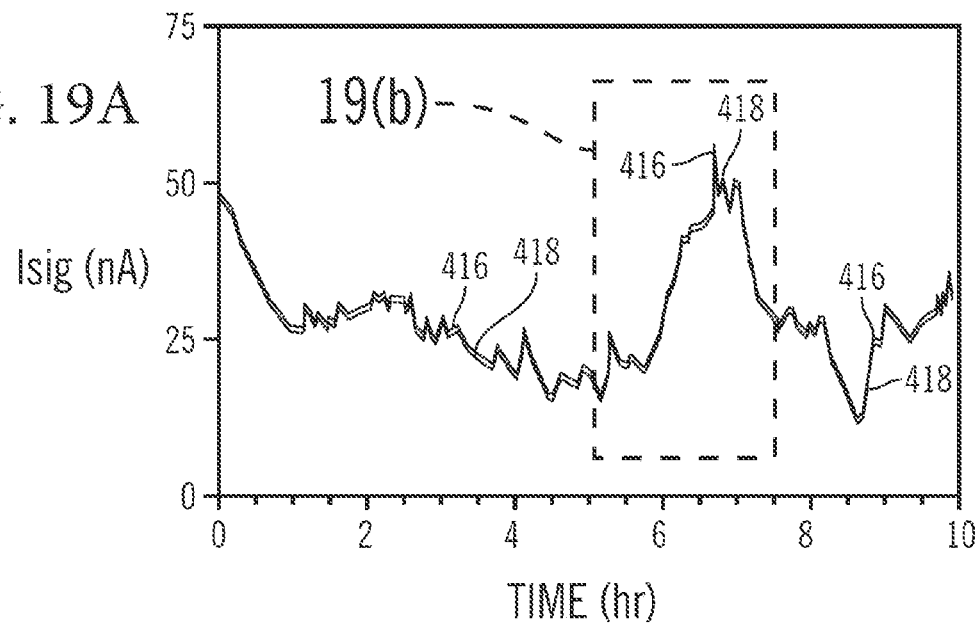
FIG. 19A is a plot of a filtered and an unfiltered sensor signal over time in accordance with an embodiment of the present invention.
Figure 19B:
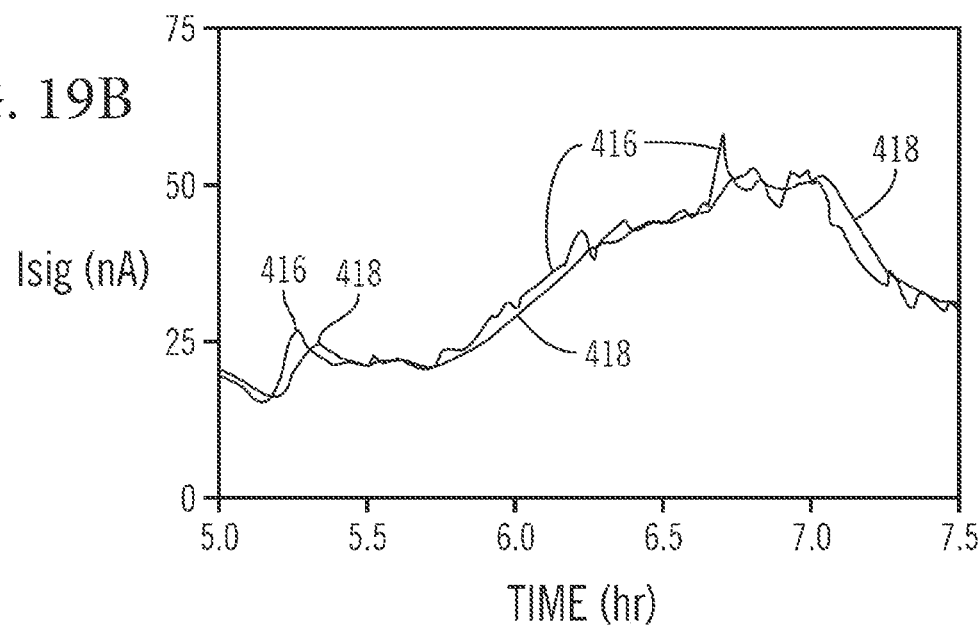
FIG. 19B is close up of a section of the plot of FIG. 19A in accordance with an embodiment of the present invention.

In preferred embodiments, the filter 402 is a finite impulse response (FIR) filter used to reduce noise. In particular embodiments, the FIR filter is a 7th order filter tuned with a pass band for frequencies from zero to 3 cycles per hour (c/hr) and a stop band for frequencies greater than about 6 c/hr, as shown in an example frequency response curve 414 in FIG. 18. However, typically FIR filters tuned with a pass band for frequencies from zero up to between about 2 c/hr and 5 c/hr and a stop band beginning at 1.2 to three times the selected pass band frequency will sufficiently reduce noise while passing the sensor signal. In particular embodiments, FIR filters tuned with a pass band for frequencies from zero up to between about 2 c/hr and 10 c/hr and a stop band beginning at 1.2 to three times the selected pass band frequency will sufficiently reduce noise. In the 7th order filter, unique weighting factors are applied to each of eight digital sensor values Dsig. The digital sensor values Dsig include the most recently sampled value and the seven previous values. The effects of a low pass filter on a digital sensor values collected at one minute intervals is shown in FIGS. 19A and B. An unfiltered sensor signal curve 416 of digital sensor values is contrasted with a curve of the same signal after the effects of a 7th order FIR filter 418. The filtered signal curve 418 is delayed and the peaks are smoother compared to the unfiltered sensor signal curve 416. In other particular embodiments, higher or lower order filters may be used. In still other particular embodiments, filter weighting coefficients may be applied to digital sensor values Dsig collected at time intervals shorter or longer than one minute depending on the desired sensor sample rate based on the body's physiology, the computational capabilities of the telemetered characteristic monitor transmitter 30, the sensor's response time, or the like. In alternative embodiments, filters with other frequency responses may be used to eliminate other noise frequencies depending on the type of sensor, noise from the power supply or other electronics, the sensor's interaction with the body, the effects of body motion on the sensor signal, or the like. In still other alternative embodiments, the filter is an infinite impulse response (IIR) filter.

In alternative embodiments, other methods are used to pre-filter the digital sensor values Dsig such as rate-of-change thresholds, rate-of-change squared thresholds, noise thresholds about a least squares fit line rather than about the average of a subset of a group's values, higher or lower noise threshold lines, or the like.

Delay Compensation Filter

Aside from noise reduction, a filter may be used to compensate for time delays. Ideally, a sensor would provide a real time, noise-free measurement of a parameter that a control system is intended to control, such as a blood glucose measurement. However, realistically there are physiological, chemical, electrical, and algorithmic sources of time delays that cause the sensor measurement to lag behind the present value of blood glucose.

A physiological delay 422 is due to the time required for glucose to move between blood plasma 420 and interstitial fluid (ISF). The delay is represented by the circled double headed arrow 422 in FIG. 20. Generally, as discussed above, the sensor 26 is inserted into the subcutaneous tissue 44 of the body 20 and the electrodes 42 near the tip of the sensor 40 are in contact with interstitial fluid (ISF). But the desired parameter to be measured is the concentration of blood glucose. Glucose is carried throughout the body in blood plasma 420. Through the process of diffusion, glucose moves from the blood plasma 420 into the ISF of the subcutaneous tissue 44 and vice versa. As the blood glucose level 18 changes so does the glucose level in the ISF. But the glucose level in the ISF lags behind the blood glucose level 18 due to the time required for the body to achieve glucose concentration equilibrium between the blood plasma 420 and the ISF. Studies show the glucose lag times between blood plasma 420 and ISF vary between 0 to 30 minutes. Some parameters that may affect the glucose lag time between blood plasma 420 and ISF are the individual's metabolism, the current blood glucose level, whether the glucose level is rising, or falling, or the like.

Figure 20:
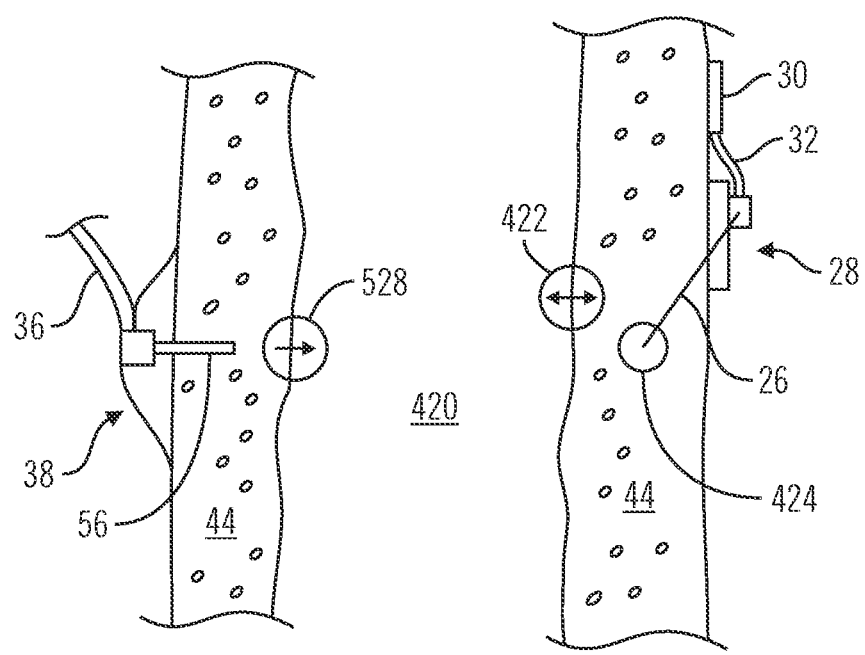
FIG. 20 is a cross-sectional view of a sensor set and an infusion set attached to the body in accordance with an embodiment of the present invention.

A chemical reaction delay 424 is introduced by the sensor response time, represented by the circle 424 surrounding the tip of the sensor 26 in FIG. 20. The sensor electrodes 42 are coated with protective membranes that keep the electrodes 42 wetted with ISF, attenuate the glucose concentration, and reduce glucose concentration fluctuations on the electrode surface. As glucose levels change, the protective membranes slow the rate of glucose exchange between the ISF and the electrode surface. In addition, there is a chemical reaction delay simply due to the reaction time for glucose to react with glucose oxidase GOX to generate hydrogen peroxide, and the reaction time for a secondary reaction, the reduction of hydrogen peroxide to water, oxygen and free electrons.

There is also a processing delay as the analog sensor signal Isig is converted to digital sensor values Dsig. In preferred embodiments, the analog sensor signal Isig is integrated over one-minute intervals and then converted to a number of counts. In essence an A/D conversion time results in an average delay of 30 seconds. In particular embodiments, the one-minute values are averaged into 5-minute values before they are sent to the controller. The resulting average delay is two and one half minutes. In alternative embodiments, longer or shorter integration times are used resulting in longer or shorter delay times. In other embodiments the analog sensor signal current Isig is continuously converted to an analog voltage Vsig and a A/D converter samples the voltage Vsig every 10 seconds. Then six 10-second values are pre-filtered and averaged to create a one-minute value. Finally, five 1-minute values are filtered and then averaged creating a five-minute value resulting in an average delay of two and one half minutes. Other embodiments use other electrical components or other sampling rates and result in other delay periods.

Filters also introduce a delay due to the time required to acquire a sufficient number of digital sensor values Dsig to operate the filter. Higher order filters, by definition, require more digital sensor values Dsig. Aside from the most recent digital sensor value Dsig, FIR filters use a number of previous values equal to the order of the filter. For example, a 7th order filter uses 8 digital sensor values Dsig. There is a time interval between each digital sensor value Dsig. To continue with the example, if the time interval between digital sensor values Dsig is one minute, then the oldest digital sensor value Dsig used in a 7th order FIR filter would be seven minutes old. Therefore, the average time delay for all of the values used in the filter is three and a half minutes. However, if the weighting factors associated with each of the values are not equal then the time delay may be longer or shorter than three and one half minutes depending on the effects of the coefficients.

Figure 21:
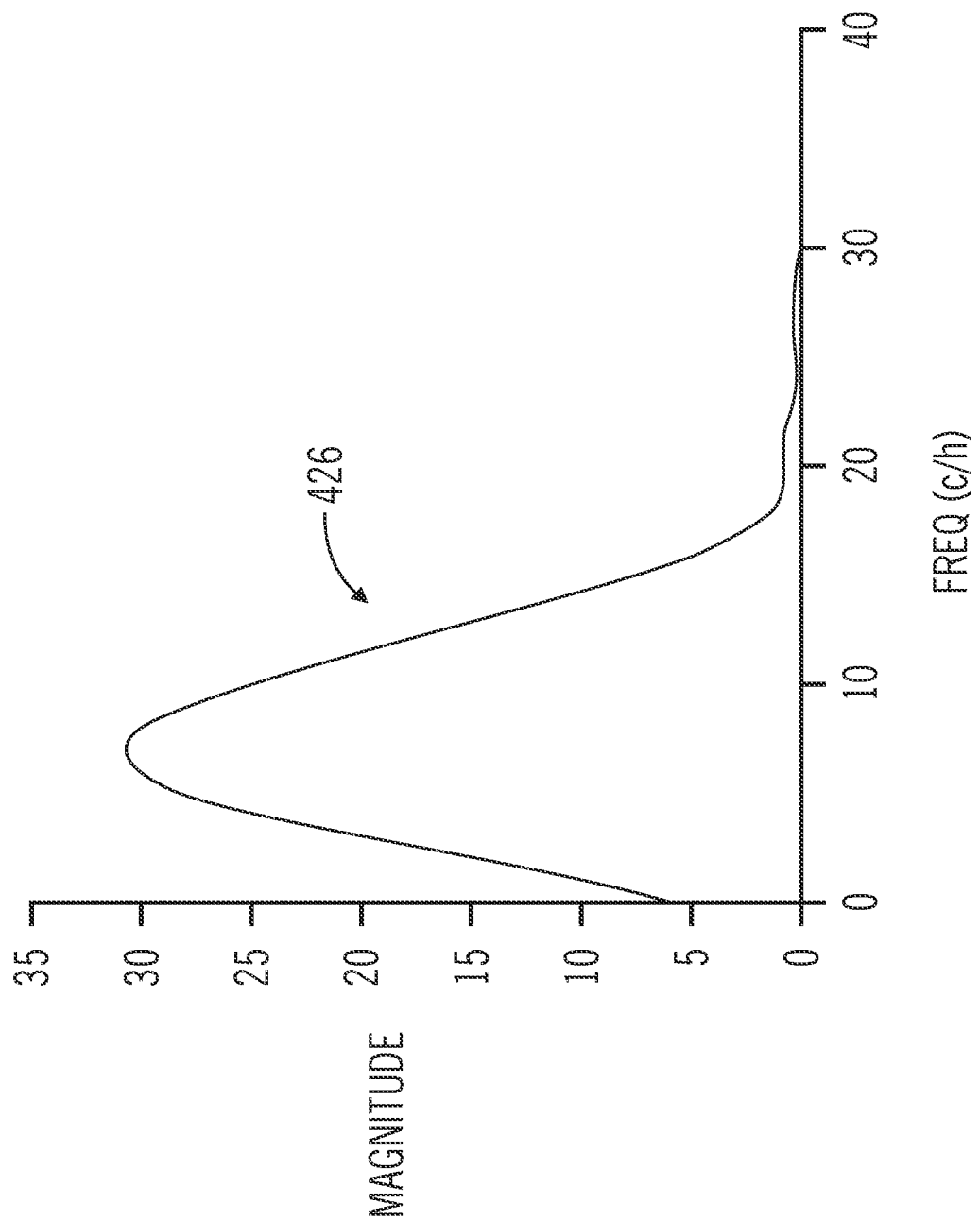
FIG. 21 is a frequency response chart of a time delay correcting Weiner filter in accordance with an embodiment of the present invention.
Figure 22:
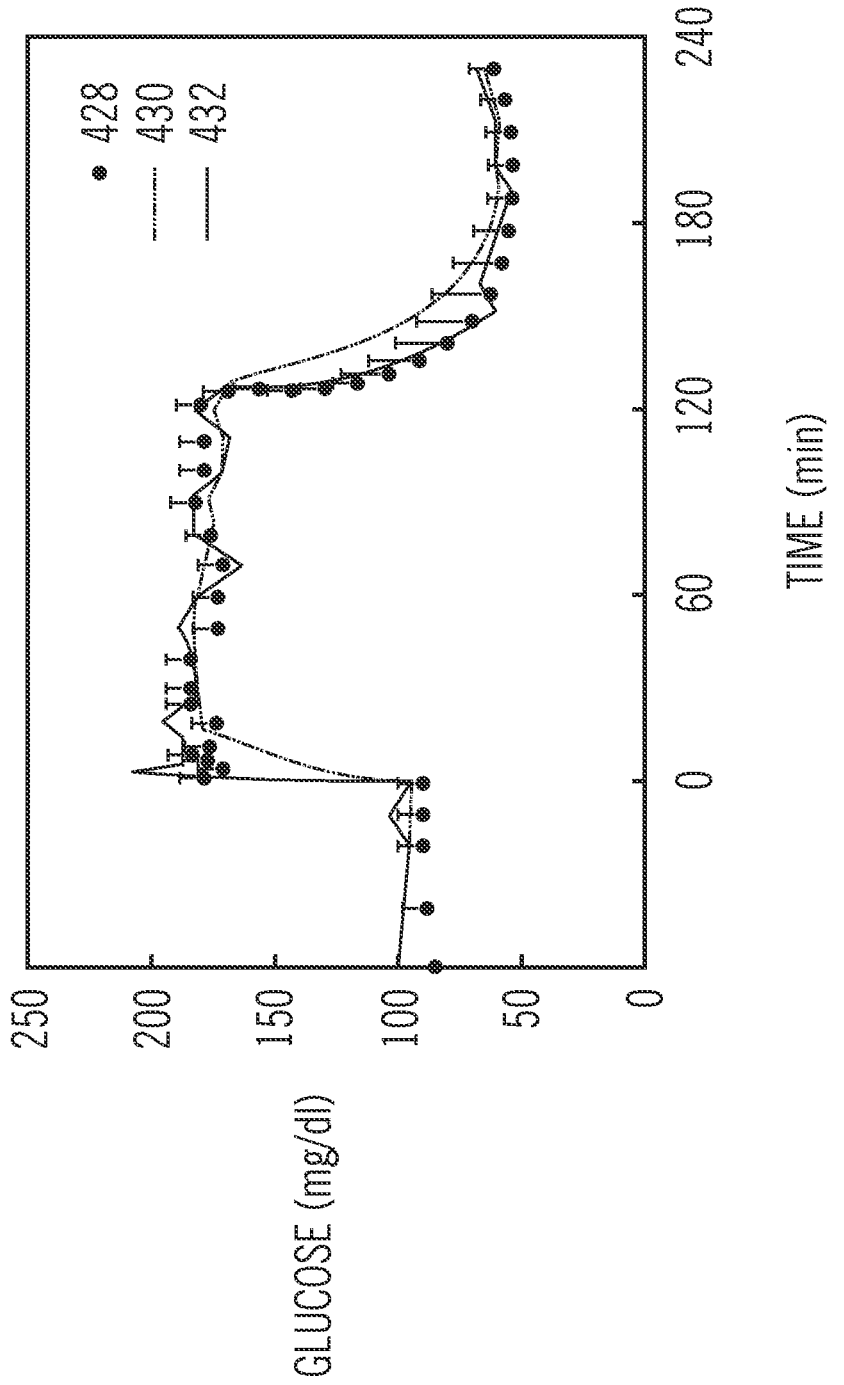
FIG. 22 is a plot of a digital sensor values Dsig before and after time delay correction compared to actual glucose measurements over time in accordance with an embodiment of the present invention.

Preferred embodiments of the invention include a FIR filter that compensates for both the various time delays, of up to about 30 minutes as discussed above, and high frequency noise, greater than about 10 c/hr also discussed above. Particular embodiments employ a 7th order Weiner type FIR filter. The coefficients for the filter are selected to correct for time lags while simultaneously reducing high frequency noise. An example of a frequency response curve 426 is shown in FIG. 21. The example frequency response curve 416 is generated for a Weiner filter with a pass band for frequencies from zero up to about 8 c/hr and a stop band for frequencies greater than about 15 c/hr for a sensor with a sensitivity of about 20 µA/100 mg/dl. A study conducted with sensors in dogs demonstrates that a FIR filter may be used to compensate for time delays. During the study a filter was used to compensate for a time delay of about 12 minutes. The results, presented in FIG. 22, show dots 428 representing actual blood plasma glucose levels measured with a blood glucose meter, a broken line 430 representing sensor measurements without delay compensation, and a solid line 432 representing sensor measurements with delay compensation. The sensor in the test was abnormally low in sensitivity. Studies with average sensitivity sensors in humans are indicating a time delay of about 3 to 10 minutes is more normal. Other filter coefficients and other orders of filters may be used to compensate for the time delay and/or noise.

In alternative embodiments, other types of filters may be used as long as they remove a sufficient portion of the noise from the sensor signal. In other alternative embodiments, no time compensation is used if the rate of change in the blood glucose level is slow compared to the time delay. For example, a five-minute delay between blood plasma glucose and a sensor measurement does not have to be corrected for a closed loop glucose control system to function.

Derivative Filter

Further embodiments may include a filter to remove noise from the derivative of the sensor signal before the controller uses it. A derivative is taken from the digital sensor values Dsig, which results in digital derivative sensor values (dDsig/dt). The digital derivative sensor values dDsig/dt are passed through a FIR filter. In particular embodiments, the derivative filter is at least a 7th order FIR filter tuned to remove high frequency noise. In alternative embodiments, higher or lower order filters may be used and the filters may be tuned to remove various frequencies of noise. In other alternative embodiments, a derivative is taken from the glucose level error $G_E$ values and then passed through a derivative filter 526, as shown in FIG. 37. In further alternative embodiments, a derivative is taken of an analog sensor signal Isig and a hardware filter is used to remove noise.

Calibration

In preferred embodiments, after filtering, the digital sensor values Dsig are calibrated with respect to one or more glucose reference values. The glucose reference values are entered into the calibrator and compared to the digital sensor values Dsig. The calibrator applies a calibration algorithm to convert the digital sensor values Dsig, which are typically in counts into blood glucose values. In particular embodiments, the calibration method is of the type described in U.S. patent application Ser. No. 09/511,580, filed on Feb. 23, 2000, entitled "GLUCOSE MONITOR CALIBRATION METHODS", which is incorporated by reference herein. In particular embodiments, the calibrator is included as part of the infusion device 34 and the glucose reference values are entered by the user into the infusion device 34. In other embodiments, the glucose reference values are entered into the telemetered characteristic monitor transmitter 30 and the calibrator calibrates the digital sensor values Dsig and transmits calibrated digital sensor values to the infusion device 34. In further embodiments, the glucose reference values are entered into a supplemental device where the calibration is executed. In alternative embodiments, a blood glucose meter is in communication with the infusion device 34, telemetered characteristic monitor transmitter 30 or supplemental device so that glucose reference values may be transmitted directly into the device that the blood glucose meter is in communication with. In additional alternative embodiments, the blood glucose meter is part of the infusion device 34, telemetered characteristic monitor transmitter 30 or supplemental device such as that shown in U.S. patent application Ser. No. 09/334,996, filed on Jun. 17, 1999, entitled "CHARACTERISTIC MONITOR WITH A CHARACTERISTIC METER AND METHOD OF USING THE SAME", which is incorporated by reference herein.

In preferred embodiments, to obtain blood glucose reference values, one or more blood samples are extracted from the body 20, and a common, over-the-counter, blood glucose meter is used to measure the blood plasma glucose concentration of the samples. Then a digital sensor value Dsig is compared to the blood glucose measurement from the meter and a mathematical correction is applied to convert the digital sensor values Dsig to blood glucose values. In alternative embodiments, a solution of a known glucose concentration is introduced into the subcutaneous tissue surrounding the sensor 26 by using methods and apparatus such as described in U.S. patent application Ser. No. 09/395,530, filed on Sep. 14, 1999, entitled "METHOD AND KIT FOR SUPPLYING A FLUID TO A SUBCUTANEOUS PLACEMENT SITE", which is incorporated by reference herein, or by using injection, infusion, jet pressure, introduction through a lumen, or the like. A digital sensor value Dsig is collected while the sensor 26 is bathed in the solution of known glucose concentration. A mathematical formula such as a factor, an offset, an equation, or the like, is derived to convert the digital sensor value Dsig to the known glucose concentration. The mathematical formula is then applied to subsequent digital sensors values Dsig to obtain blood glucose values. In alternative embodiments, the digital sensor values Dsig are calibrated before filtering. In additional alternative embodiments, the digital sensor values Dsig are calibrated after pre-filtering and before filtering. In other alternative embodiments, the sensors are calibrated before they are used in the body or do not require calibration at all.

Sensor Signal Processing Systems

Figure 10:
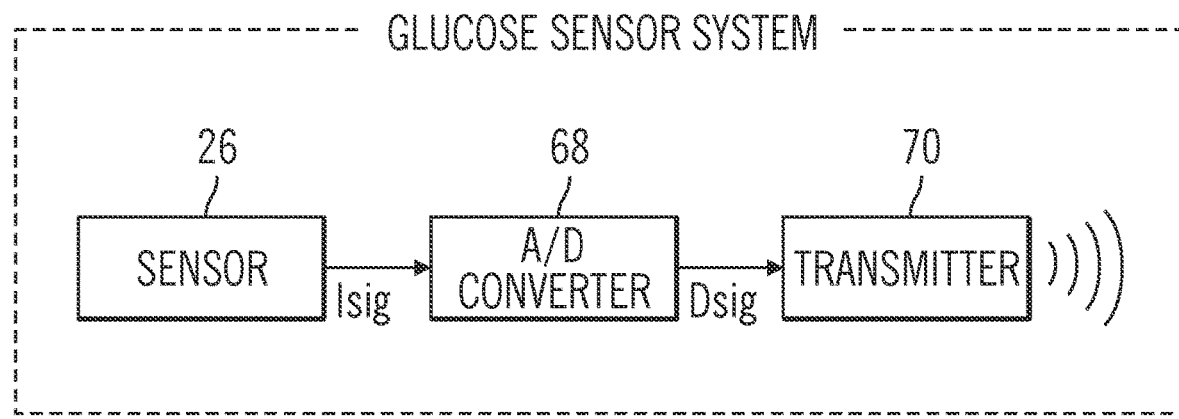
FIG. 10 is a block diagram of the glucose sensor system of FIG. 3A.
Figure 11A:
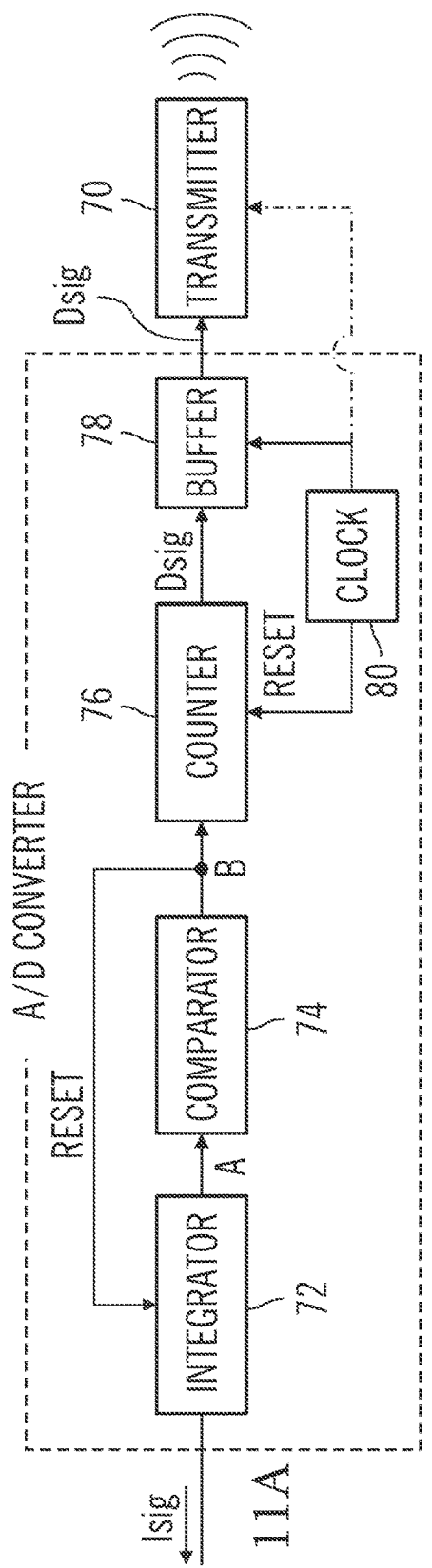
FIG. 11A is a detailed block diagram of an A/D converter for the glucose sensor system of FIG. 10 in accordance with an embodiment of the present invention.

Before filtering and calibrating, generally the sensor signal is processed to convert the sensor signal from a raw form into a form acceptable for use in the filters and/or calibrator. In preferred embodiments, as shown in FIG. 10, an analog sensor signal Isig is digitally quantified through an A/D converter 68 resulting in digital sensor values Dsig that are transmitted by a transmitter 70 from the telemetered characteristic monitor transmitter 30 to another device. In particular embodiments, the analog sensor signal Isig is an analog current value that is converted to a digital sensor value Dsig in the form of a digital frequency measurement, as shown in FIG. 11 (*a*). The general circuit includes an integrator 72, a comparator 74, a counter 76, a buffer 78, a clock 80 and the transmitter 70. The integrator 72 generates a substantially ramped voltage signal (A), and the instantaneous slope of the ramped voltage signal is proportional to the magnitude of the instantaneous analog sensor signal Isig. The comparator 74 converts the ramped voltage signal (A) from the integrator 72 into square wave pulses (B). Each pulse from the comparator 74 increments the counter 76 and also resets the integrator 72. The clock 80 periodically triggers the buffer 78 to store the present value from the counter 76 and then resets the counter 76. The values stored in the buffer 78 are the digital sensor values Dsig. The clock 80 may also periodically signal the transmitter 70 to send a value from the buffer 78. In preferred embodiments, the clock period is one minute. However, in alternative embodiments, the clock period may be adjusted based on how often measurements are needed, sensor signal noise, sensor sensitivity, required measurement resolution, the type of signal to be transmitted, or the like. In alternative embodiments, a buffer is not used.

A/D Converters

Various A/D converter designs may be used in embodiments of the present invention. The following examples are illustrative, and not limiting, since other A/D converters may be used.

I to F (Current to Frequency (Counts)), Single Capacitor, Quick Discharge

In preferred embodiments, the integrator 72 consists of a first Op-Amp 92 and a capacitor 82, shown in FIG. 12. The integrator 72 sums the analog sensor signal Isig current by charging the capacitor 82 until the capacitor voltage (A') achieves a high reference voltage (VrefH). The capacitor voltage (A') is measured at the output of the first Op-Amp 92. A second Op-Amp 94 is used as a comparator. When the capacitor voltage (A') reaches VrefH, the comparator output (B') changes from low to high. The high comparator output (B') closes a reset switch 84 that discharges the capacitor 82 through a voltage source (V+). The high comparator output (B') also triggers a reference voltage switch 88 to close, while substantially simultaneously an inverter 86 inverts the comparator output (B'). And the inverter output (C') triggers a reference voltage switch 90 to open. The result is that the reference voltage of the comparator is changed from VrefH to the low reference voltage (VrefL).

When the capacitor voltage (A') is discharged to VrefL, the comparator output (B') returns to low, thus forming a pulse. The low comparator output (B') opens the reset switch 84 allowing the capacitor 82 to begin charging again.

Virtually simultaneously, the low comparator output (B') also triggers the reference voltage switch 88 to open and the inverter output (C') triggers reference voltage switch 90 to close resulting in changing the comparator reference voltage from VrefL back to VrefH.

I to F, Single Reversible Capacitor

In alternative embodiments, two or more integrator switches are used to control the polarity of one or more capacitors. A particular embodiment is shown in FIG. 13. Generally, only one of the two integrator-switches 110 and 112 is closed and the other integrator switch is open. When the first integrator switch 110 is closed, the second integrator switch 112 is open and an integrator Op-Amp 114 sums the analog sensor signal Isig current by charging a capacitor 116 until the capacitor voltage (A") achieves a high reference voltage (VrefH). The comparator 120 compares the integrator output (A") to the reference voltage VrefH. And when the capacitor voltage (A") reaches VrefH, the comparator output (B") shifts from low to high, initiating a pulse.

The high comparator output (B") pulse causes the capacitor polarity to reverse using the following method. The high comparator output (B") triggers the second integrator switch 112 to close while virtually simultaneously the inverter 118 inverts the comparator output (B"). And the low inverter output (C") pulse triggers the first integrator switch 110 to open. Once the capacitor's polarity is reversed, the capacitor 116 discharges at a rate proportional to the analog sensor signal Isig. The high comparator output (B") pulse also triggers the reference voltage of the comparator to change form VrefH the low reference voltage (VrefL). When the capacitor voltage (A") is discharged to VrefL, the comparator output (B") returns to low. The low comparator output (B") opens the second integrator switch 112 and virtually simultaneously the high inverter output (C") closes the first integrator switch 110 allowing the capacitor 116 to begin charging again. The low comparator output (B") also triggers the comparator reference voltage to change from VrefL back to VrefH.

An advantage of this embodiment is that sensor signal errors, which may be created due to capacitor discharge time, are reduced since the magnitude of the analog sensor signal Isig drives both the charging and the discharging rates of the capacitor 116.

I to F, Dual Capacitor

In further alternative embodiments, more than one capacitor is used such that as one capacitor is charging, at a rate proportional to the magnitude of the analog sensor signal Isig, another capacitor is discharging. An example of this embodiment is shown in FIG. 14. A series of three switches are used for each capacitor. A first group of switches 210 is controlled by a latch voltage C''', and a second group of switches 212 are controlled by voltage D''', which is the inverse of C'''. Substantially, only one group of switches is closed at a time. When the first group of switches 210 is closed, the voltage across a first capacitor 216 increases at a rate proportional to the analog sensor signal Isig until the integrator voltage (A''') at the output of Op-Amp 214 achieves a reference voltage (Vref). At the same time one of the switches shorts the circuit across a second capacitor 222 causing it to discharge. A comparator 220 compares the integrator output (A''') to the reference voltage Vref And when the integrator output (A''') reaches Vref, the comparator output (B''') generates a pulse. The comparator output pulse increments a counter 76, and triggers the latch output voltage C''' from a latch 221 to toggle from a low voltage to a high voltage. The change in the latch voltage C''' causes the second group of switches 212 to close and the first group of switches 210 to open. One of the switches from the second group of switches 212 shorts the circuit across the first capacitor 216 causing it to discharge. At the same time the voltage across the second capacitor 222 increases at a rate proportional to the analog sensor signal Isig until the integrator voltage (A''') at the output of Op-Amp 214 achieves a reference voltage (Vref). Again, the comparator 220 compares the integrator output (A''') to the reference voltage Vref. And when the integrator output (A''') reaches Vref, the comparator output (B''') generates a pulse. The comparator output pulse increments the counter 76, and triggers the latch output voltage C''' to toggle from a high voltage to a low voltage, which causes the switches to return to their initial position with the first group of switches 210 closed and the second group of switches 212 to open.

In summary, as the blood glucose level 18 increases, the analog sensor signal Isig increases, which causes the voltage coming out of the integrator 72 to ramp up faster to the high reference voltage VrefH, which causes the comparator 74 to generate pulses more often, which adds counts to the counter 76 faster. Therefore, higher blood glucose levels generate more counts per minute.

The charge storage capacity for the capacitors used in the integrator 72, and the reference voltages VrefH, and VrefL are selected such that the count resolution for counts collected in a one-minute period at a glucose level of 200 mg/dl represents a blood glucose measurement error of less than 1 mg/dl. In particular embodiments, VrefH is 1.1 volts and VrefL is 0.1 volts. Higher or lower reference voltages may be selected based on the magnitude of the analog sensor signal Isig, the capacity of the capacitors, and the desired measurement resolution. The source voltage V+ is set to a voltage sufficiently high to discharge one or more capacitors quickly enough that the discharge times do not significantly reduce the number of counts per minute at a blood glucose level of 200 mg/dl.

Pulse Duration Output Feature

Figure 11B:
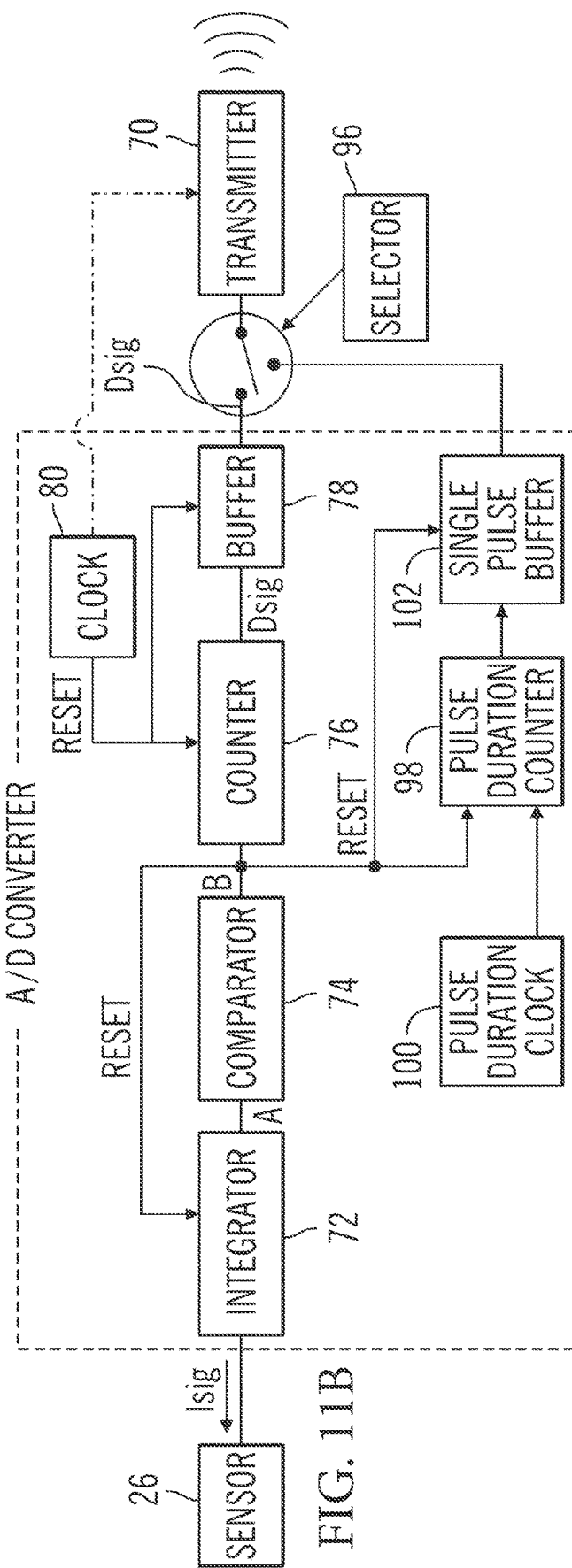
FIG. 11B is a detailed block diagram of the A/D converter for the glucose sensor system of FIG. 10 with a pulse duration output selection option in accordance with an embodiment of the present invention.

In preferred embodiments, the transmitter 70 transmits the digital sensor values Dsig from the buffer 78 whenever triggered by the clock 80. However, in particular embodiments, the user or another individual may use a selector 96 to choose other outputs to be transmitted from the transmitter 70, as shown in FIG. 11B. In preferred embodiments, the selector 96 is in the form of a menu displayed on a screen that is accessed by the user or another individual by using buttons on the surface of the telemetered characteristic monitor transmitter 30. In other embodiments, a dial selector, dedicated buttons, a touch screen, a signal transmitted to the telemetered characteristic monitor transmitter 30, or the like, may be used. Signals that may be selected to be transmitted, other than the digital sensor values Dsig, include, but are not limited to, a single pulse duration, digital sensor values before pre-filtering, digital sensor values after pre-filtering but before filtering, digital sensor values after filtering, or the like.

In particular embodiments, a pulse duration counter 98 counts clock pulses from a pulse duration clock 100 until the pulse duration counter 98 is reset by a rising or falling edge of a pulse from the comparator 74, as shown in FIG. 11B. The accumulated count at the time that the pulse duration counter 98 is reset represents the pulse duration for a portion of a single pulse from the comparator 74. The accumulated count from the pulse duration counter 98 is stored in the single pulse buffer 102 when triggered by the reset signal. When an individual selects the single pulse output, the transmitter 70 transmits the values from the single pulse buffer 102. The pulse duration clock 100 period must be sufficiently shorter than the period between individual pulse edges from the comparator 74 given a high analog sensor signal Isig to have sufficient resolution to quantify different pulse durations from the comparator 74.

I to V (Current to Voltage), Voltage A/D

Figure 15:
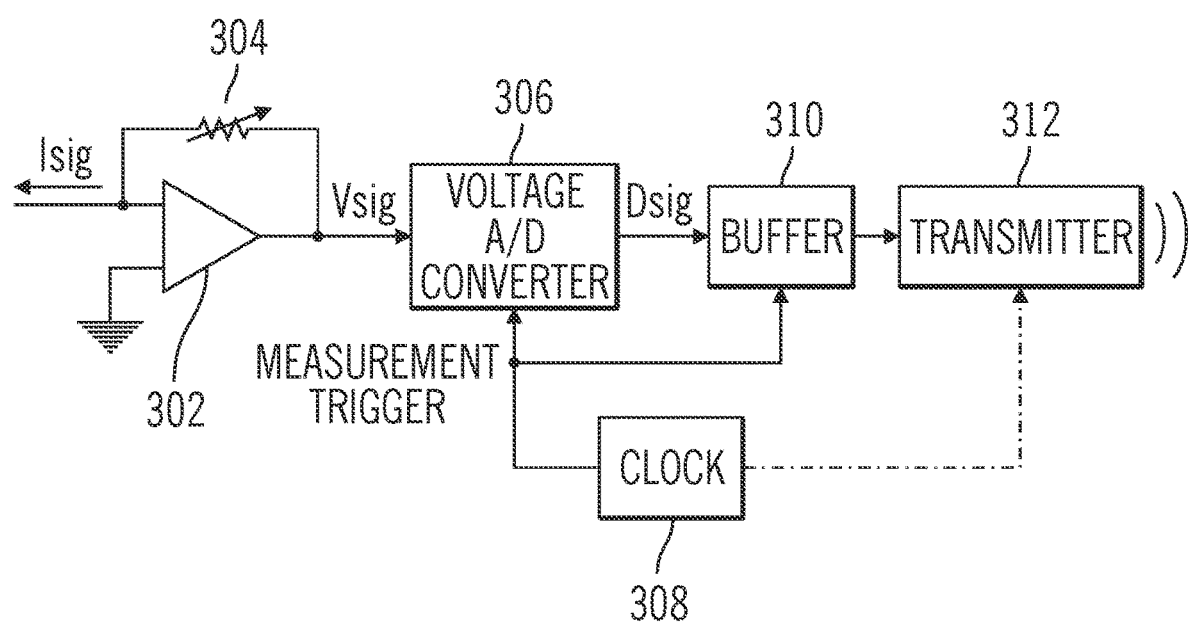
FIG. 15 is a circuit diagram of an I-V A/D converter of FIG. 10 in accordance with an embodiment of the present invention.

Alternative methods may be used to convert the analog sensor signal Isig from an analog current signal to a digital voltage signal. The analog sensor signal Isig is converted to an analog voltage Vsig using an Op Amp 302 and a resistor 304, as shown in FIG. 15. And then periodically a clock 308 triggers an A/D converter 306 to take a sample value from the analog voltage Vsig and convert it to a digital signal representing the magnitude of the voltage. The output values of the A/D converter 306 are digital sensor values Dsig. The digital sensor values Dsig are sent to a buffer 310 and then to the transmitter 70. In particular embodiments, the resistor 304 may be adjusted to scale the Vsig to use a significant portion of the range of the voltage A/D converter 306 depending on the sensor sensitivity, the maximum glucose concentration to be measured, the desired resolution from the voltage A/D converter 306, or the like.

In alternative embodiments, a buffer 310 is not needed and the digital sensor values Dsig are sent from the A/D converter directly to the transmitter 70. In other alternative embodiments, the digital sensor values Dsig are processed, filtered, modified, analyzed, smoothed, combined, averaged, clipped, scaled, calibrated, or the like, before being sent to the transmitter 70. In preferred embodiments, the clock 308 triggers a measurement every 10 seconds. In alternative embodiments, the clock 308 runs faster or slower triggering measurements more or less frequently depending on how quickly the blood glucose level can change, the sensor sensitivity, how often new measurements are needed to control the delivery system 14, or the like.

Finally, in other alternative embodiments, other sensor signals from other types of sensors, as discussed in the section "Sensor and Sensor Set" below, are converted to digital sensor values Dsig if necessary before transmitting the digital sensor values Dsig to another device.

Additional Controller Inputs

Generally, the proportional plus, integral plus, derivative (PID) insulin response controller uses only glucose (digital sensor values Dsig) as an input. Conversely, in a normally glucose tolerant human body, healthy β-cells benefit from additional inputs such as neural stimulation, gut hormone stimulation, changes in free fatty acid (FFA) and protein stimulation etc. Thus in other alternative embodiments, the PID controller, as discussed above, can be augmented with one or more additional inputs. In particular alternative embodiments, the user may manually input supplemental information such as a start of a meal, an anticipated carbohydrate content of the meal, a start of a sleep cycle, an anticipated sleep duration, a start of an exercise period, an anticipated exercise duration, an exercise intensity estimation, or the like. Then, a model predictive control feature assists the controller to use the supplemental information to anticipate changes in glucose concentration and modify the output commands accordingly. For example, in a NGT individual, neural stimulation triggers the β-cells to begin to secrete insulin into the blood stream before a meal begins, which is well before the blood glucose concentration begins to rise. So, in alternative embodiments, the user can tell the controller that a meal is beginning and the controller will begin to secrete insulin in anticipation of the meal.

In other alternative embodiments, the user or another individual may manually override the control system or select a different controller algorithm. For instance, in particular alternative embodiments, an individual may select to normalize to a basal glucose level immediately, and instead of using the β-cell emulating PID controller another controller would take over such as a PID controller with different gains, a PD controller for rapid glucose adjustment, or the like. Additional alternative embodiments allow an individual to turn off the integral component of the PID controller once the glucose level is normalized and no meals are anticipated. In other particular alternative embodiments, the user may select to turn off the controller entirely, therefore disengaging the closed loop system. Once the closed loop system is not controlling insulin dosing, the user may program the infusion device with a basal rate, variable basal rates, boluses, or the like, or the user may manually enter each individual dosage when it is needed.

In still other alternative embodiments, more than one body characteristic is measured, and the measurements are provided as inputs to a controller. Measured body characteristics that may be used by the controller include, but are not limited to, the blood glucose level, blood and/or ISF pH, body temperature, the concentration of amino acids in blood (including arginine and/or lysine, and the like), the concentration of gastrointestinal hormones in blood or ISF (including gastrin, secretin, cholecystokinin, and/or gastro inhibitory peptide, and the like), the concentration of other hormones in blood or ISF (including glucagons, growth hormone, cortisol, progesterone and/or estrogen, and the like), blood pressure, body motion, respiratory rate, heart rate, and other parameters.

In NGT individuals, the glucose-induced secretion of insulin by healthy β-cells may be as much as doubled in the presence of excess amino acids. Yet, the presence of excess amino acids alone, without elevated blood glucose, only mildly increases insulin secretions according to the Textbook of Medical Physiology, Eighth Edition, written by Arthur C. Guyton, published by W. B. Saunders Company, 1991, Ch. 78, pg. 861, section "Other Factors That Stimulate Insulin Secretion". In particular alternative embodiments, amino acid concentrations are estimated or measured, and the controller's insulin response increases when amino acid concentrations are sufficiently high.

In NGT individuals, the presence of sufficient quantities of gastrointestinal hormones in the blood causes an anticipatory increase in blood insulin, which suggests that β-cells release insulin before increases in blood glucose due to an individual's anticipation of a meal. In particular alternative embodiments, the concentration of gastrointestinal hormones is measured or estimated, and when concentrations are high enough to indicate that a meal is anticipated, the controller commands are adjusted to cause insulin introduction into the body even before the blood glucose level changes. In other alternative embodiments, the controller uses measurements or estimates of other hormones to modify the rate of insulin secretion.

In NGT individuals, the body's cells take up glucose during periods of heavy exercise with significantly lower levels of insulin. In alternative embodiments, physiologic parameters such as body motion, blood pressure, pulse rate, respiratory rate, or the like, are used to detect periods of heavy exercise by the body and therefore provide inputs to the controller that decreases (or eliminates) the amount of insulin infused into the body to compensate for glucose concentrations.

Sensor Compensation and End-of-Life Detection

Figure 31A:
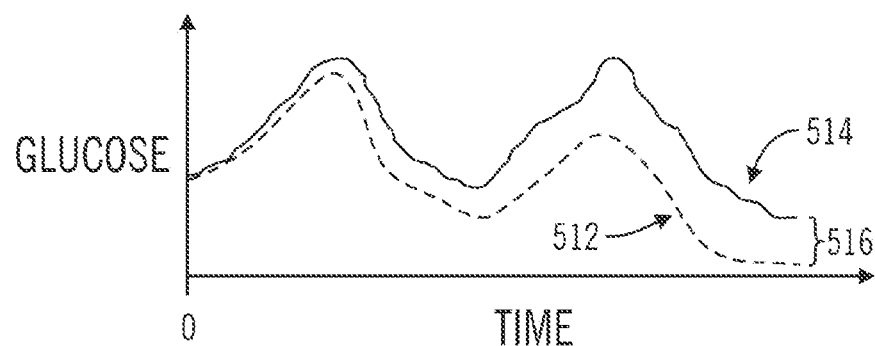
FIG. 31A is a representative drawing of blood glucose compared to sensor measured blood glucose over time in accordance with an embodiment of the present invention.
Figure 31B:
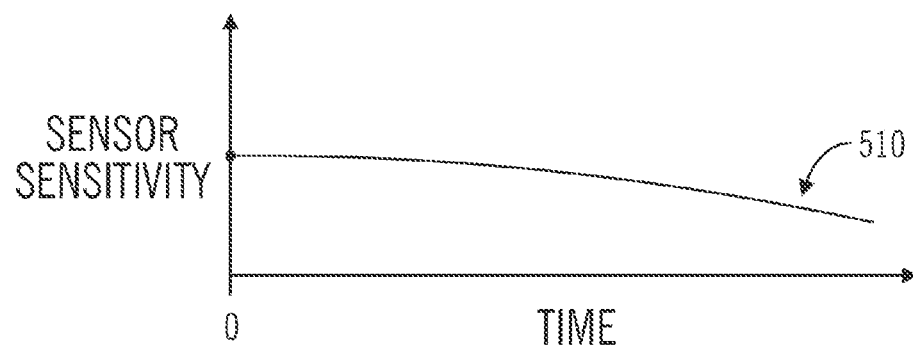
FIG. 31B is a representative drawing of sensor sensitivity over the same period of time as FIG. 31A in accordance with an embodiment of the present invention.
Figure 31C:
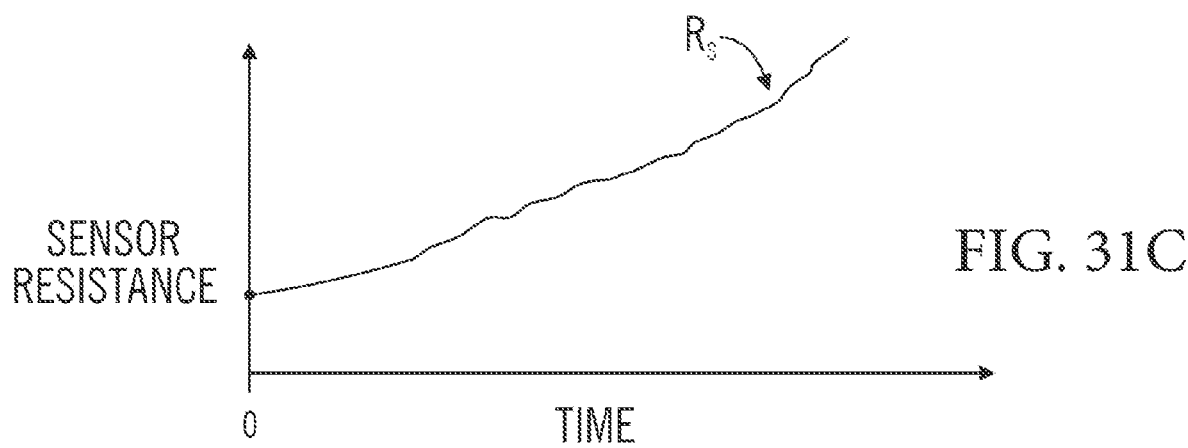
FIG. 31C is a representative drawing of sensor resistance over the same period of time as FIG. 31A in accordance with an embodiment of the present invention.

In particular embodiments, the sensor sensitivity 510 may degrade over time, as shown in FIG. 31B. As the sensor sensitivity 510 changes the sensor signal accuracy degrades. If the sensor sensitivity 510 changes significantly then the sensor must be recalibrated or replaced. A diagnostic signal may be used to evaluate whether sensor signal accuracy has changed and/or may be used to adjust the signal or to indicate when to recalibrate or replace the sensor. As the sensor sensitivity 510 decreases, the measured glucose level 512 using the sensor signal underestimates the actual blood glucose level 514, and the measurement error 516 between the measured glucose level 512 and the actual blood glucose level 514 becomes greater over time, as shown in FIG. 31A. The sensor sensitivity 510 decreases due to increases in sensor resistance Rs, as shown in FIG. 31C. The sensor resistance Rs is the resistance provided by the body between the working electrode WRK and the counter electrode CNT, shown as the sum or R1 and R2 in the circuit diagram of FIG. 7. The sensor resistance Rs can be obtained indirectly by measuring the analog sensor signal Isig and the counter electrode voltage Vcnt and then calculating the resistance, Rs=Vcnt/Isig.

As the sensor resistance Rs increases, the analog sensor signal Isig response to a given glucose concentration decreases. In preferred embodiments, the decrease in the analog sensor signal Isig may be compensated for by identifying the amount that the sensor resistance Rs has changed since the last calibration and then using the change in resistance in a correction algorithm 454 to adjust the analog sensor signal value. A compensation value calculated by the correction algorithm 454 is used to increase the sensor analog signal value. The compensation value increases over time as the sensor resistance Rs increases. The correction algorithm 454 includes at least one value that varies with changes in sensor resistance Rs. In particular embodiments, a low pass filter is applied to the sensor resistance Rs measurement to decrease high frequency noise before evaluating how much the sensor resistance Rs has changed since the last calibration.

In alternative embodiments, the sensor resistance Rs may be calculated using different equations. For instance, a sensor resistance $Rs_2$ may be calculated as:

$$Rs_2 = (V_0 - Vcnt/Isig)$$

In particular embodiments, $V_0$ is the same voltage as Vset. An advantage of this approach is that it accounts for the voltage level Vset, which can vary from sensor to sensor and/or monitor to monitor, and/or as the analog sensor signal changes. This removes the noise and/or offset associated with variations in Vset, and can provide a more accurate indication of sensor resistance. In other particular embodiments, $V_0$ is set at −0.535 volts, which is a commonly used voltage for Vset. In further embodiments, $V_0$ is calculated from paired measurements of Vcnt and Isig. Using least squares or another curve fitting method, a mathematical equation representing the curve (typically a straight line equation) is derived from the relationship between Vcnt and Isig. Then, $V_0$ is obtained by extrapolating the curve to find the value for Vcnt when Isig is zero.

Figure 38:
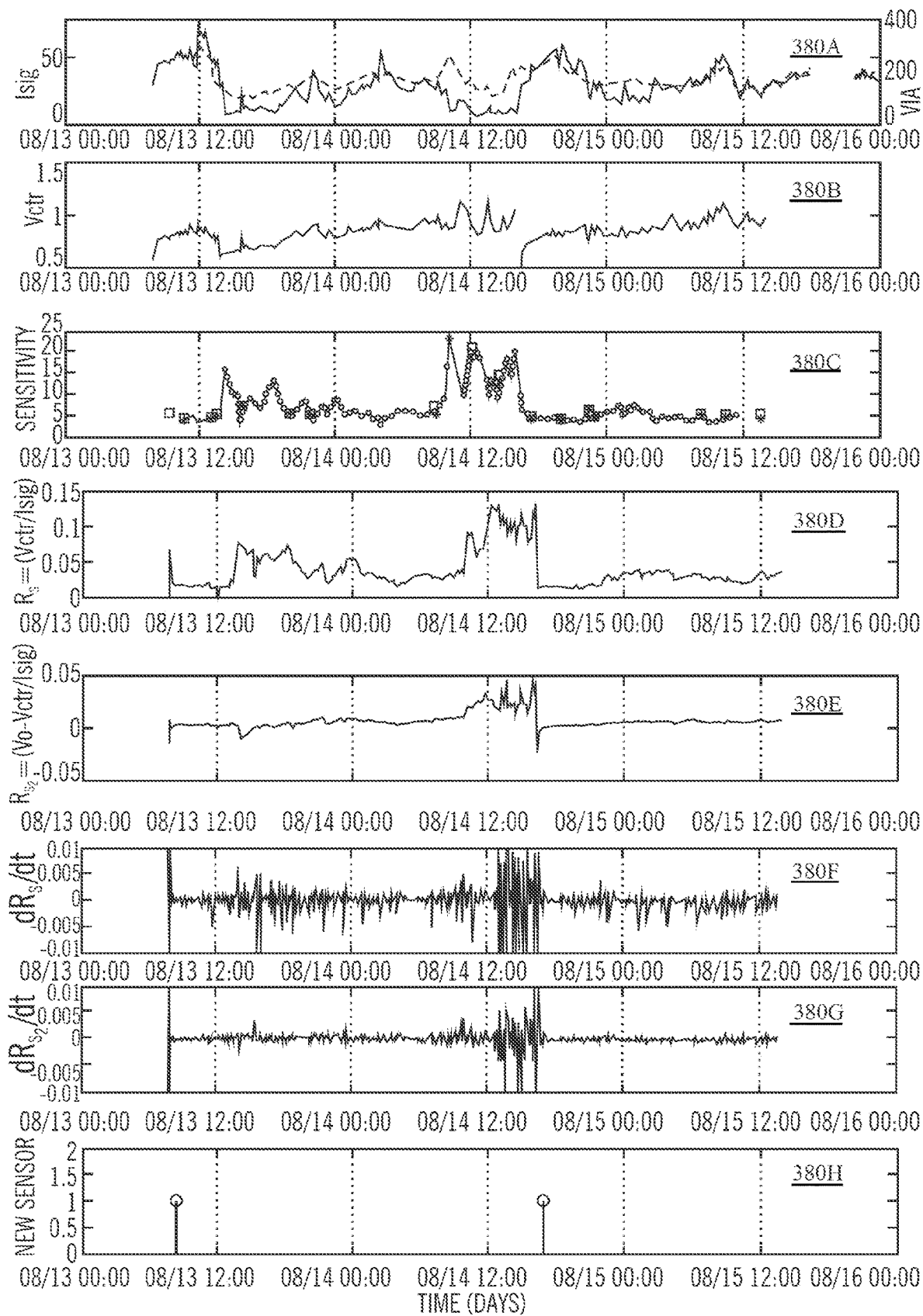
FIG. 38 depicts plots of measurements and calculations related to sensor resistance.

FIG. 38 shows a comparison between calculating the sensor resistance with $V_0$ and without $V_0$. The plot 380A is a plot of sensor signal measurements and Via measurements with respect to time in accordance with an embodiment of the present invention. The plot 380B is a plot of a measured counter electrode voltage Vcnt with respect to time in accordance with an embodiment of the present invention. The plot 380C is a plot of calculated sensor sensitivity with respect to time in accordance with an embodiment of the present invention. The plot 380D is a plot of a calculation of sensor resistance $Rs_1$ with respect to time in accordance with an embodiment of the present invention. The plot 380E is a plot of another calculation of sensor resistance $Rs_2$ with respect to time in accordance with an embodiment of the present invention. The plot 380F is a plot of the derivative of the sensor resistance $Rs_1$ (plot 380D) with respect to time in accordance with an embodiment of the present invention. The plot 380G is a plot of the derivative of the sensor resistance $Rs_2$ (plot 380E) with respect to time in accordance with an embodiment of the present invention. The plot 380H is a plot of when sensors were replaced with respect to time in accordance with an embodiment of the present invention. The plot 380G of the derivative of $Rs_2$ is cleaner and indicates the sensor failure more clearly than the plot 380F of the derivative of Rs. Hence sensor resistance $Rs_2$ may be used instead of, or in conjunction with, sensor resistance Rs described above.

Figure 32:
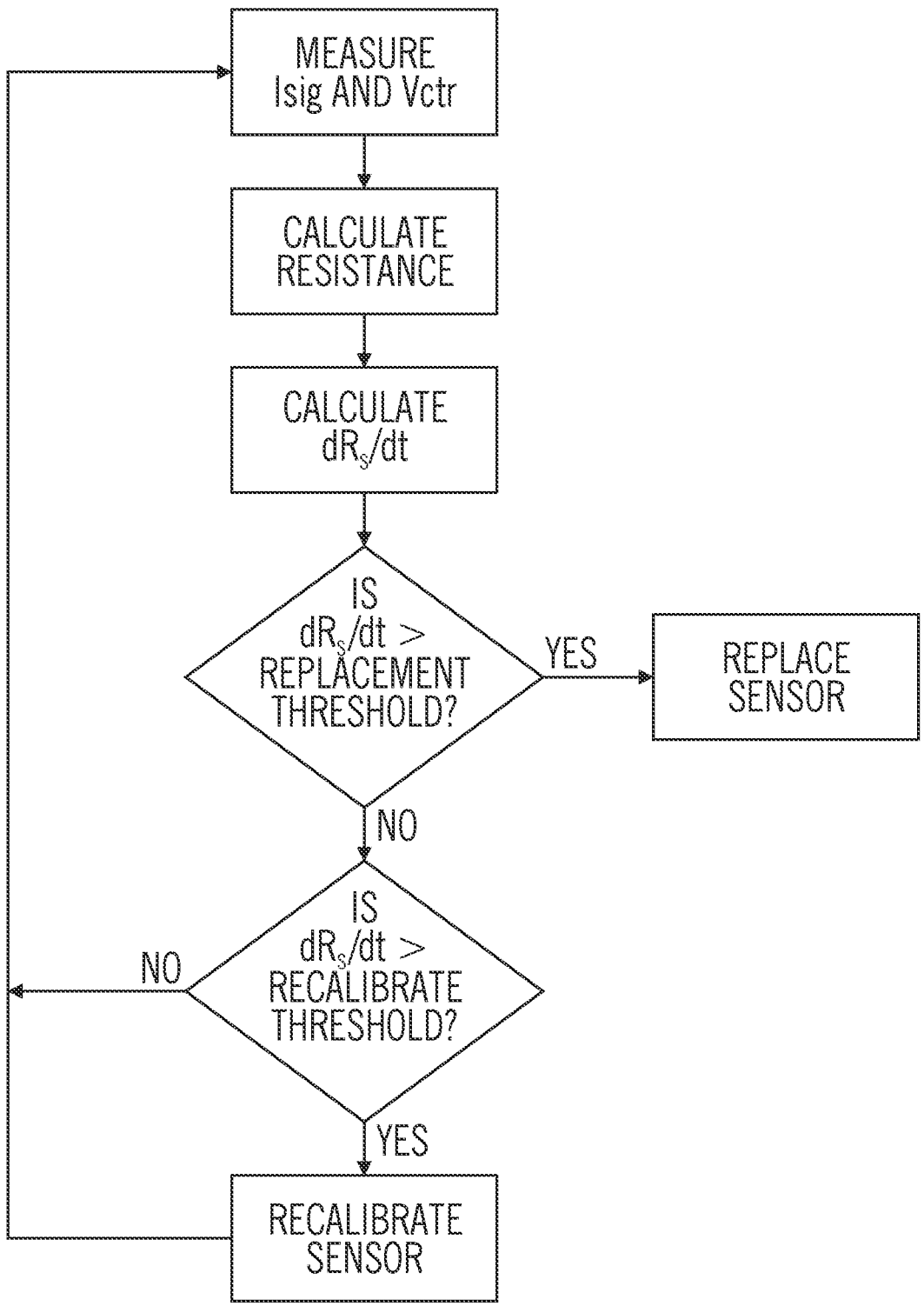
FIG. 32 is a block diagram using the derivative of sensor resistance to determine when to recalibrate or replace the sensor in accordance with an embodiment of the present invention.

In preferred embodiments, the sensor is recalibrated or replaced when the change in the sensor resistance Rs since the last calibration exceeds a threshold, or the rate of change of the sensor resistance dRs/dt exceeds another threshold. In particular embodiments, the rate of change of the sensor resistance dRs/dt may be compared to two thresholds as shown in FIG. 32. If dRs/dt exceeds a "replacement" threshold then a warning is provided to the user to replace the sensor. If dRs/dt exceeds a "recalibrate" threshold then a warning is provided to the user to recalibrate the sensor.

Figure 33A:
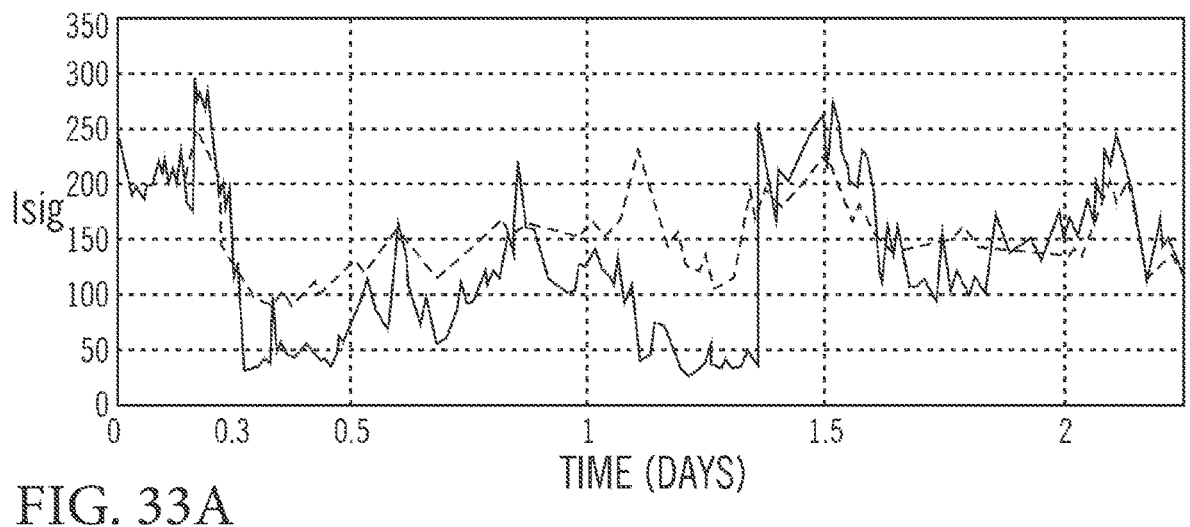
FIG. 33A is a plot of an analog sensor signal Isig over time in accordance with an embodiment of the present invention.
Figure 33B:
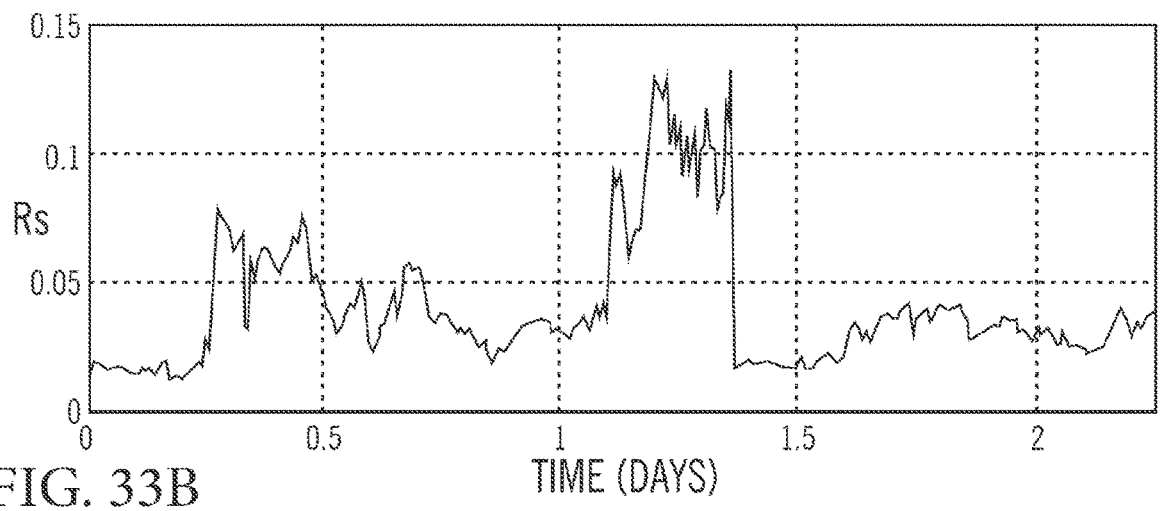
FIG. 33B is a plot of sensor resistance over the same period of time as FIG. 32A in accordance with an embodiment of the present invention.
Figure 33C:
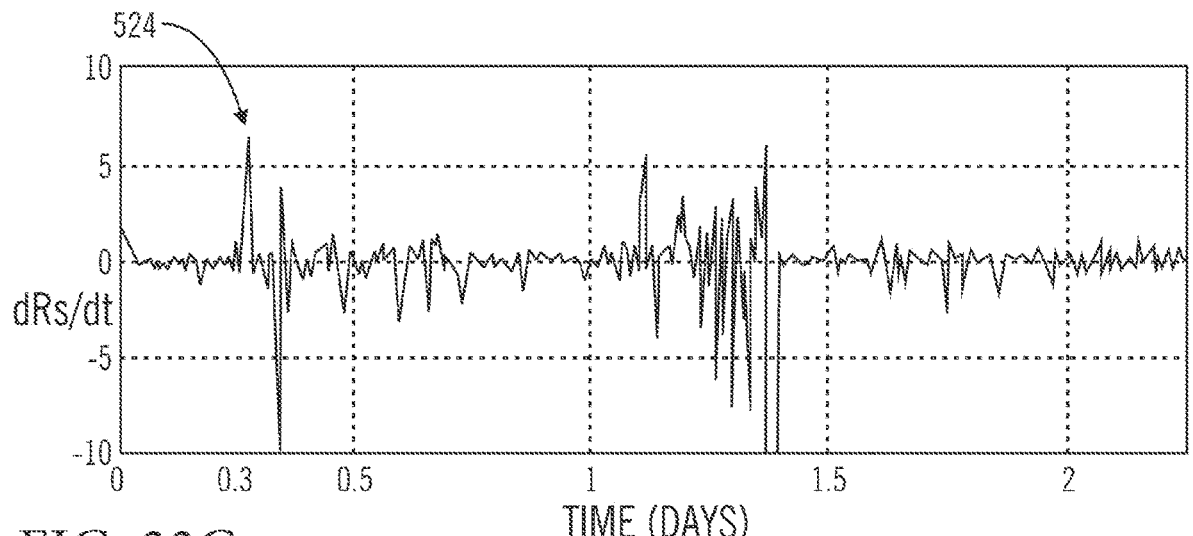
FIG. 33C is a plot of the derivative of the sensor resistance of FIG. 32B in accordance with an embodiment of the present invention.

In an example shown in FIGS. 33A-C, the analog sensor signal Isig decreases dramatically at approximately 0.3 days, as seen in FIG. 33A. Given only the analog sensor signal Isig, the user would believe that the decrease in the analog sensor signal Isig is due to a decrease in blood glucose. But in reality the drop in the analog sensor signal Isig is due to a sudden change in sensor sensitivity. The sensor resistance Rs, shown in FIG. 33A increases as the analog sensor signal Isig drops at about 0.3 days. The derivative of the sensor resistance dRs/dt, shown in FIG. 33C, clearly shows a spike 522 at about 0.3 days when the analog sensor signal Isig dropped. The spike 522 in the change in sensor resistance dRs/dt indicates a sensor anomaly rather than a realistic drop in blood glucose. If a threshold were placed at +/−4 on the dRs/dt, the user would have received a warning to replace the sensor at about 0.3 days. As seen in FIG. 33A, the sensor was not replaced until about 1.4 days. The analog sensor signal Isig was under estimating the true glucose level from about 0.3 days until the sensor was replaced at about 1.4 days.

In particular embodiments, the amount of time dt over which the derivative of the sensor resistance Rs is taken is the entire time since the last calibration. In other embodiments, the amount of time dt over which the derivative is taken is fixed, for example over the last hour, 90 minutes, 2 hours, or the like.

In alternative embodiments, the sensor is recalibrated or replaced when the integral of the sensor resistance Rs over a predetermined time window (∫Rs d/dt) exceeds a predetermined resistance integral threshold. An advantage to this approach is that it tends to filter out potential noise that could be encountered from a signal that includes occasional spikes, sudden variations in voltage levels, or the like. Preferably, the integral of the sensor resistance Rs is calculated over a time window (such as 15 minutes, or the like) based on Rs measurements obtained at set rates (such as 1 minute, 5 minutes, or the like) during the time window. In alternative embodiments, the time windows may be longer or shorter and different sampling rates may be used, with the selection being dependent on noise, response of the system, sampling rate used in the controller, or the like. In further embodiments, the time windows and sampling rates may change over time, such as when approaching the end of the expected sensor life, or as the equations indicate that the sensor is degrading, or the like.

Like above, multiple thresholds may be used. For instance, if ∫Rs d/dt exceeds a "replacement" threshold then a warning is provided to the user to replace the sensor. And if ∫Rs d/dt exceeds a "recalibrate" threshold then a warning is provided to the user to recalibrate the sensor. In further alternative embodiments, the counter electrode voltage Vcnt is used to evaluate other characteristics such as, sensor accuracy, sensor bio-fouling, sensor function, sensor voltage operating range, sensor attachment, or the like.

pH Controller Input

In alternative embodiments, the controller uses measurements of both the interstitial fluid (ISF) glucose level and a local pH in the ISF surrounding the sensor to generate commands for the infusion device. In particular alternative embodiments, a single multi-sensor 508 located in the subcutaneous tissue is used to measure both the glucose level and the pH. The tip of the multi-sensor 508 that is placed into the subcutaneous tissue with three electrodes is shown in FIG. 30. The working electrode 502 is plated with platinum black and coated with glucose oxidase (GOX). The reference electrode 506 is coated with silver-silver chloride. And the counter electrode 504 is coated with iridium oxide (Ir Ox). The analog sensor signal Isig is generated at the working electrode 502 due to the reaction between glucose oxidase GOX and the ISF glucose as described with the preferred sensor embodiment. In this alternative embodiment however, as glucose in the ISF reacts with the glucose oxidase GOX on the working electrode and gluconic acid is generated, the local pH in the ISF surrounding the sensor decreases, which changes the potential of the iridium oxide on the counter electrode 504, with respect to the reference electrode REF. So, as the pH decreases, the voltage at the counter electrode 504 increases. Therefore, as the glucose concentration increases, the local pH decreases, which causes the counter electrode voltage to increase. So, the glucose concentration may be estimated based on the counter electrode voltage. The counter electrode voltage estimate of glucose concentration can be compared to the estimate of glucose level from the analog sensor signal Isig. The two estimates of the glucose level may be combined by a weighted average or one estimate may simply be used as a check to verify that the other sensing method is functioning properly. For example, if the difference between the two estimates is 10% for a period of time and then suddenly the difference increased to 50%, a warning would be issued indicating to the user that the sensor may need to be replaced or recalibrated.

In additional alternative embodiments, the pH level near the sensor may be used to detect infection. By tracking trends in the pH over time, a dramatic change in pH may be used to identify that an infection has developed in proximity to the sensor. A warning is used to notify the user to replace the sensor.

The pH sensor may be used in other embodiments. When insulin is not available to assist the body to use glucose, the body shifts to consuming fat for energy. As the body shifts from using glucose to using almost exclusively fat for energy, concentrations of keto acids (acetoacetic acid and β-hydroxybutyric acid) increase from about 1 mEq/liter to as high as 10 mEq/liter. In particular alternative embodiments, the pH level is measured to detect increases in keto acids in the body. In embodiments of the present invention, a warning is provided to the user when the ISF pH level is too low.

A side effect of the increased of keto acid concentrations is that sodium is drawn from the body's extra cellular fluid to combine with the acids so that the body can excrete the acids. This leads to increased quantities of hydrogen ions, which greatly increases the acidosis. Severe cases lead to rapid deep breathing, acidotic coma and even death. In other alternative embodiments, an ion-selective electrode (ISE) is used to detect changes in sodium concentration. A special membrane is used to coat the ISE so that it only senses changes in sodium concentration. In particular alternative embodiments, the ISE is a fourth electrode added to the glucose sensor. In another alternative embodiment, a three-electrode system is used with a silver-silver chloride reference electrode REF, an Ir Ox counter electrode CNT, and a sodium ion-selective (Na ISE) working electrode WRK.

While pH measurements, end-of-life measurements, hormone measurements, or the like, add inputs to the controller that can significantly affect the accuracy of insulin delivery, the basic input to the controller is generally a glucose measurement. The glucose measurement is provided by the sensor system. And once the controller uses the glucose measurement to generate commands, the delivery system executes the commands. The following is a detailed description of several apparatus embodiments for the sensor system and the delivery system.

Sensor System

The sensor system provides the glucose measurements used by the controller. The sensor system includes a sensor, a sensor set to hold the sensor if needed, a telemetered characteristic monitor transmitter, and a cable if needed to carry power and/or the sensor signal between the sensor and the telemetered characteristic monitor transmitter.

Sensor and Sensor Set

In preferred embodiments, the glucose sensor system 10 includes a thin film electrochemical sensor such as the type disclosed in U.S. Pat. No. 5,391,250, entitled "METHOD OF FABRICATING THIN FILM SENSORS"; U.S. patent application Ser. No. 09/502,204, filed on Feb. 10, 2000, entitled "IMPROVED ANALYTE SENSOR AND METHOD OF MAKING THE SAME"; or other typical thin film sensors such as described in commonly assigned U.S. Pat. Nos. 5,390,671; 5,482,473; and 5,586,553 which are incorporated by reference herein. See also U.S. Pat. No. 5,299,571.

The glucose sensor system 10 also includes a sensor set 28 to support the sensor 26 such as described in U.S. Pat. No. 5,586,553, entitled "TRANSCUTANEOUS SENSOR INSERTION SET" (published as PCT Application WO 96/25088); and U.S. Pat. No. 5,954,643, entitled "INSERTION SET FOR A TRANSCUTANEOUS SENSOR" (published as PCT Application WO 98/56293); and U.S. Pat. No. 5,951,521, entitled "A SUBCUTANEOUS IMPLANTABLE SENSOR SET HAVING. THE CAPABILITY TO REMOVE OR DELIVER FLUIDS TO AN INSERTION SITE", which are incorporated by reference herein.

In preferred embodiments, the sensor 26 is inserted through the user's skin 46 using an insertion needle 58, which is removed and disposed of once the sensor is positioned in the subcutaneous tissue 44. The insertion needle 58 has a sharpened tip 59 and an open slot 60 to hold the sensor during insertion into the skin 46, as shown in FIGS. 3C and D and FIG. 4. Further description of the needle 58 and the sensor set 28 are found in U.S. Pat. No. 5,586,553, entitled "TRANSCUTANEOUS SENSOR INSERTION SET" (published as PCT Application WO 96/25088); and U.S. Pat. No. 5,954,643, entitled "INSERTION SET FOR A TRANSCUTANEOUS SENSOR" (published as PCT Application WO 98/5629), which are incorporated by reference herein.

Figure 7:
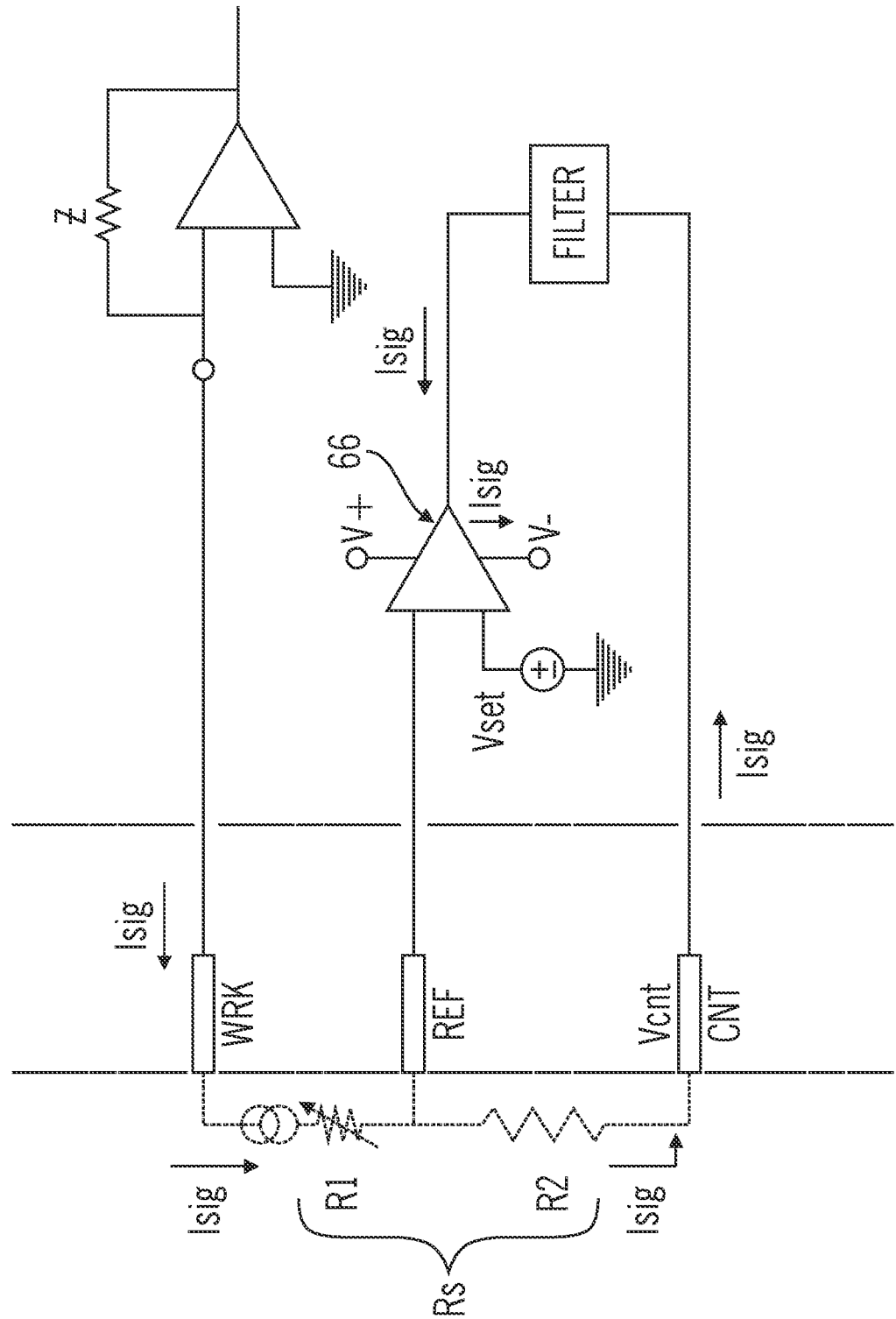
FIG. 7 is a circuit diagram of a sensor and its power supply in accordance with an embodiment of the present invention.

In preferred embodiments, the sensor 26 has three electrodes 42 that are exposed to the interstitial fluid (ISF) in the subcutaneous tissue 44 as shown in FIGS. 3D and 4. A working electrode WRK, a reference electrode REF and a counter electrode CNT are used to form a circuit, as shown in FIG. 7. When an appropriate voltage is supplied across the working electrode WRK and the reference electrode REF, the ISF provides impedance (R1 and R2) between the electrodes 42. And an analog current signal Isig flows from the working electrode WRK through the body (R1 and R2, which sum to Rs) and to the counter electrode CNT. Preferably, the working electrode WRK is plated with platinum black and coated with glucose oxidase (GOX), the reference electrode REF is coated with silver-silver chloride, and the counter electrode is plated with platinum black. The voltage at the working electrode WRK is generally held to ground, and the voltage at the reference electrode REF is substantially held at a set voltage Vset. Vset is between 300 and 700 mV, and preferably to about 535 mV.

The most prominent reaction stimulated by the voltage difference between the electrodes is the reduction of glucose as it first reacts with GOX to generate gluconic acid and hydrogen peroxide ($H_2O_2$). Then the $H_2O_2$ is reduced to water ($H_2O$) and ($O^-$) at the surface of the working electrode WRK. The $O^-$ draws a positive charge from the sensor electrical components, thus repelling an electron and causing an electrical current flow. This results in the analog current signal Isig being proportional to the concentration of glucose in the ISF that is in contact with the sensor electrodes 42. The analog current signal Isig flows from the working electrode WRK, to the counter electrode CNT, typically through a filter and back to the low rail of an op-amp 66. An input to the op-amp 66 is the set voltage Vset. The output of the op-amp 66 adjusts the counter voltage Vcnt at the counter electrode CNT as Isig changes with glucose concentration. The voltage at the working electrode WRK is generally held to ground, the voltage at the reference electrode REF is generally equal to Vset, and the voltage Vcnt at the counter electrode CNT varies as needed.

In alternative embodiments, more than one sensor is used to measure blood glucose. In particular embodiments, redundant sensors are used. The user is notified when a sensor fails by the telemetered characteristic monitor transmitter electronics. An indicator may also inform the user of which sensors are still functioning and/or the number of sensors still functioning. In other particular embodiments, sensor signals are combined through averaging or other means. If the difference between the sensor signals exceeds a threshold then the user is warned to recalibrate or replace at least one sensor. In other alternative embodiments, more than one glucose sensor is used, and the glucose sensors are not of the same design. For example, an internal glucose sensor and an external glucose sensor may be used to measure blood glucose at the same time.

In alternative embodiments, other continuous blood glucose sensors and sensor sets may be used. In particular alternative embodiments, the sensor system is a micro needle analyte sampling device such as described in U.S. patent application Ser. No. 09/460,121, filed on Dec. 13, 1999, entitled "INSERTION SET WITH MICROPIERCING MEMBERS AND METHODS OF USING THE SAME", incorporated by reference herein, or an internal glucose sensor as described in U.S. Pat. Nos. 5,497,772; 5,660,163; 5,791,344; and 5,569,186, and/or a glucose sensor that uses florescence such as described in U.S. Pat. No. 6,011,984 all of which are incorporated by reference herein. In other alternative embodiments, the sensor system uses other sensing technologies such as described in Patent Cooperation Treaty publication No. WO 99/29230, light beams, conductivity, jet sampling, micro dialysis, microporation, ultra sonic sampling, reverse iontophoresis, or the like. In still other alternative embodiments, only the working electrode WRK is located in the subcutaneous tissue and in contact with the ISF, and the counter CNT and reference REF electrodes are located external to the body and in contact with the skin. In particular embodiments, the counter electrode CNT and the reference electrode REF are located on the surface of a monitor housing 518 and are held to the skin as part of the telemetered characteristic monitor, as shown in FIG. 34A. In other particular embodiments, the counter electrode CNT and the reference electrode REF are held to the skin using other devices such as running a wire to the electrodes and taping the electrodes to the skin, incorporating the electrodes on the underside of a watch touching the skin, or the like. In more alternative embodiments, more than one working electrode WRK is placed into the subcutaneous tissue for redundancy. In additional alternative embodiments, a counter electrode is not used, a reference electrode REF is located outside of the body in contact with the skin, and one or more working electrodes WRK are located in the ISF. An example of this embodiment implemented by locating the reference electrode REF on a monitor housing 520 is shown in FIG. 34B. In other embodiments, ISF is harvested from the body of an individual and flowed over an external sensor that is not implanted in the body.

Sensor Cable

In preferred embodiments, the sensor cable 32 is of the type described in U.S. patent application Ser. No. 60/121, 656, filed on Feb. 25, 1999, entitled "TEST PLUG AND CABLE FOR A GLUCOSE MONITOR", which is incorporated by reference herein. In other embodiments, other cables may be used such as shielded, low noise cables for carrying nA currents, fiber optic cables, or the like. In alternative embodiments, a short cable may be used or the sensor may be directly connected to a device without the need of a cable.

Telemetered Characteristic Monitor Transmitter

In preferred embodiments, the telemetered characteristic monitor transmitter 30 is of the type described in U.S. patent application Ser. No. 09/465,715, filed on Dec. 17, 1999, entitled "TELEMETERED CHARACTERISTIC MONITOR SYSTEM AND METHOD OF USING THE SAME" (published as PCT Application WO 00/19887 and entitled, "TELEMETERED CHARACTERISTIC MONITOR SYSTEM"), which is incorporated by reference herein, and is connected to the sensor set 28 as shown in FIGS. 3A and B.

In alternative embodiments, the sensor cable 32 is connected directly to the infusion device housing, as shown in FIG. 8A, which eliminates the need for a telemetered characteristic monitor transmitter 30. The infusion device contains a power supply and electrical components to operate the sensor 26 and store sensor signal values.

In other alternative embodiments, the telemetered characteristic monitor transmitter includes a receiver to receive updates or requests for additional sensor data or to receive a confirmation (a hand-shake signal) indicating that information has been received correctly. Specifically, if the telemetered characteristic monitor transmitter does not receive a confirmation signal from the infusion device, then it re-sends the information. In particular alternative embodiments, the infusion device anticipates receiving blood glucose values or other information on a periodic basis. If the expected information is not supplied when required, the infusion device sends a "wake-up" signal to the telemetered characteristic monitor transmitter to cause it to re-send the information.

Insulin Delivery System
Infusion Device

Once a sensor signal 16 is received and processed through the controller 12, commands 22 are generated to operate the infusion device 34. In preferred embodiments, semi-automated medication infusion devices of the external type are used, as generally described in U.S. Pat. Nos. 4,562,751; 4,678,408; 4,685,903; and U.S. patent application Ser. No. 09/334,858, filed on Jun. 17, 1999, entitled "EXTERNAL INFUSION DEVICE WITH REMOTE PROGRAMMING, BOLUS ESTIMATOR AND/OR VIBRATION CAPABILITIES" (published as PCT application WO 00/10628), which are herein incorporated by reference. In alternative embodiments, automated implantable medication infusion devices, as generally described in U.S. Pat. Nos. 4,373,527 and 4,573,994, are used, which are incorporated by reference herein.

Insulin

In preferred embodiments, the infusion device reservoir 50 contains HUMALOG® lispro insulin to be infused into the body 20. Alternatively, other forms of insulin may be used such as HUMALIN®, human insulin, bovine insulin, porcine insulin, analogs, or other insulins such as insulin types described in U.S. Pat. No. 5,807,315, entitled "METHOD AND COMPOSITIONS FOR THE DELIVERY OF MONOMERIC PROTEINS", and U.S. Patent Application Ser. No. 60/177,897, filed on Jan. 24, 2000, entitled "MIXED BUFFER SYSTEM FOR STABILIZING POLYPEPTIDE FORMULATIONS", which are incorporated by reference herein, or the like. In further alternative embodiments, other components are added to the insulin such as polypeptides described in U.S. patent application Ser. No. 09/334,676, filed on Jun. 25, 1999, entitled "MULTIPLE ΔGENT DIABETES THERAPY", small molecule insulin mimetic materials such as described in U.S. patent application Ser. No. 09/566,877, filed on May 8, 2000, entitled "DEVICE AND METHOD FOR INFUSION OF SMALL MOLECULE INSULIN MIMETIC MATERIALS", both of which are incorporated by reference herein, or the like.

Infusion Tube

In preferred embodiments, an infusion tube 36 is used to carry the insulin 24 from the infusion device 34 to the infusion set 38. In alternative embodiments, the infusion tube carries the insulin 24 from infusion device 34 directly into the body 20. In further alternative embodiments, no infusion tube is needed, for example if the infusion device is attached directly to the skin and the insulin 24 flows from the infusion device, through a cannula or needle directly into the body. In other alternative embodiments, the infusion device is internal to the body and an infusion tube may or may not be used to carry insulin away from the infusion device location.

Infusion Set

In preferred embodiments, the infusion set 38 is of the type described in U.S. Pat. No. 4,755,173, entitled "SOFT CANNULA SUBCUTANEOUS INJECTION SET", which is incorporated by reference herein. In alternative embodiments, other infusion sets, such described in U.S. Pat. Nos. 4,373,527 and 4,573,994, are used, which are incorporated by reference herein. In alternative embodiments, other infusion sets, such as the Rapid set from Disetronic, the Silhouette from MiniMed, or the like, may be used. In further alternative embodiments, no infusion set is required, for example if the infusion device is an internal infusion device or if the infusion device is attached directly to the skin.

Configurations with Supplemental Devices

In further alternative embodiments, the pre-filter, filters, calibrator and/or controller 12 are located in a supplemental device that is in communication with both the telemetered characteristic monitor transmitter 30 and the infusion device 34. Examples of supplemental devices include, a hand held personal digital assistant such as described in U.S. patent application Ser. No. 09/487,423, filed on Jan. 20, 2000, entitled "HANDHELD PERSONAL DATA ASSISTANT (PDA) WITH A MEDICAL DEVICE AND METHOD OF USING THE SAME", which is incorporated by reference herein, a computer, a module that may be attached to the telemetered characteristic monitor transmitter 30, a module that may be attached to the infusion device 34, a RF programmer such as described in U.S. patent application Ser. No. 09/334,858, filed on Jun. 17, 1999, entitled EXTERNAL INFUSION DEVICE WITH REMOTE PROGRAMMING, BOLUS ESTIMATOR AND/OR VIBRATION CAPABILITIES (published as PCT application WO 00/10628), which is incorporated by reference herein, or the like. In particular embodiments, the supplemental device includes a post-calibration filter, a display, a recorder, and/or a blood glucose meter. In further alternative embodiments, the supplemental device includes a method for a user to add or modify information to be communicated to the infusion device 34 and/or the telemetered characteristic monitor transmitter 30 such as buttons, a keyboard, a touch screen, and the like.

In particular alternative embodiments, the supplemental device is a computer in combination with an analyte monitor and a RF programmer. The analyte monitor receives RF signals from the telemetered characteristic monitor transmitter 30, stores the signals and down loads them to a computer when needed. The RF programmer sends control signals to the infusion device 34 to reprogram the rate of insulin infusion. Both the analyte monitor and the RF programmer are placed into separate communication stations. The communication stations include IR transmitters and IR receivers to communicate with the analyte monitor and the RF programmer. The sensor signal values are transmitted via the telemetered characteristic monitor transmitter 30 to the analyte monitor located in one of the communication stations. Then the sensor signal values are communicated through the IR receiver in a first communication station and to the computer. The computer processes the sensor signal values through one or more filters, calibrators, and controllers to generate commands 22. The commands are sent to a second communication station and sent to an RF programmer by the IR transmitter in the communication station. Finally the RF programmer transmits the commands 22 to the infusion device 34. The communication station, analyte monitor and infusion device 34 may be of the type described in U.S. patent application Ser. No. 09/409,014, filed on Sep. 29, 1999 entitled COMMUNICATION STATION FOR INTERFACING WITH AN INFUSION PUMP, ANALYTE MONITOR, ANALYTE METER OR THE LIKE (published as a PCT application WO 00/18449), which is incorporated by reference herein. Alternatively, the RF programmer may be omitted and the infusion device may be placed in a communication station, or the infusion device may receive the commands without the use of an RF programmer and/or a communication station.

Overnight Closed-Loop System

A closed-loop insulin delivery system of the type described herein may utilize a variety of control algorithms to regulate the delivery of insulin to the body of the patient in a safe and predictable manner. Overnight operation of a closed-loop insulin infusion system should be carefully controlled in an automated way that need not depend on patient, user, or caregiver interaction. In this regard, a number of safeguards can be implemented with the system. These safeguards are intended to provide actionable sensor glucose readings, assess the accuracy of sensor readings, and constrain insulin delivery based upon possible sensor over-read conditions. These safeguards will alert the user and allow the patient to take appropriate actions. Therefore, these safeguards will mitigate the potential risks of overnight closed-loop control.

The control algorithm utilized by the system may be considered to be one type of safeguard in that it emulates the effect of insulin inhibiting insulin secretion. The system may also implement sensor performance safeguards. For example, a closed-loop initiation algorithm determines if the system can enter the closed-loop mode by calculating a recent calibration factor. The initiation algorithm checks the time between recent and prior calibration factors and determines the relative sensor error between the readings. As another example of a sensor safeguard, the system may employ a model supervisor during the closed-loop mode. The model supervisor checks that the sensor glucose readings are adequate for use during overnight closed-loop mode by comparing model-predicted sensor glucose values in real-time against actual sensor glucose values. If the model-predicted glucose values and the actual values differ significantly, the system triggers a fail-safe alert indicating a faulty sensor. This fail-safe alert can be generated in response to a number of sensor issues, such as sensor drift, sensor dislodgement, sensor compression artifact, etc.

The system may also implement a target glucose level safeguard. In this regard, a start-up algorithm can be deployed to provide a smooth transition between the open-loop mode and the closed-loop mode by gradually adjusting the target glucose level while in the closed-loop mode. The adjusted target glucose is used by the closed-loop control algorithm until the adjusted target glucose converges to a particular setpoint. At that time, the setpoint can be used for future dosing calculations during the closed-loop mode.

The system may also utilize at least one insulin limit as an insulin delivery and sensor performance safeguard. In this context, the insulin limit constrains the maximum amount of insulin delivered to the patient at any time in order to avoid over-delivery of insulin by the closed-loop control system due to potential sensor faults. In practice, the insulin limit is a value that is specific to each patient and is calculated based on the patient's basal rate, fasting blood glucose, and insulin sensitivity.

The system may also employ one or more insulin delivery safeguards. For example, an insulin delivery timeout continuously monitors (during closed-loop operation) if the patient is receiving insulin at the insulin limit for a prolonged period of time and, if so, triggers a fail-safe alert. This safeguard also monitors if the system is not delivering insulin for a prolonged period of time and, if so, triggers a fail-safe alert. A correction bolus is another insulin delivery safeguard. The system calculates an insulin bolus dosage for mitigating hyperglycemia at the commencement of closed-loop mode if the patient is above a designated blood glucose threshold. The determination can be achieved by acquiring a blood glucose meter reading at the initiation of closed-loop mode. The correction bolus is calculated based on the patient's insulin sensitivity, the amount of insulin on board, and a glucose target. Insulin on board (IOB) compensation is yet another insulin delivery safeguard. IOB compensation estimates the amount of insulin on board based on manual boluses administered, such that the system can effectively account for the IOB. In this regard, the manual boluses may be subtracted from the insulin dose that is calculated by the PID-IFB control algorithm.

The system may also implement one or more communication safeguards. For example, a "missed sensor transmission" feature continuously monitors data being received by the controller. For missed data packets totaling less than 15 minutes of operating time, the system remains in closed-loop mode. During this time, however, the system continues to calculate the insulin dose using the closed loop control algorithm based on the last valid sensor glucose value. For missed data packets totaling 15-60 minutes, the safeguard will switch to a pre-programmed safe basal rate, defined as half the patient's night time basal rate. If the controller starts receiving data packets during the safe basal rate timeframe, the system will again switch to the closed-loop mode. For missed data packets totaling more than 60 minutes, the system will switch to the open-loop mode where it will deliver a pre-programmed basal rate (which may be set by a caregiver).

The exemplary closed-loop control algorithms, methodologies, and techniques described in more detail below may be based around a PID control algorithm of the type presented in the preceding sections of this disclosure. In certain embodiments, the closed-loop control algorithms utilize a PID insulin feedback (PID-IFB) control algorithm. More specifically, the PID-IFB control algorithm cooperates with other algorithms, processes, and controls that represent additional safeguards that may apply during overnight use (and/or during other periods of use). These additional safeguards may include, without limitation: the use of an "Insulin Limits" parameter; a closed-loop initiation circuit that is based on glucose sensor calibration; an insulin on board (IOB) compensation algorithm; monitoring missed transmissions; and monitoring sensor glucose against predicted sensor glucose.

In practice, optimal or desired settings for the Insulin Limits parameter should be determined. In this regard, the Insulin Limits parameter serves as an input to the controller logic for each patient, and it imposes an upper limit to the insulin delivery rate as an additional safety feature to avoid over-delivery of insulin by the controller due to potential sensor error. In certain embodiments, the Insulin Limits parameter is calculated from the patient's basal rate, fasting blood glucose, and insulin sensitivity.

Referring again to FIG. 1, a closed-loop system generally includes a glucose sensor system 10, a controller 12, and an insulin delivery system 14. Although FIG. 1 depicts these primary elements as separate blocks, embodiments of the system may combine two or more of the illustrated blocks into a single physical component. For example, an investigational test configuration of the closed-loop system may include a traditional patient-worn infusion pump (corresponding to the insulin delivery system 14), a conventional continuous glucose sensor/transmitter assembly (corresponding to the glucose sensor system 10), and a mobile computing device with a suitably written software application installed thereon (corresponding to the controller 12). The mobile computing device may be, for example: a smartphone; a tablet computer; a netbook computer; a digital media player; a handheld video game device; or the like. It should be appreciated that the desired closed-loop control functionality can be carried out by way of one or more computer-executable programs or applications designed to run on the mobile computing device. An investigational test configuration may also include a translator device that serves as a data communication interface between the mobile computing device (which may utilize standard wireless data communication technologies such as the Wi-Fi or BLUETOOTH data communication protocol) and the glucose sensor system 10 (which may use a proprietary data communication protocol that is usually incompatible with the mobile computing device).

In other embodiments, the functionality of the glucose sensor system 10 could be integrated into the insulin delivery system 14, perhaps as an interchangeable disposable module that attaches to the housing of the insulin delivery system 14. In yet other embodiments, the functionality of the controller 12 could be incorporated into the insulin delivery system 14 such that a separate and distinct controller device need not be carried by the patient. Indeed, the control software utilized by the controller 12 can be ported for installation in an insulin infusion pump, a pump monitor device, or the like to implement the functionality of the controller 12 in those devices if so desired. In further embodiments, a single hardware device platform could be suitably designed to accommodate the functionality of the insulin delivery system 14, the glucose sensor system 10, and the controller 12. These and other possible implementations are contemplated by this disclosure, and the particular manner in which the closed-loop system is configured and deployed is not intended to limit or otherwise restrict the scope or application of the closed-loop control techniques described herein.

Although not shown in FIG. 1, the closed-loop system may include or cooperate with a conventional blood glucose meter (e.g., a finger stick device) that provides measured BG values to the controller 12 and/or to the insulin delivery system 14, such that the glucose sensor system 10 can be calibrated. In certain embodiments, the measured BG values are sent to the insulin delivery system 14, which in turn sends the BG value, sensor calibration factor, and calibration time to the controller 12. The controller 12 can process and analyze the received information to determine whether or not the system can enter the closed-loop operating mode. In this regard, the controller 12 may check to ensure that the calibration of the glucose sensor system 10 is within an acceptable range before allowing the system to enter the closed-loop mode.

After entering the closed-loop mode, the insulin delivery system 14 sends sensor glucose (SG) values, sensor Isig values, calibration factors, "insulin delivered" values, and other data as needed to the controller 12 in accordance with a predetermined schedule, e.g., at five minute intervals. The controller 12 determines the desired insulin dose based on the closed-loop algorithm to maintain the patient at a target glucose setpoint, and communicates suitable control data and instructions to the insulin delivery system 14. The insulin delivery system 14 responds to deliver the insulin dose specified by the controller 12 to the user.

Figure 49:
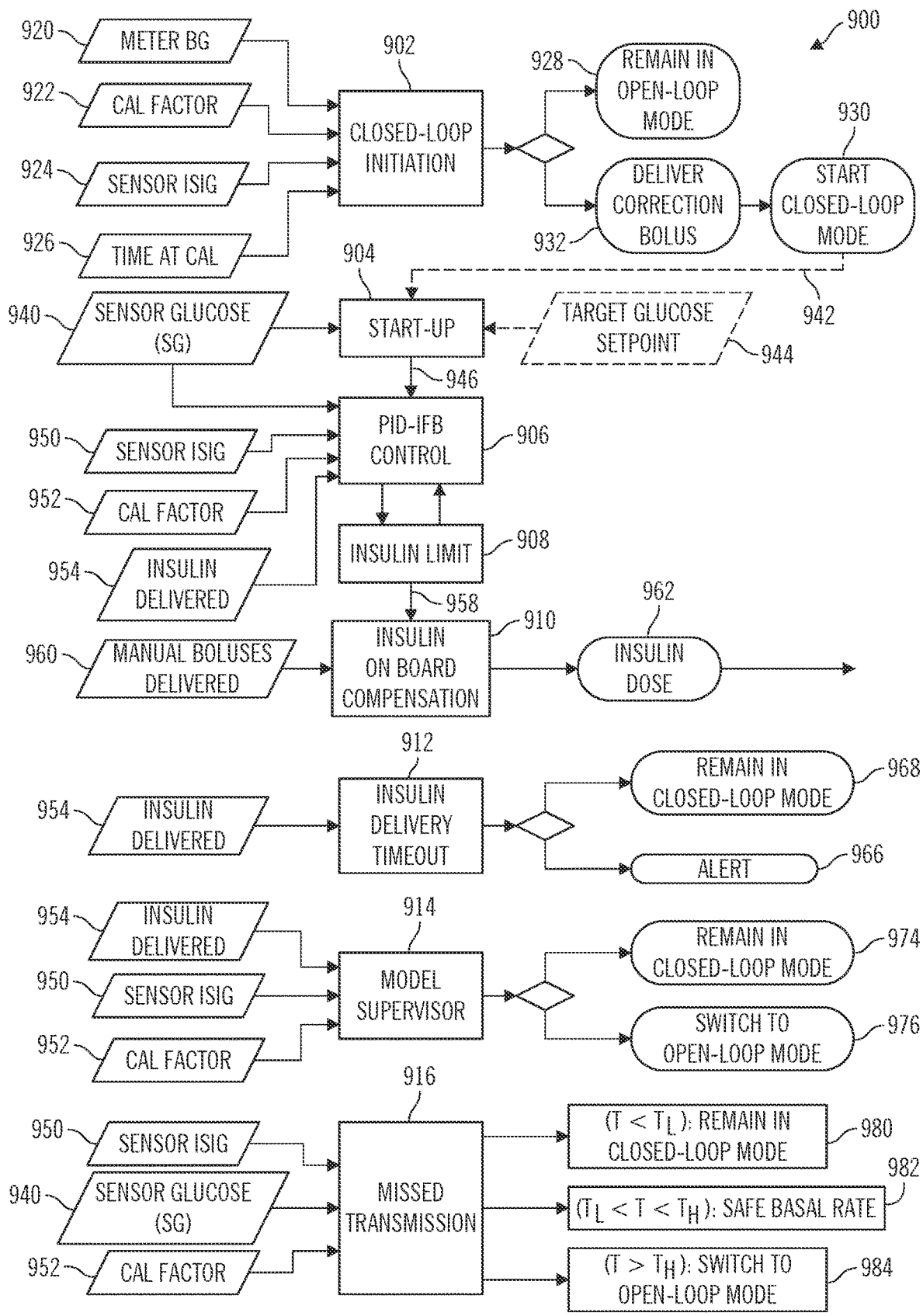
FIG. 49 is a block diagram that illustrates processing modules and algorithms of an exemplary embodiment of a closed-loop system controller.
Figure 50:
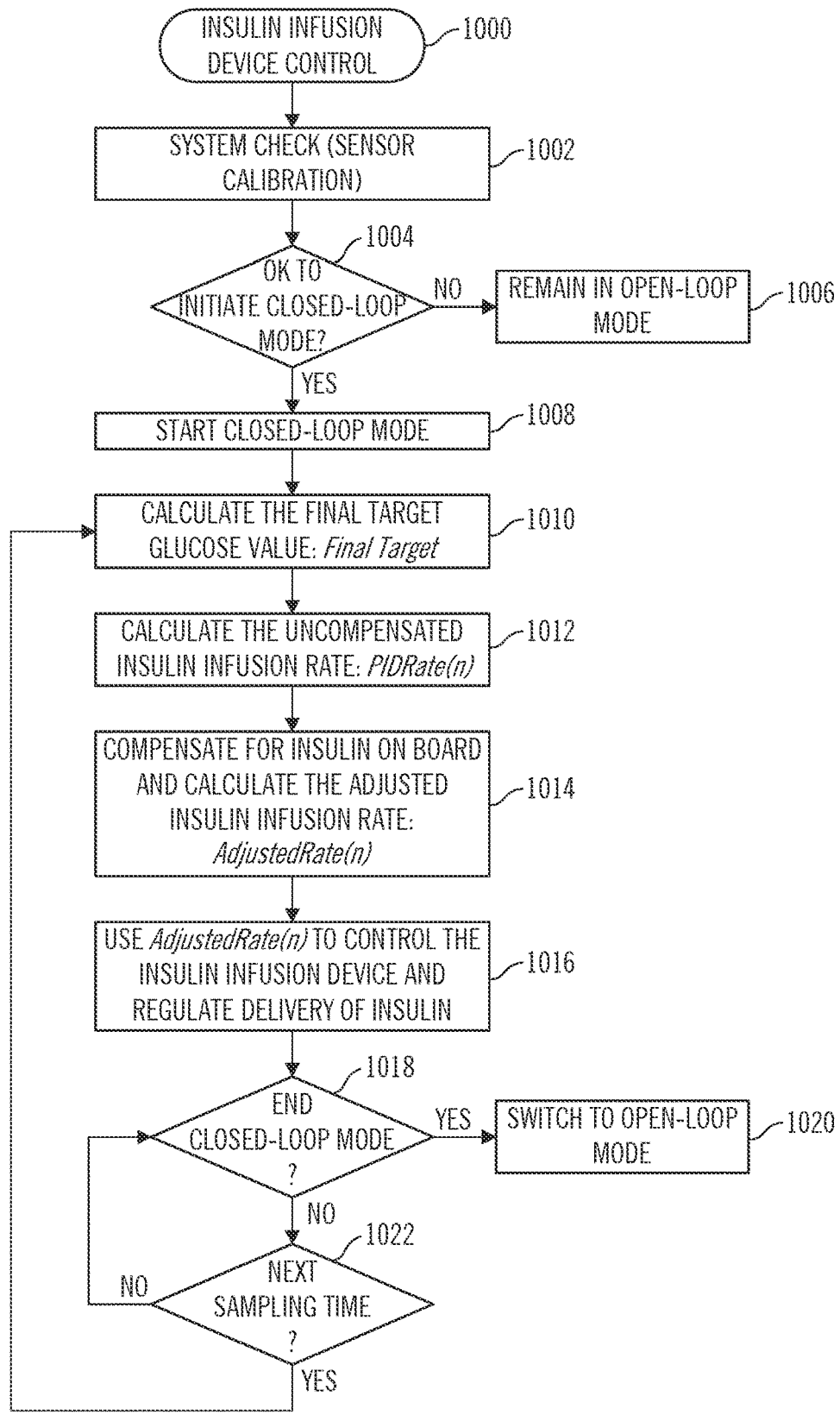
FIG. 50 is a flow chart that illustrates an exemplary embodiment of a control process for an insulin infusion device.

FIG. 49 is a block diagram that illustrates processing modules and algorithms of an exemplary embodiment of a closed-loop system controller 900, and FIG. 50 is a flow chart that illustrates an exemplary embodiment of a control process 1000 that may be performed at least in part by the controller 900 to control the insulin delivery system 14. The controller 12 shown in FIG. 1 may be configured in accordance with that shown in FIG. 49. FIG. 49 schematically depicts certain inputs and outputs of the controller 900, where the parallelograms represent the inputs, the ovals represent the outputs, and the rectangles represent the various functional modules of the controller 900. In the context of this description, a "functional module" may be any process, technique, method, algorithm, computer-executable program logic, or the like. In this regard, the controller 900 could be realized as any electronic device having a processor architecture with at least one processor device, and at least one memory element that is cooperatively associated with the processor architecture. The processor architecture is suitably configured to execute processor-executable instructions stored in the at least one memory element such that the controller 900 can perform the various control operations and methods described in detail herein.

The host electronic device that implements the controller 900 may be realized as a monitor device for an insulin infusion device, where the monitor device and the insulin infusion device are two physically distinct hardware devices. In another embodiment of the system, the host electronic device that implements the controller 900 may be realized as a portable wireless device, where the portable wireless device and the insulin infusion device are two physically distinct hardware devices. The portable wireless device in this context may be, without limitation: a mobile telephone device; a tablet computer device; a laptop computer device; a portable video game device; a digital media player device; a portable medical device; or the like. In yet other system embodiments, the host electronic device and the insulin infusion device are physically and functionally integrated into a single hardware device. In such embodiments, the insulin infusion device will include the functionality of the controller 900 as presented here.

Certain embodiments of the controller 900 include a plurality of cooperating functional modules that are designed and configured to determine the insulin dose to be delivered to keep the patient at the target glucose setpoint during an overnight closed-loop operating mode. In this regard, the illustrated embodiment of the controller 900 may include the following functional modules, without limitation: a closed-loop initiation module 902; a start-up module 904; a proportional integral derivative insulin feedback (PID-IFB) control module 906; an insulin limit module 908; an insulin on board (IOB) compensation module 910; an insulin delivery timeout module 912; a model supervisor module 914; and a missed transmission module 916.

Referring to FIG. 50, the control process 1000 may begin at any time when it is desired to enter the closed-loop operating mode. Accordingly, the control process 1000 may begin in response to a user-initiated command, automatically in response to the detection of operating conditions that are usually indicative of closed-loop operation (e.g., sleeping), or the like. Certain embodiments of the control process 1000 may begin with one or more system checks (task 1002) to confirm whether or not the system is allowed to enter the closed-loop operating mode. This particular example employs a sensor calibration check before allowing the system to proceed to the closed-loop mode. Referring to FIG. 49, the closed-loop initiation module 902 may be involved during task 1002.

In some embodiments, the closed-loop initiation module 902 may consider certain sensor performance criteria that prevents closed-loop initiation. Such criteria may include, without limitation: (1) during start-up when the calibration is not stable; (2) when the sensor sensitivity changes significantly; (3) when sensors may be calibrated with a potentially invalid meter reading thereby changing the sensor sensitivity significantly; (4) any other situation that could cause a mismatch between the sensor and meter for a number of most recent calibrations spaced over a designated period of time (e.g., the two most recent calibrations).

The illustrated embodiment of the closed-loop initiation module 902 receives at least the following items as inputs: a meter (measured) BG value 920; at least one sensor calibration factor 922 (i.e., calibration measurements, calibration data, etc.); the current sensor Isig value 924; and timestamp data 926 that indicates the calibration time associated with the BG value 920 and the sensor calibration factor 922. Some or all of this input data may be provided directly or indirectly by the insulin delivery system 14 (see FIG. 1), a translator device, a monitor device, or any device in the closed-loop system. This description assumes that a new sensor calibration factor 922 and new timestamp data 926 is generated for each measured BG value 920, wherein the sensor calibration factor 922 is associated with the calibration of the glucose sensor system 10 (see FIG. 1) that is being used to monitor the patient. In particular, the sensor calibration factor may be based on the meter BG value 920 and the corresponding sensor Isig value 924.

The closed-loop initiation module 902 analyzes the input data (both current values and historical values) to determine whether or not the system is allowed to enter into the closed-loop mode. For example, the closed-loop initiation module 902 may: check the period between two consecutive calibration timestamp values; compare recent and prior calibration factor values; and the like. The "outputs" of the closed-loop initiation module 902 correspond to two operating modes of the system. More specifically, the closed-loop initiation module 902 controls whether the system remains operating in the open-loop mode 928 or whether the system starts the closed-loop mode 930.

Referring to FIG. 50, if the closed-loop mode is not permitted (the "No" branch of query task 1004), then the control process 1000 operates the system such that it remains in the open-loop mode (task 1006). On the other hand, if the closed-loop mode is permitted (the "Yes" branch of query task 1004), then the control process 1000 can initiate and start the closed-loop mode in an appropriate manner (task 1008). Referring again to FIG. 49, a correction bolus 932 can be calculated and delivered (if needed) to mitigate hyperglycemia at the commencement of the closed-loop mode. This correction bolus 932 serves as an additional safeguard to achieve a target blood glucose level if a measured meter reading is greater than a threshold value. If the control process 1000 determines that a correction bolus is required, then an appropriate insulin dose instruction is generated for execution by the insulin delivery system at the outset of the closed-loop mode.

Referring to FIG. 49, the start-up module 904 may be called in response to a determination that the system can proceed to the closed-loop operating mode. Once the system is in the closed-loop mode, the controller retrieves historical data that can be processed and used as described in more detail below. In certain embodiments, for example, the controller obtains data for the last 24 hours (from the insulin delivery system, from a monitor, or the like). Thereafter, the controller retrieves data packets once every sampling period to obtain, without limitation: sensor glucose (SG) values; sensor Isig values; sensor calibration factors; information related to the amount of insulin delivered; information related to manual boluses delivered; and sensor calibration factors. As explained in more detail below, the received information can be used in the various safeguards, and to determine the final insulin dose.

The start-up module 904 receives sensor glucose (SG) values 940 as an input, and the functionality of the start-up module 904 may be initiated in response to the start of the closed-loop mode 930 (this trigger mechanism is represented by the dashed arrow 942 in FIG. 49). The SG values 940 may be provided directly by the glucose sensor system 10 or indirectly via the insulin delivery system 14, a translator device, or any device in the closed-loop system (see FIG. 1). This description assumes that SG values 940 are received by the start-up module 904 in an ongoing manner as they become available. The start-up module 904 may also utilize a target glucose setpoint value 944, which may be internally maintained, generated, and/or provided by the controller 900. For the implementation presented here, the target glucose setpoint value 944 represents a fixed (constant) value that the user can specify (FIG. 49 depicts the target glucose setpoint value 944 in dashed lines to indicate that the value is a user-specified parameter rather than a functional module or data received by the system).

In certain embodiments, the start-up module 904 calculates a final target glucose value 946, which serves as an input to the PID-IFB control module 906. The final target glucose value 946 enables the system to make a smoother transition between open-loop and closed-loop modes (by gradually adjusting the final target glucose value 946). The start-up module 904 may utilize the target glucose setpoint value 944 to calculate the final target glucose value 946. In this regard, the start-up module 904 elevates the final target glucose value 946 to the same level as the sensor glucose value at the start of the closed-loop mode, provided the sensor glucose is above a certain threshold. As time progresses, the final target glucose value 946 gradually decreases back to the target glucose setpoint value 944 (usually in approximately two hours). Referring to FIG. 50, the control process 1000 calculates the final target glucose value (task 1010) and continues by calculating an uncompensated insulin infusion rate, PIDRate(n), based at least in part on the final target glucose value (task 1012). For this example, the start-up module 904 may be involved during task 1010, and the PID-IFB control module 906 may be involved during task 1012.

As an additional safeguard, the insulin limit module 908 cooperates with the PID-IFB control module 906 to provide an upper insulin limit that is calculated based on the patient's basal rate, fasting blood glucose, and insulin sensitivity. This upper insulin limit imposes an upper limit to the insulin delivery rate to avoid over-delivery of insulin by the system due to potential sensor error.

The PID-IFB control module 906 may be configured to carry out the control processes described in more detail above with reference to FIGS. 1-48. In some embodiments, the PID-IFB control module 906 receives at least the following items as inputs: the SG value 940 (which may be used to calculate a rate of change value that indicates the rate of change of the SG value); the current sensor Isig value 950; the current sensor calibration factor 952; and an amount of insulin delivered 954. The inputs to the PID-IFB control module 906 may be provided directly or indirectly by the insulin delivery system 14, the glucose sensor system 10, a translator device, a monitor device, and/or any device in the closed-loop system (see FIG. 1). The PID-IFB control module 906 is suitably configured to calculate the insulin infusion rate based on the current and past SG values 940, the SG rate of change, the sensor Isig value 950, the sensor calibration factor 952, the final target glucose value 946, and the insulin delivered 954 in order to achieve euglycemia. These (and possibly other) values may be received by the PID-IFB control module 906 in an ongoing manner as they become available, e.g., in five minute intervals or in accordance with any desired schedule.

The insulin delivered 954 is a parameter or value that indicates the amount of insulin that has been delivered to the patient by the insulin delivery system. Thus, the insulin delivered 954 may indicate recent boluses (typically by Units) delivered over a period of time. In certain implementations, the insulin delivered 954 corresponds to the amount of insulin delivered in the last sampling time, which may be, without limitation: one minute; five minutes; thirty seconds; or any designated sampling time. The insulin delivered 954 may also indicate the amount of insulin delivered by the delivery system as basal or boluses in any defined period of time in the past (e.g., the last N hours) or the amount of insulin delivered by the system in the last sampling cycle. In practice, the PID-IFB control module 906 (and the IOB compensation module 910) may be "initialized" to collect and save historical values for the insulin delivered 954 as needed. Thereafter, the insulin delivered 954 can simply indicate an amount of insulin administered by the system during the last sampling time period if by a bolus or basal channels.

As mentioned above, the PID-IFB control module 906 may utilize an upper insulin limit, which is a patient-specific parameter. In certain embodiments, the upper insulin limit may be entered by the user, a caregiver, or the like. Alternatively, the insulin limit module 908 may be responsible for calculating or otherwise managing the upper insulin limit if so desired. The upper insulin limit imposes an upper limit to the insulin delivery rate as an additional safety feature to avoid over-delivery of insulin by the controller 900 due to potential sensor error. Thus, if the PID-IFB control module 906 recommends a dose higher than the insulin limit, the insulin limit will constrain the insulin delivered to the insulin limit value. In addition, the insulin limit will "freeze" the integral component of the PID to its previous value to prevent integral windup, which can cause continuous integrating of the glucose error until it reaches maximum values. In certain embodiments, the upper insulin limit has a default value set at five times the patient's basal rate. Hence, if the maximum value is reached, the PID-IFB control algorithm will be fairly aggressive in calculating an insulin dose. Accordingly, to minimize integral windup, the insulin limit is fed back to the PID-IFB control module 906 (as depicted in FIG. 49) for use in the next insulin dose calculation.

The PID-IFB control module 906 operates as described previously to calculate a current insulin dose 958 as an output value (the current insulin dose 958 is also referred to herein as the uncompensated insulin infusion rate, PIDRate(n)). In practice, the current insulin dose 958 is typically expressed as an infusion rate (Units/Hour). In the context of this description, the current insulin dose 958 represents a baseline closed-loop infusion rate, which may be subjected to further adjustment or compensation by the IOB compensation module 910. Referring again to FIG. 50, the control process 1000 may compensate for the insulin "on board" the patient by calculating an adjusted insulin infusion rate, AdjustedRate(n), based at least in part on the uncompensated insulin infusion rate (task 1014). For this example, the IOB compensation module 910 may be involved during task 1014.

The IOB compensation module 910 receives at least the following items as inputs: the current insulin dose 958; and information regarding manual boluses delivered 960. The manual boluses delivered 960 may be provided directly or indirectly by the insulin delivery system 14, a translator device, a monitor device, and/or any device in the closed-loop system (see FIG. 1). This description assumes that the manual boluses delivered 960 is received by the IOB compensation module 910 in an ongoing manner as it becomes available, e.g., in five minute intervals or in accordance with any desired schedule. The IOB compensation module 910 is suitably configured to estimate insulin on board based on manual boluses delivered, before or during closed-loop operation, in order to compensate the final infusion rate to help avoid over-delivery of insulin by the controller 900. Accordingly, the output of the IOB compensation module 910 may be a final insulin dose 962 expressed as a final infusion rate (Units/Hour). The final insulin dose 962 is also referred to herein as the adjusted insulin infusion rate, AdjustedRate(n).

Referring to FIG. 50, the control process 1000 uses the adjusted insulin infusion rate, AdjustedRate(n), to control the insulin infusion device, which in turn regulates the delivery of insulin to the body of the user (task 1016). In certain embodiments, the adjusted insulin infusion rate is communicated to the insulin infusion device in an appropriate manner (such as wireless data communication). The control process 1000 may continue as described above in an iterative and ongoing manner to monitor the condition of the user and deliver insulin as needed without user involvement. That said, if the control process 1000 determines that the closed-loop operating mode should be terminated (the "Yes" branch of query task 1018), then the control process 1000 causes the system to switch back to the open-loop mode (task 1020). The closed-loop mode may be ended in response to a user-initiated command, automatically in response to the detection of operating conditions that are usually indicative of open-loop operation, or the like.

If query task 1018 determines that the closed-loop mode should continue (the "No" branch of query task 1018), then the control process 1000 may check whether it is time to perform another iteration of the control routine. In other words, the control process 1000 may check for the next sampling time (query task 1022). If it is time for the next iteration, then the control process 1000 may return to task 1010 and repeat the computations with the next set of data values. For example, the next iteration of the control routine may obtain and process the current values of some or all of the following parameters, without limitation: the SG value 940; the SG rate of change; the sensor Isig value 924; the amount of insulin delivered 954; and the manual boluses delivered 960. This allows the control process 1000 to adjust the final insulin infusion rate in an ongoing manner in accordance with a predetermined schedule, a designated sampling rate, or the like.

The insulin delivery timeout module 912 monitors if the patient is receiving continuous delivery of insulin at the maximum insulin limit or the minimum allowable infusion of zero Units/Hour for a time specified by the controller. Accordingly, the insulin delivery timeout module 912 may receive the insulin delivered 954 as an input. If the specified time is exceeded, the system will trigger a fail-safe alert 966. Otherwise, the system remains in the closed-loop operating mode 968.

Referring back to FIG. 49, the model supervisor module 914 receives at least the following as inputs: the insulin delivered 954; sensor Isig values 950; and one or more sensor calibration factors 952. The inputs to the model supervisor module 914 may be provided directly or indirectly by the insulin delivery system 14, the glucose sensor system 10, a translator device, a monitor device, and/or any device in the closed-loop system (see FIG. 1). The model supervisor module 914 is suitably designed and configured to estimate the user's glucose concentration in real time (or substantially real time) based on the insulin delivered 954, the sensor Isig values 950, and the sensor calibration factors 952. The sensor calibration factors 952 used by the model supervisor module 914 are equal to the sensor calibration factors 922 used by the closed-loop initiation module 902. That said, the closed-loop initiation module 902 utilizes the sensor calibration factors 922 at one particular time, whereas the model supervisor module 914 considers the sensor calibration factors 952 in an ongoing and continuous manner during operation in the closed-loop mode. Should the model-predicted glucose and the sensor glucose values differ significantly, the system will exit closed loop mode. Accordingly, the model supervisor module 914 regulates whether the system remains in the closed-loop mode 974 or switches to the open-loop mode 976.

The missed transmission module 916 is suitably configured to monitor the following, without limitation: the sensor Isig values 950; the SG values 940; and the sensor calibration factors 952. More particularly, the missed transmission module 916 continuously monitors to check whether the system is receiving data packets that convey the necessary information and input values. For missed data packets totaling less than a lower threshold of time (e.g., 15 minutes), the system remains in the closed-loop mode, as indicated by block 980 in FIG. 49. During this time, the system will continue to calculate the insulin dose using the closed-loop control methodology based on the last valid sensor glucose value. For missed data packets totaling a time longer than the lower threshold and shorter than an upper threshold of time (e.g., 60 minutes), the missed transmission module 916 will switch the system to a pre-programmed safe basal rate, as indicated by block 982 in FIG. 49. In certain embodiments, this safe basal rate is defined as half the patient's overnight basal rate, and this parameter may be programmed by a caregiver or physician. If the missed transmission module 916 starts receiving data packets while the safe basal rate is being administered, the system will switch back to the closed-loop mode. For missed data packets totaling more than the upper threshold of time, the system will switch to the open-loop mode, as indicated by block 984 in FIG. 49. At this point, the system will be controlled to deliver a pre-programmed open-loop overnight basal rate.

To summarize, the controller 900 determines whether to enter into the closed-loop mode in response to at least the recent meter BG values 920, the sensor calibration factors 922, and the calibration timestamp data 926. The controller 900 utilizes the closed-loop initiation module 902 to check if the sensor calibration time between the last two calibration values is within an acceptable range, and whether any change between the two calibration values (recent and prior value) is acceptable. If so, the controller 900 will switch the system into the closed-loop mode. Once the system is in the closed-loop mode, the controller 900 will periodically receive data packets (e.g., every five minutes) that include the current SG value 940, the current sensor Isig values 950, the insulin delivered 954, the sensor calibration factors 952, and manual boluses delivered 960. In certain embodiments, each of the data packets received by the controller 900 includes data collected during the previous 24-hour period.

The start-up module 904 utilizes the SG values 940 and the target glucose setpoint value 944 to calculate the final target glucose value 946. In some embodiments, the target glucose setpoint value 944 is set to 120 mg/dL, although other settings could be used if so desired (a typical range of settings may be, for example 70-300 mg/dL). This results in a smoother transition between open-loop and closed-loop modes by gradually adjusting the final target glucose value 946. The final target glucose value 946 is sent to the PID-IFB control module 906 for use as one input to calculate the final insulin dose 962.

The PID-IFB control module 906 utilizes the final target glucose value 946, the current and past SG values 940, the SG rate of change values, and the insulin delivered 954 to determine the insulin infusion rate (final insulin dose 962) in order to achieve euglycemia. As an additional safeguard, the upper insulin limit (calculated based on the patient's basal rate, fasting blood glucose, and insulin sensitivity) from the insulin limit module 908 is input into the controller 900 for each patient to impose an upper limit to the insulin delivery rate to avoid over-delivery of insulin by the controller 900. The PID-IFB control module 906 considers the upper insulin limit before sending the final insulin dose 962 to the IOB compensation module 910, which estimates insulin on board from manual boluses, before or during closed-loop operation, in order to calculate the final insulin dose 962. The final insulin dose 962 may be communicated from the controller 900 directly or indirectly to the insulin delivery system 14 such that the final insulin dose 962 can be delivered to the patient during closed-loop operation.

Additional safeguards could be implemented to monitor the system during closed-loop operation, such that the system exits the closed-loop mode when certain criteria are not met. For example, the controller 900 may cause the system to exit the closed-loop mode if more than a designated number of consecutive data packets are missed. This assumes that the controller 900 usually receives data packets (from the insulin delivery system 14, from a monitor, from a translation device, or the like) in a continuous manner during closed-loop operation. Thus, if the controller 900 detects that more than a threshold number of consecutive data packets are not received as expected, the system will be commanded to exit the closed-loop mode. This functionality is associated with the missed transmission module 916, as described previously.

Moreover, the model supervisor module 914 estimates the user's glucose concentration in an ongoing manner, based on the insulin delivered 954, the sensor Isig values 950, and the sensor calibration factors 952. If the difference between the model-predicted glucose and the sensor glucose value is greater than a stated threshold, the controller 900 may cause the system to exit the closed-loop mode.

As summarized above, the controller 900 employs a number of modules or functions that cooperate to regulate the delivery of insulin during closed-loop operation: the closed-loop initiation module 902; the start-up module 904; the PID-IFB control module 906; the insulin limit module 908; and the IOB compensation module 910. Moreover, the controller 900 may employ a number of modules that perform various safeguarding functions during closed-loop operation. These safeguarding modules may include: the insulin delivery timeout module 912; the model supervisor module 914; and the missed transmission module 916.

Closed-Loop Initiation Module: First Representation

The closed-loop initiation module 902 checks for changes in sensor sensitivity and determines whether or not the system is allowed to enter the closed-loop mode. Referring again to FIG. 49, the inputs to the closed-loop initiation module 902 include the meter BG value 920, the sensor calibration factor 922, and the calibration timestamp data 926. The closed-loop initiation module 902 checks for a series of conditions pertaining to the sensor calibration factor values 922 and the times when the sensor calibration factor values 922 were obtained. If all the conditions are met, the controller 900 initiates the closed-loop operating mode. If this criteria is not met, the system remains in the open-loop operating mode and the controller 900 requests a new sensor calibration.

Certain embodiments of the closed-loop initiation module 902 execute one or more functions, algorithms, or methods to determine whether or not the system can proceed to the closed-loop mode. The following are the parameters and variables used by an exemplary embodiment of the closed-loop initiation module 902:

t=time when attempting to enter the closed-loop mode;

Recent Calibration Factor (CFR)=the most recent sensor calibration factor (CF) value;

tR=the time when the CFR was obtained;

Prior Calibration Factor (CFP)=the last CF value before the CFR;

tP=the time when the CFP was obtained;

CFchange=percentage change in CF from a previous CF to a current CF, for any pair of CFs. The CFchange can be calculated according to the following equation:

$$CF\ \text{change} = (\text{abs}\,(CF\ \text{current} - CF\ \text{previous})/CF\ \text{previous}) * 100 \quad (\text{eq 50})$$

tRecent=time window for the most recent calibration before attempting to start closed-loop mode (minutes)

tDiffmin=minimum time difference between the recent calibration and the calibration prior to the recent calibration (minutes)

tDiffmax=maximum time difference between the recent calibration and the prior calibration (minutes)

CFmin=minimum acceptable CF (mg/dL per nA)

CFmax=maximum acceptable CF (mg/dL per nA)

CFprevious=the CF value before CFcurrent in the pair of CF values

CFchangeTh=threshold for acceptable CFchange in % (mg/dL per nA)

In some embodiments, the closed-loop initiation module 902 is implemented in the form of a series of processing steps. Using the logic described below, the closed-loop initiation module 902 decides whether to let the system enter the closed-loop mode.

| Case A |
|---|
| If (tP is not in the time window (tR-tDiffmin : tR)), the following logic is checked.<br>  If (CFmin ≤ CFR ≤ CFmax)<br>    If (t-tRecent ≤ tR ≤ t)<br>      If (tR-tDiffmax ≤ tP ≤ tR-tDiffmin)<br>        If (CFmax ≤ CFP ≤ CFmax)<br>          Calculate CFchange with CFR as the CFcurrent and with CFP as the CFprevious in Equation 50 stated above<br>          If (CFchange ≤ CFchangeTh)<br>            Enter Closed Loop<br>          Else Cannot enter closed loop at that time<br>        Else Cannot enter closed loop at that time<br>      Else Cannot enter closed loop at that time<br>    Else Cannot enter closed loop at that time<br>  Else Cannot Enter Closed Loop |

If any of the above conditions is not met, the system remains in the open-loop mode. Thus, in order to enter the closed-loop mode, new calibration(s) that satisfy all of the conditions in Case A (or Case B as described below) will be required.

| Case B |
|---|
| If (tP is in the time window (tR-tDiffmin : tR)),<br>CFV = most recent CF value in the time window of tR-tDiffmax : tR-tDiffmin<br>tV = time when CFV was obtained<br>  If (CFmin ≤ CFR ≤ CFmax)<br>    If there is a CFV available<br>      Calculate CFchange with CFR as the CFcurrent and with CFV as the CFprevious in Equation 50 stated above<br>      If (CFV, CFR and all CF values between times tV and tR lie in the range of (CFmin:CFmax) AND CFchange between CFV and CFR is ≤ CFchangeTh)<br>        Enter closed loop<br>      Else Cannot enter closed loop at that time<br>    Else Cannot enter closed loop at that time<br>    Else Cannot enter closed loop at that time<br>  Else Cannot Enter Closed Loop |

If any of the above conditions is not met, the system remains in the open-loop mode. Thus, in order to enter the closed-loop mode, new calibration(s) that satisfy all of the conditions in Case A or Case B will be required.

In accordance with certain variations of the closed-loop initiation module 902, the system requests a meter BG and related calibration when entering the closed-loop mode. In such alternative embodiments, therefore, the closed-loop initiation module 902 uses the meter BG and Isig to calculate CFR. Thus, in such an implementation, the sensor current would also be an input to the closed-loop initiation module 902. Accordingly, because CFR is now being calculated by the closed-loop initiation module 902 itself, the conditions in Case A and Case B (i.e., checking whether t-tRecent-≤tR≤t) will always be met.

In particular implementations, some of the parameters mentioned above can be fixed. In this regard, the following values may be utilized in an exemplary embodiment. It should be appreciated that these values are provided here for illustrative purposes only, and that an implementation of the closed-loop initiation module 902 may utilize different values if so desired.

tRecent=120 minutes
tDiffmin=120 minutes
tDiffmax=480 minutes
CFmin=2.5 mg/dL per nA
CFmax=6 mg/dL per nA

Closed-Loop Initiation Module: Second Representation

In accordance with some embodiments, the functionality of the closed-loop initiation module 902 can be represented as follows. The closed-loop initiation module 902 may be implemented in the form of a series of case steps. In this regard, the closed-loop initiation module 902 first calculates the recent calibration factor value (CFR) using the most recent meter BG and Isig values as shown in the following Equation A1:

$$CFR = \text{meter } BG/(Isig - 2) \quad \text{(eq A1)}$$

Here, CFR is the recent calibration factor value, meterBG is the meter BG value, and Isig is the sensor Isig value. The "−2" in Equation A1 represents a constant offset that is used by the calibration algorithm when calculating calibration factors and sensor glucose.

Using the logic described below for Case C or Case D, the closed-loop initiation module 902 decides whether to let the system enter the closed-loop mode. Each case condition is dependent upon the time at which the most recent prior calibration factor (CFP) was obtained.

Case C

Case C corresponds to a scenario where the time of prior calibration is greater than 120 minutes before the most recent calibration. In addition, the recent calibration factor (CFR) and the prior calibration factor (CFP) are within limits as shown in the following logical expressions.

$$CF \min \leq CRF \leq CF \max \quad \text{(eq A2)}$$

$$CF \min \leq CFP \leq CF \max \quad \text{(eq A3)}$$

Here, CFR is the recent calibration factor value, CFP is the prior calibration value, CFmin is the minimum value for the calibration factor that is set as 2.5 mg/dL per nA, and CFmax is the maximum value for the calibration factor that is set as 6 mg/dL per nA.

For Case C, the time of recent calibration (tR) is within two hours of the start of closed-loop initiation as shown in the following logical expression.

$$t - t \text{ Recent} \leq tR \leq t \quad \text{(eq A4)}$$

Here, tR is the time of recent calibration, t is the time when attempting to enter the closed-loop mode, and tRecent is the time window for the most recent calibration before attempting to start the closed-loop mode (which is set to 120 minutes).

For Case C, the time of prior calibration (tP) occurs between two and eight hours before time of recent calibration factor as shown in the following logical expression.

$$tR - tDiff \max \leq tP \leq tR - tDiff \min \quad \text{(eq A5)}$$

Here, tP is the time of prior calibration, tR is the time when CFR was obtained, tDiffmax is the maximum time difference between the recent calibration and the prior calibration (which is set as 480 minutes (8 hours)), and tDiffmin is the minimum time difference between the recent calibration and the calibration prior to the recent calibration (which is set as 120 minutes (2 hours)).

For Case C, the calibration change (CFchange) is less than 35% as shown in the following logical expression, where CFchange is calculated according to Equation A6.

$$CF \text{ change} = (\text{abs }(CFR - CFP)/CFP) \times 100 \quad \text{(eq A6)}$$

$$CF \text{ change} \leq CF \text{ change } Th \quad \text{(eq A7)}$$

Here, CFchange is the percentage change in calibration factor from the previous calibration factor to a current calibration factor for any pair of calibration factors, CFchangeTh is the threshold for acceptable CFchange, (which is set to 35% for this example), CFR is the most recent calibration factor value, and CFP is the last calibration factor value before CFR.

If all of the foregoing conditions are met for Case C (Equations A2-A7), the closed-loop initiation module 902 can initiate the methodology for calculating the correction bolus (if needed). If, however, any condition is not met, the controller 900 remains in the open-loop mode. Thus, in order to enter the closed-loop mode, new calibration(s) that satisfy all of the conditions in Case C or Case D will be required.

Case D

Case D corresponds to a scenario where the time of prior calibration is less than 120 minutes before the most recent calibration. If the prior calibration is less than two hours before the recent calibration, an additional prior calibration factor (CFP2) is included in the analysis. This allows the closed-loop initiation module 902 to evaluate sensor sensitivity that has at least a two hour time span.

For Case D, the closed-loop initiation module 902 finds an earlier second prior calibration factor (CFP2) that occurs within two to eight hours before the time of the recent calibration factor (CFR) as shown in the following logical expression.

$$tR - tDiff \max \leq tP2 \leq tR - tDiff \min \quad \text{(eq A8)}$$

Here, tP2 is the time when the second prior calibration factor (CFP2) is obtained, tR is the time when CFR was obtained, tDiffmax is the maximum time difference between tP2 and tR (which is set as 480 minutes (8 hours) for this example), and tDiffmin is the minimum time difference between tP2 and tR (which is set as 120 minutes (2 hours) for this example).

For Case D, the closed-loop initiation module 902 also determines if more than one calibration factor (CF1 . . . CFn) is available between the time of the second prior calibration factor (CFP2) and the time of the recent calibration factor (CFR), as shown in the following logical expression.

$$tP2 \leq t1 \ldots tn \leq tR \quad \text{(eq A9)}$$

Here, t1 . . . tn is the time when more calibration factors (CF1 . . . CFn) are observed, tR is the time when CFR was obtained, and tP2 is the time when CFP2 is obtained.

For Case D, the time of recent calibration (tR) is within two hours of the start of closed-loop initiation, as shown in the following logical expression.

$$t - t\text{Recent} \leq tR \leq t \quad \text{(eq A10)}$$

Here, tR is the time of recent calibration, t is time when attempting to enter the closed-loop mode, and tRecent is the time window for the most recent calibration before attempting to start the closed-loop mode (which is set to 120 minutes for this example).

For Case D, all calibration factors including recent calibration factor (CFR), prior calibration factor (CFP), second prior calibration factor (CFP2) and CF1 ... CFn are within limits as shown in the following logical expressions.

$$CF\min \leq CRF \leq CF\max \quad \text{(eq A11)}$$

$$CF\min \leq CFP \leq CF\max \quad \text{(eq A12)}$$

$$CF\min \leq CFP2 \leq CF\max \quad \text{(eq A13)}$$

$$CF\min \leq CF1 \ldots CFn \leq CF\max \quad \text{(eq A14)}$$

Here, CFR is the recent calibration factor, CFP is the prior calibration factor, CFP2 is the second prior calibration factor, CF1 ... CFn are calibration factors obtained between tP2 and tR, CFmin is the minimum value for the calibration factor (which is set as 2.5 mg/dL per nA for this example), and CFmax is the maximum value for the calibration factor (which is set as 6 mg/dL per nA for this example).

For Case D, the calibration change (CFchange) between CFR and CFP2 is less than 35%, as shown in the following logical expression where CFchange is calculated according to Equation A15.

$$CF\text{change} = (\text{abs}(CFR - CFP2)/CFP2) \times 100 \quad \text{(eq A15)}$$

$$CF\text{change} \leq CF\text{change }Th \quad \text{(eq A16)}$$

Here, CFchange is the percentage change in calibration factor from the previous calibration factor to a current calibration factor for any pair of calibration factors, CFchangeTh is the threshold for acceptable CFchange (which is set to 35% for this example), CFR is the most recent calibration factor value, and CFP2 is the most recent calibration factor value in the time range described in Equation A8.

If all of the foregoing conditions are met for Case D (Equations A8-A16), the closed-loop initiation module 902 can initiate the methodology for calculating the correction bolus (if needed). If, however, any condition is not met, the controller 900 remains in the open-loop mode. Thus, in order to enter the closed-loop mode, new calibration(s) that satisfy all of the conditions in Case C or Case D will be required.

Correction Bolus with IOB Compensation

As described above, a correction bolus 932 may be commanded at the beginning of the closed-loop mode. The purpose of the correction bolus is to provide an insulin dose for mitigating hyperglycemia at the initiation of the closed-loop mode. This can be achieved by first acquiring a blood glucose meter reading value immediately prior to closed-loop initiation. If that BG meter reading value is above a certain correction threshold (CTH, which is 180 mg/dL for this example), the controller 900 will deliver an insulin dose based on the patient's insulin sensitivity (ISF, mg/dL/Units), insulin on board, and the desired target glucose level (TG, mg/dL) in order to bring the subject's glucose level to the target glucose level.

In accordance with certain implementations, the correction bolus (CB) is delivered based on the meter BG value (in mg/dL) acquired at the start of the closed-loop mode, as shown below:

$$CB = \begin{cases} \dfrac{BG - TG}{ISF} - IOB(n), & \text{if } (BG > CTH) \\ 0, & \text{if } (BG \leq CTH) \end{cases} \quad \text{(eq A17)}$$

Here, CB is the correction bolus, BG is the blood glucose meter value (mg/dL), TG is the target glucose (mg/dL), ISF (see Equation A18) is the patient's adjusted insulin sensitivity factor (mg/dL/Units), CTH is the correction threshold for blood glucose beyond which a correction bolus will be delivered (mg/dL), and IOB(n) is the active insulin on board from manual boluses (Units) where n is the current sampling point as described previously.

$$ISF = ISF \text{ factor} \times ISF_0 \quad \text{(eq A18)}$$

Here, ISF is the patient's adjusted insulin sensitivity factor (mg/dL/Units), $ISF_0$ is the patient's established insulin sensitivity factor (mg/dL/Units) and ISFfactor is an ISF adjusting factor (unit less). The default value for ISFfactor is set to one, which makes ISF $ISF_0$. However, for this particular example, ISFfactor has been assigned as an adjustable parameter with a range of 0.5 to 2 in order to provide greater flexibility for optimizing the patient's insulin sensitivity factor.

$$CB = \begin{cases} CB, & \text{if } (CB \geq 0) \\ 0, & \text{if } (CB < 0) \end{cases} \quad \text{(eq A19)}$$

Here, CB is the correction bolus expressed in Units. It should be appreciated that Equation A19 is utilized because the controller 900 can only deliver positive boluses.

Start-Up Module

The start-up module 904 processes sensor glucose (SG) values 940 and the target glucose setpoint value 944 (which is set to 120 mg/dL in certain embodiments) to calculate the final target glucose value 946, which in turn serves as an input to the PID-IFB control module 906. Accordingly, the final target glucose value 946 is sent to the PID-IFB control module 906 to calculate the final insulin dose 962. Referring again to FIG. 49, the start-up module 904 is "activated" or initiated in response to the starting of the closed-loop mode.

At the beginning of the closed-loop operating mode, the start-up module 904 calculates the difference between the current SG value 940 and the target glucose setpoint value 944, as indicated by Equation 51 below.

$$\text{Delta } Glu(n) = \begin{cases} SG(n) - \text{Set point}, & m = 1 \\ 0, & m > 1 \end{cases} \quad \text{(eq 51)}$$

In Equation 51, SG is the sensor glucose value, n is the current sampling point, Setpoint is the target glucose setpoint value defined by user, and m is the sampling time during closed-loop operation (m=1 indicates the start of the closed-loop mode, and m increases with each sample received during the closed-loop mode). DeltaGlu(n) is forced to zero when m>1 as well as in the following situation described in Equation 52.

Force DeltaGlu to zero if it is less than a certain threshold set in the controller 900 (referred to as MinDeltaGlu). Otherwise, it remains as DeltaGlu(n) if it is more than the threshold set in the controller 900, as described in Equation 52:

$$\text{Delta } Glu(n) = \begin{cases} 0, & \text{Delta } Glu \leq \text{Min Delta } Glu \\ \text{Delta } Glu(n), & \text{Delta } Glu > \text{Min Delta } Glu \end{cases} \quad \text{(eq 52)}$$

Here DeltaGlu is the difference between the current SG value 940 and the defined target glucose setpoint value 944, calculated from Equation 51 above, and MinDeltaGlu is the minimum difference (set in the controller 900) allowable between the current SG value 940 and the target glucose setpoint value 944.

The dynamic setpoint (DynSP) is calculated based on a discretized second order transfer function model as indicated in Equation 53:

$$DynSP(n) = cd_1 \cdot DynSP(n-1) + cd_2 \cdot DynSP(n-2) + \quad \text{(eq 53)}$$
$$cn_0 \cdot \text{Delta } Glu(n) + cn_1 \cdot \text{Delta } Glu(n-1)$$

Here, DynSP is the dynamic setpoint value, n is the current sampling point, n−1 is the last sampling point, and n−2 is the second to last sampling point. The parameters $cd_1$, $cd_2$, $cn_0$, and $cn_1$ are the coefficients of the setpoint model. These parameters are calculated based on the two time constants ($\tau_{sp1}$ and $\tau_{sp2}$) of the setpoint model, as indicated below:

$$cd_1 = eaxx1 + eaxx2$$
$$cd_2 = -eaxx1 \times eaxx2$$
$$cn_0 = 1$$
$$cn_1 = \frac{(axx1 \times eaxx1 - axx2 \times eaxx2)}{daxx21}$$

Where:
$$axx1 = 1/\tau_{sp1}$$
$$axx2 = 1/\tau_{sp2}$$
$$eaxx1 = e^{-axx1 \cdot Ts}$$
$$eaxx2 = e^{-axx2 \cdot Ts}$$
$$daxx21 = axx2 - axx1$$

In the above equations Ts indicates the sampling interval in minutes, and $\tau_{sp1}$ and $\tau_{sp2}$ are the time constants of the setpoint model. Moreover, axx1 is the reciprocal of the time constant $\tau_{sp1}$, axx2 is the reciprocal of the time constant tsp2, eaxx1 is the exponential decay factor for $\tau_{sp1}$, eaxx2 is the exponential decay factor for $\tau_{sp2}$, and daxx21 is the difference between the reciprocal of $\tau_{sp1}$ and $\tau_{sp2}$.

The final target glucose value 946 is obtained by adding the dynamic setpoint value (calculated in Equation 53) with the target glucose setpoint value 944 as shown in Equation 54:

$$\text{Final Target} = \text{Set point} + DynSP(n) \quad \text{(eq 54)}$$

In particular implementations, some of the parameters mentioned above for the start-up module 904 can be fixed. In this regard, the following values may be utilized in an exemplary embodiment. It should be appreciated that these values are provided here for illustrative purposes only, and that an implementation of the start-up module 904 may utilize different values if so desired.

Setpoint=120 mg/dL
MinDeltaGlu=30 mg/dL (nominal); 0 mg/dL (lower bound); 600 mg/dL (upper bound)
$\tau_{sp1}$=25 minutes (nominal); 0.1 minute (lower bound); 250 minutes (upper bound)
$\tau_{sp2}$=30 minutes (nominal); 0.1 minute (lower bound); 250 minutes (upper bound)

PID-IFB Control Module

The PID-IFB control module 906 calculates the insulin infusion rate (final insulin dose 962) based on the current and past sensor glucose values 940, the sensor Isig values 950, the rate of change of the sensor glucose values, the sensor calibration factor 952, the final target glucose value 946, the target glucose setpoint value 944, insulin limits such as the upper insulin limit, and the insulin delivered 954 in order to achieve euglycemia. In certain embodiments, the PID-IFB control module 906 receives its inputs every five minutes, therefore the calculation of the insulin feedback components considers how often the input data is being received by the controller 900.

The PID-IFB control module 906 calculates the final insulin dose 962 in accordance with Equation 55:

$$u(n) = P(n) + I(n) + D(n) - \gamma_1 I_{SC} - \gamma_2 I_p - \gamma_3 I_{EFF} \quad \text{(eq 55)}$$

Note that PIDRate(n)≡u(n). In Equation 55, the insulin infusion rate u(n) represents the final insulin dose 962 shown in FIG. 49. In Equation 55, P(n), I(n), and D(n) are, respectively, the proportional, integral, and derivative components of the PID controller. The insulin feedback components correspond to the remaining terms. The variables $\gamma_1$, $\gamma_2$, and $\gamma_3$ represent tuning coefficients. In accordance with some embodiments, $\gamma_1$=0.64935, $\gamma_2$=0.34128, and $\gamma_3$=0.0093667, although other values may be used. The parameters $I_{SC}(n)$, $I_P(n)$, and $I_{EFF}(n)$ correspond to the states of the insulin pharmacokinetic model corresponding to, respectively, the subcutaneous, plasma, and effective site compartments. Therefore, the amount of insulin delivered is reduced in proportion to the predicted insulin concentration in the different compartments.

The exemplary implementation of the control algorithm employed by the PID-IFB control module 906 is implemented in discrete (sampled) time. In the notation used, n is the current time step, where=$nT_s$, and t is the continuous time (in minutes) when using a sampling period of $T_s$.

The proportional component P(n) is calculated as follows:

$$P(n) = Kp[SG(n) - \text{Final Target}(n)] \quad \text{(eq 56)}$$

Here, Kp is the overall controller gain (expressed in Units/hour per mg/dL), SG(n) is the current sensor glucose, n indicates the current sampling point, and Final Target(n) is the calculated final target glucose setpoint from Equation 54. It should be appreciated that Kp is a patient-specific value and, therefore, the actual value of Kp will vary from one person to another. Although the range can vary depending upon the patient, in most typical scenarios, the value of Kp may be within the range of 0.008 to 0.200.

The integral component I(n) can be calculated as follows:

$$I(n) = I(n-1) + \frac{K_p \cdot T_s}{T_I}[SG(n) - \text{Final Target}(n)] \quad \text{(eq 57)}$$

Here, I(n−1) is the integral component from the previous sampling point, n indicates the current sampling point, n−1 indicates the previous sampling point, Kp is the overall controller gain, Ts is the sampling period, Ti is the integral time constant, SG(n) is the current sensor glucose, and Final Target(n) is the calculated final target glucose setpoint from Equation 54.

The derivative component D(n) can be calculated as follows:

$$D(n) = Kp \times T_D \times dSGdt(n) \quad \text{(eq 58)}$$

Here, Kp is the overall controller gain, TD is the derivative time constant, dSGdt(n) is derivative of the sensor glucose value (pre-filtered to remove noise), and n indicates the current sampling point.

The parameters that need to be set (tuned) for the controller 900 are: $K_P$, $\tau_I$, and $\tau_D$ (see Equations 56, 57, and 58). For the first three PID parameters, they will be calculated in accordance with the previous studies mentioned below (these previous approaches have resulted in good controller performance). The nominal (i.e., for the case with no insulin feedback) controller gain $K_{P0}$ is calculated based on the subject's insulin total daily dose $I_{TDD}$, (in Units/day), as indicated in Equation 59:

$$K_{P0} = \frac{60}{(90)(1500)} I_{TDD} \quad \text{(eq 59)}$$

Here, $K_{P0}$ is the default controller gain, and $I_{TDD}$ is the subject's insulin total daily dose in Units/Day.

The purpose of insulin feedback is to allow the controller 900 to deliver more insulin up-front (e.g., at the onset of a meal disturbance), but to prevent over-infusion of insulin, in a similar fashion to the bolus estimator calculations used in existing insulin pumps to prevent the stacking of boluses. Therefore, when insulin feedback is used, the controller gain $K_P$ can be adjusted so that at steady state (i.e., basal delivery conditions) the insulin delivery system will deliver the same amount of insulin as in the nominal case. This is accomplished by multiplying the nominal controller gain $K_{P0}$ (calculated for no insulin feedback) by $(1+\gamma_1+\gamma_2+\gamma_3)$ as indicated below:

$$K_P = K_P\text{factor} \cdot K_{P0} \cdot (1 + \gamma_1 + \gamma_2 + \gamma_3) \quad \text{(eq 60)}$$

Here, $K_P$ is the overall controller gain, $K_P$ factor is the gain factor for $K_P$, $K_{P0}$ is the default controller gain, $\gamma_1$ (0.64935) is a tuning coefficient for the subcutaneous insulin concentration, $\gamma_2$ (0.34128) is a tuning coefficient for plasma insulin concentration, and $\gamma_3$ (0.0093667) is a tuning coefficient for effective insulin concentration.

The integral component I(n) is also equipped with anti-windup and saturation constraints to address integral windup issues. This is achieved by calculating an integral clip value (upper limit for the integral component, IClip) as indicated by the following equations:

$$IClip(n) = \quad \text{(eq 61)}$$
$$\begin{cases} Imax(n), & (SG(n) > UnwindHigh) \\ Iramp(n), & (SG(n) > UnwindLow) \text{ and } (SG(n) < UnwindHigh) \\ Ilow(n), & (SG(n) < UnwindLow) \end{cases}$$

$$I\max(n) = I\text{maxfactor} \times \text{Basal} \times (1 + \gamma_1 + \gamma_2 + \gamma_3) \quad \text{(eq 61a)}$$

Here, Imaxfactor is the gain factor for Imax, and Basal is the subject's night time basal rate. In accordance with these expressions, IClip becomes equal to the Imax (which is a constant value) when the sensor glucose value is greater than an upper threshold (UnwindHigh). In certain embodiments, the value of Imax (expressed in Units/hour) may reach about 15. In a typical case, Imax may have a default value of 5.0. When the sensor glucose value is between the upper and lower threshold (UnwindLow), then IClip becomes equal to Iramp(n), which is calculated as indicated in Equation 62.

$$Iramp(n) = \quad \text{(eq 62)}$$
$$Kp \cdot [SG(n) - UnwindLow] \cdot \left(\frac{SG(n) - UnwindLow}{UnwindHigh - UnwindLow}\right) \cdot$$
$$(I\max - Kp \cdot [Setpoint(n) - UnwindLow])$$

Here, Kp is the overall controller gain, SG(n) is the current sensor glucose, UnwindLow is the sensor glucose lower threshold, UnwindHigh is the sensor glucose upper threshold, Imax is a constant value, and Setpoint(n) is a user-defined target glucose setpoint.

Finally, if sensor glucose is below the UnwindLow threshold, IClip assumes the value of Ilow(n), which can be calculated by Equation 61:

$$Ilow(n) = Kp[Setpoint(n) - Unwindlow] \quad \text{(eq 63)}$$

Here, Kp is the overall controller gain, Setpoint is the target glucose defined by the user, and UnwindLow is the sensor glucose lower threshold.

Figure 51:
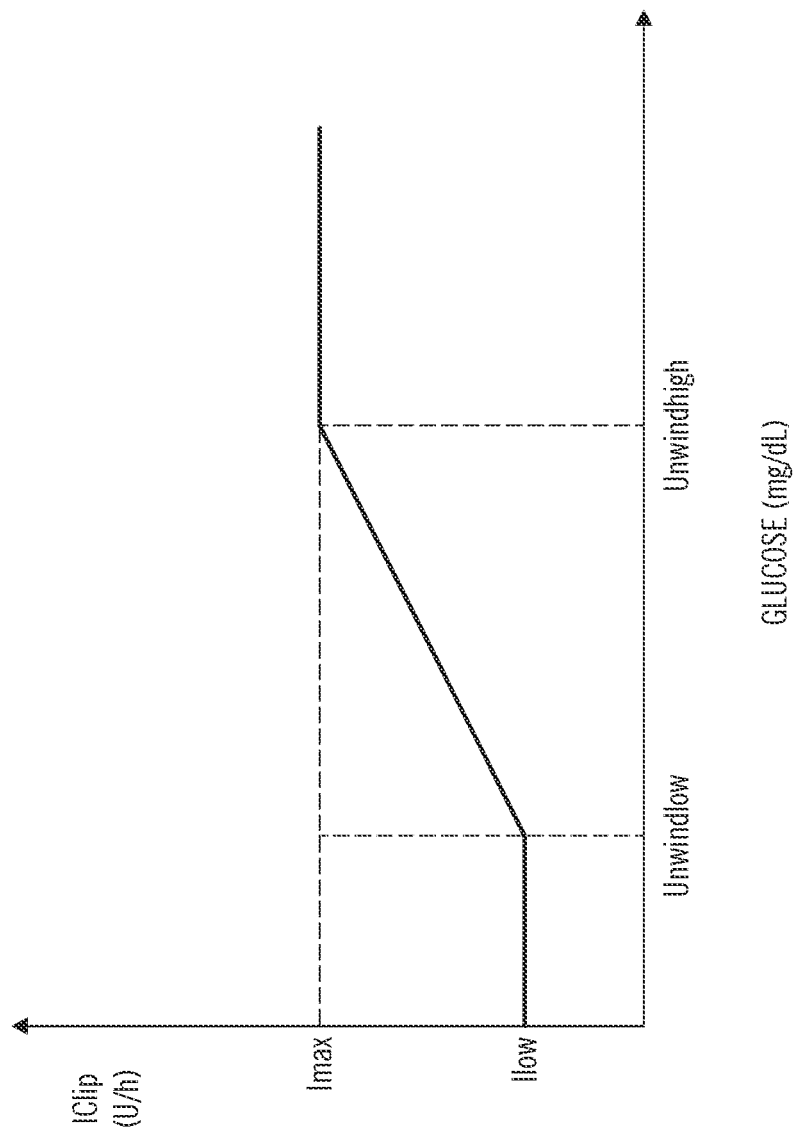
FIG. 51 is a graph of integral clip value versus sensor glucose levels.

FIG. 51 is a graph of IClip (in Units/Hour) versus sensor glucose level (in mg/dL) in accordance with one example. FIG. 51 depicts the relationships between Imax, Ilow, UnwindLow, and UnwindHigh for this particular example.

The integral component I(n) as calculated in Equation 57 must be less than or equal to the IClip value as shown in Equation 64:

$$I(n) = \begin{cases} IClip(n), & I(n) > IClip(n) \\ I(n), & I(n) \le IClip(n) \end{cases} \quad \text{(eq 64)}$$

The insulin feedback components correspond to the remaining terms. As mentioned above, for this particular example $\gamma_1$=0.64935, $\gamma_2$=0.34128, and $\gamma_3$=0.0093667 (the tuning coefficients), while the parameters $I_{SC}(n)$, $I_P(n)$, and $I_{EFF}(n)$ correspond to the states of the insulin pharmacokinetic model corresponding to, respectively, the subcutaneous, plasma, and effective site compartments. Therefore, the amount of insulin delivered is reduced in proportion to the predicted insulin concentration in the different compartments.

The model describing the insulin pharmacokinetics (insulin PK) is given by the following expressions:

$$I_{SC}(n) = \alpha_{11} \times I_{SC}(n-1) + \beta_1 \times I_D(n) \text{ where:} \quad (\text{eq } 65)$$

$$\alpha_{11} = \exp\left(-\frac{Ts}{\tau_s}\right) \quad (\text{eq } 65a)$$

$$\beta_1 = \left(\frac{60}{1}\right) \cdot \left[1 - \exp\left(-\frac{Ts}{\tau_s}\right)\right] \quad (\text{eq } 65b)$$

Here, Ts is the sampling time (which is five minutes for this example), and $\tau_s$ is the time constant for estimated subcutaneous insulin level in minutes (which is set to 50 minutes for this example).

$$I_P(n) = \alpha_{21} \times I_{SC}(n-1) + \alpha_{22} \times I_P(n-1) + \beta_2 \times I_D(n) \text{ where:} \quad (\text{eq } 65c)$$

$$\alpha_{21} = \tau_s \cdot \left[\exp\left(-\frac{Ts}{\tau_s}\right) - \exp\left(-\frac{Ts}{\tau_p}\right)\right] / (\tau_s - \tau_p) \quad (\text{eq } 65d)$$

$$\alpha_{22} = \exp\left(-\frac{Ts}{\tau_p}\right) \quad (\text{eq } 65e)$$

$$\beta_2 = \left(\frac{60}{1}\right) \cdot \left(\tau_s \cdot \left[1 - \exp\left(-\frac{Ts}{\tau_s}\right)\right] - \tau_p \cdot \left[1 - \exp\left(-\frac{Ts}{\tau_p}\right)\right]\right) / (\tau_s - \tau_p) \quad (\text{eq } 65f)$$

Here, Ts is the sampling time, which is five minutes for this example, $\tau_s$ is the time constant for estimated subcutaneous insulin level in minutes, which is set to 50 for this example, and $\tau_p$ is the time constant for estimated plasma insulin level in minutes, which is set to 70 for this example.

$$I_{EFF}(n) = \quad (\text{eq } 66)$$
$$\alpha_{31} \times I_{SC}(n-1) + \alpha_{32} \times I_P(n-1) + \alpha_{33} \times I_{EFF}(n-1) + \beta_3 \times I_D(n)$$

For Equation 66:

$$\alpha_{31} = \quad (\text{eq } 66a)$$
$$\tau_s \cdot \frac{\left[\tau_s \cdot (\tau_p - \tau_e) \cdot \exp\left(-\frac{Ts}{\tau_s}\right) - \tau_p \cdot (\tau_p - \tau_e) \cdot \exp\left(-\frac{Ts}{\tau_p}\right) + \tau_e \cdot (\tau_s - \tau_p) \cdot \exp\left(-\frac{Ts}{\tau_e}\right)\right]}{[(\tau_s - \tau_p) \cdot (\tau_s - \tau_e) \cdot (\tau_p - \tau_e)]}$$

$$\alpha_{32} = \tau_p \cdot \left[\exp\left(-\frac{Ts}{\tau_p}\right) - \exp\left(-\frac{Ts}{\tau_e}\right)\right] / (\tau_p - \tau_e) \quad (\text{eq } 66b)$$

$$\alpha_{33} = \exp\left(-\frac{Ts}{\tau_e}\right) \quad (\text{eq } 66c)$$

-continued $$\beta_3 = \left(\frac{60}{1}\right) \cdot \left(\left[\tau_s^2 \cdot (\tau_p - \tau_e) \cdot \left(1 - \exp\left(-\frac{Ts}{\tau_s}\right)\right)\right] - \tau_p^2 \cdot (\tau_s - \tau_e) \cdot \left[1 - \exp\left(-\frac{Ts}{\tau_p}\right)\right] + \tau_e^2 \cdot (\tau_s - \tau_p) \cdot \left[1 - \exp\left(-\frac{Ts}{\tau_e}\right)\right]\right) / (\tau_s - \tau_p) \cdot (\tau_s - \tau_e) \cdot (\tau_p - \tau_e) \quad (\text{eq } 66d)$$

Here, Ts is the sampling time, which is five minutes for this example, $\tau_s$ is the time constant for estimated subcutaneous insulin level in minutes, which is set to 50 for this example, $\tau_p$ is the time constant for estimated plasma insulin level in minutes, which is set to 70 for this example, and $\tau_e$ is the time constant for estimated interstitial insulin level in minutes, which is set to 55 for this example.

ID(n) is the calculated and administered insulin infusion.
The notation (n−1) indicates values at the previous time step.
$I_{SC}$ is the subcutaneous insulin model estimate/prediction.
$I_P$ is the plasma insulin model estimate/prediction.
$I_{EFF}$ is the effective site insulin model estimate/prediction.

For this particular example, the insulin PK model parameters $\alpha_{11}$, $\alpha_{21}$, $\alpha_{22}$, $\alpha_{31}$, $\alpha_{32}$, $\alpha_{33}$, $\beta_1$, $\beta_2$, and $\beta_3$ are set to 0.9802, 0.014043, 0.98582, 0.000127, 0.017889, 0.98198, 1.1881, 0.0084741, and 0.00005, respectively. These values were calculated from PK-PD data for insulin as part of an empirical study and investigation. It should be appreciated that the specific values presented here merely reflect one possible set of suitable values, and that any one or more of these values may be adjusted as appropriate for the particular embodiment.

Insulin Limit

The final infusion rate as calculated by Equation 55 is limited such that is does not exceed the maximum upper insulin limit (Umax) as indicated below in Equation 67:

$$u(n) = \begin{cases} U\max, & u(n) > U\max \\ u(n), & u(n) \leq U\max \end{cases} \quad (\text{eq } 67)$$

Umax is calculated as indicated by Equation 68:

$$U\max = I_{basal,0} + \frac{BG_{LBL} - FBG_0}{KI} \quad (\text{eq } 68)$$

Here, Umax is the upper insulin limit bounded at $BG_{LBL}$ (see Equation 68a below), and $I_{basal,0}$ is the basal rate defined for the user to bring the patient to a Fasting Blood Glucose (FBG) of the value $FBG_0$ mg/dL. $BG_{LBL}$ (mg/dL) is the lower buffer limit BG when reaching Umax, $FBG_0$ is the estimated blood glucose using meter blood glucose readings at the end of the night period, and KI is insulin gain as calculated by Equation 69 below.

$$BG_{LBL} = Setpoint - ILB \quad (\text{eq } 68a)$$

Here, $BG_{LBL}$ (mg/dL) is the lower buffer limit BG when reaching Umax, Setpoint is the target glucose setpoint value 944 (FIG. 49) that is defined by the user, and ILB is the insulin limit buffer, which is an amount (in mg/dL) that the system allows as an additional buffer to handle higher insulin needs. For example, an ILB of 50 allows the system to deliver additional insulin to lower by 50 mg/dL from the Setpoint.

$$KI = -IS * 3\left(\frac{mg}{dL} \text{ per } \frac{U}{h}\right) \qquad (eq\ 69)$$

Here, KI is insulin gain, and IS is the insulin sensitivity estimated by the 1800 rule as IS=1800/TDI (Total Daily Insulin). In certain embodiments, the value of Umax may reach 150 Units/hour. In a typical implementation, the value of Umax is calculated on a per-patient basis, and the typical range for Umax is between 0.5 to 3.0 Units/hour.

Moreover, if the insulin limit is active, then the integral component of the PID algorithm is frozen to its previous value. This feature can be employed to assist in the prevention of integral wind up. This information is passed back to the PID-IFB control module 906 for use during the next PID calculation.

$$I(n) = \begin{cases} I(n-1), & u(n) = U \max \\ I(n), & u(n) < U \max \end{cases} \qquad (eq\ 70)$$

As mentioned above, previous studies may be leveraged for purposes of configuring and/or operating the PID-IFB control module 906. A first study (Study 1; Panteleon et al., 2006) looked at the effect of changing the controller gain in a study on eight diabetic dogs. The nominal gain was calculated based on the total daily dose of insulin for one experiment; in duplicate experiments this nominal gain was increased and decreased by fifty percent. Insulin delivery in the six-hour postprandial period tended to increase with increasing gain, but this did not achieve statistical significance. This was due to feedback, with lower insulin delivered as glucose levels fell. In essence, the higher gains tended to give more insulin earlier (achieving much better glucose regulation), and reducing the infusion later, whereas the lower gains tended to keep insulin infusion above basal for a longer period of time due to the glucose levels remaining significantly above target. Note that the controller gain affects all of the components of the PID algorithm, including the integral and derivative terms.

A second study (Study 2; Steil et al., 2006) applied a PID controller to ten human subjects. In this study the nominal controller gain was about 42 percent higher than that proposed here, with the integral time constants the same (therefore also a higher integral response), but slightly lower derivative time constants (defined in terms of rising or falling blood glucose, instead of day or night response). In the proposed embodiment presented here, the night-time derivative time constant is just slightly lower than that used in Study 2.

A third study (Study 3; Weinzimer et al., 2008) applied a PID controller to seventeen human subjects. For a subset of eight subjects, no pre-meal bolus was given, while in the remaining nine subjects about 50 percent of the standard meal bolus was given about fifteen minutes before the meal. The controller tuning was the same as that proposed herein. In both cases, performance was acceptable, with the pre-meal bolus helping to lower the postprandial peak glucose excursion. When compared with home treatment using standard pump therapy, both closed-loop algorithms were superior, reducing both glucose excursions above 180 mg/dl and below 70 mg/dl.

One of the observations from Study 3 was that the meal-related insulin infusion persisted above pre-meal levels for at least four hours after the meal. This result led to the introduction of insulin feedback to the algorithm, which serves to compensate for insulin already delivered, while at the same time allowing for more aggressive action at the start of meals, where it is needed.

In particular implementations, some of the parameters mentioned above for the PID-IFB control module 906 can be fixed. In this regard, the following values may be utilized in an exemplary embodiment. It should be appreciated that these values are provided here for illustrative purposes only, and that an implementation of the PID-IFB control module 906 may utilize different values if so desired.

$\gamma_1$=0.64935
$\gamma_2$=0.34128
$\gamma_3$=0.0093667
$\alpha_{11}$=0.90483741803596
$\alpha_{21}$=0.065563404170158
$\alpha_{22}$=0.931062779704023
$\alpha_{31}$=0.00297495042963571
$\alpha_{32}$=0.083822962634882
$\alpha_{33}$=0.083822962634882
$\beta_1$=5.70975491784243
$\beta_2$=0.202428967549153
$\beta_3$=0.202428967549153

The values of the PID parameters mentioned above ($K_P$, $\tau_I$, and $\tau_D$) are not expected to change, but it may be desirable to adjust them if doing so would improve the response of the glucose excursion. The nominal values for these PID parameters, together with exemplary allowable ranges, are shown in Table 2.

TABLE 2

Adjustable Parameters For the PID-IFB Control Module

| Parameter | Nominal Value | Lower Bound | Upper Bound |
|---|---|---|---|
| Controller gain: $K_P$ | $1 \times K_{P0} \times (1 + \gamma_1 + \gamma_2 + \gamma_3)$ | $0.05 \times K_{P0} \times (1 + \gamma_1 + \gamma_2 + \gamma_3)$ | $20 \times K_{P0} \times (1 + \gamma_1 + \gamma_2 + \gamma_3)$ |
| Integral time constant: $\tau_I$ | 250 min | 10 min | 1500 min |
| Derivative time constant: $\tau_D$ | 75 min | 10 min | 500 min |
| UnwindLow (mg/dL) | 80 | 0 | 200 |
| UnwindHigh (mg/dL) | 100 | 0 | 200 |
| Imax | $2.5 \times (1 + \gamma_1 + \gamma_2 + \gamma_3) \times$ Basal Rate | 0 | $10 \times (1 + \gamma_1 + \gamma_2 + \gamma_3) \times$ Basal Rate |

The lower bound for the controller gain $K_{P0}$ would lower it by 95 percent from the nominal, resulting in an overall less aggressive response of the controller 900, and resulting in less insulin delivered for the same glucose level and trend. The upper bound allows this gain to be increased up to 20 times from the nominal. Although this would result in more insulin being given, this is always with respect to the actual glucose level and its derivative, rapidly falling blood glucose, even with an elevated blood glucose level, results in a decreased delivery of insulin due to the derivative component.

The integral time constant $\tau_I$ determines how fast a deviation in the blood glucose from the desired glucose target accumulates. A higher value results in a slower response to persistent deviations in glucose from target. Lastly, the derivative time constant TD can safely be decreased all the way to zero, as the lower it is the less insulin will be delivered. Anything much higher than the upper bound of 500 minutes would make the controller too sensitive to small changes in the rate of change of the sensor glucose, which even though it is not necessarily dangerous, is still undesirable in terms of overall performance.

IOB Compensation Module

Figure 52:
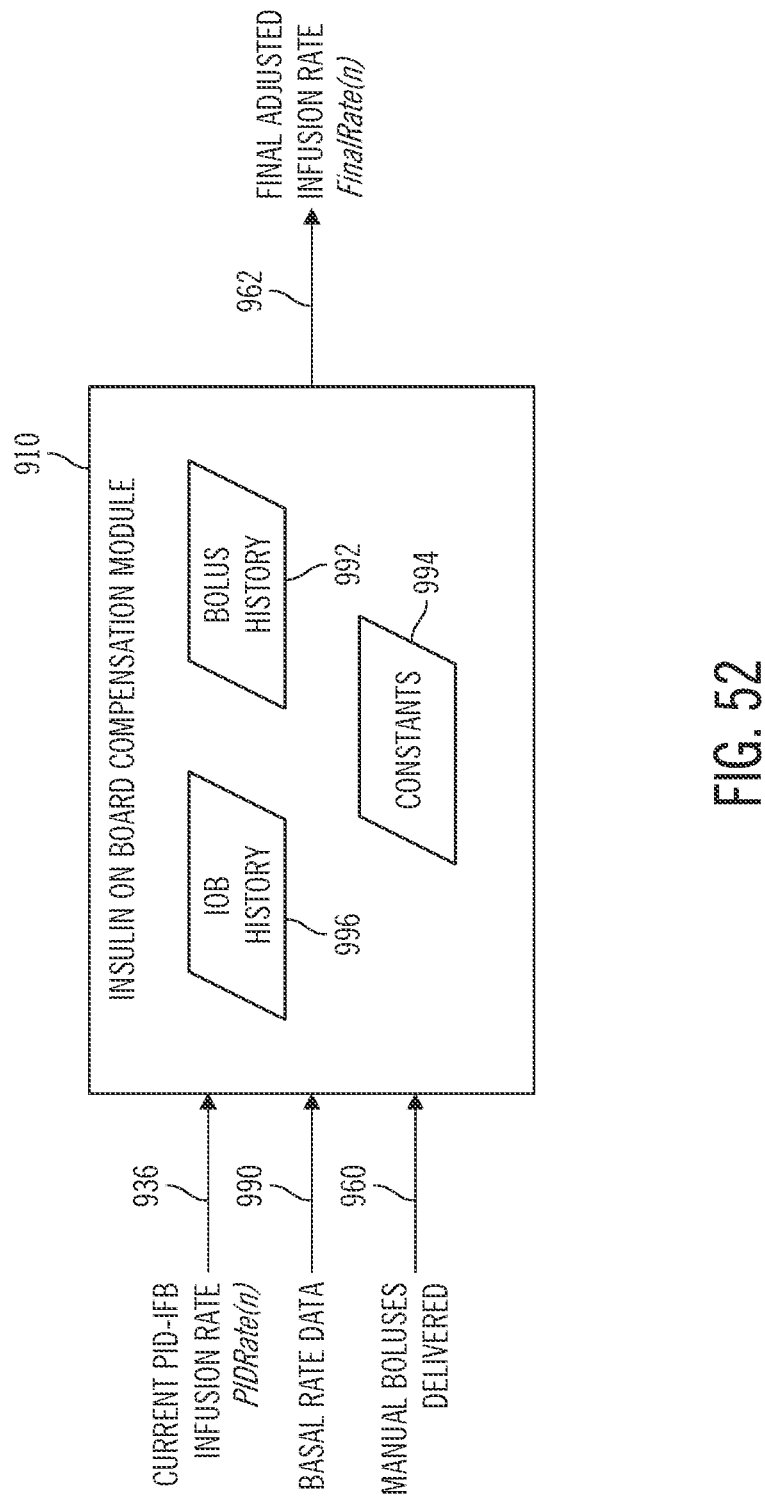
FIG. 52 is a block diagram that schematically illustrates an exemplary embodiment of an insulin on board (IOB) compensation module.

FIG. 52 is a block diagram that schematically depicts one suitable embodiment of the IOB compensation module 910 in additional detail. As mentioned briefly above, the IOB compensation module 910 adjusts the current insulin dose 958 (i.e., the insulin infusion rate as computed by the PID-IFB control module 906) as needed to generate the final insulin dose 962 (i.e., the final adjusted infusion rate used by the insulin infusion device). The IOB compensation module 910 may also receive basal rate data 990 and the information related to the manual boluses delivered 960 as input for purposes of calculating the current value of the final insulin dose 962 and/or for purposes of calculating future values of the final insulin dose 962. The basal rate data 990 may indicate the current basal rate of insulin being delivered to the user, and the manual boluses delivered 960 may indicate the amount for each bolus administered to the user, along with timestamp data corresponding to the delivery date/time of each bolus. In this regard, the manual boluses delivered 960 may include information for any number of boluses delivered in the past, and the manual boluses delivered 960 can be updated as needed in response to each bolus that is delivered going forward. Moreover, the basal rate could be dynamically adjusted if needed or desired (automatically by the system, by the user, by a caregiver, etc.).

The manual boluses delivered 960 may be collected and saved in association with the IOB compensation module 910 for use as bolus history 992. In this regard, the bolus history 992 may include any number of past bolus amounts administered during a given period of time. The IOB compensation module 910 may also use a number of constants, parameters, coefficients, configuration settings, gain values, or the like (for simplicity, the constants 994 shown in FIG. 52 are intended to encompass these and any other quantities that might be used by the IOB compensation module 910 to calculate the final insulin dose 962. FIG. 52 also depicts IOB history 996, which represents previously calculated IOB values (i.e., historical IOB values calculated for past sampling times). As explained in more detail below, the IOB history 996 and the bolus history 992 may influence the determination of the final insulin dose 962. It should be appreciated that the bolus history 992, the constants 994, and the IOB history 996 can be stored and maintained in one or more memory storage elements of the host system. FIG. 52 shows these data items "inside" the IOB compensation module 910 for simplicity and ease of description.

The IOB compensation module 910 provides an additional safeguard that estimates the insulin on board the body of the patient from manual boluses that were delivered prior to activation of the closed-loop mode, to compensate the final insulin dose 962 and help avoid over-delivery of insulin. When the system initially enters the closed-loop mode, the IOB compensation module 910 considers the manual boluses delivered 960 that have been administered over a defined period of time (e.g., the last eight hours), and subtracts the manual boluses. Thereafter, during the closed-loop mode, the IOB compensation module adjusts for manual boluses that were delivered during each sampling period (e.g., every five minutes).

Figure 53:
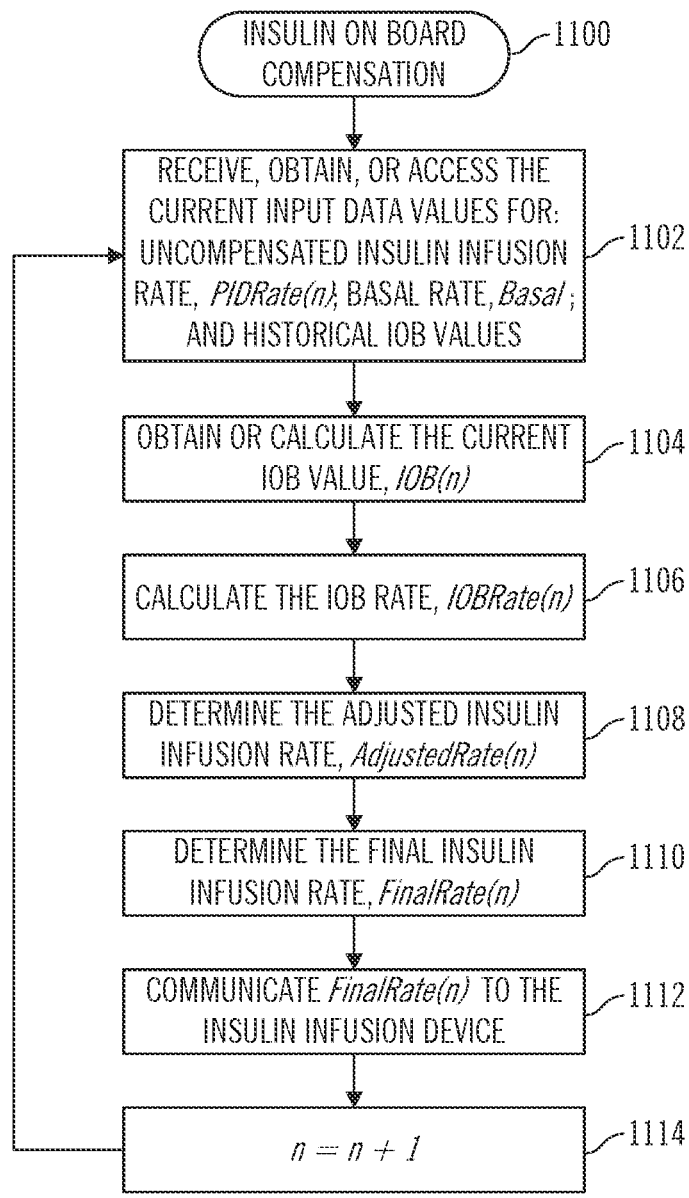
FIG. 53 is a flow chart that illustrates an exemplary embodiment of an IOB compensation process.

FIG. 53 is a flow chart that illustrates an exemplary embodiment of an IOB compensation process 1100, which may be performed by the IOB compensation module 910. The process 1100 represents one iteration that is performed for a current sampling point or time, n. Accordingly, the process 1100 receives, obtains, or accesses a variety of inputs that may have an influence on the output of the IOB compensation module (task 1102). For example, the process 1100 may utilize the current value of the uncompensated insulin infusion rate, PIDRate(n), as generated by the PID-IFB control module 906. The process 1100 may also use the current basal rate (provided with the basal rate data 990), some of the bolus history 992, and/or some of the IOB history 996 as needed.

In the context of the process 1100, the IOB compensation module 910 calculates insulin on board from manual boluses at each cycle and compensates the controller output rate (insulin infusion rate) if active IOB is greater than a certain threshold. Accordingly, the process 1100 calculates, generates, or otherwise obtains a current IOB value (task 1104) that represents an estimate of active insulin in the body of the user. In certain embodiments, the active IOB is estimated in accordance with a discretized three-compartment insulin pharmacokinetic (PK) model, as indicated below:

$$IOB(n) = ci_1 \cdot IOB(n-1) + ci_2 \cdot IOB(n-2) + ci_3 \cdot IOB(n-3) + \quad \text{(eq 71)}$$
$$cb_0 \cdot U\text{bolus}(n) + cb_1 \cdot U\text{bolus}(n-1) + cb_2 \cdot U\text{bolus}(n-2)$$

Here, IOB is the active insulin on board, Ubolus is the amount of manual bolus delivered in units per sample, n is the current sampling point, n−1 is the last sampling point, n−2 is the second to last sampling point, and n−3 is the third to last sampling point. Accordingly, the process 1100 obtains the current IOB value, IOB(n), based at least in part on historical bolus delivery data for the user (see the manual boluses delivered 960 and the bolus history 992 in FIG. 52). The parameters $ci_1$, $ci_2$, $ci_3$, $cb_0$, $cb_1$, and $cb_2$ are the coefficients of the insulin absorption model. These parameters are calculated based on the three time constants ($\tau_{sc}$, $\tau_p$, and $\tau_{eff}$) of the insulin pharmacokinetic model, as indicated below:

$$ci_1 = eaxx3 + eaxx4 + eaxx5 \quad \text{(eq 71a)}$$

$$ci_2 = -(eaxx3 \times eaxx4 + (eaxx3 + eaxx4) \times eaxx5) \quad \text{(eq 71b)}$$

$$ci_3 = eaxx3 \times eaxx4 \times eaxx5 \quad \text{(eq 71c)}$$

$$cb_0 = 1$$

$$cb_1 = \quad \text{(eq 71d)}$$
$$dprod \times (-(daxx22 \times eaxx3 + daxx22 \times eaxx4) \times axx3 \times axx4 +$$
$$(daxx31 \times eaxx3 + daxx31 \times eaxx5) \times axx3 \times axx5 -$$
$$(daxx32 \times eaxx4 + daxx32 \times eaxx5) \times axx4 \times axx5)$$

$$cb_2 = \quad \text{(eq 71e)}$$
$$dprod \times (daxx22 \times eaxx3 \times eaxx4 \times axx3 \times axx4 + daxx32 \times eaxx4 \times$$
$$eaxx5 \times axx4 \times axx5 - daxx31 \times eaxx3 \times eaxx5 \times axx3 \times axx5)$$

Where:

$$axx3 = 1/\tau_{SC} \quad \text{(eq 71f)}$$

$$axx4 = 1/\tau_p \quad \text{(eq 71g)}$$

$$axx5 = 1/\tau_{eff} \quad \text{(eq 71h)}$$

$$eaxx3 = e^{-axx3 \cdot TsC} \quad \text{(eq 71i)}$$

$$eaxx4 = e^{-axx4 \cdot TsC} \quad \text{(eq 71j)}$$

-continued $$eaxx5 = e^{-axx5 \cdot TsC} \quad \text{(eq 71k)}$$

$$daxx22 = axx4 - axx3 \quad \text{(eq 71l)}$$

$$daxx31 = axx5 - axx3 \quad \text{(eq 71m)}$$

$$daxx32 = axx5 - axx4 \quad \text{(eq 71n)}$$

$$dprod = -1/(daxx22 \times daxx31 \times daxx32) \quad \text{(eq 71o)}$$

In the above equations TsC indicates a modified sampling interval in minutes, which can be calculated as TsC=Ts*6/CurveSpeed, where Ts is the sampling interval and CurveSpeed is the insulin on board decay speed rate in hours. $\tau_{SC}$, $\tau_p$, and $\tau_{eff}$ are the respective time constants of the subcutaneous, plasma, and effective compartments of the insulin PK model.

IOB (in Units) as calculated by Equation 71 represents the residual active insulin in the body from manual boluses (that may have been administered before the start of the closed-loop mode or during closed-loop operation) which must be taken into account for calculation of the final insulin delivery rate. This is achieved by first calculating the IOB rate (task 1106) and then deducting the IOB rate from the PID-IFB calculated infusion rate, as indicated below. Accordingly, in certain situations the process 1100 determines an adjusted insulin infusion rate (task 1108) based at least in part on the calculated IOB rate and the uncompensated insulin infusion rate, PIDRate(n):

$$IOB \text{ Rate } (n) = \begin{cases} \text{Gain} IOB \times IOB(n), & IOB(n) > \text{Min } IOB \\ 0, & IOB(n) \le \text{Min } IOB \end{cases} \quad \text{(eq 72)}$$

$$\text{Adjusted Rate } (n) = \max(0, \ PID \text{ Rate } (n) - IOB \text{ Rate } (n)) \quad \text{(eq 73)}$$

Note that the process 1100 calculates the IOB rate, IOBRate (n), based at least in part on the current IOB value, IOB(n). The IOB rate, which is expressed in Units per hour (U/h), represents the amount of active insulin accumulated from manual boluses in the body per unit of time. Hence, this additional insulin which is already present in the body is deducted from the controller delivery rate (PIDRate). This accounts for all the manual boluses that have been administered by the user, and minimizes the possibility of over-delivery by the controller. Here, GainIOB is the IOB decay rate in $h^{-1}$, and MinIOB is the minimum IOB required to compensate the PIDRate (where MinIOB is expressed in Units). Thus, the IOB rate is calculated to be equal to the current IOB value multiplied by an IOB decay rate when the current IOB value is greater than a minimum IOB value, and is calculated to be equal to zero when the current IOB value is less than or equal to the minimum IOB value. In this regard, MinIOB is a minimum threshold for IOB, below which the effect of IOB on glucose is considered to be negligible; hence not needed to be compensated.

As reflected in Equation 73, the process 1100 selects the adjusted insulin infusion rate to be the maximum of zero or the difference between the uncompensated insulin infusion rate and the calculated IOB rate (from task 1106). Note that the difference between PIDRate and IOBRate could be negative, as these values are calculated from different sources. PIDRate is the controller calculated infusion rate and IOBRate is the accumulated active insulin in the body obtained from manual boluses. Accordingly, Equation 73 ensures that the AdjustedRate does not fall below zero.

Next, the process 1100 may calculate, select, or otherwise determine a final insulin infusion rate (task 1110). In certain embodiments, the final insulin infusion rate (the final insulin dose 962 in FIG. 49) is calculated as indicated below:

$$\text{Final Rate } (n) = \begin{cases} \max(\text{Basal, Adjusted Rate }(n)), & PID \text{ Rate } > \text{Basal} \\ PID \text{ Rate } (n), & PID \text{ Rate } \le \text{Basal} \end{cases} \quad \text{(eq 74)}$$

As indicated by this expression, the process 1100 selects either the adjusted insulin infusion rate (AdjustedRate(n)), the uncompensated insulin infusion rate (PIDRate(n)), or the current basal rate (Basal) to serve as the final insulin infusion rate (FinalRate(n)) for the insulin infusion device. Here, PIDRate is the insulin infusion rate as calculated by the PID-IFB control module 906 and Basal is the current pre-programmed pump basal rate. Accordingly, task 1110 selects the final insulin infusion rate to be equal to the uncompensated insulin infusion rate when the current basal rate is greater than or equal to the uncompensated insulin infusion rate. In contrast, when the current basal rate is less than the uncompensated insulin infusion rate, task 1110 selects the final insulin infusion rate to be either the current basal rate or the adjusted insulin infusion rate, whichever is higher.

In the context of task 1110, the PIDRate is used as the FinalRate (when PIDRate is less than or equal to Basal) to allow the controller to "apply brakes" (in other words, suppress insulin delivery rate) in order to prevent any potential hypoglycemia. On the other hand, when PIDRate is greater than Basal, the FinalRate will be the maximum of Basal or AdjustedRate, which ensures that the insulin adjustment only accounts for the insulin coming from boluses, and not the basal. A lower bound (i.e., the value of Basal) is applied to the FinalRate when PIDRate is greater than Basal; this lower bound is utilized to prevent over-compensation of insulin on board under these circumstances.

The process 1100 may continue by communicating or otherwise providing the final insulin infusion rate, FinalRate (n), to the insulin infusion device (task 1112). For embodiments where the process 1100 is executed natively by the insulin infusion device itself, then the process 1100 may simply provide the final insulin infusion rate to the processing logic or fluid delivery control module of the infusion device. In turn, the insulin infusion device responds by regulating delivery of insulin in accordance with the final insulin infusion rate.

This description assumes that the process 1100 is repeated for each sampling time. For the next sampling time, therefore, the value of n may be incremented by one (or by any desired amount) to establish an index for the next iteration of the process 1100 (task 1114). Thereafter, the process 1100 may return to task 1102 to obtain the newest input data values and to repeat the various tasks described above. Accordingly, the process 1100 facilitates regulation of insulin delivery to the body of the user in a controlled and ongoing manner by continuously adjusting the final insulin infusion rate while the system is operating in the closed-loop mode.

In certain embodiments, it may be desirable to adjust some of the parameters utilized by the IOB compensation module 910 if doing so would improve performance. The nominal values for these parameters, together with exemplary allowable ranges, are shown in Table 3.

TABLE 3

Adjustable Parameters For the IOB Compensation Module

| Parameter | Nominal Value | Lower Bound | Upper Bound |
|---|---|---|---|
| CurveSpeed | 6 | 1 | 8 |
| GainIOB | 1.25 | 0 | 5 |
| MinIOB | 1 | 0 | 500 |

Insulin Delivery Timeout Module

The insulin delivery timeout module 912 is suitably designed and configured to continuously monitor (during the closed-loop mode) if the patient is receiving insulin at the insulin limit (Umax) or no insulin (Umin, which may be defined as insulin delivery at little to no Units/Hour) for a prolonged period of time. If one of these insulin delivery conditions is detected, the system will issue a warning and continue operating under the closed-loop mode. As mentioned previously, the insulin delivery timeout module 912 may process the insulin delivered 960 as an input.

Accordingly, the insulin delivery timeout module 912 introduces an additional safeguard that checks for a series of steps as described below for the delivery of insulin at the insulin limit (Umax Timeout) or no insulin (Umin Timeout) for a prolonged period of time. This is achieved by calculating the total amount of insulin delivered by the system during the closed-loop mode in a pre-specified moving window that is identified as the insulin time window.

Regarding the Umin Timeout condition, once the insulin time window for Umin (which may be defined as delivering insulin at zero Units/Hour) has been reached from the start of the closed-loop mode, the system will monitor the amount of insulin being delivered at the user specified insulin time window and compare it with the amount that could have been delivered if operating at the patient's basal rate for the same time span, as shown in the following logical expression.

$$\text{Pump Delivery Rate} = \begin{cases} \text{Final Rate,} & \text{if } U_{Tot}^{WinMin} > (\text{Min Delivery } Tol/100) \times U_{Basal}^{WinMin} \\ \text{Alert,} & \text{if } U_{Tot}^{WinMin} \leq (\text{Min Delivery } Tol/100) \times U_{Basal}^{WinMin} \end{cases} \quad (\text{eq 75})$$

Here, Pump Delivery Rate (Units/Hour) is the infusion rate, which is either equal to the FinalRate from Equation 74 (i.e., the infusion rate calculated by the controller during the closed-loop mode), or a pre-programmed overnight basal rate that is used during open-loop operation. The quantity $U_{Tot}^{WinMin}$ is the total amount of insulin delivered (in Units) by the closed-loop control algorithm in a user-specified insulin time window for Umin, and the quantity $U_{Basal}^{WinMin}$ is the total amount of insulin that could be delivered if operating at a pre-programmed overnight basal rate in the same insulin time window for Umin. The parameter MinDeliveryTol is a user-specified tolerance, in percentage of $U_{Basal}^{WinMin}$, that the system has to deliver in order to stay in the closed-loop mode.

In accordance with this particular example, closed-loop control continues as long as the total amount of insulin delivered during the insulin time window (which is set to 120 minutes for this example) by the system is greater than the total amount of insulin that might have been delivered if operating at five percent (which is the default minimum tolerance for this example) of basal. Moreover, a fail-safe alert is triggered once the total amount of insulin delivered during the insulin time window (120 minutes) by the system is less than five percent of basal.

Regarding the Umax Timeout condition, once the insulin time window for Umax has been reached from the start of the closed-loop mode, the system will monitor the amount of insulin being delivered at the user specified insulin time window and compare it with the amount that might be delivered if operating at the Umax rate for the same time span, as shown in the following logical expression.

$$\text{Pump Delivery Rate} = \begin{cases} \text{Final Rate,} & \text{if } U_{Tot}^{WinMax} < (\text{Max Delivery } Tol/100) \times U_{max}^{WinMax} \\ \text{Alert,} & \text{if } U_{Tot}^{WinMax} \geq (\text{Max Delivery } Tol/100) \times U_{max}^{WinMax} \end{cases} \quad (\text{eq 76})$$

Here, Pump Delivery Rate is the infusion rate, which is equal to either the FinalRate or a pre-programmed overnight basal rate that is used during operation in the open-loop mode. The quantity $U_{Tot}^{WinMax}$ is the total amount of insulin delivered (in Units) by the closed-loop control algorithm in a user-specified insulin time window for Umax, and the quantity $U_{max}^{WinMax}$ is the total amount of insulin that could have been delivered in the user-specified moving window for Umax if operating at a calculated Umax rate. The parameter MaxDeliveryTol is a user-specified tolerance, in percentage of $U_{max}^{WinMax}$, that the system must adhere to in order to stay in the closed-loop mode.

In accordance with this particular example, closed-loop control continues as long as the total amount of insulin delivered during the insulin time window (which is set to 600 minutes for this example) by the system is less than the total amount of insulin that might have been delivered if operating at 95% (which is the default maximum tolerance for this example) of Umax. Moreover, a fail-safe alert is triggered once the total amount of insulin delivered during the insulin time window (600 minutes) by the system is greater than the total amount that might have been delivered if operating at 95% of Umax.

In certain embodiments, it may be desirable to adjust some of the parameters utilized by the insulin delivery timeout module 912 if doing so would improve performance. The nominal values for these parameters, together with exemplary allowable ranges, are shown in Table 4.

TABLE 4

Adjustable Parameters For the Insulin Delivery Timeout Module

| Parameter | Nominal Value | Lower Bound | Upper Bound |
|---|---|---|---|
| Insulin Time Window for Umin | 120 minutes | 30 minutes | 600 minutes |
| Insulin Time Window for Umax | 600 minutes | 30 minutes | 600 minutes |
| MinDeliveryTol | 5% | 0% | 100% |
| MaxDeliveryTol | 95% | 0% | 100% |

Model Supervisor Module: First Embodiment

The model supervisor module 914 is similar to the insulin delivery timeout module 912 in that it monitors and polices the system during closed-loop operation. In practice, closed-loop systems are only aware of signals (inputs) that are being provided by the measurement device(s). If measurements deviate from true values, the control system may react to the deviation. When using continuous glucose sensors for diabetes, the sensors provide the measurements to the closed-loop control system and, based on these measurements, insulin is delivered to the subject. Accordingly, sensor performance and integrity should be closely monitored. Fortunately, there is a relationship between the insulin and meal intake to the glycemic response. This relationship can be translated into a mathematical model that is able to predict the sensor glucose response based upon the insulin delivered. The sensitivity of sensor glucose to insulin delivered is patient-specific (the sensitivity can usually be learned over a period of three to six days for each patient).

The model supervisor module 914 uses a mathematical model that enables individualization of a patient's unique blood glucose time-dependent response. The model describes the sensor glucose time-dependent response as a function of insulin and meal intake. The exemplary mathematical model described herein has a number of benefits and advantages: it is linear, physiologically-based, and includes only parameters that have direct connection to measurable data (sensor glucose and insulin delivered). These features are important because a linear model is easy to analyze and predict. Moreover, a physiological-based model facilitates an understanding of the origin of the predictions (e.g., insulin sensitivity, meal intake, etc.), and use of measureable data reduces the need to estimate unobserved variables (e.g., metabolism, cell activity, etc.).

Figure 54:
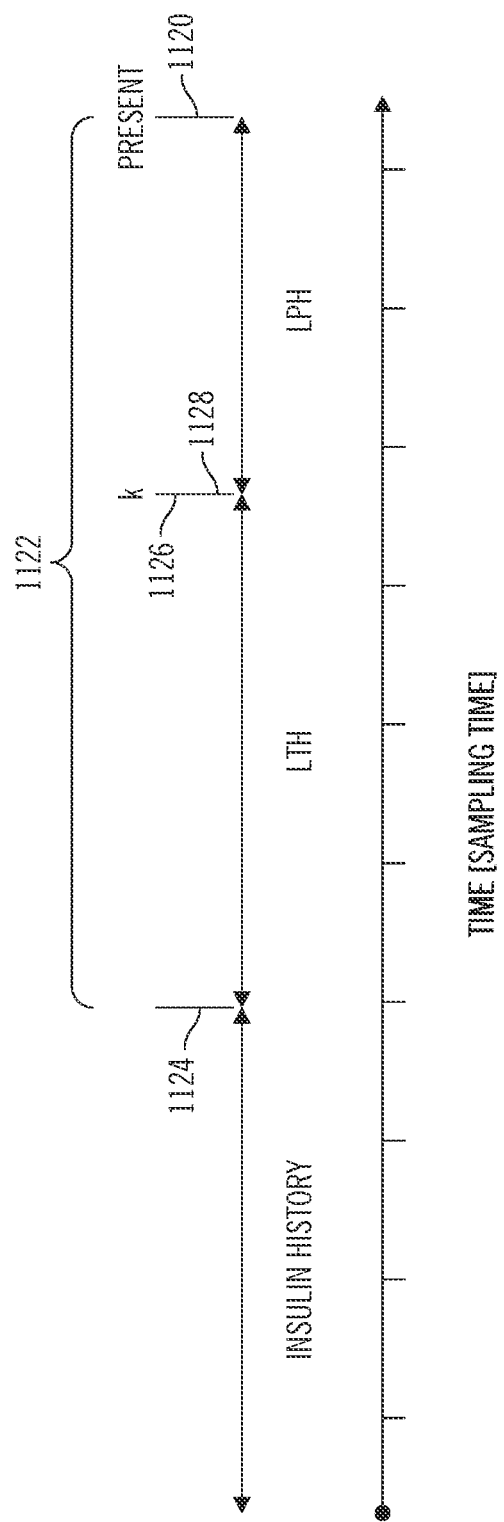
FIG. 54 is a diagram that depicts certain time events associated with the operation of a model supervisor module.

FIG. 54 is a diagram that defines certain time events for the model supervision. The label "present" indicates the most recent sampling time or sampling period 1120, and k is equal to the present sampling time minus a period corresponding to a length of prediction horizon (LPH) in sampling times. FIG. 54 also indicates a period corresponding to a length of training horizon (LTH) in sampling times, which refers to a model training period. Insulin history is defined as the length of data needed to estimate the plasma insulin. In order for the model supervisor module 914 to be able to estimate a fault, it considers the records of the insulin delivered over the past insulin history plus the LTH and the LPH sampling periods, and at least 80 percent of the Isig (electrical signal) measurements from k-LTH and k.

As described in more detail below, the model supervisor module 914 considers a "moving window" that includes a historical time period 1122 that is defined from the present (most recent sampling period 1120) back to the beginning of the LTH. The moving window considered by the model supervisor module 914 may also include insulin history that precedes the LTH, as depicted in FIG. 54. Data obtained during each window of time is processed and analyzed at or near the present time and preferably before the next sampling period has ended. Thus, at the end of each new sampling period, the "moving window" shifts by one sampling period such that the model supervisor module 914 can consider the most recently obtained data for the current sampling period while disregarding the data that no longer appears within the updated window of time (i.e., the oldest data is no longer considered). The historical time period 1122 may be defined by the LTH and the LPH, which for this example immediately follows the LTH (as shown in FIG. 54). The LPH may also be referred to herein as the "recent history period" or the "model prediction period" for reasons that will become apparent from the following description. The LTH may also be referred to herein as the "distant history period" or the "model training period" for reasons that will become apparent from the following description. In this regard, the LTH (distant history period) corresponds to a period of time from a begin-training sampling period 1124 to an end-training sampling period 1126, inclusive, while the LPH (recent history period) corresponds to a period of time from a begin-prediction sampling period 1128 to the most recent sampling period 1120, inclusive. Accordingly, by definition the current sampling period (i.e., the most recent sampling period 1120) resides within the LPH. For this particular example, the begin-prediction sampling period 1128 corresponds to the end-training sampling period 1126. Alternatively, the begin-prediction sampling period 1128 may immediately follow the end-training sampling period 1126.

Figure 55:
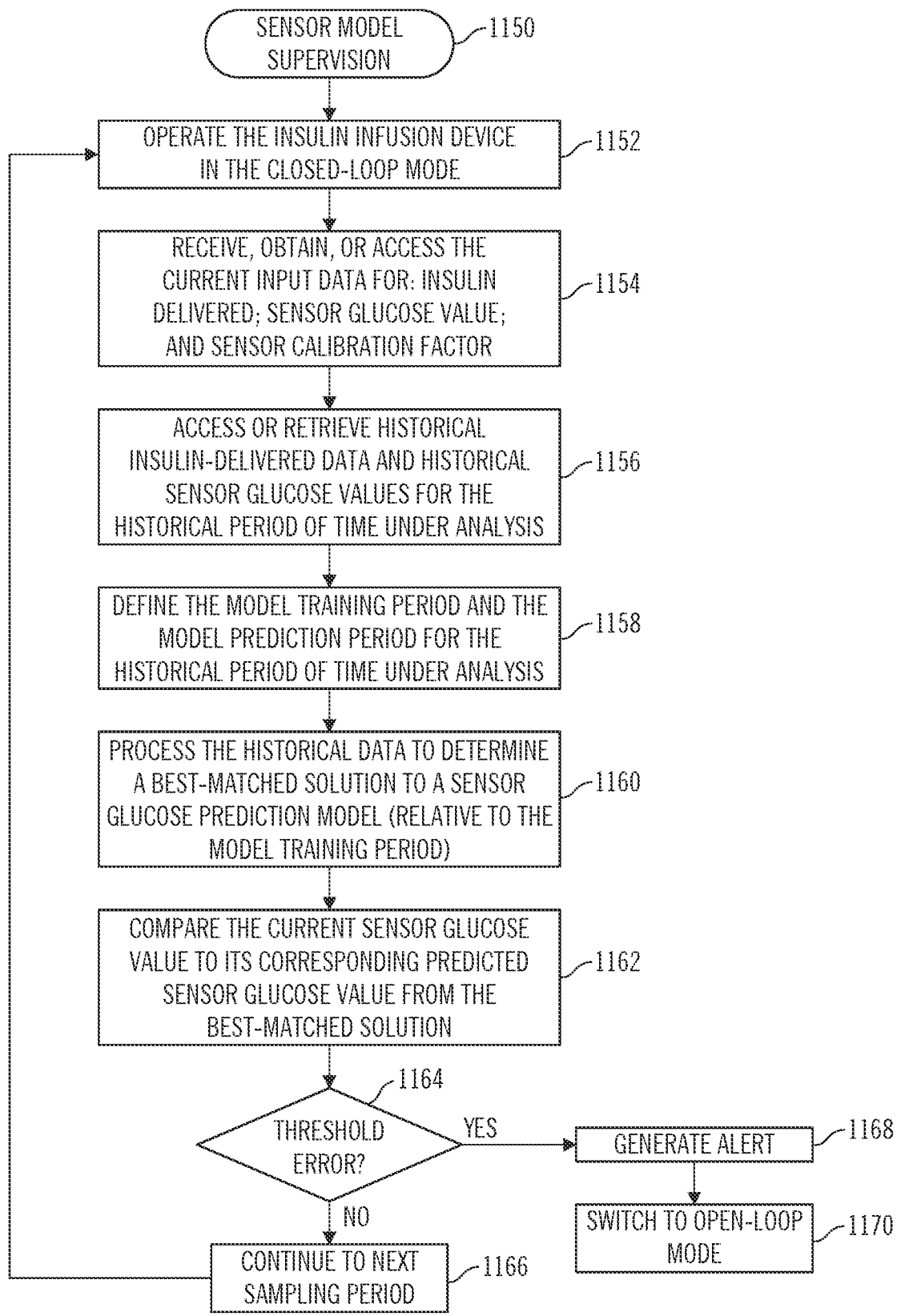
FIG. 55 is a flow chart that illustrates an exemplary embodiment of a sensor model supervision process.

FIG. 55 is a flow chart that illustrates an exemplary embodiment of a sensor model supervision process 1150, which may be performed by the model supervisor module 914. The process 1150 is shown and described in a simplified manner that focuses on functionality for ease of understanding. Certain aspects of the process 1150 are addressed in more detail below with reference to particular representations of the model supervisor module 914.

The process 1150 represents one iteration that is performed for a current sampling point or time, which corresponds to the most recent sampling period. This example assumes that the insulin infusion device is already operating in the closed-loop mode (task 1152) to deliver insulin to the body of the user, and that the process 1150 receives relevant data in accordance with a predetermined schedule (e.g., a sampling period of five minutes). Accordingly, the process 1150 receives, obtains, or accesses a variety of inputs that may have an influence on the operation of the model supervisor module 914 (task 1154). For example, the process 1150 may receive at least the following data for the current sampling period: current insulin-delivered data that indicates an amount of insulin delivered by the insulin infusion device during the most recent sampling period; current sensor data that indicates a current sensor glucose value for the user, which corresponds to the most recent sampling period; and a current sensor calibration factor, which may be needed to compensate for recent meter-based calibrations. Any amount of historical data could also be received during task 1154 if so desired. Thus, some amount of redundancy may be built into the system (which may be desirable to account for missed transmissions, lost packets, or the like). The sensor data may be received and processed in any suitable form. For example, a continuous glucose sensor may generate Isig (electrical current) values that can be mapped to sensor glucose values. The model supervisor module 914 may be suitably configured to process Isig values directly, or it could translate or map the raw Isig values into any desired representation.

The process 1150 may also access or retrieve historical data that was received for past sampling periods (task 1156). Task 1156 may represent an initialization routine that populates a grid, matrix, or other type of database structure as needed to prepare the model supervisor module 914 for the various calculations, analyses, and functions described in more detail below. It should be appreciated that subsequent iterations of the process 1150 (which are performed in an ongoing manner during the closed-loop mode) need not repeat the initialization of the historical data. Rather, task 1156 may simply adjust the data history to reflect newly received data. For the embodiments described here, the following historical data may be processed by the model supervisor module 914, without limitation: historical insulin-delivered data for the user; and historical sensor glucose values for the user. The historical insulin-delivered data may correspond to amounts of insulin delivered by the insulin infusion device during each historical sampling period of interest, and the historical sensor glucose values may correspond to respective sensor glucose measurements obtained during each historical sampling period of interest. In certain implementations, each historical sensor glucose value may be associated with or derived from a historical Isig value and a sensor calibration factor.

The process 1150 is iterative in nature, and each iteration considers data associated with the defined historical period of time (see FIG. 54). Accordingly, the process 1150 may define the model training period and the model prediction period for the historical period of time (task 1158). In this regard, task 1158 may identify or designate which data samples fall within the model training period (the LTH in FIG. 54) and/or which data samples fall within the model prediction period (the LPH in FIG. 54). Task 1158 may also serve to identify or designate "stale" data samples that need not be considered going forward. In practice, if data for the oldest sampling period is missing for some reason, then the process 1150 can make appropriate adjustments (e.g., search for the closest available data sample, wait for the next sampling period, or the like).

Next, the process 1150 processes at least some of the historical data to determine a best-matched solution to a sensor glucose prediction model (task 1160). Task 1160 may be considered to be a training procedure that finds the best-fitting sensor glucose prediction function, which in turn can be used to check (predict) the integrity and quality of the glucose sensor. In certain embodiments, the sensor glucose prediction model is expressed as a fourth order ordinary differential equation that, when solved given the initial conditions, provides model-predicted sensor glucose values. Notably, task 1160 uses the actual sensor glucose values obtained during the model training period (and does not use any of the actual sensor glucose values obtained during the model prediction period) to determine which candidate solution will be selected as the best-matched solution. Conceptually, task 1160 generates a plurality of curves (or discrete values that may be used to visualize curves for purposes of this explanation) and compares the portion of the curves within the model training period to the actual sensor glucose values obtained during the model training period. In an ideal scenario with a perfect match, one of the generated curves will precisely track the actual sensor glucose values within the model training period. In practice, however, the generated curves will deviate from the actual sensor glucose values. Accordingly, task 1160 identifies the calculated curve that best matches the actual sensor values. It should be appreciated that this best-matching curve also includes model-predicted sensor glucose values that extend beyond the model training period and into the model prediction period.

The process 1150 may continue by comparing at least one historical sensor glucose value obtained during the model prediction period to at least one corresponding predicted sensor glucose value of the best-matched solution (task 1162). In certain embodiments, task 1162 checks only one actual sensor glucose value: the current sensor glucose value obtained for the most recent sampling period. In other embodiments, any or all of the sensor glucose values obtained during the model prediction period could be analyzed during task 1162. The straightforward example described here only considers the current sensor glucose value such that the comparison in task 1162 is simple and straightforward. In this regard, task 1162 may calculate a difference between the current sensor glucose value (i.e., the most recent historical value) and the predicted current glucose value for the most recent sampling period (the difference may be expressed as an absolute value), and the process 1150 may continue by comparing the calculated difference to a threshold error amount (query task 1164). In other embodiments, the comparison performed during task 1162 may involve a more advanced methodology, e.g., curve-fitting that considers more than one sampling point in the model prediction period, statistical analyses, or the like. For example, rather than calculating error on a point-by-point basis, the process 1150 could utilize any appropriate methodology to determine whether or not the historical sensor glucose values in the model prediction period deviate (by at least a threshold amount) from the corresponding model-predicted values in the best-matched solution.

If the calculated error between the model-predicted glucose value(s) and the corresponding actual historical sensor glucose value(s) is less than or equal to the error threshold, or otherwise satisfies the predetermined criteria monitored by the model supervisor module 914, then the "No" branch of query task 1164 is followed and the process 1150 continues to the next sampling period (task 1166). At this point, the process 1150 returns to task 1152 such that the core of the process 1150 can be repeated to consider the data received for the next sampling period. Thus, the oldest data considered by the previous iteration of the process 1150 is disregarded, the newly received data is designated as the "most recent" data, and the historical time period or "analysis window" for the current iteration of the process 1150 shifts by one sampling period (see FIG. 54).

If the calculated error exceeds the threshold error amount (the "Yes" branch of query task 1164), then the process 1150 may generate an alert, an alarm, and/or a message (task 1168). In practice, an alert, alarm, or message can be initiated by the model supervisor module 914 for rendering, annunciation, delivery, playback, etc. For example, an alert could be presented at the insulin infusion device, at a remote monitoring station, at a handheld controller device, or the like. In certain embodiments, the process 1150 switches from the closed-loop mode to the open-loop mode (or to some type of safe operating mode with reduced insulin delivery) when the threshold error amount is exceeded (task 1170).

Figure 56:
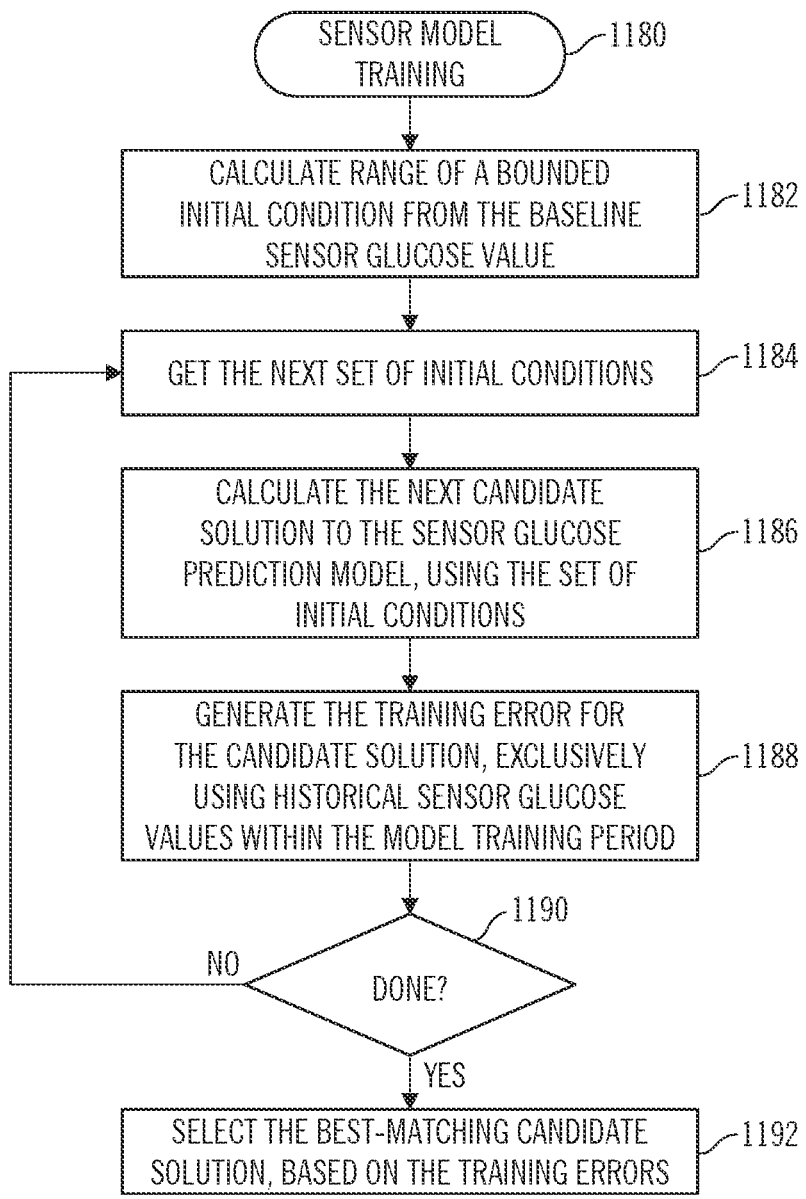
FIG. 56 is a flow chart that illustrates an exemplary embodiment of a sensor model training process, which may be performed in conjunction with the sensor model supervision process depicted in FIG. 55.

One important aspect of the process 1150 relates to the manner in which the best-matched sensor glucose prediction model is chosen (see task 1160). In this regard, FIG. 56 is a flow chart that illustrates an exemplary embodiment of a sensor model training process 1180, which may be performed in conjunction with the sensor model supervision process 1150 depicted in FIG. 55. The process 1180 is shown and described in a simplified manner for ease of understanding. Certain aspects of the process 1180 are addressed in more detail below with reference to particular implementations of the model supervisor module 914.

As mentioned previously, the exemplary sensor glucose prediction model utilized here is expressed as a fourth order ordinary differential equation. In accordance with conventional mathematics, the model-predicted sensor glucose values (G) in time are calculated as a function of the two model prediction initial conditions $G_0$ and $dG_0$. Here, $G_0$ is the estimated sensor glucose value for the begin-training sampling period 1124 (the start of LTH in FIG. 54), and $dG_0$ is the derivative of $G_0$. Therefore, different initial condition values result in different solutions to the sensor glucose prediction model; each distinct set of initial conditions corresponds to a different prediction model. For the sake of processing efficiency, the model supervisor module 914 imposes limits and boundaries on the initial condition values to calculate and analyze a manageable number of candidate solutions. In this regard, the sensor model training process

1180 may begin by calculating a range or boundary for each bounded initial condition (task 1182).

For the exemplary embodiment presented here, the initial condition $dG_0$ is bounded in a simple manner that is based on a predetermined parameter (which may be adjustable): $dG_0 = \pm \text{grad\_bound}$. In contrast, the boundary for the initial condition $G_0$ is based on (or is otherwise influenced by) a baseline historical sensor glucose value obtained during the model training period, such as the sensor glucose value that was obtained during the begin-training sampling period 1124. Thus, the process 1180 may identify, from the historical sensor glucose values, the baseline sensor glucose value to be used for purposes of calculating the boundary for the initial condition $G_0$: $G_0 = SG_{k-LTH} \pm 0.14 \cdot SG_{k-LTH}$, where $SG_{k-LTH}$ is the baseline sensor glucose value obtained for the earliest sampling period in the historical time period under analysis (see FIG. 54). Notably, the boundary for $G_0$ is a function of the baseline sensor glucose value, which may vary in an ongoing manner during operation of the system, and which may vary from one iteration of the process 1180 to another. In practice, if the sensor glucose data is missing for the begin-training sampling period 1124, then the process 1180 can take appropriate measures, e.g., search for the nearest available sensor glucose data point, wait for the next sampling period, etc.

The process 1180 may then continue by determining, calculating, or otherwise obtaining the next set of initial conditions (task 1184). The manner in which the process 1180 selects and steps through the different initial conditions is unimportant in this context. The current set of initial conditions is used to calculate a candidate solution to the sensor glucose prediction model (task 1186). As mentioned above, each candidate solution is calculated as a function of the two bounded initial conditions. Moreover, each candidate solution is calculated as a function of estimated plasma insulin for the user, which in turn is calculated as a function of an amount of insulin delivered to the user. Accordingly, task 1186 may estimate plasma insulin for the user based on: the current insulin-delivered data (obtained for the most recent sampling period); the historical insulin-delivered data; and an insulin basal rate for the user. In practice, task 1186 considers the total insulin (basal, bolus, and any other insulin delivered) for all sampling periods. This allows the process 1180 to obtain the candidate solution to the sensor glucose prediction model based at least in part on the estimated plasma insulin and based at least in part on the baseline sensor glucose value obtained at the earliest sampling period under analysis.

The process 1180 may continue by generating a training error value, quantity, or function for the candidate solution (task 1188). The training error may be calculated by comparing predicted sensor glucose values from the candidate solution to the corresponding historical sensor glucose values, to obtain a metric that indicates how closely the predicted values match the actual values. In certain embodiments, the training error is based only on predicted values and actual values for the model training period (LTH in FIG. 54), and, therefore, task 1188 does not consider any predicted or actual values for the model prediction period (LPH in FIG. 54).

If the process 1180 has considered all of the initial condition combinations (the "Yes" branch of query task 1190), then the process 1180 may proceed to a task 1192. If more sets of initial conditions remain (the "No" branch of query task 1190), then the process 1180 may return to task 1184, retrieve the next set of initial conditions, and continue as described above. Task 1192 is performed after a plurality of different candidate solutions have been calculated, using the different sets of initial conditions. Task 1192 may be performed to select the best-matching candidate solution from the plurality of calculated solutions. For this particular embodiment, the selection is based on the training errors generated during task 1188. For example, the candidate solution having the lowest training error may be selected as the best-matching solution.

It should be appreciated that the process 1180 need not be performed in the illustrated sequence, and that some tasks could be performed in parallel. For example, the calculation of the training errors (task 1188) may instead be performed after all of the candidate solutions have been obtained and saved. Moreover, the process 1180 could be designed to immediately eliminate candidate solutions (following completion of task 1188) that have a training error that exceeds a predetermined error threshold. As another option, the process 1180 could be designed to immediately designate a candidate solution as the best-matched solution if the associated training error satisfies certain criteria.

The foregoing concepts and methodologies may be implemented in a practical embodiment of the model supervisor module 914. The following description relates to two possible embodiments that implement the general concepts presented above. It should be appreciated that the particular embodiments described below are not exhaustive, and that the description of the embodiments is not intended to limit or restrict the scope or application of the subject matter presented here.

Model Supervisor Module: First Representation

The model supervisor module 914 is suitably designed and configured to detect potentially faulty sensor measurements. The model supervisor module 914 may utilize a mathematical model that is trained offline. For example, parameters that could be estimated offline estimated include, without limitation: $K_I$ (insulin gain in mg/dL per U/h; $\tau_1$ (first insulin time constant, in minutes); $\tau_2$ (second insulin time constant, in minutes); Ibasal (basal insulin, in U/h); and SGbase (blood glucose (BG) at fasting, in mg/dL, when Ibasal insulin is delivered.

The model supervisor module 914 trains the model prediction initial conditions, $G_0$ and $dG_0$ every sampling time. $G_0$ and $dG_0$ represent the BG (mg/dL) and BG derivative (mg/dL/min) estimate values at k-LTH (see FIG. 54), where LTH is the length of the training data (sampling times) and k is equal to the present sampling time minus LPH. In this context, LPH is the length of the prediction horizon in sampling times. $G_0$ and $dG_0$ estimations are bounded as formulated by the expressions collectively identified below as Equation 77. Note that these initial conditions and their boundaries were also described above with reference to task 1182 of the sensor model training process 1180.

$$G_0 = CGM_{k-LTH} \pm 0.14 \cdot CGM_{k-LTH} \qquad \text{(eq 77)}$$

$$dG_0 = \pm \text{grad\_bound}$$

For Equation 77, $CGM_{k-LTH}$ is the CGM measurement at sampling time k-LTH, and grad_bound is a predefined absolute maximum BG derivative in time (mg/dL/min).

The model supervisor module 914 estimates plasma insulin, $I_p$, at k-LTH using the insulin history records from k-LTH-insulin history and k-LTH (see FIG. 54) in accordance with Equation 81. Having the estimated $I_p$, $G_0$, and $dG_0$, a model prediction is generated from present-LTH- LPH, until present (as described above for task 1186 of the sensor model training process 1180). The model prediction enables the calculation of two values: Terr and Perr. Terr is defined as the mean sum square of errors between the model prediction and the CGM records from k-LTH and k (Equation 78). Perr is defined as the absolute mean error between the model prediction and the CGM records from k and present (Equation 79). Note that Terr is one type of training error, which was described above for task 1188 of the process 1180, and Perr is one type of prediction error, as described above for task 1162 and query task 1164 of the sensor model supervision process 1150. A fault is defined when Perr<err1 and Terr>err2 (Equation 80).

$$Terr = \sqrt{\frac{\sum_{i=k-LTH}^{k}(\text{Model}_i - CGM_i)^2}{LTH}} \quad \text{(eq 78)}$$

$$Perr = \text{abs}\left(\frac{\sum_{i=k}^{k+LPH}\text{Model}_i - CGM_i}{LPH}\right) \quad \text{(eq 79)}$$

$$\text{Fault} = \begin{cases} 1, & \text{if } Terr < err1 \text{ and } Perr > err2 \\ 0, & \text{else if } Terr \leq err2 \text{ or } Perr \geq err1 \\ -1, & \text{if not enough data records available} \end{cases} \quad \text{(eq 80)}$$

In Equation 80, Fault 1 indicates a faulty sensor, Fault 0 indicates a non-faulty sensor, and Fault −1 indicates that there is not enough information to decide. Referring again to FIG. 55, Fault 1 corresponds to the "Yes" branch of query task 1164.

In certain embodiments, some of the parameters used by the model supervisor module 914 may be adjustable. Table 5 identifies the adjustable parameters, along with some exemplary values for the parameters.

TABLE 5

Adjustable Parameters For the Model Supervisor Module

| Parameter | Symbol | Typical Starting Value | Minimum Value | Maximum Value |
|---|---|---|---|---|
| Insulin gain | $K_I$ | −100 | −500 | −1 |
| Insulin time constant | $\tau_1$ | 30 | 0.1 | 150 |
| Insulin time constant | $\tau_2$ | 150 | 0.1 | 150 |
| Fasting BG | SGbase | 120 | 50 | 300 |
| Basal insulin at fasting BG | Ibasal | 1 | 0.1 | 3 |
| Training data error | err1 | 5 | 1 | 100 |
| Prediction data error | err2 | 20 | 1 | 100 |
| Length of training data | LTH | 8 | 5 | 30 |
| Length of prediction data | LPH | 3 | 1 | 20 |
| Length of insulin data | Insulin History | 48 | 30 | 60 |
| BG maximum absolute derivative | grad_bound | 5 | 1 | 8 |

The following equations describe the mathematical model equations in Laplace transform form:

$$\hat{I}_P(s) = \frac{1}{(50s+1)(70s+1)}\left(\hat{I}_D + \hat{I}_{P0}s\,\alpha + dI_{P0}\beta\right) \quad \text{(eq 81)}$$

In this expression, $\alpha=3500$, $\beta=120$, and $\hat{I}_P$ is the IP in deviation form. $\hat{I}_{P0}$ and $dI_{P0}$ are the $\hat{I}_P$ and derivative initial conditions, respectively.

All the insulin states are formulated in deviation form from the given insulin value Ibasal as it is expressed by the following Equation 82:

$$\hat{I}_x = I_x - I\text{basal} \quad \text{(eq 82)}$$

In Equation 82, x represents D, in, or P.

The following Equation 83 expresses BG in deviation form from SGbase. Note that Equation 83 represents one suitable expression for the sensor glucose prediction model, which is a fourth order ordinary differential equation.

$$\hat{G}(s) = \frac{1}{(\tau_1 s+1)\cdot(\tau_2 s+1)} \quad \text{(eq 83)}$$

$$\left(K_1 \cdot \hat{I}_P - \frac{1}{(50s+1)(70s+1)}(\hat{G}_0 \cdot \alpha + (\hat{G}_0 \cdot s + d\hat{G}_0)\cdot \beta + \right.$$

$$\left. (\hat{G}_0 \cdot s^2 + d\hat{G}_0 \cdot s)\cdot \chi + (\hat{G}_0 \cdot s^3 + d\hat{G}_0 \cdot s^2)\cdot \delta)\right)$$

In Equation 83, the following relationships hold:

$$\alpha = 120 + \tau_1 + \tau_2$$

$$\beta = 3500 + 120\tau_1 + 120\tau_2 + \tau_1\tau_2$$

$$\chi = 3500\tau_1 + 3500\tau_2 + 120\tau_1\tau_2$$

$$\delta = 3500\tau_1\tau_2$$

Moreover, in Equation 78, $\hat{G}$, $K_I$, $\hat{G}_0$, $dG_0$, $\tau_1$, and $\tau_2$ are the BG in deviation form from SGbase, the insulin gain, the BG initial conditions in deviation form, the BG derivative initial conditions, and two time constants, respectively.

Model Supervisor Module: Second Representation

In accordance with some embodiments, the functionality of the model supervisor module 914 can be represented as follows. As mentioned above, the model supervisor module 914 estimates the user's glucose concentration in real-time based on the insulin delivered, the sensor Isig values, and sensor calibration factors. If the model-predicted sensor glucose value (SG) and the actual SG value differ significantly, the system will trigger a fail-safe alert that indicates that the collected data contains unexplained behavior, which may in turn be associated with a faulty sensor and/or insulin delivery, or an unannounced meal intake.

The time frames and reference time periods for the model supervisor module 914 are defined as shown in FIG. 54. The methodology performed by the model supervisor module 914 uses data packets received for past time frames to estimate plasma insulin and model-predicted glucose in order to estimate the fault conditions. The sampling time is the time interval between two consecutive data packets, which for this particular example is five minutes. The insulin history in FIG. 54 corresponds to a defined past time frame that is needed to estimate plasma insulin (for this example, the insulin history corresponds to four hours or 48 sampling periods). The length training horizon (LTTH) for this example includes 24 data packets, which corresponds to a past time frame of 120 minutes. The length of predicted horizon (LPH) for this example includes 24 data packets, which corresponds to a past time frame of 120 minutes. In FIG. 54, k is equal to the present number of data packets minus LPH, and "present" indicates the most recent sampling time.

The following equations describe the mathematical model in Laplace transform form. Equation 84 provides an estimate of the plasma insulin, and Equation 85 provides the model-predicted SG values. Accordingly, the model supervisor module 914 in accordance with this particular embodiment estimates the plasma insulin as follows:

$$\hat{I}_p(s) = \frac{1}{(50s+1)(70s+1)}(\hat{I}_D + \hat{I}_{P0}s\varepsilon + dI_{P0}\gamma) \quad \text{(eq 84)}$$

For this example, $\varepsilon=3500$, $\gamma=120$, $\hat{I}_P$ is the estimated plasma insulin in deviation form, (s) refers to Laplace transform form, and D is the insulin delivered from the system in deviation form. Moreover, $\hat{I}_{P0}$ is the estimated plasma insulin in deviation form for the sampling time identified as k-LTH (see FIG. 54), $dI_{P0}$ is the derivative of the estimated plasma insulin, and a and p are constants.

The insulin states described above are formulated in deviation form from a given insulin value Ibasal as it is expressed by the following equation:

$$\hat{I}_x = I_x - I\,\text{basal} \quad \text{(eq 85)}$$

In Equation 85, x represents D or P (where D refers to insulin delivered and P refers to plasma insulin), and $I_{basal,0}$ is the estimated basal rate defined for each user to bring the patient to a fasting blood glucose (FBG) of the value $FBG_0$ (in mg/dL).

For this second embodiment, the model-predicted sensor glucose value, $\hat{G}$, in time is calculated in accordance with Equation 83 and the associated relationships, as described for the first embodiment of the model supervisor module 914. In this regard, $\hat{G}$ is the model-predicted SG value in deviation form from $FBG_0$ (estimated blood glucose using meter blood glucose readings at the end of the night period), (s) refers to Laplace transform form, $\tau_1$, and $\tau$ are the two insulin time constants identified for each patient, which are related to how fast a patient reacts to insulin, $K_I$ is the insulin gain, and $\hat{I}_P$ is the estimated plasma insulin in deviation form. Moreover, $\hat{G}_0$ is the estimated SG value (in mg/dL) in deviation form for the sampling time of k-LTH (see FIG. 54), as calculated in accordance with Equation 86 below, and $dG_0$ (calculated by Equation 87 below) is the derivative of the estimated SG value (in mg/dL/min) for the sampling time of k-LTH. The constants $\alpha$, $\beta$, $\chi$, and $\delta$ are calculated as set forth above in the context of Equation 83.

The estimated blood glucose values are calculated as a function of the model prediction initial conditions, $G_0$ and $dG_0$. For this particular embodiment, the estimations for $G_0$ and $dG_0$ are bounded as formulated by the following equations. Note that these initial conditions and their boundaries were also described above with reference to task 1182 of the sensor model training process 1180.

$$G_0 = SG_{k-LTH} \pm 0.14 \cdot SG_{k-LTH} \quad \text{(eq 86)}$$

$$dG_0 = \pm grad\_bound \quad \text{(eq 87)}$$

Here, $G_0$ is the estimated SG value (in mg/dL) value for the sampling time of k-LTH, $SG_{k-LTH}$ is the SG measurement for the sampling time of k-LTH, $dG_0$ is the derivative of the estimated SG value (in mg/dL/min) for the sampling time of k-LTH, and grad_bound is a predefined absolute maximum SG derivative in time (mg/dL/min). For certain embodiments, grad_bound is a fixed parameter. For the example presented here, grad_bound has a value of 5 mg/dL/min.

The model prediction facilitates the calculation of two values: Terr and Perr. Terr is defined as the mean absolute error between the model predicted SG values and the actual SG records for the sampling time identified as k-LTH and k as calculated by Equation 88 below. Perr is defined as the mean absolute error between the model predicted SG values and the actual SG records for sampling times identified as k to present (see FIG. 54) as calculated by Equation 89 below.

$$Terr = \frac{\sum_{i=k-LTH}^{k} \text{abs}(Model_i - SG_i)}{LTH} \quad \text{(eq 88)}$$

Here, Terr is defined as the mean absolute error between the model predicted SG values ($Model_i$) and the SG records ($SG_i$) for the sampling time identified as k-LTH and k.

$$Perr = \frac{\text{abs}(Model_{present} - SG_{present})}{SG_{present}} \cdot 100\% \quad \text{(eq 89)}$$

Here, Perr is defined as the percentage of error between the model prediction and the SG measurement at the present (most recent) sampling time.

In accordance with this particular implementation, the model supervisor module 914 estimates the fault scenario based on Equation 90, where Fault 1 signifies a faulty sensor, Fault 0 indicates a non-faulty sensor, Fault 3 indicates a training error, and Fault −1 indicates that there is not enough data available to make a determination.

$$\text{Fault} = \begin{cases} 1, & \text{if } Terr < err1 \text{ and } Perr > err2 \\ 0, & \text{if } Perr \le err2 \text{ or } Terr \ge err1 \\ 3, & \text{if } Terr > err3 \\ -1, & \text{if not enough data available} \end{cases} \quad \text{(eq 90)}$$

In Equation 90, err1 is the upper threshold for the mean absolute error (see Equation 88). Thus, if the training error is above this threshold, a fault cannot be triggered because the credibility of the training is suspect. The err2 is the lower threshold for Equation 89. If the prediction value of the model and the sensor measurement at present are above this threshold and the training error is less than err1, then a fault will be triggered. The err3 defines a lower threshold for the training period. If Equation 88 indicates a value that is above this threshold, then a warning associated with poor training can be triggered.

Figure 57:
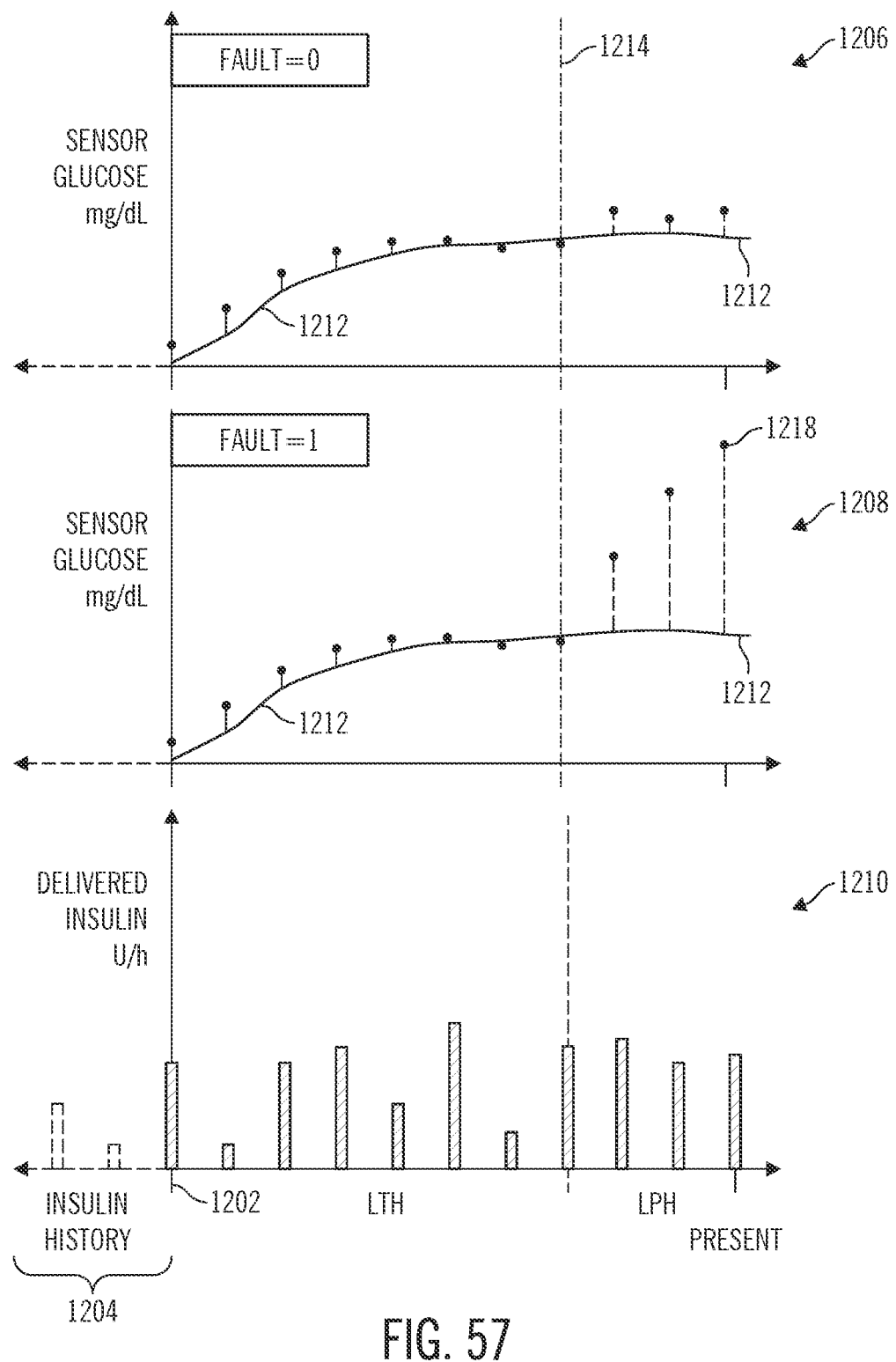
FIG. 57 is a diagram that illustrates two exemplary fault conditions that can be detected by the model supervisor module.

FIG. 57 is a diagram that illustrates exemplary sensor conditions corresponding to a non-faulty sensor (Fault 0) and a faulty sensor (Fault 1). The common horizontal axis indicates the present sampling time at the far right, along with the time periods identified by LPH and LTH. The sampling time 1202 corresponds to the oldest data considered by the model supervisor module 914 at the present time. Accordingly, historical data 1204 for sampling times that occurred before the sampling time 1202 is disregarded.

The top plot 1206 in FIG. 57 is indicative of a non-faulty sensor (Fault 0), the middle plot 1208 is indicative of a faulty sensor (Fault 1), and the bottom plot 1210 depicts the insulin administered, which is needed in order to estimate the plasma insulin and to generate the model predicted SG values. In the plots 1206, 1208, the solid line 1212 represents the model-predicted SG values, and the dots represent the actual SG measurements. The dashed vertical line 1214 represents the demarcation between the LTH time frame and the LPH time frame. The lines between the solid line 1212 and the dots represent the difference (error) between the model-predicted SG values and the actual SG measurements. Dashed lines are utilized in the LPH time frame, which corresponds to fifteen minutes or three sampling periods for this example.

Referring to the top plot 1206, there is good agreement between the model predicted SG values (represented by the solid line 1212) and the actual SG measurements (represented by the dots). In other words, the actual measurements do not deviate significantly from the predicted values. In certain embodiments, the model supervisor module 914 only compares actual measurement values that are within the LPH time frame. In accordance with one exemplary embodiment, the model supervisor module 914 determines the fault status based solely on the most recently obtained data, i.e., the information received for the last sampling time. For this example depicted in FIG. 55, Perr is less than or equal to err2. Thus, in accordance with Equation 90, the model supervisor module 914 returns Fault 1 and the system is commanded to remain in the closed-loop mode.

Referring to the middle plot 1208, of FIG. 57, there is good agreement between the model predicted SG values and the actual SG measurements in the LTH time period (for this period, Terr is less than err1 in Equation 90). Note, however, that there is a significant difference observed between the model predicted SG last value and the actual last SG measurement 1218 (Perr is greater than err2 in Equation 90). In this scenario, therefore, the model supervisor module 914 will issue a fail-safe alert and/or take other appropriate measures.

In certain embodiments, some of the parameters used by the model supervisor module 914 may be adjustable. Table 6 identifies some adjustable parameters for this embodiment, along with some exemplary values for the parameters.

TABLE 6

Adjustable Parameters For the Model Supervisor Module

| Parameter | Default Value | Lower Bound | Upper Bound |
|---|---|---|---|
| $K_I$ (mg/dL/U/H) | −100 | −360 | −49 |
| $FBG_0$ (mg/dL) | 120 | 50 | 300 |
| Ibasal (U/H) | 1 | 0.1 | 3 |
| err1 (mg/dL) | 5 | 1 | 30 |
| err2 (%) | 50 | 20 | 100 |
| err3 (mg/dL) | 10 | 1 | 30 |
| LTH (sampling times) | 24 | 4 | 48 |
| LPH (sampling times) | 24 | 1 | 48 |

Alternative Model Supervisor Module

Another embodiment of a model supervisor module and related operating methodologies are presented in this section. The general theory of operation and functionality of the alternative model supervisor module is similar to that described above. In other words, the alternative module supervisor module is active during closed loop operation of the insulin infusion device, and it estimates the accuracy of the sensor glucose measurement in real-time. The alternative model supervisor module calculates the model-predicted sensor glucose value (SGp) and compares SGp against the actual sensor glucose (SG) value obtained from the continuous glucose sensor. If SGp and SG differ significantly, the alternative model supervisor module can generate (or cause the system to generate) appropriate alerts, warnings, or otherwise take corrective action as needed. For example, if the alternative model supervisor determines that SG is significantly lower than SGp (i.e., the alternative model supervisor detects a "sensor under-reading" condition), then an appropriate alert can be generated and the insulin infusion device can be automatically controlled to enter a safe basal rate mode of operation, to exit the closed-loop operating mode, or take other safeguarding measures.

The alternative model supervisor module differs from that described in the preceding section (for the first embodiment of the model supervisor module) in several ways. For example, the alternative model supervisor module presented here does not utilize the sensor model training technique that was described above with reference to FIGS. 54-56. Instead, the alternative model supervisor module employs a simpler methodology that considers historical data (such as SG values, BG meter values, insulin history, etc.) without explicitly training the sensor model. The alternative model supervisor module performs a calibration routine to calibrate the sensor model whenever a BG meter reading is obtained. This approach differs from the previously described embodiment that uses SG values to train and calibrate the sensor model. The alternative model supervisor module reacts to an "under-reading" sensor condition to transition the insulin infusion device out of the closed loop mode, but does not react or generate a fault in response to an "over-reading" sensor condition. Moreover, the alternative model supervisor module considers SG values obtained during fasting periods, whereas the previously described version of the model supervisor module considers BG meter values.

Figure 58:
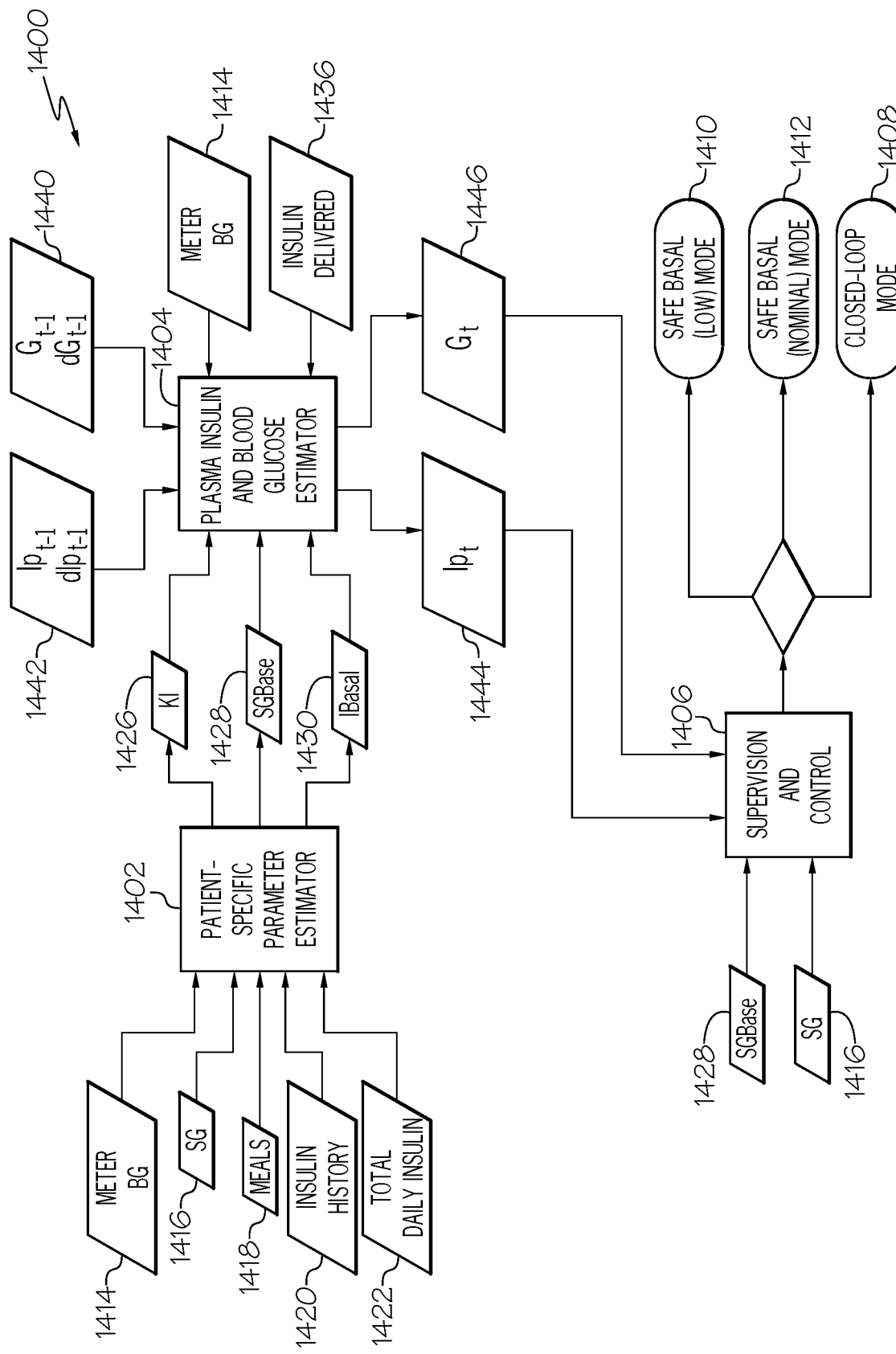
FIG. 58 is a block diagram that schematically illustrates an exemplary data flow and processing scheme associated with a model supervisor module.

FIG. 58 is a block diagram that schematically illustrates an exemplary data flow and processing scheme associated with a model supervisor module 1400. The model supervisor module 1400 can include processing logic, computer-readable instructions, and algorithms needed to perform the alternative model supervisor methodology described in more detail below. For ease of illustration and description, FIG. 58 depicts three "components" of the model supervisor module 1400: a patient-specific parameter estimator 1402; a plasma insulin and blood glucose estimator (hereinafter referred to as the insulin/glucose estimator 1404); and a supervision and control module 1406. The parameter estimator 1402 generates various patient-specific parameters, some of which serve as inputs to the insulin/glucose estimator 1404 and the supervision and control module 1406. The insulin/glucose estimator 1404 estimates the patient's plasma insulin and blood glucose concentrations in a dynamic and adaptive manner. The estimated blood glucose value (Gt) for the current sampling time and the estimated plasma insulin value (Ipt) for the current sampling time serve as inputs to the supervision and control module 1406. Each of the primary components of the model supervisor module 1400 is described in more detail below.

At least some of the inputs to the model supervisor module 1400 may be provided directly or indirectly by the insulin delivery system 14, the glucose sensor system 10, a translator device, a monitor device, and/or any device in the closed-loop system (see FIG. 1). The model supervisor module 1400 processes the various inputs in an ongoing manner during closed-loop operation, determines the current status, state, or condition of the glucose sensor based on the processing of the inputs, and regulates whether the system remains in the closed-loop mode 1408 or switches out of the closed-loop mode 1408 to a designated safe basal mode. The example described here supports two different safe basal modes, which are designated as the safe basal (low) mode 1410 and the safe basal (nominal) mode 1412.

Patient-Specific Parameter Estimator

The patient-specific parameter estimator 1402 calculates a variety of patient-specific parameters using historical data obtained from the insulin infusion device. In accordance with certain exemplary embodiments, the infusion system is initialized with data collected during two to six days of operation. Thereafter (e.g., from the second or third night of operation and onwards), the system will update itself with new data obtained from the insulin infusion device every 24 hours. The data collected and considered by the parameter estimator 1402 can include, without limitation: blood glucose meter data 1414; sensor glucose (SG) data 1416; meal-related data 1418; insulin history data 1420, which refers to all insulin delivery sequences in a predefined historical period of time; and total daily insulin data 1422 (expressed in Units), which represents the sum of all insulin delivery sequences over a 24 hour period, such as from midnight to midnight. It should be appreciated that the model supervisor module 1400 need not rely or use all of this information. For example, fasting sensor glucose measurements and plasma insulin estimates are collected in real time and, therefore, the insulin history data 1420 need not be considered to evaluate the fasting values.

For the model supervisor module 1400, the parameter estimator 1402 calculates or assigns the following patient-specific parameters (which are described in more detail below): insulin gain (KI) 1426; estimated basal rate at fasting blood glucose (IBasal) 1428; and fasting blood glucose (SGBase) 1430. These values are updated once every 24 hours, for example, at midnight. It should be appreciated that the parameter estimator 1402 can also calculate or estimate other parameters, which may be utilized by other processing modules of the system.

The insulin gain KI is calculated based on the "1800 rule" as follows:

$$KI = -3 * 1800/I_{TDD} \qquad \text{(eq 91)}$$

In Equation 91, $I_{TDD}$ is the daily insulin requirement, which can be calculated by the parameter estimator 1402. $I_{TDD}$ is calculated as follows:

Step 1: Use the latest six full-day total daily insulin 1422 (U/day) obtained from the insulin infusion device. The total daily insulin 1422 is the total amount of insulin delivered by the infusion device from midnight to midnight (or any designated 24 hour period), and it is reported at 0:00 hours every day. In order to successfully calculate $I_{TDD}$, a minimum of two days of total daily insulin 1422 is required. If the available total daily insulin 1422 from the infusion device is associated with less than two full days, then $I_{TDD}$ is not calculated.

Step 2: Delete the total daily insulin 1422 value if it is above a maximum value (such as 250 U) or below a minimum value (such as 5 U).

Step 3: If the number of total daily insulin 1422 entries is less than two, then $I_{TDD}$ is not calculated.

Step 4: Take the median of available total daily insulin 1422 values to calculate $I_{TDD}$ as follows:

$$I_{TDD} = \text{median}(\text{Daily Insulin Total}_{i=1:N}) \qquad \text{(eq 92)}$$

Here, i represents the index for individual days, and N represents the total number of days. For this particular embodiment, N has a maximum value of six and a minimum value of two.

The patient-specific parameter estimator 1402 calculates two related parameters: IBasal 1430 and SGBase 1428. In this regard, IBasal 1430 is the estimated basal rate at the fasting blood glucose value SGBase, and SGBase 1428 is the estimated fasting blood glucose at the basal rate IBasal. In other words, IBasal is the estimated basal rate to bring the patient to SGBase. For the exemplary embodiment described here, the values of IBasal and SGBase are calculated in the following manner.

The fasting glucose (FG) values are determined using the following logic:
(a) At midnight (or any designated time of day), start searching for the best fasting glucose value of the day until the next midnight (24 hours).
  i. There should be at least two hours of historical sensor and insulin delivery data before the candidate fasting SG.
  ii. The sum of all carbohydrates announced in meals over the last five hours prior to the candidate fasting SG must be ≤20 grams. The carbohydrate information is included in or represented by the meal-related data 1418.
  ii. The SG must be in a predetermined range (such as 70 to 250 mg/dL).
b) If the above conditions are met, continue with the following:
  iv. Access or review the analytical response for Plasma Insulin values by analyzing two hours of stored data prior to the candidate fasting SG (see Equation 100 and Equation 102, below).
  v. If 20 out of 24 Isig measurements (or any desired percentage) are available in the two hours prior to the candidate fasting SG, calculate the mean rate of change (ROC) in the prior two hours (e.g., 24 sampling times), and its high-to-low ROC (the maximum possible absolute rate of change between any two available SG measurements in the prior two hours, 24 sampling times) for the candidate fasting SG.
  vi. ROC Calculation:
    a. Loop through all valid Isig values (minimum of 20, maximum of 24), get the most recent calibration factor, CF, and compute the rate of change according to the following relationship: ROC=(next_ISIG−current_ISIG)*CF/(delta_T_minutes).
    b. Compute the mean of the ROC values when done.
    c. Calculate the ROC between the highest and lowest SG values encountered in the valid SG data set. In the case where multiple minimum SG or maximum SG values are encountered, calculate all permutations and keep the one with the highest ROC (if identical values exist pick the first encountered value).
  vii. If ROC computation was possible (more than 20 Isig measurements are available in the two hours prior to the candidate fasting SG), check if the mean ROC value is below 0.4 mg/dL/min and check if the high-to-low ROC value is below 0.8 mg/dL/min.

viii. If the ROC values are within range, check whether the difference between the maximum and minimum estimated plasma insulin (Ip) values over the previous two hours is less than 20% of the default Ibasal (which is calculated in accordance with Equation 93 below).

c) If all conditions above passed, check whether a fasting SG has already been found for that day.
 i. If no fasting SG is found, store the current SG as an FG of that day, save the Ip value at the time stamp of the current SG, and save the calculated ROC.
 ii. If a fasting SG is found, and if the current ROC is greater than the previous ROC, then do not store the FG.
 iii. If a fasting SG is found, and if the current ROC is less than the previous ROC, then store the FG and delete the previous value, save the Ip value at the time stamp of the current SG, and save the calculated ROC.

d) An array of FG entries is formed (only containing the last six full days), one FG per day. A corresponding array of plasma insulin can also be created (FG_vec and Plasma_vec).

If no FG values are available, compute the IBasal and SGBase parameters as follows:

$$IBasal = I_{TDD}/48 \qquad \text{(eq 93)}$$
$$SGBase = 120$$

Here, IBasal is the calculated insulin delivery rate to bring the fasting blood glucose to 120 mg/dL, $I_{TDD}$ is the daily insulin requirement (Equation 92), and SGBase is the predicted fasting blood glucose if insulin is delivered at the rate of IBasal.

If only one FG value is available, compute the IBasal and SGBase parameters as follows:

$$IBasal = \qquad \text{(eq 94)}$$
plasma insulin estimate at time of the associated fasting $SG$ Here, IBasal is the calculated insulin delivery rate to bring the fasting blood glucose to the value of SGBase mg/dL, and "plasma insulin estimate at time of associated fasting SG" is the plasma insulin estimate (calculated by Equation 100, which is described below) associated with the fasting SG, and SGBase is the predicted fasting blood glucose if insulin is delivered at the rate of IBasal.

If more than one FG value is available, compute the IBasal and SGBase parameters in the following manner.

Compute the normalized vector of FG as follows:

$$FG\_vec\_\text{normalized} = \qquad \text{(eq 95)}$$
$$(FG\_vec - \min(FG\_vec))/((\max(FG\_vec) - \min(FG\_vec))$$

Here, FG_vec is the vector of all collected daily FG values, and FG_vec_normalized is the normalized vector of FG_vec using the maximum and minimum FG values.

Compute IBasal as follows:

$$IBasal = \text{Mean value of the Plasma\_vec} \qquad \text{(eq 96)}$$

Here, IBasal is the calculated insulin delivery rate to bring the fasting blood glucose to SGBase mg/dL, and Plasma_vec is all plasma insulin estimates at the corresponding FG values.

Compute SGBase as follows:

$$SGBase = KI * IBasal + b2 \qquad \text{(eq 97)}$$

Here, SGBase is the predicted fasting blood glucose if insulin is delivered at the rate of IBasal, KI is the insulin gain (Equation 91 above), IBasal is the calculated insulin delivery rate to bring the fasting blood glucose to SGBase mg/dL, and b2 is a free constant of the weighted linear regressing that is calculated as indicated below:

$$\text{(eq 98)}$$
$$b2 = \text{sum of } [(FG\_vec - (KI * \text{Plasma\_vec})) * FG\_vec\_\text{normalized}]/$$
$$\text{sum of } [FG\_vec\_\text{normalized}]$$

Here, b2 is a free constant of the weighted linear regressing, KI is insulin gain, Plasma_vec is all plasma insulin estimates at the corresponding FG values, FG_vec is the fasting blood glucose values that were collected, and FG_vec_normalized is obtained by normalizing FG_vec by using the minimum and maximum values of FG_vec.

To briefly summarize, SGBase and IBasal are two related patient-specific parameters that are calculated once per day (e.g., at midnight each day). These parameters are calculated based on a plurality of fasting sample points, and SGBase serves as a baseline or "zero" point for the glucose model, for purposes of comparisons. This, along with other aspects described in more detail below, allows the glucose model to dynamically adjust and adapt in an ongoing manner.

Notably, the patient-specific parameters generated by the parameter estimator 1402 are dynamic and adaptive in nature in that they are calculated in an ongoing manner for the particular patient/user. The patient-specific parameters are calculated using no fixed parameters, because they are all calculated based on historical data based on operation of the insulin infusion device.

Plasma Insulin and Blood Glucose Estimator

The insulin/glucose estimator 1404 estimates the plasma insulin and blood glucose concentrations of the patient based on data that is available from the insulin infusion device and/or data that is calculated by the parameter estimator 1402. In accordance with the exemplary embodiment described here, the insulin/glucose estimator 1404 obtains and considers the following as inputs: the insulin delivered 1436 by the infusion device since the last sampling time (for this example, the insulin delivered 1436 corresponds to the amount delivered during the previous five minutes, because the insulin/glucose estimator 1404 is active once every five minutes); the blood glucose meter data 1414 (which also serves as an input to the parameter estimator 1402); the estimated blood glucose value at the previous sampling time ($G_{t-1}$) and the derivative of the estimated blood glucose at the previous sampling time ($dG_{t-1}$) (depicted as estimated blood glucose data 1440 in FIG. 58); and the estimated plasma insulin value at the previous sampling time ($Ip_{t-1}$) and the derivative of the estimated plasma insulin at the previous sampling time ($dIp_{t-1}$) (depicted as estimated plasma insulin data 1442 in FIG. 58). The insulin/glucose estimator 1404 also obtains and utilizes the current values of KI 1426, SGBase 1428, and IBasal 1430 generated by the parameter estimator 1402, as schematically depicted in FIG. 58. The output of the insulin/glucose estimator 1404 includes the following values: estimated plasma insulin ($Ip_t$) 1444; its derivative ($dIp_t$); estimated blood glucose ($G_t$) 1446, and its derivative ($dG_t$). The values of $dIp_t$ and $dG_t$ can be used with one or more of the other processing modules described previously; the exemplary embodiment of the model supervisor module 1400 uses the values of Gt and $Ip_t$ and does not require their derivatives. Although not shown in FIG. 58, the output values generated by the insulin/glucose estimator 1404 are fed back for use in calculating the next estimated values. In this way, operation of the insulin/glucose estimator 1404 is adaptive and iterative in nature.

In order to accurately estimate the plasma insulin ($Ip_t$), the plasma insulin derivative ($dIp_t$), the blood glucose ($G_t$), and the blood glucose derivative ($dG_t$) every sampling time (which is once every five minutes for this particular embodiment), certain initial conditions are used. More specifically, the insulin/glucose estimator 1404 uses the following initial conditions from the previous sampling time (indicated by the t−1 index): the estimated plasma insulin ($Ip_{t-1}$), the plasma insulin derivative ($dIp_{t-1}$), the estimated blood glucose ($G_{t-1}$), and the blood glucose derivative ($dG_{t-1}$).

When a new BG meter measurement is present, then $G_{t-1}$ is reset by the following equation:

$$G_{t-1} = MBG - SGBase \quad \text{(eq 99)}$$

Here, $G_{t-1}$ is the estimated blood glucose in deviation form at the t−1 sampling time, MBG is the most recent meter BG measurement, and SGBase is the predicted fasting blood glucose if insulin is delivered at the rate of IBasal, as described above. The resetting of $G_{t-1}$ in this manner serves to calibrate the glucose prediction model based on the most recent BG meter reading.

When a new insulin infusion device is deployed, or when a currently deployed insulin infusion device is reset, the values of $Ip_{t-1}$, $dIp_{t-1}$, $G_{t-1}$, and $dG_{t-1}$ are reset to zero. Thereafter, (e.g., following a warmup period for the infusion device) the closed-loop operating mode will not be available for at least five hours.

In accordance with the exemplary embodiment described here, the plasma insulin and blood glucose are estimated in the following manner. For each sampling time (e.g., one minute, five minutes, or the like), the estimated plasma insulin at the present sampling time ($Ip_t$), the estimated plasma insulin derivative at the present sampling time ($dIp_t$), the initial blood glucose in deviation form at the present sampling time ($G_t$), and the derivative of the blood glucose at the present sampling time ($dG_t$) are calculated as follows:

$$Ip_t = \quad \text{(eq 100)}$$

$$Iin + (TauIp1 * \exp(-t/TauIp1) * (Ip_{t-1} - Iin + dIp_{t-1} * TauIp2))/$$

$$(TauIp1 - TauIp2) -$$

-continued $$(TauIp2 * \exp(-t/TauIp2) * (Ip_{t-1} - Iin + dIp0_{t-1} * TauIp1))/$$

$$(TauIp1 - TauIp2)$$

$$Iptotal = Ip_t + IBasal \quad \text{(eq 101)}$$

Here, $Ip_t$ is the estimation of plasma insulin in deviation form at the sampling time t, IBasal (expressed in U/h) is the patient-specific parameter described above, Iin is the insulin delivered 1436 (since the last sampling time, e.g., during the last five minutes) minus IBasal, $Ip_{t-1}$ is the estimated plasma insulin in deviation form at the sampling time of t−1, TauIp1 (min) is a fixed parameter representing a time constant (TauIp1 (min) for this example has a value of 50), and TauIp2 (min) is another fixed parameter representing a time constant (TauIp2 (min) for this example has a value of 70), and Iptotal is the estimated plasma insulin in its nominal value.

$$dIp_t = \exp(-t/TauIp2) * (Ip_{t-1} - Iin + dIp_{t-1} * TauIp1))/ \quad \text{(eq 102)}$$

$$(TauIp1 - TauIp2) \ldots -$$

$$(\exp(-t/TauIp1) * (Ip_{t-1} - Iin + dIp_{t-1} * TauIp2))/$$

$$(TauIp1 - TauIp2)$$

The parameters and variables in Equation 102 are described and/or defined above.

$$G_t = Ip_t * KI + (TauG1 * \exp(-t/TauG1) * \quad \text{(eq 103)}$$

$$(G_{t-1} + dG_{t-1} * TauG2 - Ip_t * KI))/(TauG1 - TauG2) -$$

$$(TauG2 * \exp(-t/TauG2) *$$

$$(G_{t-1} + dG0_{t-1} * TauG1 - Ip_t * KI))/(TauG1 - TauG2)$$

Most of the variables and parameters in Equation 103 were described and/or defined previously. TauG1 (min) is a fixed parameter representing a time constant (which is set to 50 for this example), and TauG2 (min) is another fixed parameter representing a time constant (which is set to 100 for this example).

$$dG_t = (\exp(-t/TauG2) * \quad \text{(eq 104)}$$

$$(G_{t-1} + dG_{t-1} * TauG1 - Ip * KI))/(TauG1 - TauG2) -$$

$$(\exp(-t/TauG1) *$$

$$(G_{t-1} + dG_{t-1} * TauG2 - Ip_t * KI))/(TauG1 - TauG2)$$

The parameters and variables in Equation 104 were described and/or defined previously.

Supervision and Control Module

The current values of the estimated plasma insulin ($Ip_t$) 1444 and the estimated blood glucose (Gr) 1446 (as calculated by the insulin/glucose estimator 1404) serve as inputs to the supervision and control module 1406. The current sensor glucose value SG 1416, and the current value of SGBase 1428 (as calculated by the parameter estimator 1402) also serve as inputs to the supervision and control module 1406. As mentioned previously, the goal of the model supervisor module 1400 is to estimate the accuracy of the sensor glucose measurement in real-time. The supervision and control module 1406 generates the model-predicted sensor glucose (SGp) and compares it against the actual SG 1416. The result of this comparison is used to determine whether the insulin infusion device should remain in the closed-loop mode 1408, transition to the safe basal (low) mode 1410, or transition to the safe basal (nominal) mode 1412.

Figure 59:
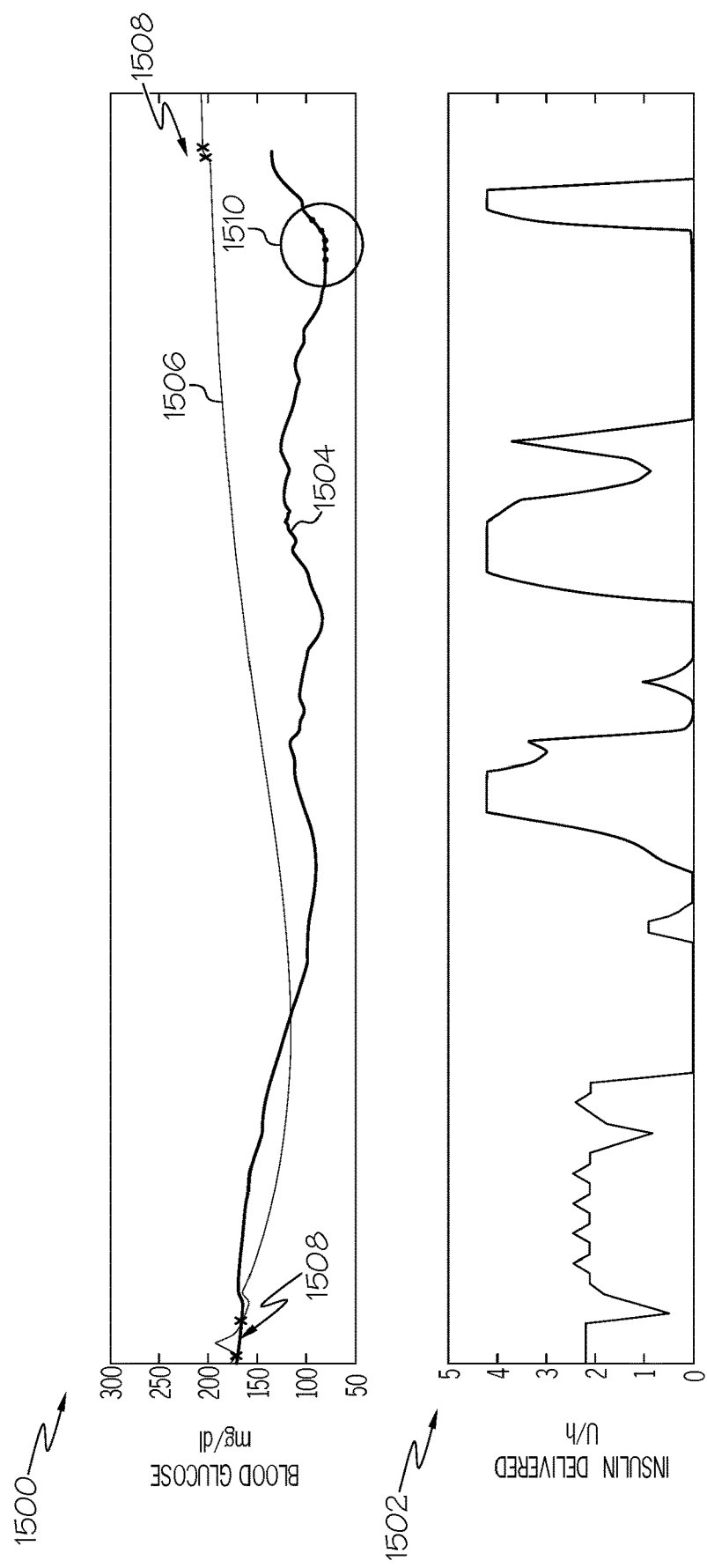
FIG. 59 shows a graph of different blood glucose readings versus time, along with a corresponding graph of insulin as delivered over the same period of time.

The model supervisor module 1400 is unique in that it can be configured to disregard "over-reading" sensor conditions that are typically indicative of meal consumption and an associated insulin bolus. Accordingly, the embodiment described here concentrates on the detection of only one actionable condition, namely, an "under-reading" sensor condition. In this regard, FIG. 59 shows a graph 1500 of blood glucose versus time, along with a corresponding graph 1502 of insulin as delivered over the same period of time. The graph 1500 indicates blood glucose values in mg/dL, and the graph 1502 depicts the associated insulin delivery profile in U/h.

The plot 1504 represents SG measurements, and the plot 1506 represents the corresponding SGp values as generated by the model supervisor module 1400. The graph 1500 also includes blood glucose meter readings 1508, which are depicted as small "X" marks (two appearing at the left side of the graph 1500 and two appearing at the right side of the graph 1500). The blood glucose meter readings 1508 indicate actual blood glucose measurements obtained from the patient's blood samples.

The scenario represented by the graph 1500 includes a period during which the model supervisor module 1400 detects an under-reading sensor condition. In accordance with this particular example, the under-reading sensor condition is flagged when the SGp value exceeds the SG value (by at least 50% of the SG value) for more than five sequential sampling times. The circled region 1510 of the plot 1504 corresponds to a detected under-reading sensor condition; the five dots in the circled region 1510 represent the five sequential sampling times. FIG. 59 illustrates a scenario where the SGp values are accurately tracking the blood glucose meter readings 1508 (at the beginning and end of the time period under analysis). Consequently, the illustrated scenario assumes that the model supervisor module 1400 has detected a true under-reading sensor condition. In other words, the continuous glucose sensor reading is lower than the estimated or modeled glucose sensor output, and is lower than the actual glucose meter data.

As mentioned above, the supervision and control module 1406 uses Gt as an input. The supervision and control module 1406 calculates the predicted sensor glucose value (SGp) in accordance with Equation 105:

$$SGp = G_t + SG\,\text{Base} \qquad (\text{eq 105})$$

In Equation 105, SGp is the predicted sensor glucose value, Gt is the estimated blood glucose at the sampling time t (as determined by the insulin/glucose estimator 1404) and SGBase is the calculated fasting blood glucose as determined by the parameter estimator 1402.

As explained above, an over-reading sensor condition occurs when the supervision and control module 1406 detects SG values that are significantly higher than the corresponding SGp values. In other words, the glucose sensor output is higher than predicted. This condition can be associated with mealtime because: (1) the consumption of meals is accompanied by an insulin bolus; and (2) the sensor model, which is based on fasting periods, does not consider meals. The supervision and control module 1406 is suitably configured to detect such "meal consumed" conditions, but it need not take any corrective action other than setting a flag or recording the occurrence.

In accordance with certain embodiments, the supervision and control module 1406 analyzes the input data in the following manner. The mean relative error between the current sensor glucose (SG) measurements and predicted sensor glucose (SGp) at the present sampling time is calculated and defined as last_measure_error:

$$\text{last\_measure\_error} = \bigl((SG - SGp)/\max([SG(n), SGp])\bigr) * 100\% \qquad (\text{eq 106})$$

Here, last_measure_error is the relative error between the sensor glucose (SG) value and the predicted sensor glucose (SGp) value at the present sampling time, SG is the measured sensor glucose at the current sampling time, and SGp is the predicted sensor glucose at the present sampling time.

If last_measure_error>maxErrPredict, or if last_measure_error<−maxErrPredict, then the supervision and control module 1406 can flag, identify, or otherwise record the occurrence of a corresponding state or condition, as described below. Otherwise, the supervision and control module 1406 assumes that the glucose sensor is functioning properly. For the embodiment described here, the supervision and control module sets a flag (MSFlag) to an appropriate value as needed. If the supervision and control module 1406 determines that the glucose sensor is functioning properly, then MSFlag is set to "No Fault".

If last_measure_error>maxErrPredict and no meal has been recorded in the previous four hours (or any selected or designated period of time), then:

$$\text{set } MS \text{ Flag to "Sensor Over-Reading"} \qquad (\text{eq 107})$$

This condition is flagged because the actual SG values obtained from the glucose sensor are significantly higher than the corresponding predicted values. In this context, last_measure_error is the mean relative error between the current sensor glucose (SG) value and the predicted sensor glucose (SGp) value at the present sampling time (Equation 105), and maxErrPredict is the threshold of the upper acceptable error (which is 50% for this example).

If last_measure_error>maxErrPredict for at least 24 sequential time samples (or any specified number of sequential time samples), and if SG(n) is valid, then:

$$\text{set } G_{t-1} = SG - SG\,\text{Base; and} \qquad (\text{eq 108})$$

$$\text{reset } MS \text{ Flag to "No Fault"}$$

Here, $G_{t-1}$ is the blood glucose in deviation form at the sampling time of t−1, SG is the sensor glucose, SGBase is the fasting blood glucose calculated by the system, and the flag is triggered by the model supervisor module as needed. For this example, the 24 sequential time samples corresponds to a continuous period of two hours (with five minutes being the sampling period). Thus, if the conditions of an over-reading sensor continue for two hours, then the system cancels the "Sensor Over-Reading" flag and resets it to "No Fault". Moreover, the model supervisor module 1400 is recalibrated in accordance with the sensor glucose value (this recalibration is performed under the assumption that detection of an over-reading sensor condition for two continuous hours is indicative of a meal rather than a sensor issue). The system checks if there is a current (valid) value of SG because there can be situations where the system does not have a current sensor reading. It should be appreciated that Equation 108 represents a check that is performed regardless of whether a meal event has actually been recorded.

If last_measure_error<−maxErrPredict for at least six sequential time samples (or any specified number of sequential time samples), then:

$$\text{set } MS \text{ Flag to "Sensor Under-Reading"} \quad \text{(eq 109)}$$

else:

$$\text{set } MS \text{ Flag to "No Fault"} \quad \text{(eq 110)}$$

Supervision and Control Module: Triggered Actions

The model supervisor module 1400 provides additional safeguard checks during closed-loop operation of the insulin infusion system. The exemplary embodiment presented here is suitably configured to detect or determine at least three conditions or scenarios that may bear some relationship to the operating integrity of the continuous glucose sensor. In practice, each detectable condition can be associated with the setting, designating, or saving of an associated MSFlag value for purposes of documentation and/or to trigger certain types of corrective action if so desired. For example, the model supervisor module 1400 can select an appropriate operating mode for the insulin infusion device (e.g., closed-loop mode, open-loop mode, a safe basal mode, or the like). The details of the three different scenarios handled by the model supervisor module 1400 are described below with reference to Case 1, Case 2, and Case 3.

Case 1: Sensor Over-Reading Flagged

If MSFlag is set to "Sensor Over-Reading" (see Equation 107), then the supervision and control module 1406 commands the system to continue operating in the normal closed-loop mode 1412, and to deliver insulin to the body of the user in accordance with the closed-loop mode 1412.

Case 2: Sensor Under-Reading Flagged

If MSFlag is set to "Sensor Under-Reading (see Equation 109), then the supervision and control module 1406 will select either a safe low basal mode or a safe nominal basal mode, where the safe nominal basal mode represents a higher basal rate of insulin relative to the safe low basal mode. To this end, the supervision and control module 1406 checks the difference between the predicted sensor glucose value (SGp) and a low threshold value (Low Threshold), as follows:

$$SGpThDiff = SGp - \text{Low Threshold} \quad \text{(eq 111)}$$

Here, SGpThDiff is the calculated difference, and Low Threshold is the desired low glucose threshold, which for this particular example is set to 70 mg/dL. The calculated difference (SGpThDiff) can be used to determine how best to proceed. In this regard, at least two different scenarios are contemplated for Case 2.

One scenario (Case 2a) is associated with the following relationship:

$$\text{If } (\textit{Temp Target} == \text{true OR } \textit{SGpThDiff} < 0), \quad \text{(eq 112)}$$
$$\text{Then: Deliver Safe Basal Low}$$

Here, Temp Target is true when the set point is raised to 150 mg/dL by the user, SGpThDiff is the difference between SGp and Low Threshold (see Equation 111), and SafeBasalLow is the calculated rate of insulin (U/h) that will bring the fasting blood glucose to a designated or predetermined value, for example, 200 mg/dL. In certain embodiments, SafeBasalLow is based on the value of the patient's insulin total daily dose ($I_{TDD}$), which is also referred to as the daily insulin requirement (see Equation 92). For this particular example, SafeBasalLow $I_{TDD}$/166. Referring to FIG. 58, the supervision and control module 1406 triggers a transition from the closed-loop mode 1408 to the safe basal (low) mode 1410, which in turn causes the insulin infusion device to deliver insulin in accordance with the SafeBasalLow value. The system may deliver at the SafeBasalLow rate for up to 90 minutes (or any specified period of time as appropriate to the particular embodiment) before automatically transitioning back to the open-loop mode. During this time, a BG entry that passes the closed-loop initiation check (as described above) will return the system to the normal closed-loop mode 1408.

Another scenario (Case 2b) is associated with the following:

$$\text{If } (\textit{Temp Target} == \text{false AND } \textit{SGpThDiff} \geq 0), \quad \text{(eq 113)}$$
$$\text{Then: } Ip \text{ Basal } Diff = Ip_t - \text{Basal Factor} \times \text{Safe Basal}$$

In other words, if neither of the conditions in Equation 112 is satisfied, then the supervision and control module 1406 calculates the value of IpBasalDiff in accordance with Equation 113. Here, IpBasalDiff is the difference between the plasma insulin and the safe basal rate, $Ip_t$ is the estimated plasma insulin obtained from the insulin/glucose estimator 1404, SafeBasal is the calculated rate of insulin (U/h) that will bring the fasting blood glucose to a designated or predetermined value, for example, 120 mg/dL, and BasalFactor is a tolerance factor for the basal rate. In certain embodiments, SafeBasal is based on the value of the patient's insulin total daily dose ($I_{TDD}$), which is also referred to as the daily insulin requirement (see Equation 92). For this particular example, SafeBasal=$I_{TDD}$/48.

Next, depending on the calculated value of IpBasalDiff the supervision and control module 1406 determines whether to select SafeBasal or SafeBasalLow as the insulin delivery rate. For this particular embodiment, the delivery rate is selected based on the following:

$$\text{If } Ip \text{ Basal } Diff \leq 0, \text{ Then deliver Safe Basal rate} \quad \text{(eq 114)}$$
$$\text{Else } (Ip \text{ Basal } Diff > 0), \text{ Then deliver Safe Basal Low rate}$$

Referring again to FIG. 58, the supervision and control module 1406 triggers a transition from the closed-loop mode 1408 to either the safe basal (nominal) mode 1412 or the safe basal (low) mode 1410, based on the result of Equation 114. In this regard, the safe basal (nominal) mode 1412 is associated with insulin delivery at the SafeBasal rate, and the safe basal (low) mode 1410 is associated with insulin delivery at the SafeBasalLow rate. The system may deliver at either the SafeBasal rate or the SafeBasalLow rate for up to 90 minutes (or any specified period time as appropriate to the particular embodiment) before automatically transitioning back to the open-loop mode. During this time, a BG entry that passes the closed-loop initiation check (described previously) will return the system to the normal closed-loop mode 1408.

To briefly summarize, there are three scenarios where the supervision and control module 1406 will initiate a transition to the safe basal (low) mode 1408 rather than the safe basal (nominal) mode 1412. In one scenario, the temporary target glucose value (Temp Target) is raised to 150 mg/dL, which is usually associated with a planned period of exercise. In another scenario, the predicted sensor glucose value (SGp) is below 70 mg/dL. Consequently, although there may be a sensor issue the system transitions to the safe basal (low) mode 1410 to avoid a hypoglycemic condition. In a third scenario, the estimated plasma insulin ($Ip_t$) is above a typical basal rate. Although this by itself does not always indicate a sensor issue, the system still enters the safe basal (low) mode 1408 under certain flagged conditions because the estimate indicates that there is a relatively large amount of insulin in the patient's plasma.

Case 3: No Fault Flagged

For this scenario, if MSFlag is set to "No Fault" (see Equation 110), then the supervision and control module 1406 commands the system to remain in the closed-loop mode 1408. In other words, operation of the insulin infusion device continues without transitioning out of the closed-loop mode 1408.

The above description of the alternative model supervisor module 1400 refers to exemplary values, thresholds, constants, ranges, and quantities that are suitable for use with certain exemplary implementations. It should be appreciated that the specific values presented here are not intended to be limiting or exhaustive, and that an exemplary embodiment of the model supervisor module 1400 can employ different values if so desired, to suit the needs of the particular application.

Missed Transmission Module

The missed transmission module 916 continuously checks whether the controller receiving data packets (including SG values) for processing. The missed transmission module 916 keeps the system operating in the closed-loop mode for when less than a stated number of data packets are missed (e.g., less than four data packets in a row, a total number of data packets that represent a timespan of less than 15 minutes, or the like). During this time, the system will continue to calculate the insulin dose using the closed-loop control algorithm based on the last valid sensor glucose value or sensor Isig value. For missed data packets that represent a time longer than a lower time threshold and longer than an upper time threshold (e.g., between 15 and 60 minutes), the missed transmission module 916 switches the system to a pre-programmed safe basal rate, which may be defined as half the patient's nighttime basal rate. If the controller starts receiving data packets during the safe basal rate timeframe, the system will switch back to the closed-loop mode. For missed data packets that represent a time longer than the upper time threshold, however, the missed transmission module 916 switches the system to the open-loop mode to deliver a pre-programmed nighttime basal rate, which may be set by a healthcare provider or a caregiver.

The missed transmission module 916 checks for different scenarios pertaining to when and what kind of packet is lost during transmission. Different steps are executed depending on the type of lost transmission. The details of four different scenarios are described below.

Case 1

If the sensor Isig value and the SG value are both received by the controller, then:
(a) the sensor Isig is saved by the controller;
(b) the SG value is saved by the controller;
(c) a Zero Order Hold (ZOH) count is set to zero; and
(d) the system remains in the closed-loop mode as described previously.

Case 2

If the sensor Isig value is not received, but the SG value is received by the controller, then:
(a) the ZOH count is set to zero;
(b) Isig is calculated by Equation 91 (see below) using the SG value and the sensor calibration factor; and
(c) the system remains in the closed-loop mode.

$$Isig_{calc} = (SG/CF') + 2 \qquad (\text{eq } 115)$$

Case 3

If the sensor Isig value is received, but the SG value is not received by the controller, then:
(a) the ZOH count is set to zero;
(b) SG is calculated by Equation 116 (see below) using the Isig value and the sensor calibration factor; and
(c) the system remains in the closed-loop mode.

$$SG_{calc} = (Isig - 2) \times CF' \qquad (\text{eq } 116)$$

Case 4a

If neither the sensor Isig value nor the SG value are received by the controller (i.e., both values are not received), and if:

$$ZOH \text{ Count} \le ZOH \text{ Count Max}$$

then:
(a) the ZOH count for the sensor Isig and SG is calculated based on previous values;
(b) ZOH Count=ZOH Count+1;
(c) TimeoutCount=0; and
(d) the system remains in the closed-loop mode.

Case 4b

If neither the sensor Isig value nor the SG value are received by the controller (i.e., both values are not received), and if:

$$ZOH \text{ Count} > ZOH \text{ Count Max}$$

then:
(a) an "invalid" place holder for the sensor Isig and SG value is saved;

(b) the system remains in the closed-loop mode, but switches to a temporary safe basal rate, which is half the patient's night time basal rate when in the open-loop mode;
(c) if a packet is received by the system while it is delivering the safe basal rate, the system will transition back to the closed-loop mode;
(d) for every minute that the system is delivering the safe basal rate, a TimeoutCount is incremented: TimeoutCount TimeoutCount+1;
(e) if TimeoutCount>Timeout Count Max, then the system switches to the open-loop mode.

In accordance with certain embodiments, ZOH Count Max has a fixed value of two, and Timeout Count Max has a fixed value of 45, although different values may be used as appropriate to the particular implementation. Moreover, the safe basal rate used by the missed transmission module 916 may be adjustable. In this regard, the safe basal rate may be adjustable within a range of about zero to five Units/Hour.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A method of operating an insulin infusion device to regulate delivery of insulin to a body of a user, the method comprising:
   obtaining, from a continuous glucose sensor, sensor glucose (SG) values for the user;
   operating in a first mode of operation or a second mode of operation, wherein the mode of operation is dependent on one or more of: a sensor underread condition being met, a sensor overread condition being met, the SG values for the user, a minimum lower limit of insulin to be delivered (UMIN) time limit being exceeded, or a maximum upper limit of insulin to be delivered (UMAX) limit being exceeded; and
   automatically operating the insulin infusion device to control delivery of insulin from the insulin infusion device to the body of the user, in accordance with the mode of operation.

2. The method of claim 1, further comprising:
   determining a correction bolus dosage while in the first mode of operation; and
   causing delivery of insulin at the correction bolus dosage.

3. The method of claim 1, further comprising:
   responsive to detecting the UMAX time limit being exceeded or the UMIN time limit being exceeded, causing an alert to be presented to the user; and
   operating in the second mode of operation.

4. The method of claim 1, wherein operating in the first mode of operation or the second mode of operation dependent on the SG values for the user comprises determining a difference between a model-predicted glucose value for the user and the SG values for the user.

5. The method of claim 1, wherein operating in the first mode of operation or the second mode of operation is dependent on whether SG values for the user have not been received for more than a predetermined threshold of time.

6. The method of claim 5, further comprising transitioning to the second mode of operation responsive to the SG values for the user having not been received for more than the predetermined threshold of time, wherein the second mode of operation corresponds to a safe basal delivery mode of operation.

7. The method of claim 6, further comprising transitioning to a third mode of operation responsive to operation of the insulin infusion device in the safe basal delivery mode of operation for more than a second predetermined threshold of time, wherein the third mode of operation comprises an open-loop mode of operation.

8. The method of claim 5, wherein determining whether the SG values for the user have not been received for more than a predetermined threshold of time is based on data packets received at the insulin infusion device from the continuous glucose sensor.

9. The method of claim 1, wherein the sensor underread condition and/or the sensor overread condition are determined based on a comparison of the SG values for the user to model-predicted glucose values for the user.

10. A system comprising:
    one or more processors; and
    one or more processor-readable media storing instructions which, when executed by one or more processors, cause performance of:
      obtaining, from a continuous glucose sensor, sensor glucose (SG) values for a user;
      operating in a first mode of operation or a second mode of operation, wherein the mode of operation is dependent on one or more of: a sensor underread condition being met, a sensor overread condition being met, the SG values for the user, a minimum lower limit of insulin to be delivered (UMIN) time limit being exceeded, or a maximum upper limit of insulin to be delivered (UMAX) limit being exceeded; and
      automatically operating an insulin infusion device to control delivery of insulin from the insulin infusion device to a body of the user, in accordance with the mode of operation.

11. The system of claim 10, wherein the instructions further cause performance of:
    determining a correction bolus dosage while in the first mode of operation; and
    causing delivery of insulin at the correction bolus dosage.

12. The system of claim 10, wherein the instructions further cause performance of:
    responsive to detecting the UMAX time limit being exceeded or the UMIN time limit being exceeded, causing an alert to be presented to the user; and
    operating in the second mode of operation.

13. The system of claim 10, wherein operating in the first mode of operation or the second mode of operation dependent on the SG values for the user comprises determining a difference between a model-predicted glucose value for the user and the SG values for the user.

14. The system of claim 10, wherein operating in the first mode of operation or the second mode of operation is dependent on whether SG values for the user have not been received for more than a predetermined threshold of time.

15. The system of claim 14, wherein the instructions further cause performance of transitioning to the second mode of operation responsive to the SG values for the user having not been received for more than the predetermined threshold of time, wherein the second mode of operation corresponds to a safe basal delivery mode of operation.

16. The system of claim 15, wherein the instructions further cause performance of transitioning to a third mode of operation responsive to operation of the insulin infusion device in the safe basal delivery mode of operation for more than a second predetermined threshold of time, wherein the third mode of operation comprises an open-loop mode of operation.

17. The system of claim 14, wherein determining whether the SG values for the user have not been received for more than a predetermined threshold of time is based on data packets received at the insulin infusion device from the continuous glucose sensor.

18. The system of claim 10, wherein the sensor underread condition and/or the sensor overread condition are determined based on a comparison of the SG values for the user to model-predicted glucose values for the user.

19. A method comprising:
receiving a temporary setpoint value to be used for a specified period of time to regulate fluid delivery to a patient during operation of a fluid delivery device, wherein the temporary setpoint value is greater than a default setpoint value; and
responsive to receiving the temporary setpoint value, causing operation of the fluid delivery device to transition from a first mode of operation to a second mode of operation, wherein the second mode of operation comprises automatically delivering fluid to the patient based on a difference between the temporary setpoint value and measured glucose values of the patient.

20. The method of claim 19, wherein automatically delivering fluid to the patient while in the second mode of operation causes a reduction in fluid delivery to the patient relative to the first mode of operation.

* * * * *